United States Patent
Bland-Ward et al.

(10) Patent No.: US 9,868,790 B2
(45) Date of Patent: *Jan. 16, 2018

(54) SYNERGISTIC COMBINATIONS OF OX40L ANTIBODIES FOR THE TREATMENT OF GVHD

(71) Applicant: Kymab Limited, Cambridge (GB)

(72) Inventors: Philip Bland-Ward, Cambridge (GB); Miha Kosmac, Cambridge (GB); Steve Holmes, Cambridge (GB); Ian Kirby, Cambridge (GB); Jamie Campbell, Cambridge (GB)

(73) Assignee: Kymab Limited (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/661,584

(22) Filed: Jul. 27, 2017

(65) Prior Publication Data

US 2017/0327586 A1    Nov. 16, 2017

Related U.S. Application Data

(63) Continuation of application No. 15/604,495, filed on May 24, 2017, which is a continuation of application No. 15/333,517, filed on Oct. 25, 2016, which is a continuation of application No. 15/142,538, filed on Apr. 29, 2016, now Pat. No. 9,512,229, which is a continuation-in-part of application No. PCT/GB2016/050565, filed on Mar. 3, 2016, and a continuation-in-part of application No. PCT/GB2015/050614, filed on Mar. 3, 2015, and a continuation-in-part of application No. 14/935,937, filed on Nov. 9, 2015, now Pat. No. 9,434,785, which is a continuation of application No. 14/811,163, filed on Jul. 28, 2015, now Pat. No. 9,234,043, which is a continuation of application No. 14/700,896, filed on Apr. 30, 2015, now Pat. No. 9,139,653, said application No. 15/142,538 is a continuation-in-part of application No. 14/955,843, filed on Dec. 1, 2015, now abandoned, which is a continuation of application No. 14/811,163, filed on Jul. 28, 2015, now Pat. No. 9,234,043, which is a continuation of application No. 14/700,896, filed on Apr. 30, 2015, now Pat. No. 9,139,653.

(30) Foreign Application Priority Data

Sep. 9, 2015  (GB) .................................. 1516008.8

(51) Int. Cl.
| | |
|---|---|
| A61K 39/395 | (2006.01) |
| C07K 16/28 | (2006.01) |
| A61K 45/06 | (2006.01) |
| A61K 31/436 | (2006.01) |
| G01N 33/483 | (2006.01) |
| A61K 39/00 | (2006.01) |

(52) U.S. Cl.
CPC ........ *C07K 16/2875* (2013.01); *A61K 31/436* (2013.01); *A61K 39/3955* (2013.01); *A61K 45/06* (2013.01); *G01N 33/4833* (2013.01); *A61K 2039/505* (2013.01); *A61K 2039/507* (2013.01); *C07K 2317/21* (2013.01); *C07K 2317/22* (2013.01); *C07K 2317/24* (2013.01); *C07K 2317/31* (2013.01); *C07K 2317/33* (2013.01); *C07K 2317/54* (2013.01); *C07K 2317/55* (2013.01); *C07K 2317/565* (2013.01); *C07K 2317/622* (2013.01); *C07K 2317/624* (2013.01); *C07K 2317/76* (2013.01); *C07K 2317/90* (2013.01)

(58) Field of Classification Search
None
See application file for complete search history.

(56) References Cited

U.S. PATENT DOCUMENTS

| | | | |
|---|---|---|---|
| 6,528,055 | B2 | 3/2003 | Godfrey et al. |
| 6,528,623 | B2 | 3/2003 | Godfrey et al. |
| 7,098,184 | B2 | 8/2006 | Godfrey et al. |
| 7,291,331 | B1 | 11/2007 | Croft et al. |
| 7,304,033 | B2 | 12/2007 | Larsen et al. |
| 7,501,496 | B1 | 3/2009 | Endl et al. |
| 7,812,133 | B2 | 10/2010 | Martin |
| 7,868,141 | B2 | 1/2011 | Endl et al. |
| 8,101,175 | B1 | 1/2012 | Croft et al. |
| 8,551,477 | B1 | 10/2013 | Croft et al. |
| 8,956,615 | B1 | 2/2015 | Croft et al. |
| 8,962,807 | B2 | 2/2015 | Verdonck et al. |
| 9,139,653 | B1 | 9/2015 | Campbell et al. |
| 9,234,043 | B1 | 1/2016 | Campbell et al. |

(Continued)

FOREIGN PATENT DOCUMENTS

| | | |
|---|---|---|
| WO | WO 85/04880 A1 | 11/1985 |
| WO | WO 1995/021915 A1 | 8/1995 |

(Continued)

OTHER PUBLICATIONS

Carraway et al. New targets for therapy in breast cancer: Mammalian target of rapamycin (mTOR) antagonists. Breast Cancer Res 2004, 6: 219-224.*

Abouelnasr et al., "Defining the role of sirolimus in the management of graft-versus-host disease: from prophylaxis to treatment", Bioi Blood Marrow Transplant, 19(1):12-21 (2013).

Akiba et al., "CD28-independent costimulation of T cells by OX40 ligand and CD70 on activated B cells", J Immunol, 162(12):7058-66 (1999).

Biasco et al., "In vivo tracking of T cells in humans unveils decade-long survival and activity of genetically modified T memory stem cells", Sci Transl Med, 7(273):273ra13 (2015).

(Continued)

*Primary Examiner* — Ilia I Ouspenski

(74) *Attorney, Agent, or Firm* — Finnegan, Henderson, Farabow, Garrett & Dunner, LLP

(57) ABSTRACT

The present invention relates to anti-human OX40L antibodies, new medical uses and methods.

29 Claims, 9 Drawing Sheets

(56) References Cited

U.S. PATENT DOCUMENTS

| | | | |
|---|---|---|---|
| 9,428,570 | B2 | 8/2016 | Lawson et al. |
| 9,434,785 | B1 | 9/2016 | Bland-Ward et al. |
| 9,512,229 | B2 | 12/2016 | Bland-Ward et al. |
| 9,587,030 | B2 | 3/2017 | Campbell et al. |
| 2002/0114814 | A1 | 8/2002 | Gray et al. |
| 2003/0158402 | A1 | 8/2003 | Hall et al. |
| 2006/0002929 | A1 | 1/2006 | Khare et al. |
| 2007/0292440 | A1 | 12/2007 | Kenyon et al. |
| 2008/0279862 | A1 | 11/2008 | Khare |
| 2009/0053230 | A1 | 2/2009 | Martin |
| 2009/0252749 | A1 | 10/2009 | Leister et al. |
| 2010/0098712 | A1 | 4/2010 | Adler et al. |
| 2010/0183591 | A1 | 7/2010 | Baron et al. |
| 2010/0183612 | A1 | 7/2010 | Peach et al. |
| 2011/0033451 | A1 | 2/2011 | Carreno et al. |
| 2011/0070239 | A1 | 3/2011 | Endl et al. |
| 2012/0027751 | A1 | 2/2012 | Rennert |
| 2013/0095109 | A1 | 4/2013 | Nadler et al. |
| 2013/0183315 | A1 | 7/2013 | Attinger et al. |
| 2014/0044703 | A1 | 2/2014 | Kato et al. |
| 2014/0086932 | A1 | 3/2014 | Traber et al. |
| 2014/0093497 | A1 | 4/2014 | Reimann et al. |
| 2014/0286897 | A1 | 9/2014 | Podack et al. |
| 2016/0361364 | A1 | 12/2016 | Corbascio |
| 2017/0037137 | A1 | 2/2017 | Bland-Ward et al. |

FOREIGN PATENT DOCUMENTS

| | | |
|---|---|---|
| WO | WO-2008-106116 | 5/2003 |
| WO | WO 2005/094879 A2 | 10/2005 |
| WO | WO 2006/029879 A2 | 3/2006 |
| WO | WO 2006/030220 A1 | 3/2006 |
| WO | WO 2007/133290 A2 | 11/2007 |
| WO | WO 2009/141239 A1 | 11/2009 |
| WO | WO 2011/073180 A1 | 6/2011 |
| WO | WO 2013/008171 A1 | 1/2013 |
| WO | WO 2015/132580 A1 | 9/2015 |
| WO | WO 2015/153514 A1 | 10/2015 |
| WO | WO 2016/022468 A1 | 2/2016 |
| WO | WO 2016/139482 A1 | 9/2016 |

OTHER PUBLICATIONS

Blazar et al., "Ligation of OX40 (CD134) regulates graft-versus-host disease (GVHD) and graft rejection in allogeneic bone marrow transplant recipients", Blood, 101:3741-3748 (2003).

Burrows et al., "OX40 blockade inhibits house dust mite driven allergic lung inflammation in mice and in vitro allergic responses in humans", Eur. J. Immunol pp. 1-13 (2015).

Burrows et al., "Peer Review Correspondence: OX40 blockade inhibits house dust mite driven allergic lung inflammation in mice and in vitro allergic responses in humans", European Journal of Immunology, (2014).

Chen et al. "Ox40-ligand has a critical costimulatory role in dendritic cell: T cell interactions", Immunity, 11:689-698 (1999).

Cieri et al., "IL-7 and IL-15 instruct the generation of human memory stem T cells from naive precursors", Blood, 121 (4):573-584 (2013).

Cieri et al., "Generation of human memory stem T cells after haploidentical T-replete hematopoietic stem cell transplantation", Blood, 125(18):2865-2874 (2015).

Croft et al., "Control of Immunity by the TNFR-Related molecule OX40 (CD134)", Annu. Rev. Immunol. 28:57-78 (2010).

Dai et al., "Anti-OX40L monoclonal antibody prolongs secondary heart allograft survival based on CD40/CD40L and LFA-1/ICAM-1 blockade", Transplant Immunology {2015), http://dx.doi.org/10.1016/j.trim.2015.01.001.

Damayanti et al., "Serial OX40 engagement on CD+4 T cells and natural killer T cells causes allergic airway inflammation", Am J Respir Crit Care Med 181(7):688-698 (2010).

Findlay et al., "OX40L blockade is therapeutic in arthritis despite promoting osteoclastogenesis", PNAS, 111 (6):2289-2294 (2014).

Foks et al., "Interruption of the OX40-OX40 ligand pathway in LDL receptor-deficient mice causes regression of atherosclerosis", J. Immunol. 191:4573-4580 (2013).

Gallego-Pinazo et al., "Update on the principles and novel local and systemic therapies for the treatment of non-infectious uveitis", Inflamm Allergy Drug Targets, 12(1):38-45 (2013).

Garnett et al., "Treatment and management of graft-versus-host disease: improving response and survival", Ther Adv Hematol 4(6):366-78 (2013).

Gattinoni et al., "A human memory T cell subset with stem cell-like properties", Nat Med, 17(10):1290-1297 (2011).

Gattinoni, L. & Restifo, N.P., Comment on "Moving T memory stem cells to the clinic", Blood, 121(4):567-568 (2013).

Gauvreau et al., "OX40L blockade and allergen-induced airway responses in subjects with mild asthma", Clinical Experimental Allergy, 44:29-37 (2013).

Ge et al., "CDI34-Allodepletion allows selective elimination of alloreactive human T cells without loss of virus-specific and leukemia-specific effectors", Biology of Blood and Marrow Transplantation 14:518-530 (2008).

Hattori et al., "Blockade of the OX40 ligand prolongs corneal allograft survival", Eur. J. Immunol. 37:3597-3604 (2007).

Hitt, "FDA Approves Belatacept for Kidney Transplant Patients." Accessed at http://www.medscape.com/viewarticle/744723 on Jun. 17, 2017, 2 pages.

Hoshino et al., "Critical role for OX40 ligand in the development of pathogenic Th2 cells in a murine model of asthma", Eur J Immunol, 33(4):861-9 (2003).

Jacquemin et al., OX40 ligand contributes to human lupus pathogenesis by promoting T follicular helper response, Immunity, 4:1-12 (2015).

Kitchens et al., "Interruption of OX40L signaling prevents costimulation blockade-resistant allograft rejection", JCI Insight 2(5):e90317 (2017) https://doi.org/10.1172/jci.insight.90317.

Kotani et al., "Correlation of peripheral blood OX40+(CD134+) T cells with chronic graft-versus-host disease in patients who underwent allogeneic hematopoietic stem cell transplantation: Presented in part at the 42nd Annual Meeting and Exposition of the America Society of Hematology", Blood, 98(10):3160-3164 (2001).

Laustsen et al., "Soluble OX40L is associated with presence of autoantibodies in early rheumatoid arthritis", Arthritis Research & Therapy 16:747 (2014).

Levine et al., "A prognostic score for acute graft-versus-host disease based on biomarkers: a multicentre study", Haematology, 2:e21-e29 (2015).

Martin-Orozco et al., "Paradoxical dampening of anti-islet self-reactivity but promotion of diabetes by OX40 ligand", J Immunol. 171:6954-6960 (2003).

Miura et al., "Molecular cloning and characterization of a novel glycoprotein, gp34, that is specifically induced by the human T-cell leukemia virus type 1 transactivator p40 tax", Molecular and Cellular Biology 11 (3): 1313-1325 (1991).

Nohara et al., "Amelioration of experimental autoimmune encephalomyelitis with anti-OX40 ligand monoclonal antibody: a critical role for OX40 ligand in migration, but not development, of pathogenic T cells", J Immunol, 166 (3):2108-15 (2001).

Pakala et al., "Prevention of diabetes in NOD mice at a late stage by targeting OX40/OX40 ligand interactions", Eur. J. Immunol. 34:3039-3046 (2004).

Polte et al., "Different roles of C30 in the development of acute and chronic airways inflammation in a murine asthma model", Eur. J. 39:1736-1742 (2009).

Przepiorka et al., "1994 Consensus Conference on Acute GVHD Grading", Bone Marrow Transplant, 15(6):825-8 (1995).

Qian et al., "Advances in the treatment of acute graft-versus-host disease", J Cell Mol Med, 17(8):966-75 (2013).

Roberto et al., "Role of naive-derived T memory stem cells in T-cell reconstitution following allogeneic transplantation", Blood, 125(18):2855-2864 (2015).

Ruutu et al., "Prophylaxis and treatment of GVHD: EBMT-ELN working group recommendations for a standardized practice", Bone Marrow Transplant, 49(2):168-73 (2014).

(56) References Cited

OTHER PUBLICATIONS

Salek-Ardakani et al., "OX40 (CD134) controls memory T helper 2 cells that drive lung inflammation", J Exp Med, 198(2):315-24 (2003).
Seshasayee et al., "In vivo blockade of OX40 ligand inhibits thymic stromal lymphopoietin driven atopic inflammation", J. Clin. Invest. 117:3868-3878 (2007).
Song et al., "Small-molecule modulators of the OX40-OX40 ligand co-stimulatory protein-protein interaction", British Journal of Pharmacology 171:4955-4969 (2014).
Soroosh et al., "OX40-OX40 ligand interaction though T cell-T cell contact contributes to CD4 T Cell longevity", J. Immunol. 176:5975-5987 (2006).
Souza et al., "Expression of lymphocyte-endothelial receptor-ligand pairs, 4beta7/MAdCAM-1 and OX40/OX40 ligand in the colon and jejunum of patients with inflammatory bowel disease", Gut 45:856-863 (1999).
Stallone et al., "mTOR inhibitors effects on regulatory T cells and on dendritic cells", J Transl Med, 14(1):152 (2016)_ 9pp.
Strom et al., "Therapeutic approach to organ transplantation" (Therapeutic Immunology, Austen et al. (Ed.) Blackwell Science, Cambridge MA, 1996, p. 451-456).
Stuber et al.,"Involvement of OX40-OX40L interactions in the intestinal manifestations of the murine acute graft-versus-host disease", Gastroenterology, 115(5):1205-15 (1998).
Sugamura et al., "Therapeutic targeting of the effector T-cell co-stimulatory molecule OX40", Nat Rev Immunol, 4(6):420-31 (2004).
Summary of PubMed search results, Nov. 2016, 1 page.
Sun et al., "Prevention of Chronic Rejection in Mouse Aortic Allografts by Combined Treatment with CTLA4-Ig and Anti-CD40 Ligand Monoclonal Antibody," Transplantation 64:1838-56 (1997).
Tanaka et al., "Generation and characterization of monoclonal antibodies against multiple epitopes on the c-terminal half of envelope gp46 of human t-cell leukemia virus type-I (HTLV-I)", Int. J. Cancer, 46:675-681 (1990).
Totsuka et al., "Therapeutic effect of anti-OX40L and anti-TNF-beta MAbs in a murine model of chronic colitis", Am Physiol Gastrointest Liver Physiol. 284:G595-G603 (2003).
Tsukada et al., "Blockade of CD134 (OX40)-CD143L interaction ameliorates lethal acute graft-versus-host in a murine model of allogeneic bone marrow transplantation", Blood, 95:2434-2439 (2000).
Ueno et al., "OX40/OX40L axis: not a friend in autoimmunity", Obcotgarget, 6(26): 21779-21780 (2015).
Ukyo et al., "Costimulation through OX40 is crucial for induction of an alloreactive human T-cell response", Immunology, 109:226-231 (2003).
Xu et al., "The roles of stem cell memory T cells in hematological malignancies", J Hematol Oncol, 8:113 (2015).
Zhang et al., "Activation of OX40 augments Th17 cytokine expression and antigen-specific uveitis", The American Journal of Pathology, 177(6):2912-2920 (2010).
Akimova et al. Differing effects of rapamycin or calcineurin inhibitor on T-regulatory cells in pediatric liver and kidney transplant recipients. Am. J. Transplant. 12, 3449-3461 (2012).
Alignment of Amgen Publication Heavy Chain Sequence SEQ ID No. 22 and Kymab Application HCDR3 Sequences SEQ ID No. 106. Alignment generated using BLAST on Aug. 10, 2017.
R. Bourgon, R. Gentleman, W. Huber, Independent filtering Increases detection power for high-throughput experiments, Proc. Natl. Sci. U.S.A. 107, 9546-9551 (2010).
Charbonnier et al. CTLA4-Ig restores rejection of MHC class-II mismatched allografts by disabling IL-2-expanded regulatory T cells. Am. J. Transplant. 12, 2313-2321 (2012).
Chen, X. et al, Blockade of Interleukin-6 signaling augments regulatory T-cell reconstitution and attenuates the severity of graft-versus-host disease. Blood114, 891-900 (2009).
Culhane et al. MADE4: An R package for multivariate analysis of gene expression data. Bioinformatics 21, 2789-2790 (2005).
Cutler et al. Tacrolimus/sirolimus vs tacrolimus/methotrexate as GVHD prophylaxis after matched, related donor allogeneic HCT, Blood 124, 1372-1377 (2014).
Diamond et al. The broad-spectrum antiviral functions of IFIT and IFITM proteins. Nat. Rev. Immunol. 13, 46-57 (2013).
Duan et al. Large scale analysis of positional effects of single-base mismatches on microarray gene expression data. BioData Min. 3, 2 (2010).
Golub et al. Molecular classification of cancer. Class discovery and class prediction by gene expression monitoring. Science 286, 531-537 (1999).
Guo et al. The type I IFN induction pathway constrains Th17-mediated autoimmune inflammation in mice. J. Clin. Invest. 118, 1680-1690 (2008).
Hitt, "FDA Approves Beletacept for Kidney Transplant Patients" Accessed at http://www.medscape.com/viewarticle/744723 on Jun. 17, 2017, 2 pages.
Horkheimer et al, Induction of type I IFN is required for overcoming tumor-specific T-cell tolerance after stem cell transplantation. Blood 113, 5330-5339 (2009).
Hsieh et al. Allogeneic hematopoletic stem-cell transplantation for sickle cell disease. N. Engl. J. Med. 361, 2309-2317 (2009).
Huang et al. Systematic and integrative analysis of large gene lists using DAVID bioinformatics resources. Nat. Protoc. 4, 44-57 (2009).
Huang et al. Bioinformatics enrichment tools: Paths toward the comprehensive functional analysis of large gene lists, Nucleic Acids Res. 37, 1-13 (2009).
Irizarry et al. Exploration, normalization, and summaries of high density oligonucleotide array probe level data, Biostatistics 4, 249-264 (2003).
Johnson, W.E., Adjusting batch effects in microarray expression data using empirical Bayes methods. Biostatistics 8, 118-127 (2007).
Johnson, Z.P., et al, Immunogenetic management software: A new tool for visualization and analysis of complex immunogenetic datasets. Immmunogenetics 64, 329-336 (2012).
Johnston et al. Sirolimus and mycophenolate mofetil as GVHD prophylaxis in myeloablative, matched-related donor hematopoietic cell transplantation. Bone Marrow Transplant. 47, 581-588 (2012).
Kabelitz, Expression and function of Toll-like receptors in T lymphocytes, Curr. Opin. Immunol. 19, 39-45 (2007).
Kinnear et al. A diametric role for OX40 in the response of effector/memory CD4+ T cells and regulatory T cells to alloantigen. J. Immunol. 191, 1465-1475 (2013).
Kole et al. Type I IFNs regulate effector and regulatory T cell accummulation and anti-inflammatory cytokine production during T cell-mediated colitis. J. Immunol. 191, 2771-2779 (2013).
Kopf et al. OX40-deficient mice are defective in Th cell proliferation but are competent in generating B cell and CTL Responses after virus infection. Immunity 11, 699-706 (1999).
Koura et al. In vivo T cell costimulation blockade with abatacept for acute graft-versus-host disease prevention: A first-in-disease trial. Biol. BloodMarrow Transplant. 19, 1638-1649 (2013).
Kroemer et al. OX40 controls functionally different T cell subsets and their resistance to depletion therapy. J. Immunol. 179, 5584-5591 (2007).
Lank et al. Ultra-high resolution HLA genotyping arid allele discovery by highly multiplexed cDNA amplicon pyrosequencing. BMC Genomics 13, 378 (2012).
Larsen et al. An MHC-defined primate model reveals significant rejection of bone marrow after mixed chimerism induction despite full MHC matching. Am. J. Transplant. 10, 2396-2409 (2010).
Lee, E.-C. et al. Complete humanization of the mouse immunoglobulin loci enables efficient therapeutic antibody discovery. Nat. Biotechnol. 32, 356-363 (2014).
LeE, J.S. et al. Recruitment of Sprouty1 to immune synapse regulates T cell receptor signaling. J. Immunol. 183, 7178-7186 (2009).
Miller et al. GVHD after hapioidentical transplantation: A novel, MHC-defined rhesus macaque model identifies CD28-CD8+ T cells

(56) References Cited

OTHER PUBLICATIONS as a reservoir of breakthrough T-cell proliferation during costimulation blockade and sirolimus-based immunosuppression. *Blood* 116, 5403-5418 (2010).
Mootha et al. PGC-1a-responsive genes involved in oxidative phosphorylation are coordinately downregulated in human diabetes. *Nat. Genet.* 34, 267-273 (2003).
Moschen et al. Interferon-alpha controls IL-17 expression in vitro and in vivo. *Immunobiology* 213, 779-787 (2008).
Munson, An improved technique for calculating relative response in cellular proliferation experiments. *Cytometry A* 77, 909-910 (2010).
Murata et al. Impairment of antigen-presenting cell function in mice lacking expression of OX40 ligand. *J. Exp. Med.* 191, 365-374 (2000).
Newcomb et al, Human TH17 cells express a functional IL-13 receptor and IL-13 altenuates IL-17A production. *J. Allergy Clin. Immunol.* 127, 1006-1013 (2011).
Newman et al Modification of the Fc region of a primatized IgG antibody to human CD4 retains its ability to modulate CD4 receptors but does not deplete CD4+ T cells in chimpanzees. *Clin. Immunol.* 98, 164-174 (2001).
Peccatori et al. Sirolimus-based graft-versus-host disease prophylaxis promotes the in vivo expandion of regulatory T cells and permits peripheral blood stem cell transplantion from haploidentical donors. *Leukemia* 29, 396-405 (2015).
Piconese et al. OX40 triggering blocks suppression by regulatory T cells and facilitates tumor rejection. *J. Exp. Med.* 205, 825-839 (2008).
Piconese et al. A non-redundant role for OX40 in the competitive fitness of Treg in response to IL-2. *Eur. J. Immunol.* 40, 2902-2913 (2010).
Pidala et al. A randomized phase II study to evaluate tacrolimus in combination with sirolimus or methotrexate after allogeneic hematopoletic cell transplantation. *Haematologica* 97, 1882-1889 (2012).
Rawlings et al. The JAK/STAT signaling pathway. *J. Cell Sci.* 117, 1281-1283 (2004).
Riella el al. Deleterious effect of CTLA4-Ig on a Treg dependent transplant model. *Am. J. Transplant.* 12, 846-855 (2012).
Robb et al. Type I-IFNs control GVHD and GVL responses after transplantation. *Blood* 118, 3399-3409 (2011).
Robb et al. The Interferon-dependent orchestration of innate and adaptive immunity after transplantation. *Blood* 119. 5351-5358 (2012).
Ruby et al. Cutting edge: OX40 agonists can drive regulatory T cell expansion if the cytokine milleu is right. *J. Immunol.* 163, 4853-4857 (2009).
Salek-Ardakani et al. OX40:OX40L Axis: Emerging Targets for Immunotherapy of Human Disease, *Current Immunology Reviews* 2. 37-53 (2006).
Sanchez et al Kinetic of regulatory CD25high and activated CD134+ (OX40) T lymphocytes during acute and chronic graft-versus-host disease after allogeneic bone marrow transplantation. *Br. J. Haematol.* 126. 697-703 (2004).
Schoggins et al. Interferon-stimulated genes and their antiviral effector functions. *Curr. Opin Virol.* 1, 519-525 (2011).
Shinohara et al. Engagement of the type I interferon receptor on dendritic cells inhibits T helper 17 cell development: Role of Intracellular osteopontin. *Immunity* 29, 68-78 (2008).
Spoerl et al. Activity of therapeutic JAK 1/2 blockade in graft-versus-host disease. *Blood* 123, 3832-3842 (2014).
Stewart et al. Interferon-dependent IL-10 production by Tregs limits tumor Th17 inflammation. *J. Clin. Invest.* 123, 4859-4874 (2013).
Subramanian et al. Gene set enrichment analysis: A kowledge-based approach for interpreting genome-wide expression profiles. *Proc. Natl. Acad. Sci. U.S.A.* 102, 15545-15550 (2005).
Sun et al., Prevention of Chronic Rejection in Mouse Aortic Allografts by Combined Treatment with CTLA4-Ig and Anti-CD40 Ligand Monoclonal Antibody, *Transplantation* 64, 1838-1856 (1997).
Vu et al. OX40 costimulation turns off Foxp3+ Tregs. *Blood* 110, 2501-2510 (2007).
Wing et al. CTLA-4 control over Foxp3+ regulatory T cell function. *Science* 322, 271-275 (2008).
Wiseman et al. Major histocompatibility complex genotyping with massively parallel pyrosequencing. *Nat. Med.* 15, 1322-1326 (2009).
Yuan et al. The Role of hte CD134-CD134 Ligand Costimulatory Pathsway in Alloimmune Responses In Vivo, *J. Immunol.* 170, 2949-2955 (2003).
Zhang et al. An obligate cell-intrinsic function for CD28 in Tregs. *J. Clin. Invest.* 123, 580-593 (2013).

* cited by examiner

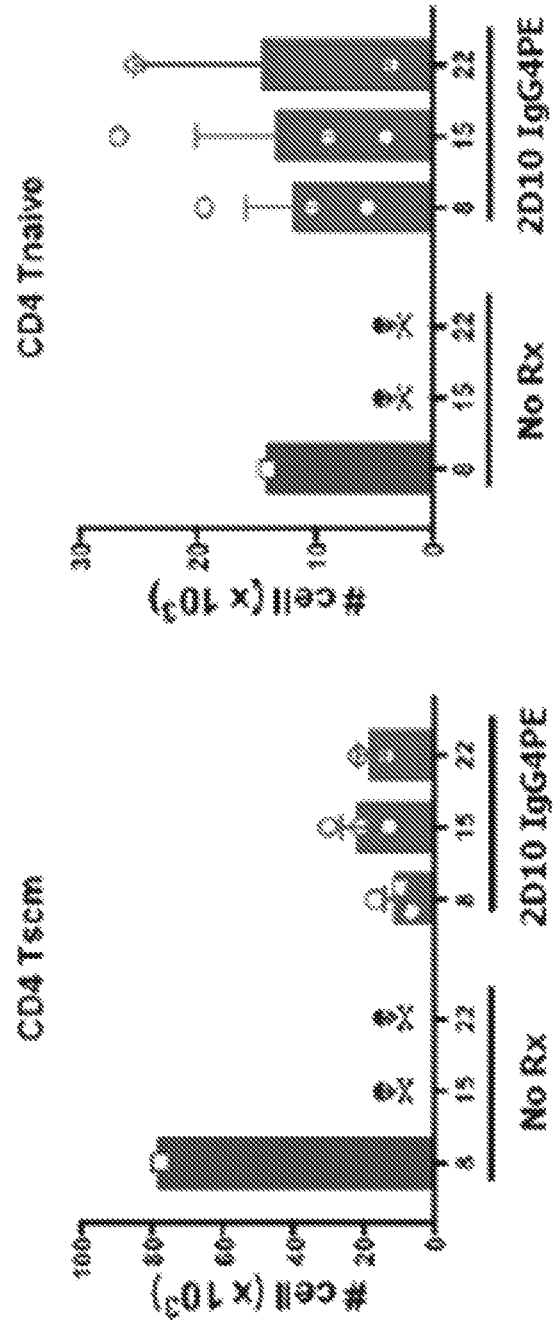

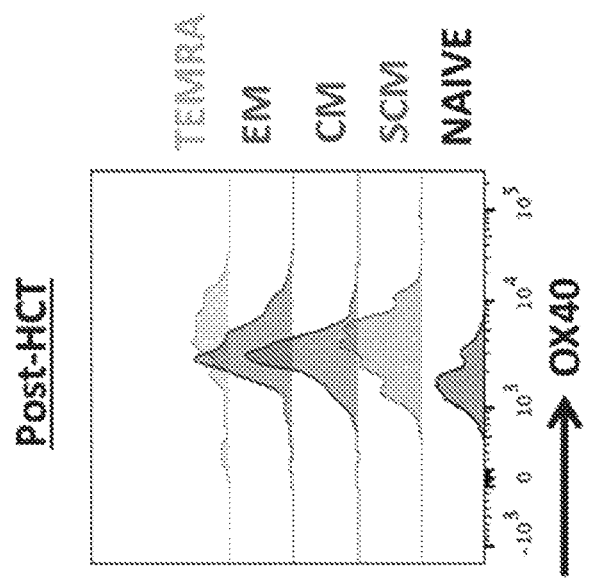
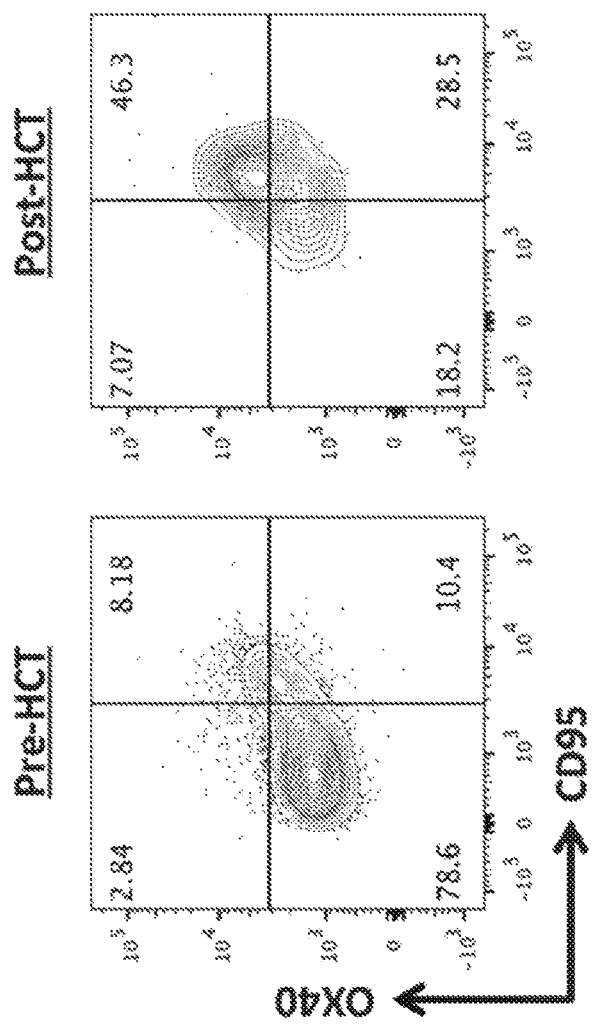

SEQUENCE LISTING

<160> NUMBER OF SEQ ID NOS: 234

<210> SEQ ID NO 1
<211> LENGTH: 384
<212> TYPE: DNA
<213> ORGANISM: Homo Sapiens

<400> SEQUENCE: 1
gaggtgcaac tggtggagtc tgggggagtc ttggtacagc cggggggggtc cctgagactc        60 tcctgtgcag cctctggatt cacctttagc agttatatta tgacttgggt ccgccaggct       120
ccagggaagg ggctggagtg ggtctcaggt attagtggta gtggtggtgg tacatactac       180
gcagactcca tgaagggccg gttcaccatc tccagagaca attccaagaa cacgctgtat       240
ctgcagatga acagcctgag agtcgaggac acggccgtat attactgtgc gaaagatcgg       300
ttaggtccga ttactttggt tcggggggggc tattactacg gtatggacgt ctggggccaa       360
gggaccacgg tcaccgtctc ctca                                              384

<210> SEQ ID NO 2
<211> LENGTH: 128
<212> TYPE: PRT
<213> ORGANISM: Homo Sapiens

<400> SEQUENCE: 2

Glu Val Gln Leu Val Glu Ser Gly Gly Val Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Thr Trp Val Arg Gln Ala Pro Gly Lys Gly Leu Glu Trp Val
        35                  40                  45

Ser Gly Ile Ser Gly Ser Gly Gly Gly Thr Tyr Tyr Ala Asp Ser Met
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Lys Asp Arg Leu Gly Pro Ile Thr Leu Val Arg Gly Tyr Tyr
            100                 105                 110

Tyr Gly Met Asp Val Trp Gly Gln Gly Thr Thr Val Thr Val Ser Ser
        115                 120                 125

<210> SEQ ID NO 3
<211> LENGTH: 24
<212> TYPE: DNA
<213> ORGANISM: Homo Sapiens

<400> SEQUENCE: 3
ggattcacct ttagcagtta tatt                                               24

<210> SEQ ID NO 4
<211> LENGTH: 8
<212> TYPE: PRT
<213> ORGANISM: Homo Sapiens

<400> SEQUENCE: 4

Gly Phe Thr Phe Ser Ser Tyr Ile
1               5

<210> SEQ ID NO 5

```
<211> LENGTH: 24
<212> TYPE: DNA
<213> ORGANISM: Homo Sapiens

<400> SEQUENCE: 5
attagtggta gtggtggtgg taca                                          24

<210> SEQ ID NO 6
<211> LENGTH: 8
<212> TYPE: PRT
<213> ORGANISM: Homo Sapiens

<400> SEQUENCE: 6

Ile Ser Gly Ser Gly Gly Gly Thr
1               5

<210> SEQ ID NO 7
<211> LENGTH: 63
<212> TYPE: DNA
<213> ORGANISM: Homo Sapiens

<400> SEQUENCE: 7
gcgaaagatc ggttaggtcc gattactttg gttcgggggg gctattacta cggtatggac   60
gtc                                                                 63

<210> SEQ ID NO 8
<211> LENGTH: 21
<212> TYPE: PRT
<213> ORGANISM: Homo Sapiens

<400> SEQUENCE: 8

Ala Lys Asp Arg Leu Gly Pro Ile Thr Leu Val Arg Gly Gly Tyr Tyr
1               5                   10                  15

Tyr Gly Met Asp Val
            20

<210> SEQ ID NO 9
<211> LENGTH: 15
<212> TYPE: DNA
<213> ORGANISM: Homo Sapiens

<400> SEQUENCE: 9
agttatatta tgact                                                    15

<210> SEQ ID NO 10
<211> LENGTH: 5
<212> TYPE: PRT
<213> ORGANISM: Homo Sapiens

<400> SEQUENCE: 10

Ser Tyr Ile Met Thr
1               5

<210> SEQ ID NO 11
<211> LENGTH: 51
<212> TYPE: DNA
<213> ORGANISM: Homo Sapiens

<400> SEQUENCE: 11
ggtattagtg gtagtggtgg tggtacatac tacgcagact ccatgaaggg c             51

<210> SEQ ID NO 12
<211> LENGTH: 17
```

```
<212> TYPE: PRT
<213> ORGANISM: Homo Sapiens

<400> SEQUENCE: 12

Gly Ile Ser Gly Ser Gly Gly Thr Tyr Tyr Ala Asp Ser Met Lys
1               5                   10                  15

Gly

<210> SEQ ID NO 13
<211> LENGTH: 57
<212> TYPE: DNA
<213> ORGANISM: Homo Sapiens

<400> SEQUENCE: 13
gatcggttag gtccgattac tttggttcgg gggggctatt actacggtat ggacgtc      57

<210> SEQ ID NO 14
<211> LENGTH: 19
<212> TYPE: PRT
<213> ORGANISM: Homo Sapiens

<400> SEQUENCE: 14

Asp Arg Leu Gly Pro Ile Thr Leu Val Arg Gly Tyr Tyr Tyr Gly
1               5                   10                  15

Met Asp Val

<210> SEQ ID NO 15
<211> LENGTH: 321
<212> TYPE: DNA
<213> ORGANISM: Homo Sapiens

<400> SEQUENCE: 15
gacatccaga tgacccagtc tccatcctcc ctgtctgcat ctgtaggaga cagagtcacc      60
atcacttgcc gggcaagtca gagcattagc gactatttaa attggtatca gcagaaacca     120
gggaaagccc ctaagttcct gatctatgct gcatccagtt tgcaaagtgg agtcccatca     180
aggttcagtg gcagtggatc tgggacagat ttcactctca ccgtcagcag tctgcaacct     240
gaagattttg caacttacta ctgtcaacag agttacagta cccctcggac gttcggccaa     300
gggaccaggg tggaaatcaa a                                               321

<210> SEQ ID NO 16
<211> LENGTH: 107
<212> TYPE: PRT
<213> ORGANISM: Homo Sapiens

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asp Tyr
                20                  25                  30

Leu Asn Trp Tyr Gln Gln Lys Pro Gly Lys Ala Pro Lys Phe Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Val Ser Ser Leu Gln Pro
65                  70                  75                  80

Glu Asp Phe Ala Thr Tyr Tyr Cys Gln Gln Ser Tyr Ser Thr Pro Arg
                85                  90                  95
```

Thr Phe Gly Gln Gly Thr Arg Val Glu Ile Lys
            100                 105

<210> SEQ ID NO 17
<211> LENGTH: 18
<212> TYPE: DNA
<213> ORGANISM: Homo Sapiens

<400> SEQUENCE: 17
cagagcatta gcgactat                                                 18

<210> SEQ ID NO 18
<211> LENGTH: 6
<212> TYPE: PRT
<213> ORGANISM: Homo Sapiens

<400> SEQUENCE: 18

Gln Ser Ile Ser Asp Tyr
1               5

<210> SEQ ID NO 19
<211> LENGTH: 9
<212> TYPE: DNA
<213> ORGANISM: Homo Sapiens

<400> SEQUENCE: 19 gctgcatcc                                                            9

<210> SEQ ID NO 20
<211> LENGTH: 3
<212> TYPE: PRT
<213> ORGANISM: Homo Sapiens

<400> SEQUENCE: 20

Ala Ala Ser
1

<210> SEQ ID NO 21
<211> LENGTH: 27
<212> TYPE: DNA
<213> ORGANISM: Homo Sapiens

<400> SEQUENCE: 21
caacagagtt acagtacccc tcggacg                                       27

<210> SEQ ID NO 22
<211> LENGTH: 9
<212> TYPE: PRT
<213> ORGANISM: Homo Sapiens

<400> SEQUENCE: 22

Gln Gln Ser Tyr Ser Thr Pro Arg Thr
1               5

<210> SEQ ID NO 23
<211> LENGTH: 33
<212> TYPE: DNA
<213> ORGANISM: Homo Sapiens

<400> SEQUENCE: 23
cgggcaagtc agagcattag cgactattta aat                                33

<210> SEQ ID NO 24
<211> LENGTH: 11

```
<212> TYPE: PRT
<213> ORGANISM: Homo Sapiens

<400> SEQUENCE: 24

Arg Ala Ser Gln Ser Ile Ser Asp Tyr Leu Asn
1               5                   10

<210> SEQ ID NO 25
<211> LENGTH: 21
<212> TYPE: DNA
<213> ORGANISM: Homo Sapiens

<400> SEQUENCE: 25
gctgcatcca gtttgcaaag t                                              21

<210> SEQ ID NO 26
<211> LENGTH: 7
<212> TYPE: PRT
<213> ORGANISM: Homo Sapiens

<400> SEQUENCE: 26

Ala Ala Ser Ser Leu Gln Ser
1               5

<210> SEQ ID NO 27
<211> LENGTH: 27
<212> TYPE: DNA
<213> ORGANISM: Homo Sapiens

<400> SEQUENCE: 27
caacagagtt acagtacccc tcggacg                                        27

<210> SEQ ID NO 28
<211> LENGTH: 9
<212> TYPE: PRT
<213> ORGANISM: Homo Sapiens

<400> SEQUENCE: 28

Gln Gln Ser Tyr Ser Thr Pro Arg Thr
1               5

<210> SEQ ID NO 29
<211> LENGTH: 1365
<212> TYPE: DNA
<213> ORGANISM: Homo Sapiens

<400> SEQUENCE: 29
gaggtccagc tcgtggaaag cggaggagtg ctcgtgcagc ctggaggcag cctcaggctg     60
tcctgtgccg cctccggctt caccttcagc agctacatca tgacctgggt gaggcaggct    120
cccggaaaag gcctggagtg ggtgtccggc atctccggat ccggaggagg cacatactac    180
gccgacagca tgaagggccg gttcaccatc agcggacaa atagcaagaa tacctctac     240 ctgcaaatga acagcctgcg ggtggaggat accgccgtgt actactgcgc caaagatagg    300
ctgggcccca ttaccctcgt gagggggagc tattactacg gcatggatgt gtggggccag    360
ggcaccaccg tgacagtgtc cagcgccagc accaagggcc cttccgtgtt ccccctggcc    420
ccttgcagca ggagcaccct cgaatccaca gctgccctgg gctgtctggt gaaggactac    480
tttcccgagc ccgtgaccgt gagctggaac agcggcgctc tgacatccgg cgtccacacc    540
tttcctgccg tcctgcagtc ctccggcctc tactccctgt cctccgtggt gaccgtgcct    600
agctcctccc tcggcaccaa gacctacacc tgtaacgtgg accacaaacc ctccaacacc    660
```

-continued

```
aaggtggaca aacgggtcga gagcaagtac ggccctccct gccctccttg tcctgccccc        720
gagttcgaag gcggacccag cgtgttcctg ttccctccta agcccaagga caccctcatg        780
atcagccgga cacccgaggt gacctgcgtg gtggtggatg tgagccagga ggaccctgag        840
gtccagttca actggtatgt ggatggcgtg gaggtgcaca acgccaagac aaagcccgg         900 gaagagcagt tcaactccac ctacagggtg gtcagcgtgc tgaccgtgct gcatcaggac        960
tggctgaacg gcaaggagta caagtgcaag gtcagcaata agggactgcc cagcagcatc       1020
gagaagacca tctccaaggc taaaggccag ccccgggaac tcaggtgta cccctgcct         1080 cccagccagg aggagatgac caagaaccag gtgagcctga cctgcctggt gaagggattc       1140 taccttccg acatcgccgt ggagtgggag tccaacggcc agcccgagaa caattataag        1200 accaccctc ccgtcctcga cagcgacgga tccttctttc tgtactccag gctgaccgtg        1260
gataagtcca ggtggcagga aggcaacgtg ttcagctgct ccgtgatgca cgaggccctg       1320
cacaatcact acacccagaa gtccctgagc ctgtccctgg aaaag                       1365
```

<210> SEQ ID NO 30  
<211> LENGTH: 455  
<212> TYPE: PRT  
<213> ORGANISM: Homo Sapiens

<400> SEQUENCE: 30

```
Glu Val Gln Leu Val Glu Ser Gly Gly Val Leu Val Gln Pro Gly Gly
1               5                   10                  15

Ser Leu Arg Leu Ser Cys Ala Ala Ser Gly Phe Thr Phe Ser Ser Tyr
            20                  25                  30

Ile Met Thr Trp Val Arg Gln Ala Pro Gly Lys Gly Leu Glu Trp Val
        35                  40                  45

Ser Gly Ile Ser Gly Gly Gly Thr Tyr Tyr Ala Asp Ser Met
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Val Glu Asp Thr Ala Val Tyr Tyr Cys
                85                  90                  95

Ala Lys Asp Arg Leu Gly Pro Ile Thr Leu Val Arg Gly Gly Tyr Tyr
            100                 105                 110

Tyr Gly Met Asp Val Trp Gly Gln Gly Thr Thr Val Thr Val Ser Ser
        115                 120                 125

Ala Ser Thr Lys Gly Pro Ser Val Phe Pro Leu Ala Pro Cys Ser Arg
    130                 135                 140

Ser Thr Ser Glu Ser Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Leu Gly Thr Lys Thr
        195                 200                 205

Tyr Thr Cys Asn Val Asp His Lys Pro Ser Asn Thr Lys Val Asp Lys
    210                 215                 220

Arg Val Glu Ser Lys Tyr Gly Pro Pro Cys Pro Pro Cys Pro Ala Pro
225                 230                 235                 240

Glu Phe Glu Gly Gly Pro Ser Val Phe Leu Phe Pro Pro Lys Pro Lys
```

```
                    245                 250                 255
Asp Thr Leu Met Ile Ser Arg Thr Pro Glu Val Thr Cys Val Val Val
                260                 265                 270

Asp Val Ser Gln Glu Asp Pro Glu Val Gln Phe Asn Trp Tyr Val Asp
            275                 280                 285

Gly Val Glu Val His Asn Ala Lys Thr Lys Pro Arg Glu Glu Gln Phe
        290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
            420                 425                 430

Cys Ser Val Met His Glu Ala Leu His Asn His Tyr Thr Gln Lys Ser
        435                 440                 445

Leu Ser Leu Ser Leu Gly Lys
    450                 455

<210> SEQ ID NO 31
<211> LENGTH: 642
<212> TYPE: DNA
<213> ORGANISM: Homo Sapiens

<400> SEQUENCE: 31
gacatccaga tgacccagtc cccttcctcc ctgtccgcct ccgtgggaga cagggtgacc      60
atcacctgcc gggccagcca gtccatcagc gactacctga actggtatca gcagaagccc     120
ggcaaggccc ctaagttcct gatctacgcc gcttcctccc tgcagtccgg agtgcccagc     180
aggttttccg gctccggatc cggcaccgac ttcaccctga ccgtgtccag cctgcagccc     240
gaggacttcg ccacctacta ctgccagcag agctacagca cccccaggac atttggccag     300
ggcacccggg tggagatcaa gaggaccgtc gctgcccct  ccgtgtttat cttcccccc      360 agcgacgagc agctgaaatc cggcaccgcc tccgtggtct gcctgctgaa taacttctac     420
cctcgggagg ccaaggtgca gtggaaggtg gacaacgccc tgcagagcgg aaactcccag     480
gagagcgtga ccgagcagga ctccaaggac tccacatact ccctgtcctc cacccctgaca    540 ctgtccaagg ccgattacga gaagcacaag gtgtacgcct gcgaggtgac ccaccaggga    600
ctgtcctccc ccgtgaccaa gtccttcaac cggggcgagt gc                        642

<210> SEQ ID NO 32
<211> LENGTH: 214
<212> TYPE: PRT
<213> ORGANISM: Homo Sapiens

<400> SEQUENCE: 32
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asp Tyr
            20                  25                  30

Leu Asn Trp Tyr Gln Gln Lys Pro Gly Lys Ala Pro Lys Phe Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Val Ser Ser Leu Gln Pro
65              70                  75                  80

Glu Asp Phe Ala Thr Tyr Tyr Cys Gln Gln Ser Tyr Ser Thr Pro Arg
                85                  90                  95

Thr Phe Gly Gln Gly Thr Arg Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 33
<211> LENGTH: 381
<212> TYPE: DNA
<213> ORGANISM: Homo Sapiens

<400> SEQUENCE: 33
gaggtgcagt tggtggagtc tgggggaggc ttggtacagc ctggggggtc cctgagactc      60
tcctgtgcag cctctggatt cacttttagc aactatgcca tgaactgggt ccgccaggct     120
ccagggaagg gctggagtg gtctcaact attagcggaa gtggtggtgc acaaggtat        180 gcagactccg tgaagggccg attccacata tccagacaca ttccaggaaa cacggtgtat     240
ctgcaaatga acagcctgag agtcgaggac acggccgttt tttactgtac gaaagatcgg     300
ctcattatgg ctacggttcg ggacccctat tactacggta tggacgtctg gggccaaggg     360
accacggtca ccgtctcctc a                                               381

<210> SEQ ID NO 34
<211> LENGTH: 127
<212> TYPE: PRT
<213> ORGANISM: Homo Sapiens

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Asn Trp Val Arg Gln Ala Pro Gly Lys Gly Leu Glu Trp Val

```
              35                  40                  45

Ser Thr Ile Ser Gly Ser Gly Gly Ala Thr Arg Tyr Ala Asp Ser Val
    50                  55                  60

Lys Gly Arg Phe Thr Ile Ser Arg Asp Asn Ser Arg Asn Thr Val Tyr
 65                  70                  75                  80

Leu Gln Met Asn Ser Leu Arg Val Glu Asp Thr Ala Val Phe Tyr Cys
                 85                  90                  95

Thr Lys Asp Arg Leu Ile Met Ala Thr Val Arg Gly Pro Tyr Tyr Tyr
            100                 105                 110

Gly Met Asp Val Trp Gly Gln Gly Thr Thr Val Thr Val Ser Ser
        115                 120                 125

<210> SEQ ID NO 35
<211> LENGTH: 24
<212> TYPE: DNA
<213> ORGANISM: Homo Sapiens

<400> SEQUENCE: 35
ggattcactt ttagcaacta tgcc                                           24

<210> SEQ ID NO 36
<211> LENGTH: 8
<212> TYPE: PRT
<213> ORGANISM: Homo Sapiens

<400> SEQUENCE: 36

Gly Phe Thr Phe Ser Asn Tyr Ala
1               5

<210> SEQ ID NO 37
<211> LENGTH: 24
<212> TYPE: DNA
<213> ORGANISM: Homo Sapiens

<400> SEQUENCE: 37
attagcggaa gtggtggtgc caca                                           24

<210> SEQ ID NO 38
<211> LENGTH: 8
<212> TYPE: PRT
<213> ORGANISM: Homo Sapiens

<400> SEQUENCE: 38

Ile Ser Gly Ser Gly Gly Ala Thr
1               5

<210> SEQ ID NO 39
<211> LENGTH: 60
<212> TYPE: DNA
<213> ORGANISM: Homo Sapiens

<400> SEQUENCE: 39
acgaaagatc ggctcattat ggctacggtt cggggaccct attactacgg tatggacgtc   60

<210> SEQ ID NO 40
<211> LENGTH: 20
<212> TYPE: PRT
<213> ORGANISM: Homo Sapiens

<400> SEQUENCE: 40

Thr Lys Asp Arg Leu Ile Met Ala Thr Val Arg Gly Pro Tyr Tyr Tyr
1               5                   10                  15
```

Gly Met Asp Val
          20

<210> SEQ ID NO 41
<211> LENGTH: 15
<212> TYPE: DNA
<213> ORGANISM: Homo Sapiens

<400> SEQUENCE: 41
aactatgcca tgaac                                                    15

<210> SEQ ID NO 42
<211> LENGTH: 5
<212> TYPE: PRT
<213> ORGANISM: Homo Sapiens

<400> SEQUENCE: 42

Asn Tyr Ala Met Asn
1               5

<210> SEQ ID NO 43
<211> LENGTH: 51
<212> TYPE: DNA
<213> ORGANISM: Homo Sapiens

<400> SEQUENCE: 43
actattagcg gaagtggtgg tgccacaagg tatgcagact ccgtgaaggg c             51

<210> SEQ ID NO 44
<211> LENGTH: 17
<212> TYPE: PRT
<213> ORGANISM: Homo Sapiens

<400> SEQUENCE: 44

Thr Ile Ser Gly Ser Gly Gly Ala Thr Arg Tyr Ala Asp Ser Val Lys
1               5                   10                  15

Gly

<210> SEQ ID NO 45
<211> LENGTH: 54
<212> TYPE: DNA
<213> ORGANISM: Homo Sapiens

<400> SEQUENCE: 45
gatcggctca ttatggctac ggttcgggga ccctattact acggtatgga cgtc         54

<210> SEQ ID NO 46
<211> LENGTH: 18
<212> TYPE: PRT
<213> ORGANISM: Homo Sapiens

<400> SEQUENCE: 46

Asp Arg Leu Ile Met Ala Thr Val Arg Gly Pro Tyr Tyr Tyr Gly Met
1               5                   10                  15

Asp Val

<210> SEQ ID NO 47
<211> LENGTH: 321
<212> TYPE: DNA
<213> ORGANISM: Homo Sapiens

<400> SEQUENCE: 47

```
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaacctcct gatctatgct gcatccagtt tgcaaagtgg ggtcccatca   180
aggttcagtg gcagtggatc tgagacagat tcactctca ccatcagcag tctgcaacct    240
gaagattttg caacttacta ctgtcaacag agtcacagtg tctcattcac tttcggccct   300
gggaccaaag tggatatcaa a                                             321
```

<210> SEQ ID NO 48
<211> LENGTH: 107
<212> TYPE: PRT
<213> ORGANISM: Homo Sapiens

<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Asn Leu Leu Ile
        35                  40                  45

Tyr Ala Ala Ser Ser Leu Gln Ser Gly Val Pro Ser Arg Phe Ser Gly
    50                  55                  60

Ser Gly Ser Glu Thr Asp Phe Thr Leu Thr Ile Ser Ser Leu Gln Pro
65                  70                  75                  80

Glu Asp Phe Ala Thr Tyr Tyr Cys Gln Gln Ser His Ser Val Ser Phe
                85                  90                  95

Thr Phe Gly Pro Gly Thr Lys Val Asp Ile Lys
            100                 105

<210> SEQ ID NO 49
<211> LENGTH: 18
<212> TYPE: DNA
<213> ORGANISM: Homo Sapiens

<400> SEQUENCE: 49
cagagcatta gcagctat                                                  18

<210> SEQ ID NO 50
<211> LENGTH: 6
<212> TYPE: PRT
<213> ORGANISM: Homo Sapiens

<400> SEQUENCE: 50

Gln Ser Ile Ser Ser Tyr
1               5

<210> SEQ ID NO 51
<211> LENGTH: 9
<212> TYPE: DNA
<213> ORGANISM: Homo Sapiens

<400> SEQUENCE: 51 gctgcatcc                                                             9

<210> SEQ ID NO 52
<211> LENGTH: 3
<212> TYPE: PRT
<213> ORGANISM: Homo Sapiens

<400> SEQUENCE: 52

Ala Ala Ser
1

<210> SEQ ID NO 53
<211> LENGTH: 27
<212> TYPE: DNA
<213> ORGANISM: Homo Sapiens

<400> SEQUENCE: 53
caacagagtc acagtgtctc attcact                        27

<210> SEQ ID NO 54
<211> LENGTH: 9
<212> TYPE: PRT
<213> ORGANISM: Homo Sapiens

<400> SEQUENCE: 54

Gln Gln Ser His Ser Val Ser Phe Thr
1               5

<210> SEQ ID NO 55
<211> LENGTH: 33
<212> TYPE: DNA
<213> ORGANISM: Homo Sapiens

<400> SEQUENCE: 55
cgggcaagtc agagcattag cagctattta aat                  33

<210> SEQ ID NO 56
<211> LENGTH: 11
<212> TYPE: PRT
<213> ORGANISM: Homo Sapiens

<400> SEQUENCE: 56

Arg Ala Ser Gln Ser Ile Ser Ser Tyr Leu Asn
1               5                   10

<210> SEQ ID NO 57
<211> LENGTH: 21
<212> TYPE: DNA
<213> ORGANISM: Homo Sapiens

<400> SEQUENCE: 57
gctgcatcca gtttgcaaag t                              21

<210> SEQ ID NO 58
<211> LENGTH: 7
<212> TYPE: PRT
<213> ORGANISM: Homo Sapiens

<400> SEQUENCE: 58

Ala Ala Ser Ser Leu Gln Ser
1               5

<210> SEQ ID NO 59
<211> LENGTH: 27
<212> TYPE: DNA
<213> ORGANISM: Homo Sapiens

<400> SEQUENCE: 59
caacagagtc acagtgtctc attcact                        27

<210> SEQ ID NO 60

<211> LENGTH: 9
<212> TYPE: PRT
<213> ORGANISM: Homo Sapiens

<400> SEQUENCE: 60

Gln Gln Ser His Ser Val Ser Phe Thr
1               5

<210> SEQ ID NO 61
<211> LENGTH: 1362
<212> TYPE: DNA
<213> ORGANISM: Homo Sapiens

<400> SEQUENCE: 61

```
gaagtgcaac tggtggagtc cggaggaggc ctggtgcagc ctggaggaag cctgaggctg      60
agctgtgccg ccagcggctt caccttcagc aactacgcca tgaactgggt gaggcaggcc     120
cctggcaagg gactggagtg ggtctccacc atcagcggct ccggaggcgc tacacggtac     180
gccgatagcg tgaagggccg gtttaccatt tcccgggaca actccggaaa caccgtgtac     240
ctccagatga acagcctgag ggtggaggat accgccgtgt ctactgcac caaggacagg     300
ctgattatgg ccaccgtgag gggacttac tactatggca tggatgtgtg gggccagggc     360
acaaccgtca ccgtgtcctc cgcctccacc aagggaccta gcgtgttccc tctcgccccc     420
tgttccaggt ccacaagcga gtccaccgct gccctcggct gtctggtgaa agactacttt     480
cccgagcccg tgaccgtctc ctggaatagc ggagccctga cctccggcgt gcacacattt     540
ccggccgtgc tgcagagcag cggactgtat agcctgagca gcgtggtgac cgtgcccagc     600
tccagcctcg gcaccaaaac ctacacctgc aacgtggacc acaagccctc caacaccaag     660
gtggacaagc gggtggagag caagtacggc ccccccttgcc ctccttgtcc tgcccctgag     720
ttcgagggag accctccgt gttcctgttt ccccccaaac ccaaggacac cctgatgatc     780
tcccggacac ccgaggtgac ctgtgtggtc gtggacgtca gccaggagga ccccgaggtg     840
cagttcaact ggtatgtgga cggcgtggag gtgcacaatg ccaaaaccaa gcccagggag     900
gagcagttca attccaccta cagggtggtg agcgtgctga ccgtcctgca tcaggattgg     960
ctgaacggca aggagtacaa gtgcaaggtg tccaacaagg gactgccag ctccatcgag    1020
aagaccatca gcaaggctaa gggccagccg agggagcccc aggtgtatac cctgcctcct    1080
agccaggaag agatgaccaa gaaccaagtg tccctgacct gcctggtgaa gggattctac    1140
ccctccgaca tcgccgtgga gtgggagagc aatggccagc ccgagaacaa ctacaaaaca    1200
acccctcccg tgctcgatag cgacggcagc ttctttctct acagccggct gacagtggac    1260
aagagcaggt ggcaggaggg caacgtgttc tcctgttccg tgatgcacga ggccctgcac    1320
aatcactaca cccagaagag cctctcccctg tccctgggca ag                     1362
```

<210> SEQ ID NO 62
<211> LENGTH: 454
<212> TYPE: PRT
<213> ORGANISM: Homo Sapiens

<400> SEQUENCE: 62

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Asn Trp Val Arg Gln Ala Pro Gly Lys Gly Leu Glu Trp Val
        35                  40                  45

Ser Thr Ile Ser Gly Ser Gly Gly Ala Thr Arg Tyr Ala Asp Ser Val
    50                  55                  60

Lys Gly Arg Phe Thr Ile Ser Arg Asp Asn Ser Arg Asn Thr Val Tyr
 65                  70                  75                  80

Leu Gln Met Asn Ser Leu Arg Val Glu Asp Thr Ala Val Phe Tyr Cys
                 85                  90                  95

Thr Lys Asp Arg Leu Ile Met Ala Thr Val Arg Gly Pro Tyr Tyr Tyr
                100                 105                 110

Gly Met Asp Val Trp Gly Gln Gly Thr Thr Val Thr Val Ser Ser Ala
                115                 120                 125

Ser Thr Lys Gly Pro Ser Val Phe Pro Leu Ala Pro Cys Ser Arg Ser
    130                 135                 140

Thr Ser Glu Ser Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
                180                 185                 190

Ser Ser Val Val Thr Val Pro Ser Ser Ser Leu Gly Thr Lys Thr Tyr
            195                 200                 205

Thr Cys Asn Val Asp His Lys Pro Ser Asn Thr Lys Val Asp Lys Arg
    210                 215                 220

Val Glu Ser Lys Tyr Gly Pro Pro Cys Pro Pro Cys Pro Ala Pro Glu
225                 230                 235                 240

Phe Glu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
                260                 265                 270

Val Ser Gln Glu Asp Pro Glu Val Gln Phe Asn Trp Tyr Val Asp Gly
            275                 280                 285

Val Glu Val His Asn Ala Lys Thr Lys Pro Arg Glu Glu Gln Phe Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Gly Leu Pro
                325                 330                 335

Ser Ser Ile Glu Lys Thr Ile Ser Lys Ala Lys Gly Gln Pro Arg Glu
                340                 345                 350

Pro Gln Val Tyr Thr Leu Pro Pro Ser Gln Glu Glu Met Thr Lys Asn
            355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Arg
                405                 410                 415

Leu Thr Val Asp Lys Ser Arg Trp Gln Glu Gly Asn Val Phe Ser Cys
                420                 425                 430

Ser Val Met His Glu Ala Leu His Asn His Tyr Thr Gln Lys Ser Leu
            435                 440                 445

Ser Leu Ser Leu Gly Lys
    450

<210> SEQ ID NO 63
<211> LENGTH: 642
<212> TYPE: DNA
<213> ORGANISM: Homo Sapiens

<400> SEQUENCE: 63

```
gacatccaga tgacccagtc cccttcctcc ctgagcgcta gcgtgggaga tagggtgacc      60
atcacctgca gggcctccca aagcatctcc tcctacctga actggtacca gcagaaaccc     120
ggcaaggccc ccaacctgct gatctacgct gcctcctccc tccagtccgg cgtgcctagc     180
aggtttagcg gctccggaag cgagaccgac ttcaccctga ccatctcctc cctgcagccc     240
gaggacttcg ccacctacta ctgccagcaa tcccacagcg tgtccttcac cttcggcccc     300
ggcaccaagg tggacatcaa gaggaccgtg gccgccccct ccgtgttcat ctttcccccc     360
tccgatgaac agctgaagag cggcaccgct agcgtggtgt gcctgctgaa caacttctac     420
cccagggagg ccaaggtgca gtggaaggtg gacaatgccc tgcagtccgg caacagccag     480
gagagcgtga ccgagcagga ctccaaggac agcacctaca gcctgtcctc cacccctgacc    540
ctgtccaagg ccgactacga gaagcacaaa gtgtacgcct gcgaagtgac ccatcagggc     600
ctgagctccc ccgtgaccaa gtcctttaac aggggcgagt gc                        642
```

<210> SEQ ID NO 64
<211> LENGTH: 214
<212> TYPE: PRT
<213> ORGANISM: Homo Sapiens

<400> SEQUENCE: 64

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Asn Leu Leu Ile
        35                  40                  45

Tyr Ala Ala Ser Ser Leu Gln Ser Gly Val Pro Ser Arg Phe Ser Gly
    50                  55                  60

Ser Gly Ser Glu Thr Asp Phe Thr Leu Thr Ile Ser Ser Leu Gln Pro
65                  70                  75                  80

Glu Asp Phe Ala Thr Tyr Tyr Cys Gln Gln Ser His Ser Val Ser Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 65
<211> LENGTH: 372
<212> TYPE: DNA
<213> ORGANISM: Homo Sapiens

<400> SEQUENCE: 65

```
caggtgcagc tggtggagtc tgggggaggc ttggtcaagc ctggagggtc cctgagactc        60
tcctgtgcag cctctcgatt caccctcagt gactactaca tgacctggat ccgccaggct       120
ccagggaagg ggctggagtg ggtttcatac attagtagta gtggtaatac catatactac       180
gcagactctg tgaagggccg attcaccatc tccaggaca acgccaagaa ctcactgtat        240
ctgcaaatga acagcctgag agccgaggac acggccgtgt attactgtgc gagagatctg       300
agtgggagct actgggacta ctactacggt atggacgtct ggggccaagg gaccacggtc       360
accgtctcct ca                                                           372
```

<210> SEQ ID NO 66
<211> LENGTH: 124
<212> TYPE: PRT
<213> ORGANISM: Homo Sapiens

<400> SEQUENCE: 66

```
Gln Val Gln Leu Val Glu Ser Gly Gly Gly Leu Val Lys Pro Gly Gly
1               5                   10                  15

Ser Leu Arg Leu Ser Cys Ala Ala Ser Arg Phe Thr Leu Ser Asp Tyr
            20                  25                  30

Tyr Met Thr Trp Ile Arg Gln Ala Pro Gly Lys Gly Leu Glu Trp Val
        35                  40                  45

Ser Tyr Ile Ser Ser Ser Gly Asn Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Ser Gly Ser Tyr Trp Asp Tyr Tyr Tyr Gly Met Asp
            100                 105                 110

Val Trp Gly Gln Gly Thr Thr Val Thr Val Ser Ser
        115                 120
```

<210> SEQ ID NO 67
<211> LENGTH: 24
<212> TYPE: DNA
<213> ORGANISM: Homo Sapiens

<400> SEQUENCE: 67

```
cgattcaccc tcagtgacta ctac                                               24
```

<210> SEQ ID NO 68
<211> LENGTH: 8
<212> TYPE: PRT
<213> ORGANISM: Homo Sapiens

<400> SEQUENCE: 68

```
Arg Phe Thr Leu Ser Asp Tyr Tyr
1               5
```

<210> SEQ ID NO 69
<211> LENGTH: 24

```
<212> TYPE: DNA
<213> ORGANISM: Homo Sapiens

<400> SEQUENCE: 69
attagtagta gtggtaatac cata                                          24

<210> SEQ ID NO 70
<211> LENGTH: 8
<212> TYPE: PRT
<213> ORGANISM: Homo Sapiens

<400> SEQUENCE: 70

Ile Ser Ser Ser Gly Asn Thr Ile
1               5

<210> SEQ ID NO 71
<211> LENGTH: 51
<212> TYPE: DNA
<213> ORGANISM: Homo Sapiens

<400> SEQUENCE: 71
gcgagagatc tgagtgggag ctactgggac tactactacg gtatggacgt c            51

<210> SEQ ID NO 72
<211> LENGTH: 17
<212> TYPE: PRT
<213> ORGANISM: Homo Sapiens

<400> SEQUENCE: 72

Ala Arg Asp Leu Ser Gly Ser Tyr Trp Asp Tyr Tyr Tyr Gly Met Asp
1               5                   10                  15

Val

<210> SEQ ID NO 73
<211> LENGTH: 15
<212> TYPE: DNA
<213> ORGANISM: Homo Sapiens

<400> SEQUENCE: 73
gactactaca tgacc                                                    15

<210> SEQ ID NO 74
<211> LENGTH: 5
<212> TYPE: PRT
<213> ORGANISM: Homo Sapiens

<400> SEQUENCE: 74

Asp Tyr Tyr Met Thr
1               5

<210> SEQ ID NO 75
<211> LENGTH: 51
<212> TYPE: DNA
<213> ORGANISM: Homo Sapiens

<400> SEQUENCE: 75
tacattagta gtagtggtaa taccatatac tacgcagact ctgtgaaggg c            51

<210> SEQ ID NO 76
<211> LENGTH: 17
<212> TYPE: PRT
<213> ORGANISM: Homo Sapiens

<400> SEQUENCE: 76
```

```
Tyr Ile Ser Ser Gly Asn Thr Ile Tyr Tyr Ala Asp Ser Val Lys
1               5                   10                  15

Gly

<210> SEQ ID NO 77
<211> LENGTH: 45
<212> TYPE: DNA
<213> ORGANISM: Homo Sapiens

<400> SEQUENCE: 77
gatctgagtg ggagctactg ggactactac tacggtatgg acgtc              45

<210> SEQ ID NO 78
<211> LENGTH: 15
<212> TYPE: PRT
<213> ORGANISM: Homo Sapiens

<400> SEQUENCE: 78

Asp Leu Ser Gly Ser Tyr Trp Asp Tyr Tyr Gly Met Asp Val
1               5                   10                  15

<210> SEQ ID NO 79
<211> LENGTH: 321
<212> TYPE: DNA
<213> ORGANISM: Homo Sapiens

<400> SEQUENCE: 79
gccatccagt tgacccagtc tccatcctcc ctgtctacat ctgtaggaga cagagtcacc      60
atcgcttgcc gggcaagtca ggcattaac  aatgctttag cctggtatca gcagaaacca     120
gggaaagctc ctaagctcct gatctatgat gcctccagtt tggaaagtgg ggtcccatca     180
aggttcagcg gcagtggatc tgggacagat ttcactctca ccatcagcag cctgcagcct     240
gaagattttg caacttatta ctgtcaacag tttaatagtt accctcggac gttcggccaa     300
gggaccaagg tggaaatcaa a                                                321

<210> SEQ ID NO 80
<211> LENGTH: 107
<212> TYPE: PRT
<213> ORGANISM: Homo Sapiens

<400> SEQUENCE: 80

Ala Ile Gln Leu Thr Gln Ser Pro Ser Ser Leu Ser Thr Ser Val Gly
1               5                   10                  15

Asp Arg Val Thr Ile Ala Cys Arg Ala Ser Gln Gly Ile Asn Asn Ala
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Pro Arg
                85                  90                  95

Thr Phe Gly Gln Gly Thr Lys Val Glu Ile Lys
            100                 105

<210> SEQ ID NO 81
<211> LENGTH: 18
```

```
<212> TYPE: DNA
<213> ORGANISM: Homo Sapiens

<400> SEQUENCE: 81
cagggcatta acaatgct                                              18

<210> SEQ ID NO 82
<211> LENGTH: 6
<212> TYPE: PRT
<213> ORGANISM: Homo Sapiens

<400> SEQUENCE: 82

Gln Gly Ile Asn Asn Ala
1               5

<210> SEQ ID NO 83
<211> LENGTH: 9
<212> TYPE: DNA
<213> ORGANISM: Homo Sapiens

<400> SEQUENCE: 83 gatgcctcc                                                         9

<210> SEQ ID NO 84
<211> LENGTH: 3
<212> TYPE: PRT
<213> ORGANISM: Homo Sapiens

<400> SEQUENCE: 84

Asp Ala Ser
1

<210> SEQ ID NO 85
<211> LENGTH: 27
<212> TYPE: DNA
<213> ORGANISM: Homo Sapiens

<400> SEQUENCE: 85
caacagttta atagttaccc tcggacg                                    27

<210> SEQ ID NO 86
<211> LENGTH: 9
<212> TYPE: PRT
<213> ORGANISM: Homo Sapiens

<400> SEQUENCE: 86

Gln Gln Phe Asn Ser Tyr Pro Arg Thr
1               5

<210> SEQ ID NO 87
<211> LENGTH: 33
<212> TYPE: DNA
<213> ORGANISM: Homo Sapiens

<400> SEQUENCE: 87
cgggcaagtc agggcattaa caatgcttta gcc                             33

<210> SEQ ID NO 88
<211> LENGTH: 11
<212> TYPE: PRT
<213> ORGANISM: Homo Sapiens

<400> SEQUENCE: 88

Arg Ala Ser Gln Gly Ile Asn Asn Ala Leu Ala
```

<210> SEQ ID NO 89
<211> LENGTH: 21
<212> TYPE: DNA
<213> ORGANISM: Homo Sapiens

<400> SEQUENCE: 89
gatgcctcca gtttggaaag t                                            21

<210> SEQ ID NO 90
<211> LENGTH: 7
<212> TYPE: PRT
<213> ORGANISM: Homo Sapiens

<400> SEQUENCE: 90

Asp Ala Ser Ser Leu Glu Ser
1               5

<210> SEQ ID NO 91
<211> LENGTH: 27
<212> TYPE: DNA
<213> ORGANISM: Homo Sapiens

<400> SEQUENCE: 91
caacagttta atagttaccc tcggacg                                      27

<210> SEQ ID NO 92
<211> LENGTH: 9
<212> TYPE: PRT
<213> ORGANISM: Homo Sapiens

<400> SEQUENCE: 92

Gln Gln Phe Asn Ser Tyr Pro Arg Thr
1               5

<210> SEQ ID NO 93
<211> LENGTH: 369
<212> TYPE: DNA
<213> ORGANISM: Homo Sapiens

<400> SEQUENCE: 93
gaggtgcagc tggtggagtc tgggggaggc ttggtaaagc ctgggggggtc ccttagactc    60 tcctgtgcag cctctggatt cactttcagt aacgcctgga tgagctgggt ccgccaggct   120
ccagggaagg ggctggagtg ggttggccgt attaaaagca aaactgaagg tgggacaaca   180
gactacgctg cacccgtgaa aggcagattc accatctcaa gagatgattc aaaaaacacg   240
ctgtatctgc aaatgaacag cctgaaaacc gaggacacag ccgtgtatta ctgtaccaca   300
gattttctat ggttcgggga gttccctttt gactactggg gccagggaac cctggtcacc   360
gtctcctca                                                          369

<210> SEQ ID NO 94
<211> LENGTH: 123
<212> TYPE: PRT
<213> ORGANISM: Homo Sapiens

<400> SEQUENCE: 94

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
            35                  40                  45

Gly Arg Ile Lys Ser Lys Thr Glu Gly Gly Thr Thr Asp Tyr Ala Ala
        50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Asp Phe Leu Trp Phe Gly Glu Phe Pro Phe Asp Tyr
            100                 105                 110

Trp Gly Gln Gly Thr Leu Val Thr Val Ser Ser
            115                 120

<210> SEQ ID NO 95
<211> LENGTH: 24
<212> TYPE: DNA
<213> ORGANISM: Homo Sapiens

<400> SEQUENCE: 95
ggattcactt tcagtaacgc ctgg                                        24

<210> SEQ ID NO 96
<211> LENGTH: 8
<212> TYPE: PRT
<213> ORGANISM: Homo Sapiens

<400> SEQUENCE: 96

Gly Phe Thr Phe Ser Asn Ala Trp
1               5

<210> SEQ ID NO 97
<211> LENGTH: 30
<212> TYPE: DNA
<213> ORGANISM: Homo Sapiens

<400> SEQUENCE: 97
attaaaagca aaactgaagg tgggacaaca                                  30

<210> SEQ ID NO 98
<211> LENGTH: 10
<212> TYPE: PRT
<213> ORGANISM: Homo Sapiens

<400> SEQUENCE: 98

Ile Lys Ser Lys Thr Glu Gly Gly Thr Thr
1               5                   10

<210> SEQ ID NO 99
<211> LENGTH: 42
<212> TYPE: DNA
<213> ORGANISM: Homo Sapiens

<400> SEQUENCE: 99
accacagatt ttctatggtt cggggagttc cctttttgact ac                   42

<210> SEQ ID NO 100
<211> LENGTH: 14
<212> TYPE: PRT
<213> ORGANISM: Homo Sapiens

<400> SEQUENCE: 100

```
Thr Thr Asp Phe Leu Trp Phe Gly Glu Phe Pro Phe Asp Tyr
 1               5                  10
```

<210> SEQ ID NO 101
<211> LENGTH: 15
<212> TYPE: DNA
<213> ORGANISM: Homo Sapiens

<400> SEQUENCE: 101
aacgcctgga tgagc                                            15

<210> SEQ ID NO 102
<211> LENGTH: 5
<212> TYPE: PRT
<213> ORGANISM: Homo Sapiens

<400> SEQUENCE: 102

```
Asn Ala Trp Met Ser
 1               5
```

<210> SEQ ID NO 103
<211> LENGTH: 57
<212> TYPE: DNA
<213> ORGANISM: Homo Sapiens

<400> SEQUENCE: 103
cgtattaaaa gcaaaactga aggtgggaca acagactacg ctgcacccgt gaaaggc   57

<210> SEQ ID NO 104
<211> LENGTH: 19
<212> TYPE: PRT
<213> ORGANISM: Homo Sapiens

<400> SEQUENCE: 104

```
Arg Ile Lys Ser Lys Thr Glu Gly Gly Thr Thr Asp Tyr Ala Ala Pro
 1               5                  10                  15

Val Lys Gly
```

<210> SEQ ID NO 105
<211> LENGTH: 36
<212> TYPE: DNA
<213> ORGANISM: Homo Sapiens

<400> SEQUENCE: 105
gattttctat ggttcgggga gttcccttt gactac                      36

<210> SEQ ID NO 106
<211> LENGTH: 12
<212> TYPE: PRT
<213> ORGANISM: Homo Sapiens

<400> SEQUENCE: 106

```
Asp Phe Leu Trp Phe Gly Glu Phe Pro Phe Asp Tyr
 1               5                  10
```

<210> SEQ ID NO 107
<211> LENGTH: 321
<212> TYPE: DNA
<213> ORGANISM: Homo Sapiens

<400> SEQUENCE: 107
gacatccaga tgacccagtc tccatcctcc ctgtctgcat ctgtaggaga cagagtcacc   60
atcacttgcc gggcgagtca gggcattagc aattatttag cctggtatca gcagaaacca  120

```
gggaaaattc ctaagctcct gatctatgct gcatccactt tgcaatcagg ggtcccatct    180
cggttcagtg gcagtggatc tgggacagat ttcactctca ccatcagcag cctgcagcct    240
gaagatgttg caacttatta ctgtcaaaag tataacagtg cccctcggac gttcggccaa    300
gggaccaagg tggaaatcaa a                                              321
```

```
<210> SEQ ID NO 108
<211> LENGTH: 107
<212> TYPE: PRT
<213> ORGANISM: Homo Sapiens

<400> SEQUENCE: 108

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Ile Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Arg
                85                  90                  95

Thr Phe Gly Gln Gly Thr Lys Val Glu Ile Lys
            100                 105
```

```
<210> SEQ ID NO 109
<211> LENGTH: 18
<212> TYPE: DNA
<213> ORGANISM: Homo Sapiens

<400> SEQUENCE: 109
cagggcatta gcaattat                                                  18
```

```
<210> SEQ ID NO 110
<211> LENGTH: 6
<212> TYPE: PRT
<213> ORGANISM: Homo Sapiens

<400> SEQUENCE: 110

Gln Gly Ile Ser Asn Tyr
1               5
```

```
<210> SEQ ID NO 111
<211> LENGTH: 9
<212> TYPE: DNA
<213> ORGANISM: Homo Sapiens

<400> SEQUENCE: 111 gctgcatcc                                                             9
```

```
<210> SEQ ID NO 112
<211> LENGTH: 3
<212> TYPE: PRT
<213> ORGANISM: Homo Sapiens

<400> SEQUENCE: 112

Ala Ala Ser
1
```

<210> SEQ ID NO 113
<211> LENGTH: 27
<212> TYPE: DNA
<213> ORGANISM: Homo Sapiens

<400> SEQUENCE: 113
caaaagtata acagtgcccc tcggacg 27

<210> SEQ ID NO 114
<211> LENGTH: 9
<212> TYPE: PRT
<213> ORGANISM: Homo Sapiens

<400> SEQUENCE: 114

Gln Lys Tyr Asn Ser Ala Pro Arg Thr
1               5

<210> SEQ ID NO 115
<211> LENGTH: 33
<212> TYPE: DNA
<213> ORGANISM: Homo Sapiens

<400> SEQUENCE: 115
cgggcgagtc agggcattag caattattta gcc 33

<210> SEQ ID NO 116
<211> LENGTH: 11
<212> TYPE: PRT
<213> ORGANISM: Homo Sapiens

<400> SEQUENCE: 116

Arg Ala Ser Gln Gly Ile Ser Asn Tyr Leu Ala
1               5                   10

<210> SEQ ID NO 117
<211> LENGTH: 21
<212> TYPE: DNA
<213> ORGANISM: Homo Sapiens

<400> SEQUENCE: 117
gctgcatcca ctttgcaatc a 21

<210> SEQ ID NO 118
<211> LENGTH: 7
<212> TYPE: PRT
<213> ORGANISM: Homo Sapiens

<400> SEQUENCE: 118

Ala Ala Ser Thr Leu Gln Ser
1               5

<210> SEQ ID NO 119
<211> LENGTH: 27
<212> TYPE: DNA
<213> ORGANISM: Homo Sapiens

<400> SEQUENCE: 119
caaaagtata acagtgcccc tcggacg 27

<210> SEQ ID NO 120
<211> LENGTH: 9
<212> TYPE: PRT
<213> ORGANISM: Homo Sapiens

<400> SEQUENCE: 120

Gln Lys Tyr Asn Ser Ala Pro Arg Thr
1               5

<210> SEQ ID NO 121
<211> LENGTH: 981
<212> TYPE: DNA
<213> ORGANISM: Homo Sapiens

<400> SEQUENCE: 121

```
gcttccacca agggcccatc cgtcttcccc ctggcgccct gctccaggag cacctccgag    60
agcacagccg ccctgggctg cctggtcaag gactacttcc ccgaaccggt gacggtgtcg   120
tggaactcag gcgccctgac cagcggcgtg cacaccttcc cggctgtcct acagtcctca   180
ggactctact ccctcagcag cgtggtgacc gtgccctcca gcagcttggg cacgaagacc   240
tacacctgca acgtagatca caagcccagc aacaccaagg tggacaagag agttgagtcc   300
aaatatggtc ccccatgccc atcatgccca gcacctgagt tcctgggggg accatcagtc   360
ttcctgttcc ccccaaaacc caaggacact ctcatgatct cccggacccc tgaggtcacg   420
tgcgtggtgg tggacgtgag ccaggaagac cccgaggtcc agttcaactg gtacgtggat   480
ggcgtggagg tgcataatgc caagacaaag ccgcgggagg agcagttcaa cagcacgtac   540
cgtgtggtca gcgtcctcac cgtcctgcac caggactggc tgaacggcaa ggagtacaag   600
tgcaaggtct ccaacaaagg cctcccgtcc tccatcgaga aaaccatctc caaagccaaa   660
gggcagcccc gagagccaca ggtgtacacc ctgcccccat cccaggagga gatgaccaag   720
aaccaggtca gcctgacctg cctggtcaaa ggcttctacc ccagcgacat cgccgtggag   780
tgggagagca atgggcagcc ggagaacaac tacaagacca cgcctcccgt gctggactcc   840
gacggctcct tcttcctcta cagcaggcta accgtggaca agagcaggtg gcaggagggg   900
aatgtcttct catgctccgt gatgcatgag gctctgcaca accactacac acagaagagc   960
ctctccctgt ctctgggtaa a                                             981
```

<210> SEQ ID NO 122
<211> LENGTH: 327
<212> TYPE: PRT
<213> ORGANISM: Homo Sapiens

<400> SEQUENCE: 122

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

```
Asp Thr Leu Met Ile Ser Arg Thr Pro Glu Val Thr Cys Val Val Val
        130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 123
<211> LENGTH: 981
<212> TYPE: DNA
<213> ORGANISM: Homo Sapiens

<400> SEQUENCE: 123
gcttccacca agggcccatc cgtcttcccc ctggcgccct gctccaggag cacctccgag      60
agcacagccg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacgaagacc     240
tacacctgca acgtagatca caagcccagc aacaccaagg tggacaagag agttgagtcc     300
aaatatggtc ccccgtgccc atcatgccca gcacctgagt tcctggggggg accatcagtc     360 ttcctgttcc ccccaaaacc caaggacact ctcatgatct cccggacccc tgaggtcacg     420
tgcgtggtgg tggacgtgag ccaggaagac cccgaggtcc agttcaactg gtacgtggat     480
ggcgtggagg tgcataatgc caagacaaag ccgcgggagg agcagttcaa cagcacgtac     540
cgtgtggtca gcgtcctcac cgtcgtgcac caggactggc tgaacggcaa ggagtacaag     600
tgcaaggtct ccaacaaagg cctcccgtcc tccatcgaga aaaccatctc caaagccaaa     660
gggcagcccc gagagccaca ggtgtacacc ctgcccccat cccaggagga gatgaccaag     720
aaccaggtca gcctgacctg cctggtcaaa ggcttctacc ccagcgacat cgccgtggag     780
tgggagagca atgggcagcc ggagaacaac tacaagacca cgcctcccgt gctggactcc     840
gacggctcct tcttcctcta cagcaggcta accgtggaca agagcaggtg gcaggagggg     900
aatgtcttct catgctccgt gatgcatgag gctctgcaca accactacac gcagaagagc     960
```
ctctccctgt ctctgggtaa a                                                          981

<210> SEQ ID NO 124
<211> LENGTH: 327
<212> TYPE: PRT
<213> ORGANISM: Homo Sapiens

<400> SEQUENCE: 124

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Val His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 125
<211> LENGTH: 981
<212> TYPE: DNA
<213> ORGANISM: Homo Sapiens

<400> SEQUENCE: 125

```
gcttccacca agggcccatc cgtcttcccc ctggcgccct gctccaggag cacctccgag      60
agcacagccg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacgaagacc     240
tacacctgca acgtagatca caagcccagc aacaccaagg tggacaagag agttgagtcc     300
aaatatggtc ccccatgccc atcatgccca gcacctgagt tcctgggggg accatcagtc     360
ttcctgttcc ccccaaaacc caaggacact ctcatgatct cccggacccc tgaggtcacg     420
tgcgtggtgg tggacgtgag ccaggaagac cccgaggtcc agttcaactg gtacgtggat     480
ggcgtggagg tgcataatgc caagacaaag ccgcgggagg agcagttcaa cagcacgtac     540
cgtgtggtca gcgtcctcac cgtcctgcac caggactggc tgaacggcaa ggagtacaag     600
tgcaaggtct ccaacaaagg cctcccgtcc tccatcgaga aaaccatctc caaagccaaa     660
gggcagcccc gagagccaca ggtgtacacc ctgcccccat cccaggagga gatgaccaag     720
aaccaggtca gcctgacctg cctggtcaaa ggcttctacc ccagcgacat cgccgtggag     780
tgggagagca atgggcagcc ggagaacaac tacaagacca cgcctcccgt gctggactcc     840
gacggctcct tcttcctcta cagcaagctc accgtggaca agagcaggtg gcaggagggg     900
aacgtcttct catgctccgt gatgcatgag gctctgcaca accactacac gcagaagagc     960
ctctcccctgt ctctgggtaa a                                              981
```

<210> SEQ ID NO 126
<211> LENGTH: 327
<212> TYPE: PRT
<213> ORGANISM: Homo Sapiens

<400> SEQUENCE: 126

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
```

```
              180                 185                 190
Trp Leu Asn Gly Lys Glu Tyr Lys Cys Lys Val Ser Asn Lys Gly Leu
            195                 200                 205
Pro Ser Ser Ile Glu Lys Thr Ile Ser Lys Ala Lys Gly Gln Pro Arg
        210                 215                 220
Glu Pro Gln Val Tyr Thr Leu Pro Pro Ser Gln Glu Met Thr Lys
225                 230                 235                 240
Asn Gln Val Ser Leu Thr Cys Leu Val Lys Gly Phe Tyr Pro Ser Asp
                245                 250                 255
Ile Ala Val Glu Trp Glu Ser Asn Gly Gln Pro Glu Asn Asn Tyr Lys
            260                 265                 270
Thr Thr Pro Pro Val Leu Asp Ser Asp Gly Ser Phe Phe Leu Tyr Ser
        275                 280                 285
Lys Leu Thr Val Asp Lys Ser Arg Trp Gln Glu Gly Asn Val Phe Ser
    290                 295                 300
Cys Ser Val Met His Glu Ala Leu His Asn His Tyr Thr Gln Lys Ser
305                 310                 315                 320
Leu Ser Leu Ser Leu Gly Lys
                325

<210> SEQ ID NO 127
<211> LENGTH: 981
<212> TYPE: DNA
<213> ORGANISM: Homo Sapiens

<400> SEQUENCE: 127
gcctccacca agggcccatc cgtcttcccc ctggcgccct gctccaggag cacctccgag    60
agcacggccg ccctgggctg cctggtcaag gactacttcc ccgaaccagt gacggtgtcg   120
tggaactcag gcgccctgac cagcggcgtg cacaccttcc cggctgtcct acagtcctca   180
ggactctact ccctcagcag cgtggtgacc gtgccctcca gcagcttggg cacgaagacc   240
tacacctgca acgtagatca caagcccagc aacaccaagg tggacaagag agttgagtcc   300
aaatatggtc ccccatgccc accatgccca gcgcctgaat ttgagggggg accatcagtc   360
ttcctgttcc cccaaaaacc caaggacact ctcatgatct cccggacccc tgaggtcacg   420
tgcgtggtgg tggacgtgag ccaggaagac cccgaggtcc agttcaactg gtacgtggat   480
ggcgtggagg tgcataatgc caagacaaag ccgcgggagg agcagttcaa cagcacgtac   540
cgtgtggtca gcgtcctcac cgtcctgcac caggactggc tgaacggcaa ggagtacaag   600
tgcaaggtct ccaacaaagg cctcccgtca tcgatcgaga aaaccatctc caaagccaaa   660
gggcagcccc gagagccaca ggtgtacacc ctgcccccat cccaggagga gatgaccaag   720
aaccaggtca gcctgacctg cctggtcaaa ggcttctacc ccagcgacat cgccgtggag   780
tgggagagca atgggcagcc ggagaacaac tacaagacca cgcctcccgt gctggactcc   840
gacggatcct tcttcctcta cagcaggcta accgtggaca agagcaggtg gcaggagggg   900
aatgtcttct catgctccgt gatgcatgag gctctgcaca accactacac acagaagagc   960
ctctcccctgt ctctgggtaa a                                             981

<210> SEQ ID NO 128
<211> LENGTH: 327
<212> TYPE: PRT
<213> ORGANISM: Homo Sapiens

<400> SEQUENCE: 128
```

```
Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
             20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
             100                 105                 110

Glu Phe Glu Gly Gly Pro Ser Val Phe Leu Phe Pro Pro Lys Pro Lys
         115                 120                 125

Asp Thr Leu Met Ile Ser Arg Thr Pro Glu Val Thr Cys Val Val Val
 130                 135                 140

Asp Val Ser Gln Glu Asp Pro Glu Val Gln Phe Asn Trp Tyr Val Asp
 145                 150                 155                 160

Gly Val Glu Val His Asn Ala Lys Thr Lys Pro Arg Glu Glu Gln Phe
                 165                 170                 175

Asn Ser Thr Tyr Arg Val Val Ser Val Leu Thr Val Leu His Gln Asp
             180                 185                 190

Trp Leu Asn Gly Lys Glu Tyr Lys Cys Lys Val Ser Asn Lys Gly Leu
         195                 200                 205

Pro Ser Ser Ile Glu Lys Thr Ile Ser Lys Ala Lys Gly Gln Pro Arg
 210                 215                 220

Glu Pro Gln Val Tyr Thr Leu Pro Pro Ser Gln Glu Glu Met Thr Lys
 225                 230                 235                 240

Asn Gln Val Ser Leu Thr Cys Leu Val Lys Gly Phe Tyr Pro Ser Asp
                 245                 250                 255

Ile Ala Val Glu Trp Glu Ser Asn Gly Gln Pro Glu Asn Asn Tyr Lys
             260                 265                 270

Thr Thr Pro Pro Val Leu Asp Ser Asp Gly Ser Phe Phe Leu Tyr Ser
         275                 280                 285

Arg Leu Thr Val Asp Lys Ser Arg Trp Gln Glu Gly Asn Val Phe Ser
 290                 295                 300

Cys Ser Val Met His Glu Ala Leu His Asn His Tyr Thr Gln Lys Ser
 305                 310                 315                 320

Leu Ser Leu Ser Leu Gly Lys
                 325
```

<210> SEQ ID NO 129
<211> LENGTH: 981
<212> TYPE: DNA
<213> ORGANISM: Homo Sapiens

<400> SEQUENCE: 129

```
gcctccacca agggacctag cgtgttccct ctcgcccct gttccaggtc cacaagcgag     60
tccaccgctg ccctcggctg tctggtgaaa gactactttc ccgagcccgt gaccgtctcc    120
tggaatagcg gagccctgac ctccggcgtg cacacatttc ccgccgtgct gcagagcagc    180
ggactgtata gcctgagcag cgtggtgacc gtgcccagct ccagcctcgg caccaaaacc    240
```

-continued

| | |
|---|---|
| tacacctgca acgtggacca caagccctcc aacaccaagg tggacaagcg ggtggagagc | 300 |
| aagtacggcc cccttgccc tccttgtcct gccctgagt tcgagggagg accctccgtg | 360 |
| ttcctgtttc cccccaaacc caaggacacc ctgatgatct cccggacacc cgaggtgacc | 420 |
| tgtgtggtcg tggacgtcag ccaggaggac cccgaggtgc agttcaactg gtatgtggac | 480 |
| ggcgtggagg tgcacaatgc caaaaccaag cccagggagg agcagttcaa ttccacctac | 540 |
| agggtggtga gcgtgctgac cgtcctgcat caggattggc tgaacggcaa ggagtacaag | 600 |
| tgcaaggtgt ccaacaaggg actgcccagc tccatcgaga agaccatcag caaggctaag | 660 |
| ggccagccga gggagcccca ggtgtatacc ctgcctccta gccaggaaga gatgaccaag | 720 |
| aaccaagtgt ccctgacctg cctggtgaag ggattctacc cctccgacat cgccgtggag | 780 |
| tgggagagca atggccagcc cgagaacaac tacaaaacaa cccctcccgt gctcgatagc | 840 |
| gacggcagct tctttctcta cagccggctg acagtggaca agagcaggtg gcaggagggc | 900 |
| aacgtgttct cctgttccgt gatgcacgag gccctgcaca atcactacac ccagaagagc | 960 |
| ctctccctgt ccctgggcaa g | 981 |

<210> SEQ ID NO 130
<211> LENGTH: 981
<212> TYPE: DNA
<213> ORGANISM: Homo Sapiens

<400> SEQUENCE: 130

| | |
|---|---|
| gccagcacca agggcccttc cgtgttcccc ctggccccctt gcagcaggag cacctccgaa | 60 |
| tccacagctg ccctgggctg tctggtgaag gactactttc ccgagccgt gaccgtgagc | 120 |
| tggaacagcg gcgctctgac atccggcgtc cacacctttc ctgccgtcct gcagtcctcc | 180 |
| ggcctctact cccgtgtcctc cgtggtgacc gtgcctagct cctccctcgg caccaagacc | 240 |
| tacacctgta acgtggacca caaaccctcc aacaccaagg tggacaaacg ggtcgagagc | 300 |
| aagtacggcc ctccctgccc tccttgtcct gcccccgagt tcgaaggcgg acccagcgtg | 360 |
| ttcctgttcc ctcctaagcc caaggacacc ctcatgatca gccggacacc cgaggtgacc | 420 |
| tgcgtggtgg tggatgtgag ccaggaggac cctgaggtcc agttcaactg gtatgtggat | 480 |
| ggcgtggagg tgcacaacgc caagacaaag ccccgggaag agcagttcaa ctccacctac | 540 |
| agggtggtca gcgtgctgac cgtgctgcat caggactggc tgaacggcaa ggagtacaag | 600 |
| tgcaaggtca gcaataaggg actgcccagc agcatcgaga agaccatctc caaggctaaa | 660 |
| ggccagcccc gggaacctca ggtgtacacc ctgcctccca gccaggagga gatgaccaag | 720 |
| aaccaggtga gcctgacctg cctggtgaag ggattctacc cttccgacat cgccgtggag | 780 |
| tgggagtcca acggccagcc cgagaacaat tataagacca cccctcccgt cctcgacagc | 840 |
| gacggatcct tctttctgta ctccaggctg accgtggata agtccaggtg gcaggaaggc | 900 |
| aacgtgttca gctgctccgt gatgcacgag gccctgcaca atcactacac ccagaagtcc | 960 |
| ctgagcctgt ccctgggaaa g | 981 |

<210> SEQ ID NO 131
<211> LENGTH: 981
<212> TYPE: DNA
<213> ORGANISM: Homo Sapiens

<400> SEQUENCE: 131

| | |
|---|---|
| gcctccacca agggcccatc cgtcttcccc ctggcgccct gctccaggag cacctccgag | 60 |
| agcacggccg ccctgggctg cctggtcaag gactacttcc ccgaaccagt gacggtgtcg | 120 |

```
tggaactcag gcgccctgac cagcggcgtg cacaccttcc cggctgtcct acagtcctca    180
ggactctact ccctcagcag cgtggtgacc gtgccctcca gcagcttggg cacgaagacc    240
tacacctgca acgtagatca caagcccagc aacaccaagg tggacaagag agttgagtcc    300
aaatatggtc ccccatgccc accatgccca gcgcctccag ttgcgggggg accatcagtc    360
ttcctgttcc ccccaaaacc caaggacact ctcatgatct cccggacccc tgaggtcacg    420
tgcgtggtgg tggacgtgag ccaggaagac cccgaggtcc agttcaactg gtacgtggat    480
ggcgtggagg tgcataatgc caagacaaag ccgcgggagg agcagttcaa cagcacgtac    540
cgtgtggtca gcgtcctcac cgtcctgcac caggactggc tgaacggcaa ggagtacaag    600
tgcaaggtct ccaacaaagg cctcccgtca tcgatcgaga aaaccatctc caaagccaaa    660
gggcagcccc gagagccaca ggtgtacacc ctgcccccat cccaggagga gatgaccaag    720
aaccaggtca gcctgacctg cctggtcaaa ggcttctacc ccagcgacat cgccgtggag    780
tgggagagca atgggcagcc ggagaacaac tacaagacca cgcctcccgt gctggactcc    840
gacggatcct tcttcctcta cagcaggcta accgtggaca agagcaggtg gcaggagggg    900
aatgtcttct catgctccgt gatgcatgag gctctgcaca accactacac acagaagagc    960
ctctccctgt ctctgggtaa a                                              981
```

<210> SEQ ID NO 132
<211> LENGTH: 327
<212> TYPE: PRT
<213> ORGANISM: Homo Sapiens

<400> SEQUENCE: 132

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Pro Val Ala Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
```

```
                210                 215                 220
Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325
```

<210> SEQ ID NO 133
<211> LENGTH: 990
<212> TYPE: DNA
<213> ORGANISM: Homo Sapiens

<400> SEQUENCE: 133

```
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agtggagccc     300
aaatcttgtg acaaaactca cacatgccca ccgtgcccag cacctgaact cgcggggggca     360
ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcgggagga gcagtacaac     540
agcacgtacc gtgtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag ggcagccccg agaaccacag gtgtacaccc tgcccccatc ccgggatgag     720
ctgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctac agcaagctca ccgtggacaa gagcaggtgg     900
cagcagggga acgtcttctc atgctccgtg atgcatgagg ctctgcacaa ccactacacg     960
cagaagagcc tctccctgtc tccgggtaaa                                     990
```

<210> SEQ ID NO 134
<211> LENGTH: 330
<212> TYPE: PRT
<213> ORGANISM: Homo Sapiens

<400> SEQUENCE: 134

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
             100                 105                 110

Pro Ala Pro Glu Leu Ala Gly Ala Pro Ser Val Phe Leu Phe Pro Pro
             115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 135
<211> LENGTH: 321
<212> TYPE: DNA
<213> ORGANISM: Homo Sapiens

<400> SEQUENCE: 135
cgtacggtgg ccgctccctc cgtgttcatc ttcccacctt ccgacgagca gctgaagtcc      60
ggcaccgctt ctgtcgtgtg cctgctgaac aacttctacc ccgcgaggc caaggtgcag     120 tggaaggtgg acaacgccct gcagtccggc aactcccagg aatccgtgac cgagcaggac     180
tccaaggaca gcacctactc cctgtcctcc accctgaccc tgtccaaggc cgactacgag     240
aagcacaagg tgtacgcctg cgaagtgacc caccagggcc tgtctagccc cgtgaccaag     300
tctttcaacc ggggcgagtg t                                              321

<210> SEQ ID NO 136
```

```
<211> LENGTH: 107
<212> TYPE: PRT
<213> ORGANISM: Homo Sapiens

<400> SEQUENCE: 136

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 137
<211> LENGTH: 321
<212> TYPE: DNA
<213> ORGANISM: Homo Sapiens

<400> SEQUENCE: 137
cgaactgtgg ctgcaccatc tgtcttcatc ttcccgccat ctgatgagca gttgaaatct     60
ggaactgcct ctgttgtgtg cctgctgaat aacttctatc ccagagaggc caaagtacag    120
tggaaggtgg ataacgccct ccaatcgggt aactcccagg agagtgtcac agagcaggag    180
agcaaggaca gcacctacag cctcagcagc accctgacgc tgagcaaagc agactacgag    240
aaacacaaag tctacgccgg cgaagtcacc catcagggcc tgagctcgcc cgtcacaaag    300
agcttcaaca ggggagagtg t                                              321

<210> SEQ ID NO 138
<211> LENGTH: 107
<212> TYPE: PRT
<213> ORGANISM: Homo Sapiens

<400> SEQUENCE: 138

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Glu Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Gly Glu Val Thr His Gln Gly Leu Ser Ser
                85                  90                  95

Pro Val Thr Lys Ser Phe Asn Arg Gly Glu Cys
            100                 105

<210> SEQ ID NO 139
<211> LENGTH: 321
```

<212> TYPE: DNA
<213> ORGANISM: Homo Sapiens

<400> SEQUENCE: 139

```
cgaactgtgg ctgcaccatc tgtcttcatc ttcccgccat ctgatgagca gttgaaatct    60
ggaactgcct ctgttgtgtg cctgctgaat aacttctatc ccagagaggc caaagtacag   120
cggaaggtgg ataacgccct ccaatcgggt aactcccagg agagtgtcac agagcaggag   180
agcaaggaca gcacctacag cctcagcagc accctgacgc tgagcaaagc agactacgag   240
aaacacaaag tctacgcctg cgaagtcacc catcagggcc tgagctcgcc cgtcacaaag   300
agcttcaaca ggggagagtg t                                             321
```

<210> SEQ ID NO 140
<211> LENGTH: 107
<212> TYPE: PRT
<213> ORGANISM: Homo Sapiens

<400> SEQUENCE: 140

```
Arg Thr Val Ala Ala Pro Ser Val Phe Ile Phe Pro Pro Ser Asp Glu
 1               5                  10                  15
Gln Leu Lys Ser Gly Thr Ala Ser Val Val Cys Leu Leu Asn Asn Phe
            20                  25                  30
Tyr Pro Arg Glu Ala Lys Val Gln Arg Lys Val Asp Asn Ala Leu Gln
        35                  40                  45
Ser Gly Asn Ser Gln Glu Ser Val Thr Glu Gln Ser Lys Asp Ser
    50                  55                  60
Thr Tyr Ser Leu Ser Ser Thr Leu Thr Leu Ser Lys Ala Asp Tyr Glu
 65                  70                  75                  80
Lys His Lys Val Tyr Ala Cys Glu Val Thr His Gln Gly Leu Ser Ser
                85                  90                  95
Pro Val Thr Lys Ser Phe Asn Arg Gly Glu Cys
            100                 105
```

<210> SEQ ID NO 141
<211> LENGTH: 321
<212> TYPE: DNA
<213> ORGANISM: Homo Sapiens

<400> SEQUENCE: 141

```
cgaactgtgg ctgcaccatc tgtcttcatc ttcccgccat ctgatgagca gttgaaatct    60
ggaactgcct ctgttgtgtg cctgctgaat aacttctatc ccagagaggc caaagtacag   120
tggaaggtgg ataacgccct ccaatcgggt aactcccagg agagtgtcac agagcaggac   180
agcaaggaca gcacctacag cctcagcagc accctgacgc tgagcaaagc agactacgag   240
aaacacaaac tctacgcctg cgaagtcacc catcagggcc tgagctcgcc cgtcacaaag   300
agcttcaaca ggggagagtg t                                             321
```

<210> SEQ ID NO 142
<211> LENGTH: 107
<212> TYPE: PRT
<213> ORGANISM: Homo Sapiens

<400> SEQUENCE: 142

```
Arg Thr Val Ala Ala Pro Ser Val Phe Ile Phe Pro Pro Ser Asp Glu
 1               5                  10                  15
Gln Leu Lys Ser Gly Thr Ala Ser Val Val Cys Leu Leu Asn Asn Phe
            20                  25                  30
```

```
Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Leu Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 143
<211> LENGTH: 321
<212> TYPE: DNA
<213> ORGANISM: Homo Sapiens

<400> SEQUENCE: 143

```
cgaactgtgg ctgcaccatc tgtcttcatc ttcccgccat ctgatgagca gttgaaatct      60
ggaactgcct ctgttgtgtg cctgctgaat aacttctatc ccagagaggc caaagtacag     120
tggaaggtgg ataacgccct ccaatcgggt aactcccagg agagtgtcac agagcaggac     180
agcaaggaca gcacctacag cctcagcaac accctgacgc tgagcaaagc agactacgag     240
aaacacaaag tctacgcctg cgaagtcacc catcagggcc tgagctcgcc cgtcacaaag     300
agcttcaaca ggggagagtg c                                                321
```

<210> SEQ ID NO 144
<211> LENGTH: 107
<212> TYPE: PRT
<213> ORGANISM: Homo Sapiens

<400> SEQUENCE: 144

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
            35                  40                  45

Ser Gly Asn Ser Gln Glu Ser Val Thr Glu Gln Asp Ser Lys Asp Ser
    50                  55                  60

Thr Tyr Ser Leu Ser Asn Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 145
<211> LENGTH: 312
<212> TYPE: DNA
<213> ORGANISM: Homo Sapiens

<400> SEQUENCE: 145

```
cccaaggcca accccacggt cactctgttc ccgccctcct ctgaggagct ccaagccaac      60
aaggccacac tagtgtgtct gatcagtgac ttctacccgg gagctgtgac agtggcttgg     120
aaggcagatg gcagccccgt caaggcggga gtggagacga ccaaaccctc caaacagagc     180
```
aacaacaagt acgcggccag cagctacctg agcctgacgc ccgagcagtg gaagtcccac    240
agaagctaca gctgccaggt cacgcatgaa gggagcaccg tggagaagac agtggcccct    300
acagaatgtt ca    312

<210> SEQ ID NO 146
<211> LENGTH: 104
<212> TYPE: PRT
<213> ORGANISM: Homo Sapiens

<400> SEQUENCE: 146

Pro Lys Ala Asn Pro Thr Val Thr Leu Phe Pro Pro Ser Ser Glu Glu
1               5                   10                  15

Leu Gln Ala Asn Lys Ala Thr Leu Val Cys Leu Ile Ser Asp Phe Tyr
            20                  25                  30

Pro Gly Ala Val Thr Val Ala Trp Lys Ala Asp Gly Ser Pro Val Lys
        35                  40                  45

Ala Gly Val Glu Thr Thr Lys Pro Ser Lys Gln Ser Asn Asn Lys Tyr
    50                  55                  60

Ala Ala Ser Ser Tyr Leu Ser Leu Thr Pro Glu Gln Trp Lys Ser His
65                  70                  75                  80

Arg Ser Tyr Ser Cys Gln Val Thr His Glu Gly Ser Thr Val Glu Lys
                85                  90                  95

Thr Val Ala Pro Thr Glu Cys Ser
            100

<210> SEQ ID NO 147
<211> LENGTH: 318
<212> TYPE: DNA
<213> ORGANISM: Homo Sapiens

<400> SEQUENCE: 147
ggtcagccca aggccaaccc cactgtcact ctgttcccgc cctcctctga ggagctccaa     60
gccaacaagg ccacactagt gtgtctgatc agtgacttct acccgggagc tgtgacagtg    120
gcctggaagg cagatggcag ccccgtcaag gcgggagtgg agaccaccaa acccctccaaa  180 cagagcaaca acaagtacgc ggccagcagc tacctgagcc tgacgccccga gcagtggaag   240 tcccacagaa gctacagctg ccaggtcacg catgaaggga gcaccgtgga agacagtg    300 gcccctacag aatgttca    318

<210> SEQ ID NO 148
<211> LENGTH: 106
<212> TYPE: PRT
<213> ORGANISM: Homo Sapiens

<400> SEQUENCE: 148

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val

Glu Lys Thr Val Ala Pro Thr Glu Cys Ser
            85              90              95
                100                  105

<210> SEQ ID NO 149
<211> LENGTH: 318
<212> TYPE: DNA
<213> ORGANISM: Homo Sapiens

<400> SEQUENCE: 149
ggtcagccca aggccaaccc cactgtcact ctgttcccgc cctcctctga ggagctccaa    60
gccaacaagg ccacactagt gtgtctgatc agtgacttct acccgggagc tgtgacagtg   120
gcctggaagg cagatggcag ccccgtcaag gcgggagtgg agaccaccaa accctccaaa   180
cagagcaaca caagtacgc ggccagcagc tacctgagcc tgacgcccga gcagtggaag   240
tcccacagaa gctacagctg ccaggtcacg catgaaggga gcaccgtgga agacagtg    300 gcccctacag aatgttca                                                 318

<210> SEQ ID NO 150
<211> LENGTH: 318
<212> TYPE: DNA
<213> ORGANISM: Homo Sapiens

<400> SEQUENCE: 150
ggccagccta aggccgctcc ttctgtgacc ctgttccccc catcctccga ggaactgcag    60
gctaacaagg ccaccctcgt gtgcctgatc agcgacttct accctggcgc cgtgaccgtg   120
gcctggaagg ctgatagctc tcctgtgaag gccggcgtgg aaaccaccac ccttccaag    180 cagtccaaca caaatacgc cgcctcctcc tacctgtccc tgaccctga gcagtggaag    240 tcccaccggt cctacagctg ccaagtgacc cacgagggct ccaccgtgga aagaccgtg   300 gctcctaccg agtgctcc                                                 318

<210> SEQ ID NO 151
<211> LENGTH: 318
<212> TYPE: DNA
<213> ORGANISM: Homo Sapiens

<400> SEQUENCE: 151
ggccagccta aagctgcccc cagcgtcacc ctgtttcctc cctccagcga ggagctccag    60
gccaacaagg ccaccctcgt gtgcctgatc tccgacttct atcccggcgc tgtgaccgtg   120
gcttggaaag ccgactccag ccctgtcaaa gccggcgtgg agaccaccac accctccaag   180
cagtccaaca caagtacgc cgcctccagc tatctctccc tgaccctga gcagtggaag    240 tcccaccggt cctactcctg tcaggtgacc cacgagggct ccaccgtgga aagaccgtc   300 gccccaccg agtgctcc                                                  318

<210> SEQ ID NO 152
<211> LENGTH: 106
<212> TYPE: PRT
<213> ORGANISM: Homo Sapiens

<400> SEQUENCE: 152

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
            35                  40                  45

Val Lys Ala Gly Val Glu Thr Thr Lys Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
            100                 105

<210> SEQ ID NO 153
<211> LENGTH: 318
<212> TYPE: DNA
<213> ORGANISM: Homo Sapiens

<400> SEQUENCE: 153
ggtcagccca aggctgcccc ctcggtcact ctgttcccgc cctcctctga ggagcttcaa      60
gccaacaagg ccacactggt gtgtctcata agtgacttct acccgggagc cgtgacagtg     120
gcctggaagg cagatagcag ccccgtcaag gcgggagtgg agaccaccac accctccaaa     180
caaagcaaca acaagtacgc ggccagcagc tatctgagcc tgacgcctga gcagtggaag     240
tcccacagaa gctacagctg ccaggtcacg catgaaggga gcaccgtgga agacagtg      300 gcccctacag aatgttca                                                   318

<210> SEQ ID NO 154
<211> LENGTH: 106
<212> TYPE: PRT
<213> ORGANISM: Homo Sapiens

<400> SEQUENCE: 154

Gly Gln Pro Lys Ala Ala Pro Ser Val Thr Leu Phe Pro Pro Ser Ser
 1               5                  10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
            35                  40                  45

Val Lys Ala Gly Val Glu Thr Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
            100                 105

<210> SEQ ID NO 155
<211> LENGTH: 312
<212> TYPE: DNA
<213> ORGANISM: Homo Sapiens

<400> SEQUENCE: 155
cccaaggctg ccccctcggt cactctgttc ccaccctcct ctgaggagct tcaagccaac      60
aaggccacac tggtgtgtct cataagtgac ttctacccgg gagccgtgac agttgcctgg     120
aaggcagata gcagccccgt caaggcgggg gtggagacca ccacaccctc caaacaaagc     180
aacaacaagt acgcggccag cagctacctg agcctgacgc ctgagcagtg gaagtcccac     240
aaaagctaca gctgccaggt cacgcatgaa gggagcaccg tggagaagac agttgcccct    300
acggaatgtt ca    312

<210> SEQ ID NO 156
<211> LENGTH: 104
<212> TYPE: PRT
<213> ORGANISM: Homo Sapiens

<400> SEQUENCE: 156

Pro Lys Ala Ala Pro Ser Val Thr Leu Phe Pro Ser Ser Glu Glu
1               5                   10                  15

Leu Gln Ala Asn Lys Ala Thr Leu Val Cys Leu Ile Ser Asp Phe Tyr
            20                  25                  30

Pro Gly Ala Val Thr Val Ala Trp Lys Ala Asp Ser Ser Pro Val Lys
        35                  40                  45

Ala Gly Val Glu Thr Thr Thr Pro Ser Lys Gln Ser Asn Asn Lys Tyr
    50                  55                  60

Ala Ala Ser Ser Tyr Leu Ser Leu Thr Pro Glu Gln Trp Lys Ser His
65                  70                  75                  80

Lys Ser Tyr Ser Cys Gln Val Thr His Glu Gly Ser Thr Val Glu Lys
                85                  90                  95

Thr Val Ala Pro Thr Glu Cys Ser
            100

<210> SEQ ID NO 157
<211> LENGTH: 318
<212> TYPE: DNA
<213> ORGANISM: Homo Sapiens

<400> SEQUENCE: 157
ggtcagccca aggctgcccc ctcggtcact ctgttcccac cctcctctga ggagcttcaa    60
gccaacaagg ccacactggt gtgtctcata agtgacttct acccgggggcc agtgacagtt    120 gcctggaagg cagatagcag ccccgtcaag gcggggggtgg agaccaccac accctccaaa    180
caaagcaaca caagtacgc ggccagcagc tacctgagcc tgacgcctga gcagtggaag    240
tcccacaaaa gctacagctg ccaggtcacg catgaaggga gcaccgtgga agacagtg    300 gcccctacgg aatgttca    318

<210> SEQ ID NO 158
<211> LENGTH: 106
<212> TYPE: PRT
<213> ORGANISM: Homo Sapiens

<400> SEQUENCE: 158

Gly Gln Pro Lys Ala Ala Pro Ser Val Thr Leu Phe Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Lys Ser Tyr Ser Cys Gln Val Thr His Glu Gly Ser Thr Val
                85                  90                  95

```
Glu Lys Thr Val Ala Pro Thr Glu Cys Ser
            100                 105

<210> SEQ ID NO 159
<211> LENGTH: 318
<212> TYPE: DNA
<213> ORGANISM: Homo Sapiens

<400> SEQUENCE: 159
ggtcagccca aggctgcccc ctcggtcact ctgttcccac cctcctctga ggagcttcaa      60
gccaacaagg ccacactggt gtgtctcata agtgacttct acccgggagc cgtgacagtg     120
gcctggaagg cagatagcag ccccgtcaag gcgggagtgg agaccaccac accctccaaa     180
caaagcaaca acaagtacgc ggccagcagc tacctgagcc tgacgcctga gcagtggaag     240
tcccacaaaa gctacagctg ccaggtcacg catgaaggga gcaccgtgga aagacagtg      300 gcccctacag aatgttca                                                   318

<210> SEQ ID NO 160
<211> LENGTH: 106
<212> TYPE: PRT
<213> ORGANISM: Homo Sapiens

<400> SEQUENCE: 160

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Lys Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 161
<211> LENGTH: 318
<212> TYPE: DNA
<213> ORGANISM: Homo Sapiens

<400> SEQUENCE: 161
ggtcagccca aggctgcccc ctcggtcact ctgttcccgc cctcctctga ggagcttcaa      60
gccaacaagg ccacactggt gtgtctcata agtgacttct acccgggagc cgtgacagtg     120
gcctggaagg cagatagcag ccccgtcaag gcgggagtgg agaccaccac accctccaaa     180
caaagcaaca acaagtacgc ggccagcagc tacctgagcc tgacgcctga gcagtggaag     240
tcccacagaa gctacagctg ccaggtcacg catgaaggga gcaccgtgga aagacagtg      300 gcccctacag aatgttca                                                   318

<210> SEQ ID NO 162
<211> LENGTH: 106
<212> TYPE: PRT
<213> ORGANISM: Homo Sapiens
```

<400> SEQUENCE: 162

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 163
<211> LENGTH: 318
<212> TYPE: DNA
<213> ORGANISM: Homo Sapiens

<400> SEQUENCE: 163
ggtcagccca aggctgcccc atcggtcact ctgttcccgc cctcctctga ggagcttcaa     60
gccaacaagg ccacactggt gtgcctgatc agtgacttct acccgggagc tgtgaaagtg    120
gcctggaagg cagatggcag ccccgtcaac acgggagtgg agaccaccac accctccaaa    180
cagagcaaca acaagtacgc ggccagcagc tacctgagcc tgacgcctga gcagtggaag    240
tcccacagaa gctacagctg ccaggtcacg catgaaggga gcaccgtgga agacagtgtg    300
gcccctgcag aatgttca                                                  318

<210> SEQ ID NO 164
<211> LENGTH: 106
<212> TYPE: PRT
<213> ORGANISM: Homo Sapiens

<400> SEQUENCE: 164

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Lys Val Ala Trp Lys Ala Asp Gly Ser Pro
        35                  40                  45

Val Asn Thr Gly Val Glu Thr Thr Thr Pro Ser Lys Gln Ser Asn Asn
50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Ala Glu Cys Ser
            100                 105

<210> SEQ ID NO 165
<211> LENGTH: 318
<212> TYPE: DNA
<213> ORGANISM: Homo Sapiens

<400> SEQUENCE: 165

```
ggtcagccca aggctgcccc atcggtcact ctgttcccac cctcctctga ggagcttcaa      60
gccaacaagg ccacactggt gtgtctcgta agtgacttct acccgggagc cgtgacagtg     120
gcctggaagg cagatggcag ccccgtcaag gtgggagtgg agaccaccaa accctccaaa     180
caaagcaaca caagtatgc ggccagcagc tacctgagcc tgacgcccga gcagtggaag      240
tcccacagaa gctacagctg ccgggtcacg catgaaggga gcaccgtgga agacagtg      300 gcccctgcag aatgctct                                                   318
```

<210> SEQ ID NO 166
<211> LENGTH: 106
<212> TYPE: PRT
<213> ORGANISM: Homo Sapiens

<400> SEQUENCE: 166

```
Gly Gln Pro Lys Ala Ala Pro Ser Val Thr Leu Phe Pro Pro Ser Ser
1               5                  10                  15

Glu Glu Leu Gln Ala Asn Lys Ala Thr Leu Val Cys Leu Val Ser Asp
            20                  25                  30

Phe Tyr Pro Gly Ala Val Thr Val Ala Trp Lys Ala Asp Gly Ser Pro
        35                  40                  45

Val Lys Val Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Arg Val Thr His Glu Gly Ser Thr Val
                85                  90                  95

Glu Lys Thr Val Ala Pro Ala Glu Cys Ser
            100                 105
```

<210> SEQ ID NO 167
<211> LENGTH: 615
<212> TYPE: DNA
<213> ORGANISM: Homo Sapiens

<400> SEQUENCE: 167

```
atgggctggt cctgcatcat cctgtttctg gtggccaccg ccaccggcgt gcacagcgat      60
tacaaggatg acgacgataa gcgtatgaaa cagatcgaag ataaaattga agagatcttg     120
agcaaaatct atcatatcga aacgaaatt gcgcgtatca aaaagctgat ggcgaacgt      180 ggcggtggca gcgtggcggt tagcggcggt ggcagccagg tgtcccaccg ataccccagg     240
atccagtcca tcaaggtcca gttcaccgag tacaaaaagg agaagggatt catcctgacc     300
tcccaaaagg aggacgagat catgaaggtg caaaacaact ccgtgatcat caactgcgac     360
ggcttctacc tgatctccct gaagggctac ttctcccagg aggtgaacat ctccctgcac     420
taccagaagg acgaggagcc cctgttccag ctgaagaagg tgaggtccgt gaattccctg     480
atggtggcca gcctgaccta caaggacaag gtctacctga acgtgaccac cgacaacacc     540
agcctggacg acttccatgt caacggcggc gagctgatcc tgatccatca gaaccccggc     600
gagttttgcg tcctg                                                     615
```

<210> SEQ ID NO 168
<211> LENGTH: 205
<212> TYPE: PRT
<213> ORGANISM: Homo Sapiens

<400> SEQUENCE: 168

```
Met Gly Trp Ser Cys Ile Ile Leu Phe Leu Val Ala Thr Ala Thr Gly
1               5                   10                  15

Val His Ser Asp Tyr Lys Asp Asp Asp Lys Arg Met Lys Gln Ile
            20                  25                  30

Glu Asp Lys Ile Glu Glu Ile Leu Ser Lys Ile Tyr His Ile Glu Asn
        35                  40                  45

Glu Ile Ala Arg Ile Lys Lys Leu Ile Gly Glu Arg Gly Gly Gly Ser
    50                  55                  60

Gly Gly Gly Ser Gly Gly Ser Gln Val Ser His Arg Tyr Pro Arg
65              70                  75                  80

Ile Gln Ser Ile Lys Val Gln Phe Thr Glu Tyr Lys Lys Glu Lys Gly
            85                  90                  95

Phe Ile Leu Thr Ser Gln Lys Glu Asp Glu Ile Met Lys Val Gln Asn
            100                 105                 110

Asn Ser Val Ile Ile Asn Cys Asp Gly Phe Tyr Leu Ile Ser Leu Lys
            115                 120                 125

Gly Tyr Phe Ser Gln Glu Val Asn Ile Ser Leu His Tyr Gln Lys Asp
            130                 135                 140

Glu Glu Pro Leu Phe Gln Leu Lys Lys Val Arg Ser Val Asn Ser Leu
145                 150                 155                 160

Met Val Ala Ser Leu Thr Tyr Lys Asp Lys Val Tyr Leu Asn Val Thr
                165                 170                 175

Thr Asp Asn Thr Ser Leu Asp Asp Phe His Val Asn Gly Gly Glu Leu
            180                 185                 190

Ile Leu Ile His Gln Asn Pro Gly Glu Phe Cys Val Leu
            195                 200                 205

<210> SEQ ID NO 169
<211> LENGTH: 615
<212> TYPE: DNA
<213> ORGANISM: Homo Sapiens

<400> SEQUENCE: 169
atgggctggt cctgcatcat cctgtttctg gtggccaccg ccaccggcgt gcacagcgat       60
tacaaggatg acgacgataa gcgtatgaaa cagatcgaag ataaaattga agagatcttg      120
agcaaaatct atcatatcga aaacgaaatt gcgcgtatca aaaagctgat tggcgaacgt      180
ggcggtggca gcggtggcgg tagcggcggt ggcagccagg tgtcccacca ataccccagg      240
atccagtcca tcaaggtcca gttcaccgag tacaaaaagg aggagggatt catcctgacc      300
tcccaaaagg aggacgagat catgaaggtg caaaacaact ccgtgatcat caactgcgac      360
ggcttctacc tgatctccct gaagggctac ttctcccagg aggtgaacat ctccctgcac      420
taccagaagg acgaggagcc cctgttccag ctgaagaagg tgaggtccgt gaattccctg      480
atggtggcca gcctgaccta caaggacaag gtctacctga acgtgaccac cgacaacacc      540
agcctggacg acttccatgt caacggcggc gagctgatcc tgatccatca gaaccccggc      600
gagttttgcg tcctg                                                      615

<210> SEQ ID NO 170
<211> LENGTH: 205
<212> TYPE: PRT
<213> ORGANISM: Homo Sapiens

<400> SEQUENCE: 170

Met Gly Trp Ser Cys Ile Ile Leu Phe Leu Val Ala Thr Ala Thr Gly
```

```
                1               5                       10                      15
            Val His Ser Asp Tyr Lys Asp Asp Asp Lys Arg Met Lys Gln Ile
                        20                      25                      30

Glu Asp Lys Ile Glu Glu Ile Leu Ser Lys Ile Tyr His Ile Glu Asn
                        35                      40                      45

Glu Ile Ala Arg Ile Lys Lys Leu Ile Gly Glu Arg Gly Gly Gly Ser
                        50                      55                      60

Gly Gly Gly Ser Gly Gly Ser Gln Val Ser His Gln Tyr Pro Arg
            65                      70                      75                      80

Ile Gln Ser Ile Lys Val Gln Phe Thr Glu Tyr Lys Lys Glu Gly
                                85                      90                      95

Phe Ile Leu Thr Ser Gln Lys Glu Asp Glu Ile Met Lys Val Gln Asn
                        100                     105                     110

Asn Ser Val Ile Ile Asn Cys Asp Gly Phe Tyr Leu Ile Ser Leu Lys
                        115                     120                     125

Gly Tyr Phe Ser Gln Glu Val Asn Ile Ser Leu His Tyr Gln Lys Asp
                        130                     135                     140

Glu Glu Pro Leu Phe Gln Leu Lys Lys Val Arg Ser Val Asn Ser Leu
            145                     150                     155                     160

Met Val Ala Ser Leu Thr Tyr Lys Asp Lys Val Tyr Leu Asn Val Thr
                        165                     170                     175

Thr Asp Asn Thr Ser Leu Asp Asp Phe His Val Asn Gly Gly Glu Leu
                        180                     185                     190

Ile Leu Ile His Gln Asn Pro Gly Glu Phe Cys Val Leu
                        195                     200                     205

<210> SEQ ID NO 171
<211> LENGTH: 1332
<212> TYPE: DNA
<213> ORGANISM: Homo Sapiens

<400> SEQUENCE: 171
atgggctggt cctgcatcat cctgtttctg gtggccaccg ccaccggcgt gcacagcctg      60
cattgcgtgg cgacaccta tccctccaac gacaggtgct gccacgagtg caggcctgga    120
aacggcatgg tgagcaggtg cagccggtcc cagaataccg tgtgtaggcc ctgcggcccc    180
ggctttaca cgacgtggt gtcctccaag ccctgcaagc cctgcacatg gtgcaacctg    240
cggtccggca gcgagaggaa gcagctctgc acagccaccc aggacaccgt ctgtaggtgt    300
agggctggca cccagcctct ggactcctac aagcccggcg tggattgtgc tccttgccct    360
cccggccatt tctcccctgg cgacaaccag gcttgcaagc cctggaccaa ctgtaccctg    420
gccggcaagc atacactgca gcctgcttcc aactcctccg acgctatctg cgaggatagg    480
gaccccctg ccacacaacc ccaggagaca cagggccctc ctgctaggcc catcacagtc    540
caacccaccg aagcctggcc caggacatcc caaggccctt ccaccaggcc tgtggaagtg    600
cctggaggaa gggctgtggc cattgaaggt cgtatggatg aacccaagtc ctgcgacaag    660
acccacacct gtccccttg tctgcccct gaactgctgg gcggaccttc cgtgttcctg    720
ttccccccaa agcccaagga caccctgatg atctcccgga ccccgaagt gacctgcgtg    780
gtggtggatg tgtcccacga ggaccctgaa gtgaagttca ttggtacgt ggacggcgtg    840
gaagtgcaca cgccaagac caagcctaga gaggaacagt acaactccac ctaccgggtg    900
gtgtccgtgc tgaccgtgct gcaccaggat tggctgaacg gcaaagagta caagtgcaag    960
gtgtccaaca aggccctgcc tgccccatc gaaaagacca tctccaaggc caagggccag   1020
```

-continued

```
cccgggaac cccaggtgta cacactgccc cctagcaggg acgagctgac caagaaccag    1080
gtgtccctga cctgtctcgt gaaaggcttc taccctccg atatcgccgt ggaatgggag    1140
tccaacggcc agcctgagaa caactacaag accacccccc ctgtgctgga ctccgacggc    1200
tcattcttcc tgtacagcaa gctgacagtg gacaagtccc ggtggcagca gggcaacgtg    1260
ttctcctgct ccgtgatgca cgaggccctg cacaaccact acacccagaa gtccctgtcc    1320
ctgagcccct ga                                                        1332
```

<210> SEQ ID NO 172
<211> LENGTH: 443
<212> TYPE: PRT
<213> ORGANISM: Homo Sapiens

<400> SEQUENCE: 172

```
Met Gly Trp Ser Cys Ile Ile Leu Phe Leu Val Ala Thr Ala Thr Gly
1               5                   10                  15

Val His Ser Leu His Cys Val Gly Asp Thr Tyr Pro Ser Asn Asp Arg
            20                  25                  30

Cys Cys His Glu Cys Arg Pro Gly Asn Gly Met Val Ser Arg Cys Ser
        35                  40                  45

Arg Ser Gln Asn Thr Val Cys Arg Pro Cys Gly Pro Gly Phe Tyr Asn
    50                  55                  60

Asp Val Val Ser Ser Lys Pro Cys Lys Pro Cys Thr Trp Cys Asn Leu
65                  70                  75                  80

Arg Ser Gly Ser Glu Arg Lys Gln Leu Cys Thr Ala Thr Gln Asp Thr
                85                  90                  95

Val Cys Arg Cys Arg Ala Gly Thr Gln Pro Leu Asp Ser Tyr Lys Pro
            100                 105                 110

Gly Val Asp Cys Ala Pro Cys Pro Pro Gly His Phe Ser Pro Gly Asp
        115                 120                 125

Asn Gln Ala Cys Lys Pro Trp Thr Asn Cys Thr Leu Ala Gly Lys His
    130                 135                 140

Thr Leu Gln Pro Ala Ser Asn Ser Ser Asp Ala Ile Cys Glu Asp Arg
145                 150                 155                 160

Asp Pro Pro Ala Thr Gln Pro Gln Glu Thr Gln Gly Pro Pro Ala Arg
                165                 170                 175

Pro Ile Thr Val Gln Pro Thr Glu Ala Trp Pro Arg Thr Ser Gln Gly
            180                 185                 190

Pro Ser Thr Arg Pro Val Glu Val Pro Gly Gly Arg Ala Val Ala Ile
        195                 200                 205

Glu Gly Arg Met Asp Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285

Pro Arg Glu Glu Gln Tyr Asn Ser Thr Tyr Arg Val Val Ser Val Leu
    290                 295                 300

Thr Val Leu His Gln Asp Trp Leu Asn Gly Lys Glu Tyr Lys Cys Lys
```

```
            305                 310                 315                 320
Val Ser Asn Lys Ala Leu Pro Ala Pro Ile Glu Lys Thr Ile Ser Lys
                    325                 330                 335

Ala Lys Gly Gln Pro Arg Glu Pro Gln Val Tyr Thr Leu Pro Pro Ser
                340                 345                 350

Arg Asp Glu Leu Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
        370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro
        435                 440
```

<210> SEQ ID NO 173
<211> LENGTH: 552
<212> TYPE: DNA
<213> ORGANISM: Homo Sapiens

<400> SEQUENCE: 173

```
atggagaggg tgcagcccct cgaggagaac gtgggaaacg ccgccaggcc taggttcgag    60
aggaacaagc tgctgctggt ggcttccgtg atccaaggac tcggcctgct gctctgcttc   120
acctacatct gcctccactt cagcgccctg caggtgtccc accgataccc caggatccag   180
tccatcaagg tccagttcac cgagtacaaa aaggagaagg gattcatcct gacctcccaa   240
aaggaggacg agatcatgaa ggtgcaaaac aactccgtga tcatcaactg cgacggcttc   300
tacctgatct ccctgaaggg ctacttctcc caggaggtga acatctccct gcactaccag   360
aaggacgagg agcccctgtt ccagctgaag aaggtgaggt ccgtgaattc cctgatggtg   420
gccagcctga cctacaagga caaggtctac ctgaacgtga ccaccgacaa caccagcctg   480
gacgacttcc atgtcaacgg cggcgagctg atcctgatcc atcagaaccc cggcgagttt   540
tgcgtcctgt aa                                                      552
```

<210> SEQ ID NO 174
<211> LENGTH: 181
<212> TYPE: PRT
<213> ORGANISM: Homo Sapiens

<400> SEQUENCE: 174

```
Met Glu Arg Val Gln Pro Leu Glu Glu Asn Val Gly Asn Ala Ala Arg
1               5                   10                  15

Pro Arg Phe Glu Arg Asn Lys Leu Leu Leu Val Ala Ser Val Ile Gln
            20                  25                  30

Gly Leu Gly Leu Leu Leu Cys Phe Thr Tyr Ile Cys Leu His Phe Ser
        35                  40                  45

Ala Leu Gln Val Ser His Arg Tyr Pro Arg Ile Gln Ser Ile Lys Val
    50                  55                  60

Gln Phe Thr Glu Tyr Lys Lys Glu Lys Gly Phe Ile Leu Thr Ser Gln
65                  70                  75                  80

Lys Glu Asp Glu Ile Met Lys Val Gln Asn Asn Ser Val Ile Ile Asn
                85                  90                  95
```

```
Cys Asp Gly Phe Tyr Leu Ile Ser Leu Lys Gly Tyr Phe Ser Gln Glu
            100                 105                 110

Val Asn Ile Ser Leu His Tyr Gln Lys Asp Glu Glu Pro Leu Phe Gln
            115                 120                 125

Leu Lys Lys Val Arg Ser Val Asn Ser Leu Met Val Ala Ser Leu Thr
        130                 135                 140

Tyr Lys Asp Lys Val Tyr Leu Asn Val Thr Thr Asp Asn Thr Ser Leu
145                 150                 155                 160

Asp Asp Phe His Val Asn Gly Gly Glu Leu Ile Leu Ile His Gln Asn
                165                 170                 175

Pro Gly Glu Phe Cys
            180

<210> SEQ ID NO 175
<211> LENGTH: 834
<212> TYPE: DNA
<213> ORGANISM: Homo Sapiens

<400> SEQUENCE: 175
atgtgcgtgg gggctcggcg gctgggccgc gggccgtgtg cggctctgct cctcctgggc      60
ctggggctga gcaccgtgac ggggctccac tgtgtcgggg acacctaccc cagcaacgac     120
cggtgctgcc acgagtgcag gccaggcaac gggatggtga ccgctgcag ccgctcccag     180
aacacggtgt gccgtccgtg cggggccggg c ttctacaacg acgtggtcag ctccaagccg    240
tgcaagccct gcacgtggtg taacctcaga agtgggagtg agcggaagca gctgtgcacg     300
gccacacagg acacagtctg ccgctgccgg gcgggcaccc agccctgga cagctacaag     360
cctggagttg actgtgcccc ctgccctcca gggcacttct ccccaggcga caaccaggcc     420
tgcaagccct ggaccaactg caccttggct gggaagcaca ccctgcagcc ggccagcaat     480
agctcggacg caatctgtga ggacagggac cccccagcca cgcagcccca ggagacccag     540
ggccccccgg ccaggcccat cactgtccag cccactgaag cctggcccag aacctcacag     600
ggaccctcca cccggcccgt ggaggtcccc ggggccgtg cggttgccgc atcctgggc       660
ctgggcctgg tgctggggct gctgggcccc ctggccatcc tgctggccct gtacctgctc     720
cggagggacc agaggctgcc cccgatgcc cacaagcccc tgggggagg cagtttccgg       780
accccatcc aagaggagca ggccgacgcc cactccaccc tggccaagat ctga           834

<210> SEQ ID NO 176
<211> LENGTH: 277
<212> TYPE: PRT
<213> ORGANISM: Homo Sapiens

<400> SEQUENCE: 176

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
            20                  25                  30

Gly Asp Thr Tyr Pro Ser Asn Asp Arg Cys Cys His Glu Cys Arg Pro
        35                  40                  45

Gly Asn Gly Met Val Ser Arg Cys Ser Arg Ser Gln Asn Thr Val Cys
    50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
```

```
                    85                  90                  95
Gln Leu Cys Thr Ala Thr Gln Asp Thr Val Cys Arg Cys Arg Ala Gly
                100                 105                 110

Thr Gln Pro Leu Asp Ser Tyr Lys Pro Gly Val Asp Cys Ala Pro Cys
            115                 120                 125

Pro Pro Gly His Phe Ser Pro Gly Asp Asn Gln Ala Cys Lys Pro Trp
        130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
        195                 200                 205

Val Pro Gly Gly Arg Ala Val Ala Ala Ile Leu Gly Leu Gly Leu Val
    210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
        275

<210> SEQ ID NO 177
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 177

Glu Val Gln Leu Val Glu Ser Gly Gly Gly Leu Val Gln Ala Gly Gly
1               5                   10                  15

Ser Leu Arg Leu Ser Cys Ala Ala Ser Arg Ser Ile Gly Arg Leu Asp
            20                  25                  30

Arg Met Gly Trp Tyr Arg His Arg Thr Gly Glu Pro Arg Glu Leu Val
        35                  40                  45

Ala Thr Ile Thr Gly Gly Ser Ser Ile Asn Tyr Gly Asp Phe Val Lys
    50                  55                  60

Gly Arg Phe Thr Ile Ser Ile Asp Asn Ala Lys Asn Thr Val Tyr Leu
65                  70                  75                  80

Gln Met Asn Asn Leu Lys Pro Glu Asp Thr Ala Val Tyr Tyr Cys Asn
                85                  90                  95

Phe Asn Lys Tyr Val Thr Ser Arg Asp Thr Trp Gly Gln Gly Thr Gln
            100                 105                 110

Val Thr Val Ser Ser
        115

<210> SEQ ID NO 178
<211> LENGTH: 128
<212> TYPE: PRT
<213> ORGANISM: Artificial Sequence
<220> FEATURE:
```

-continued

<223> OTHER INFORMATION: Description of Artificial Sequence: Synthetic
     polypeptide

<400> SEQUENCE: 178

Glu Val Gln Leu Val Glu Ser Gly Gly Gly Leu Val Gln Ala Gly Gly
1               5                   10                  15

Ser Leu Arg Leu Ser Cys Val Ala Ser Gly Arg Ser Phe Ser Thr Tyr
            20                  25                  30

Ile Met Gly Trp Phe Arg Gln Ala Pro Gly Lys Glu Arg Glu Phe Val
        35                  40                  45

Ala Thr Ile Ser Arg Ser Gly Ile Thr Ile Arg Ser Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Ala Val Tyr Tyr Cys
                85                  90                  95

Ala Ala Gly Pro Tyr Val Glu Gln Thr Leu Gly Leu Tyr Gln Thr Leu
            100                 105                 110

Gly Pro Trp Asp Tyr Trp Gly Gln Gly Thr Gln Val Thr Val Ser Ser
        115                 120                 125

<210> SEQ ID NO 179
<211> LENGTH: 124
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 179

Glu Val Gln Leu Val Glu Ser Gly Gly Gly Leu Val Gln Ala Gly Gly
1               5                   10                  15

Ser Leu Arg Leu Ser Cys Ala Ala Ser Gly Arg Thr Phe Ser Ser Ile
            20                  25                  30

Tyr Ala Lys Gly Trp Phe Arg Gln Ala Pro Gly Lys Glu Arg Glu Phe
        35                  40                  45

Val Ala Ala Ile Ser Arg Ser Gly Arg Ser Thr Ser Tyr Ala Asp Ser
    50                  55                  60

Val Lys Gly Arg Phe Thr Ile Ser Arg Asp Asn Ala Lys Asn Thr Val
65                  70                  75                  80

Tyr Leu Gln Met Asn Ser Leu Lys Pro Glu Asp Thr Ala Val Tyr Tyr
                85                  90                  95

Cys Ala Ala Val Gly Gly Ala Thr Thr Val Thr Ala Ser Glu Trp Asp
            100                 105                 110

Tyr Trp Gly Leu Gly Thr Gln Val Thr Val Ser Ser
        115                 120

<210> SEQ ID NO 180
<211> LENGTH: 125
<212> TYPE: PRT
<213> ORGANISM: Artificial Sequence
<220> FEATURE:
<223> OTHER INFORMATION: Description of Artificial Sequence: Synthetic
     polypeptide

<400> SEQUENCE: 180

Glu Val Gln Leu Val Glu Ser Gly Gly Gly Leu Val Gln Ala Gly Asp
1               5                   10                  15

Ser Leu Arg Leu Ser Cys Ala Ala Ser Gly Leu Thr Phe Ser Ser Phe

```
            20                  25                  30
Ala Met Gly Trp Phe Arg Gln Ala Pro Gly Lys Glu Arg Glu Phe Val
            35                  40                  45

Ala Ala Ile Ser Arg Ser Gly Tyr Gly Thr Ser Glu Ala Asp Ser Val
    50                  55                  60

Arg Asp Arg Phe Ile Ile Ser Arg Asp Asn Ala Lys Asn Thr Val Thr
65                  70                  75                  80

Leu His Leu Ser Arg Leu Lys Pro Glu Asp Thr Ala Val Tyr Tyr Cys
                85                  90                  95

Ala Ala Glu His Thr Leu Gly Arg Pro Ser Arg Ser Gln Ile Asn Tyr
            100                 105                 110

Leu Tyr Trp Gly Gln Gly Thr Gln Val Thr Val Ser Ser
        115                 120                 125

<210> SEQ ID NO 181
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 181

Glu Val Gln Leu Val Glu Ser Gly Gly Gly Leu Val Gln Ala Gly Gly
1               5                   10                  15

Ser Leu Arg Leu Ser Cys Ala Ala Ser Arg Asn Ile Leu Ser Leu Asn
            20                  25                  30

Thr Met Gly Trp Tyr Arg His Ala Pro Gly Lys Pro Arg Glu Leu Val
            35                  40                  45

Ala Arg Ile Ser Ser Asn Ser Lys Thr Asp Tyr Ala Asp Ser Val Lys
    50                  55                  60

Gly Arg Phe Thr Ile Ser Arg Asp Asn Ala Lys Asn Thr Val Leu Leu
65                  70                  75                  80

Gln Met Asn Ser Leu Lys Pro Glu Asp Thr Gly Val Tyr Tyr Cys Asn
                85                  90                  95

Leu Asn Val Trp Arg Thr Ser Ser Asp Tyr Trp Gly Gln Gly Thr Gln
            100                 105                 110

Val Thr Val Ser Ser
        115

<210> SEQ ID NO 182
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 182

Glu Val Gln Leu Val Glu Ser Gly Gly Gly Leu Val Gln Ala Gly Gly
1               5                   10                  15

Ser Leu Arg Leu Ser Cys Ala Ala Ser Gly Phe Thr Leu Asp Asp Tyr
            20                  25                  30

Ala Ile Ala Trp Phe Arg Gln Ala Pro Gly Lys Glu Arg Glu Gly Val
            35                  40                  45

Ser Arg Ile Lys Ile Ser Asn Gly Arg Thr Thr Tyr Ala Gly Ser Val
    50                  55                  60

Lys Gly Arg Phe Thr Ile Ser Ser Asp Asn Ala Lys Asn Thr Val Tyr
```

-continued

```
              65                  70                  75                  80
Leu Gln Met Asn Ser Leu Asn Ala Glu Asp Thr Ala Val Tyr Tyr Cys
                    85                  90                  95

Ala Ala Asp Arg Ser Leu Leu Phe Gly Ser Asn Trp Asp Arg Lys
                100                 105                 110

Ala Arg Tyr Asp Tyr Trp Gly Gln Gly Thr Gln Val Thr Val Ser Ser
            115                 120                 125
```

<210> SEQ ID NO 183
<211> LENGTH: 125
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 183

```
Glu Val Gln Leu Val Glu Ser Gly Gly Gly Leu Val Gln Ala Gly Ala
1               5                   10                  15

Ser Leu Arg Leu Ser Cys Ala Ala Ser Gly Arg Arg Phe Ile Ser Asn
                20                  25                  30

Tyr Ala Met Gly Trp Phe Arg Gln Ala Pro Gly Gln Glu Arg Ala Phe
            35                  40                  45

Val Ala Ala Ile Ser Arg Ser Gly Ser Ile Thr Tyr Tyr Thr Asp Ser
        50                  55                  60

Val Lys Gly Arg Phe Ser Ile Ser Arg Asp Tyr Ala Lys Ser Thr Val
65                  70                  75                  80

Tyr Leu Gln Met Asp Asn Leu Lys Pro Glu Thr Ala Val Tyr Tyr
                85                  90                  95

Cys Ala Ala Asp Gly Gly Ala Val Arg Asp Leu Thr Thr Asn Leu Pro
                100                 105                 110

Asp Tyr Trp Gly Arg Gly Thr Gln Val Thr Val Ser Ser
            115                 120                 125
```

<210> SEQ ID NO 184
<211> LENGTH: 128
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 184

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Ser Phe Ser Thr Tyr
                20                  25                  30

Ile Met Gly Trp Phe Arg Gln Ala Pro Gly Lys Glu Arg Glu Phe Val
            35                  40                  45

Ala Thr Ile Ser Arg Ser Gly Ile Thr Thr Arg Ser Ala Asp Ser Val
        50                  55                  60

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Ala Gly Pro Tyr Val Glu Gln Thr Leu Gly Leu Tyr Gln Thr Leu
                100                 105                 110

Gly Pro Trp Asp Tyr Trp Gly Gln Gly Thr Leu Val Thr Val Ser Ser
```

-continued

<210> SEQ ID NO 185
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 185

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Ile
            20                  25                  30

Tyr Ala Lys Gly Trp Phe Arg Gln Ala Pro Gly Lys Glu Arg Glu Phe
        35                  40                  45

Val Ala Ala Ile Ser Arg Ser Gly Arg Ser Thr Ser Tyr Ala Asp Ser
    50                  55                  60

Val Lys Gly Arg Phe Thr Ile Ser Arg Asp Asn Ala Lys Asn Thr Val
65                  70                  75                  80

Tyr Leu Gln Met Asn Ser Leu Arg Pro Glu Asp Thr Ala Val Tyr Tyr
                85                  90                  95

Cys Ala Ala Val Gly Gly Ala Thr Thr Val Thr Ala Ser Glu Trp Asp
            100                 105                 110

Tyr Trp Gly Leu Gly Thr Leu Val Thr Val Ser Ser
        115                 120

<210> SEQ ID NO 186
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 186

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Ile
            20                  25                  30

Tyr Ala Lys Gly Trp Phe Arg Gln Ala Pro Gly Lys Glu Arg Glu Phe
        35                  40                  45

Val Ala Ala Ile Ser Arg Ser Gly Arg Ser Thr Ser Tyr Ala Asp Ser
    50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Pro Glu Asp Thr Ala Val Tyr Tyr
                85                  90                  95

Cys Ala Ala Val Gly Gly Ala Thr Thr Val Thr Ala Ser Glu Trp Asp
            100                 105                 110

Tyr Trp Gly Leu Gly Thr Leu Val Thr Val Ser Ser
        115                 120

<210> SEQ ID NO 187
<211> LENGTH: 124
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 187

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Ile
            20                  25                  30

Tyr Ala Lys Gly Trp Phe Arg Gln Ala Pro Gly Lys Glu Arg Glu Phe
        35                  40                  45

Val Ala Ala Ile Ser Arg Ser Gly Arg Ser Thr Ser Tyr Ala Asp Ser
50                  55                  60

Val Lys Gly Arg Phe Thr Ile Ser Arg Asp Asn Ala Lys Asn Thr Val
65                  70                  75                  80

Tyr Leu Gln Met Asn Ser Leu Arg Pro Glu Asp Thr Ala Val Tyr Tyr
                85                  90                  95

Cys Ala Ala Val Gly Gly Ala Thr Thr Val Thr Ala Ser Glu Trp Asp
            100                 105                 110

Tyr Trp Gly Gln Gly Thr Leu Val Thr Val Ser Ser
        115                 120

<210> SEQ ID NO 188
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 188

Glu Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Ile
            20                  25                  30

Tyr Ala Lys Gly Trp Phe Arg Gln Ala Pro Gly Lys Glu Arg Glu Phe
        35                  40                  45

Val Ala Ala Ile Ser Arg Ser Gly Arg Ser Thr Ser Tyr Ala Asp Ser
50                  55                  60

Val Lys Gly Arg Phe Thr Ile Ser Arg Asp Asn Ser Lys Asn Thr Val
65                  70                  75                  80

Tyr Leu Gln Met Asn Ser Leu Arg Pro Glu Asp Thr Ala Val Tyr Tyr
                85                  90                  95

Cys Ala Ala Val Gly Gly Ala Thr Thr Val Thr Ala Ser Glu Trp Asp
            100                 105                 110

Tyr Trp Gly Gln Gly Thr Leu Val Thr Val Ser Ser
        115                 120

<210> SEQ ID NO 189
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Asp Val Gln Leu Val Glu Ser Gly Gly Gly Leu Val Gln Pro Gly Gly
1               5                   10                  15

Ser Leu Arg Leu Ser Cys Ala Ala Ser Gly Arg Thr Phe Ser Ser Ile
            20                  25                  30

```
Tyr Ala Lys Gly Trp Phe Arg Gln Ala Pro Gly Lys Glu Arg Glu Phe
            35                  40                  45

Val Ala Ala Ile Ser Arg Ser Gly Arg Ser Thr Ser Tyr Ala Asp Ser
 50                  55                  60

Val Lys Gly Arg Phe Thr Ile Ser Arg Asp Asn Ala Lys Asn Thr Val
 65                  70                  75                  80

Tyr Leu Gln Met Asn Ser Leu Arg Pro Glu Asp Thr Ala Val Tyr Tyr
                85                  90                  95

Cys Ala Ala Val Gly Gly Ala Thr Thr Val Thr Ala Ser Glu Trp Asp
                100                 105                 110

Tyr Trp Gly Leu Gly Thr Leu Val Thr Val Ser Ser
            115                 120

<210> SEQ ID NO 190
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 190

Asp Val Gln Leu Val Glu Ser Gly Gly Gly Leu Val Gln Pro Gly Gly
 1               5                  10                  15

Ser Leu Arg Leu Ser Cys Ala Ala Ser Gly Arg Thr Phe Ser Ser Ile
                20                  25                  30

Tyr Ala Lys Gly Trp Phe Arg Gln Ala Pro Gly Lys Glu Arg Glu Phe
            35                  40                  45

Val Ala Ala Ile Ser Arg Ser Gly Arg Ser Thr Ser Tyr Ala Asp Ser
 50                  55                  60

Val Lys Gly Arg Phe Thr Ile Ser Arg Asp Asn Ser Lys Asn Thr Val
 65                  70                  75                  80

Tyr Leu Gln Met Asn Ser Leu Arg Pro Glu Asp Thr Ala Val Tyr Tyr
                85                  90                  95

Cys Ala Ala Val Gly Gly Ala Thr Thr Val Thr Ala Ser Glu Trp Asp
                100                 105                 110

Tyr Trp Gly Gln Gly Thr Leu Val Thr Val Ser Ser
            115                 120

<210> SEQ ID NO 191
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 191

Asp Val Gln Leu Val Glu Ser Gly Gly Gly Leu Val Gln Ala Gly Gly
 1               5                  10                  15

Ser Leu Arg Leu Ser Cys Ala Ala Ser Arg Ser Ile Gly Arg Leu Asp
                20                  25                  30

Arg Met Gly Trp Tyr Arg His Arg Thr Gly Glu Pro Arg Glu Leu Val
            35                  40                  45

Ala Thr Ile Thr Gly Gly Ser Ser Ile Asn Tyr Gly Asp Phe Val Lys
 50                  55                  60

Gly Arg Phe Thr Ile Ser Ile Asp Asn Ala Lys Asn Thr Val Tyr Leu
 65                  70                  75                  80
```

```
Gln Met Asn Asn Leu Lys Pro Glu Asp Thr Ala Val Tyr Tyr Cys Asn
                85                  90                  95

Phe Asn Lys Tyr Val Thr Ser Arg Asp Thr Trp Gly Gln Gly Thr Gln
            100                 105                 110

Val Thr Val Ser Ser
        115

<210> SEQ ID NO 192
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 192

Asp Val Gln Leu Val Glu Ser Gly Gly Gly Leu Val Gln Pro Gly Gly
1               5                   10                  15

Ser Leu Arg Leu Ser Cys Ala Ala Ser Arg Ser Ile Gly Arg Leu Asp
            20                  25                  30

Arg Met Gly Trp Tyr Arg His Arg Thr Gly Glu Pro Arg Glu Leu Val
        35                  40                  45

Ala Thr Ile Thr Gly Gly Ser Ser Ile Asn Tyr Gly Asp Phe Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Asn
                85                  90                  95

Phe Asn Lys Tyr Val Thr Ser Arg Asp Thr Trp Gly Gln Gly Thr Leu
            100                 105                 110

Val Thr Val Ser Ser
        115

<210> SEQ ID NO 193
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Asp Val Gln Leu Val Glu Ser Gly Gly Gly Leu Val Gln Pro Gly Gly
1               5                   10                  15

Ser Leu Arg Leu Ser Cys Ala Ala Ser Arg Ser Ile Gly Arg Leu Asp
            20                  25                  30

Arg Met Gly Trp Tyr Arg His Ala Thr Gly Glu Pro Arg Glu Leu Val
        35                  40                  45

Ala Thr Ile Thr Gly Gly Ser Ser Ile Asn Tyr Gly Asp Phe Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Asn
                85                  90                  95

Phe Asn Lys Tyr Val Thr Ser Arg Asp Thr Trp Gly Gln Gly Thr Leu
            100                 105                 110

Val Thr Val Ser Ser
        115
```

<210> SEQ ID NO 194
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 194

Asp Val Gln Leu Val Glu Ser Gly Gly Gly Leu Val Gln Pro Gly Gly
1               5                   10                  15

Ser Leu Arg Leu Ser Cys Ala Ala Ser Arg Ser Ile Gly Arg Leu Asp
            20                  25                  30

Arg Met Gly Trp Tyr Arg His Arg Pro Gly Glu Pro Arg Glu Leu Val
        35                  40                  45

Ala Thr Ile Thr Gly Gly Ser Ser Ile Asn Tyr Gly Asp Phe Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Asn
                85                  90                  95

Phe Asn Lys Tyr Val Thr Ser Arg Asp Thr Trp Gly Gln Gly Thr Leu
            100                 105                 110

Val Thr Val Ser Ser
        115

<210> SEQ ID NO 195
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 195

Asp Val Gln Leu Val Glu Ser Gly Gly Gly Leu Val Gln Pro Gly Gly
1               5                   10                  15

Ser Leu Arg Leu Ser Cys Ala Ala Ser Arg Ser Ile Gly Arg Leu Asp
            20                  25                  30

Arg Met Gly Trp Tyr Arg His Arg Thr Gly Lys Pro Arg Glu Leu Val
        35                  40                  45

Ala Thr Ile Thr Gly Gly Ser Ser Ile Asn Tyr Gly Asp Phe Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Asn
                85                  90                  95

Phe Asn Lys Tyr Val Thr Ser Arg Asp Thr Trp Gly Gln Gly Thr Leu
            100                 105                 110

Val Thr Val Ser Ser
        115

<210> SEQ ID NO 196
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 196

Asp Val Gln Leu Val Glu Ser Gly Gly Gly Leu Val Gln Pro Gly Gly
1               5                   10                  15

Ser Leu Arg Leu Ser Cys Ala Ala Ser Arg Ser Ile Gly Arg Leu Asp
            20                  25                  30

Arg Met Gly Trp Tyr Arg His Ala Pro Gly Glu Pro Arg Glu Leu Val
        35                  40                  45

Ala Thr Ile Thr Gly Gly Ser Ser Ile Asn Tyr Gly Asp Phe Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Asn
                85                  90                  95

Phe Asn Lys Tyr Val Thr Ser Arg Asp Thr Trp Gly Gln Gly Thr Leu
            100                 105                 110

Val Thr Val Ser Ser
        115

<210> SEQ ID NO 197
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 197

Asp Val Gln Leu Val Glu Ser Gly Gly Gly Leu Val Gln Pro Gly Gly
1               5                   10                  15

Ser Leu Arg Leu Ser Cys Ala Ala Ser Arg Ser Ile Gly Arg Leu Asp
            20                  25                  30

Arg Met Gly Trp Tyr Arg His Ala Thr Gly Lys Pro Arg Glu Leu Val
        35                  40                  45

Ala Thr Ile Thr Gly Gly Ser Ser Ile Asn Tyr Gly Asp Phe Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Asn
                85                  90                  95

Phe Asn Lys Tyr Val Thr Ser Arg Asp Thr Trp Gly Gln Gly Thr Leu
            100                 105                 110

Val Thr Val Ser Ser
        115

<210> SEQ ID NO 198
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 198

Asp Val Gln Leu Val Glu Ser Gly Gly Gly Leu Val Gln Pro Gly Gly
1               5                   10                  15

Ser Leu Arg Leu Ser Cys Ala Ala Ser Arg Ser Ile Gly Arg Leu Asp
            20                  25                  30

```
Arg Met Gly Trp Tyr Arg His Arg Pro Gly Lys Pro Arg Glu Leu Val
            35                  40                  45

Ala Thr Ile Thr Gly Gly Ser Ser Ile Asn Tyr Gly Asp Phe Val Lys
 50                      55                  60

Gly Arg Phe Thr Ile Ser Arg Asp Asn Ser Lys Asn Thr Val Tyr Leu
 65                  70                  75                  80

Gln Met Asn Ser Leu Arg Pro Glu Asp Thr Ala Val Tyr Tyr Cys Asn
                 85                  90                  95

Phe Asn Lys Tyr Val Thr Ser Arg Asp Thr Trp Gly Gln Gly Thr Leu
                100                 105                 110

Val Thr Val Ser Ser
            115

<210> SEQ ID NO 199
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 199

Asp Val Gln Leu Val Glu Ser Gly Gly Gly Leu Val Gln Pro Gly Gly
 1               5                  10                  15

Ser Leu Arg Leu Ser Cys Ala Ala Ser Arg Ser Ile Gly Arg Leu Asp
             20                  25                  30

Arg Met Gly Trp Tyr Arg His Ala Pro Gly Lys Pro Arg Glu Leu Val
            35                  40                  45

Ala Thr Ile Thr Gly Gly Ser Ser Ile Asn Tyr Gly Asp Phe Val Lys
 50                      55                  60

Gly Arg Phe Thr Ile Ser Arg Asp Asn Ser Lys Asn Thr Val Tyr Leu
 65                  70                  75                  80

Gln Met Asn Ser Leu Arg Pro Glu Asp Thr Ala Val Tyr Tyr Cys Asn
                 85                  90                  95

Phe Asn Lys Tyr Val Thr Ser Arg Asp Thr Trp Gly Gln Gly Thr Leu
                100                 105                 110

Val Thr Val Ser Ser
            115

<210> SEQ ID NO 200
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 200

Asp Val Gln Leu Val Glu Ser Gly Gly Gly Leu Val Gln Pro Gly Gly
 1               5                  10                  15

Ser Leu Arg Leu Ser Cys Ala Ala Ser Arg Ser Ile Gly Arg Leu Asp
             20                  25                  30

Arg Met Gly Trp Tyr Arg His Arg Thr Gly Glu Pro Arg Glu Leu Val
            35                  40                  45

Ala Thr Ile Thr Gly Gly Ser Ser Ile Asn Tyr Ala Asp Phe Val Lys
 50                      55                  60

Gly Arg Phe Thr Ile Ser Arg Asp Asn Ser Lys Asn Thr Val Tyr Leu
 65                  70                  75                  80
```

```
Gln Met Asn Ser Leu Arg Pro Glu Asp Thr Ala Val Tyr Tyr Cys Asn
                85                  90                  95

Phe Asn Lys Tyr Val Thr Ser Arg Asp Thr Trp Gly Gln Gly Thr Leu
            100                 105                 110

Val Thr Val Ser Ser
        115

<210> SEQ ID NO 201
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 201

Asp Val Gln Leu Val Glu Ser Gly Gly Gly Leu Val Gln Pro Gly Gly
1               5                   10                  15

Ser Leu Arg Leu Ser Cys Ala Ala Ser Arg Ser Ile Gly Arg Leu Asp
            20                  25                  30

Arg Met Gly Trp Tyr Arg His Arg Thr Gly Glu Pro Arg Glu Leu Val
        35                  40                  45

Ala Thr Ile Thr Gly Gly Ser Ser Ile Asn Tyr Gly Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Asn
                85                  90                  95

Phe Asn Lys Tyr Val Thr Ser Arg Asp Thr Trp Gly Gln Gly Thr Leu
            100                 105                 110

Val Thr Val Ser Ser
        115

<210> SEQ ID NO 202
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 202

Asp Val Gln Leu Val Glu Ser Gly Gly Gly Leu Val Gln Pro Gly Gly
1               5                   10                  15

Ser Leu Arg Leu Ser Cys Ala Ala Ser Arg Ser Ile Gly Arg Leu Asp
            20                  25                  30

Arg Met Gly Trp Tyr Arg His Arg Thr Gly Glu Pro Arg Glu Leu Val
        35                  40                  45

Ala Thr Ile Thr Gly Gly Ser Ser Ile Asn Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Asn
                85                  90                  95

Phe Asn Lys Tyr Val Thr Ser Arg Asp Thr Trp Gly Gln Gly Thr Leu
            100                 105                 110

Val Thr Val Ser Ser
        115
```

<210> SEQ ID NO 203
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 203

Asp Val Gln Leu Val Glu Ser Gly Gly Gly Leu Val Gln Pro Gly Gly
1               5                   10                  15

Ser Leu Arg Leu Ser Cys Ala Ala Ser Arg Ser Ile Gly Arg Leu Asp
            20                  25                  30

Arg Met Gly Trp Tyr Arg His Arg Thr Gly Glu Pro Arg Glu Leu Val
        35                  40                  45

Ala Thr Ile Thr Gly Gly Ser Ser Ile Asn Tyr Gly Asp Phe Val Lys
    50                  55                  60

Gly Arg Phe Thr Ile Ser Ile Asp Asn Ser Lys Asn Thr Val Tyr Leu
65                  70                  75                  80

Gln Met Asn Ser Leu Arg Pro Glu Asp Thr Ala Val Tyr Tyr Cys Asn
                85                  90                  95

Phe Asn Lys Tyr Val Thr Ser Arg Asp Thr Trp Gly Gln Gly Thr Leu
            100                 105                 110

Val Thr Val Ser Ser
        115

<210> SEQ ID NO 204
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 204

Asp Val Gln Leu Val Glu Ser Gly Gly Gly Leu Val Gln Pro Gly Gly
1               5                   10                  15

Ser Leu Arg Leu Ser Cys Ala Ala Ser Arg Ser Ile Gly Arg Leu Asp
            20                  25                  30

Arg Met Gly Trp Tyr Arg His Arg Thr Gly Glu Pro Arg Glu Leu Val
        35                  40                  45

Ala Thr Ile Thr Gly Gly Ser Ser Ile Asn Tyr Gly Asp Phe Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Arg Pro Glu Asp Thr Ala Val Tyr Tyr Cys Asn
                85                  90                  95

Phe Asn Lys Tyr Val Thr Ser Arg Asp Thr Trp Gly Gln Gly Thr Leu
            100                 105                 110

Val Thr Val Ser Ser
        115

<210> SEQ ID NO 205
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 205

Asp Val Gln Leu Val Glu Ser Gly Gly Gly Leu Val Gln Pro Gly Gly
1               5                   10                  15

Ser Leu Arg Leu Ser Cys Ala Ala Ser Arg Ser Ile Gly Arg Leu Asp
            20                  25                  30

Arg Met Gly Trp Tyr Arg His Arg Thr Gly Glu Pro Arg Glu Leu Val
        35                  40                  45

Ala Thr Ile Thr Gly Gly Ser Ser Ile Asn Tyr Gly Asp Phe Val Lys
    50                  55                  60

Gly Arg Phe Thr Ile Ser Arg Asp Asn Ser Lys Asn Thr Val Tyr Leu
65                  70                  75                  80

Gln Met Asn Asn Leu Arg Pro Glu Asp Thr Ala Val Tyr Tyr Cys Asn
                85                  90                  95

Phe Asn Lys Tyr Val Thr Ser Arg Asp Thr Trp Gly Gln Gly Thr Leu
            100                 105                 110

Val Thr Val Ser Ser
        115

<210> SEQ ID NO 206
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 206

Asp Val Gln Leu Val Glu Ser Gly Gly Gly Leu Val Gln Pro Gly Gly
1               5                   10                  15

Ser Leu Arg Leu Ser Cys Ala Ala Ser Arg Ser Ile Gly Arg Leu Asp
            20                  25                  30

Arg Met Gly Trp Tyr Arg His Arg Pro Gly Lys Pro Arg Glu Leu Val
        35                  40                  45

Ala Thr Ile Thr Gly Gly Ser Ser Ile Asn Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Pro Glu Asp Thr Ala Val Tyr Tyr Cys Asn
                85                  90                  95

Phe Asn Lys Tyr Val Thr Ser Arg Asp Thr Trp Gly Gln Gly Thr Leu
            100                 105                 110

Val Thr Val Ser Ser
        115

<210> SEQ ID NO 207
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 207

Asp Val Gln Leu Val Glu Ser Gly Gly Gly Leu Val Gln Pro Gly Gly
1               5                   10                  15

Ser Leu Arg Leu Ser Cys Ala Ala Ser Arg Ser Ile Gly Arg Leu Asp
            20                  25                  30

Arg Met Gly Trp Tyr Arg His Arg Pro Gly Lys Pro Arg Glu Leu Val

```
                35                  40                  45

Ala Thr Ile Thr Gly Gly Ser Ser Ile Asn Tyr Ala Asp Ser Val Lys
    50                  55                  60

Gly Arg Phe Thr Ile Ser Ile Asp Asn Ser Lys Asn Thr Val Tyr Leu
65                  70                  75                  80

Gln Met Asn Ser Leu Arg Pro Glu Asp Thr Ala Val Tyr Tyr Cys Asn
                85                  90                  95

Phe Asn Lys Tyr Val Thr Ser Arg Asp Thr Trp Gly Gln Gly Thr Leu
                100                 105                 110

Val Thr Val Ser Ser
        115

<210> SEQ ID NO 208
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 208

Asp Val Gln Leu Val Glu Ser Gly Gly Gly Leu Val Gln Pro Gly Gly
1               5                   10                  15

Ser Leu Arg Leu Ser Cys Ala Ala Ser Arg Ser Ile Gly Arg Leu Asp
                20                  25                  30

Arg Met Gly Trp Tyr Arg His Arg Pro Gly Lys Pro Arg Glu Leu Val
            35                  40                  45

Ala Thr Ile Thr Gly Gly Ser Ser Ile Asn Tyr Ala Asp Ser Val Lys
    50                  55                  60

Gly Arg Phe Thr Ile Ser Arg Asp Asn Ser Lys Asn Thr Val Tyr Leu
65                  70                  75                  80

Gln Met Asn Asn Leu Arg Pro Glu Asp Thr Ala Val Tyr Tyr Cys Asn
                85                  90                  95

Phe Asn Lys Tyr Val Thr Ser Arg Asp Thr Trp Gly Gln Gly Thr Leu
                100                 105                 110

Val Thr Val Ser Ser
        115

<210> SEQ ID NO 209
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 209

Asp Val Gln Leu Val Glu Ser Gly Gly Gly Leu Val Gln Pro Gly Gly
1               5                   10                  15

Ser Leu Arg Leu Ser Cys Ala Ala Ser Arg Ser Ile Gly Arg Leu Asp
                20                  25                  30

Arg Met Gly Trp Tyr Arg His Arg Pro Gly Lys Pro Arg Glu Leu Val
            35                  40                  45

Ala Thr Ile Thr Gly Gly Ser Ser Ile Asn Tyr Ala Asp Ser Val Lys
    50                  55                  60

Gly Arg Phe Thr Ile Ser Ile Asp Asn Ser Lys Asn Thr Val Tyr Leu
65                  70                  75                  80

Gln Met Asn Asn Leu Arg Pro Glu Asp Thr Ala Val Tyr Tyr Cys Asn
```

```
                    85                  90                  95
Phe Asn Lys Tyr Val Thr Ser Arg Asp Thr Trp Gly Gln Gly Thr Leu
                100                 105                 110

Val Thr Val Ser Ser
        115

<210> SEQ ID NO 210
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 210

Glu Val Gln Leu Val Glu Ser Gly Gly Gly Leu Val Gln Pro Gly Gly
1               5                   10                  15

Ser Leu Arg Leu Ser Cys Ala Ala Ser Arg Ser Ile Gly Arg Leu Asp
                20                  25                  30

Arg Met Gly Trp Tyr Arg His Arg Pro Gly Glu Pro Arg Glu Leu Val
            35                  40                  45

Ala Thr Ile Thr Gly Gly Ser Ser Ile Asn Tyr Gly Asp Ser Val Lys
        50                  55                  60

Gly Arg Phe Thr Ile Ser Ile Asp Asn Ser Lys Asn Thr Val Tyr Leu
65                  70                  75                  80

Gln Met Asn Ser Leu Arg Pro Glu Asp Thr Ala Val Tyr Tyr Cys Asn
                85                  90                  95

Phe Asn Lys Tyr Val Thr Ser Arg Asp Thr Trp Gly Gln Gly Thr Leu
                100                 105                 110

Val Thr Val Ser Ser
        115

<210> SEQ ID NO 211
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 211

Glu Val Gln Leu Val Glu Ser Gly Gly Gly Leu Val Gln Pro Gly Gly
1               5                   10                  15

Ser Leu Arg Leu Ser Cys Ala Ala Ser Arg Ser Ile Gly Arg Leu Asp
                20                  25                  30

Arg Met Gly Trp Tyr Arg His Arg Pro Gly Lys Pro Arg Glu Leu Val
            35                  40                  45

Ala Thr Ile Thr Gly Gly Ser Ser Ile Asn Tyr Gly Asp Ser Val Lys
        50                  55                  60

Gly Arg Phe Thr Ile Ser Ile Asp Asn Ser Lys Asn Thr Val Tyr Leu
65                  70                  75                  80

Gln Met Asn Ser Leu Arg Pro Glu Asp Thr Ala Val Tyr Tyr Cys Asn
                85                  90                  95

Phe Asn Lys Tyr Val Thr Ser Arg Asp Thr Trp Gly Gln Gly Thr Leu
                100                 105                 110

Val Thr Val Ser Ser
        115
```

```
<210> SEQ ID NO 212
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 212

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Ser Tyr
            20                  25                  30

Ala Met Ser Trp Val Arg Gln Ala Pro Gly Lys Gly Leu Glu Trp Val
        35                  40                  45

Ser Leu Ile Ser Gly Ser Gly Gly Phe Thr Tyr Tyr Ala Asp Ser Val
    50                  55                  60

Lys Gly Arg Phe Thr Ile Ser Arg Asp Asn Ser Arg Thr Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Val Ala Pro Gly Thr Phe Asp Tyr Trp Gly Gln
            100                 105                 110

Gly Ala Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365
```

```
Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 213
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 213

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 214
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 214

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Tyr
                85                  90                  95

Thr Phe Gly Gln Gly Thr Lys Leu Glu Ile Lys
            100                 105

<210> SEQ ID NO 215
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 215

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asn Ser Tyr
            20                  25                  30

Ala Met Ser Trp Val Arg Gln Ala Pro Gly Lys Gly Leu Glu Trp Val
        35                  40                  45

Ser Ile Ile Ser Gly Ser Gly Gly Phe Thr Tyr Tyr Ala Asp Ser Val
    50                  55                  60

Lys Gly Arg Phe Thr Ile Ser Arg Asp Asn Ser Arg Thr Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Leu Val Ala Pro Gly Thr Phe Asp Tyr Trp Gly Gln
            100                 105                 110

Gly Ala Leu Val Thr Val Ser Ser
        115                 120

<210> SEQ ID NO 216
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 216

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

```
Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Phe
                85                  90                  95

Thr Phe Gly Pro Gly Thr Lys Val Asp Ile Lys
            100                 105
```

<210> SEQ ID NO 217
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 217

```
Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Asn Phe
            20                  25                  30

Gly Met His Trp Val Arg Gln Ala Pro Gly Lys Gly Leu Glu Trp Val
        35                  40                  45

Ala Ala Ile Trp Tyr Asp Gly His Asp Lys Tyr Tyr Ser Tyr Tyr Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Arg Asp Ser Ser Ser Trp Tyr Arg Tyr Phe Asp Tyr Trp Gly Gln
            100                 105                 110

Gly Thr Leu Val Thr Val Ser Ser
        115                 120
```

<210> SEQ ID NO 218
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 218

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Phe
                85                  90                  95

Thr Phe Gly Pro Gly Thr Lys Val Asp Ile Lys
            100                 105
```

<210> SEQ ID NO 219
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 219

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Phe
            20                  25                  30

Gly Met His Trp Val Arg Gln Ala Pro Gly Lys Gly Leu Glu Trp Val
        35                  40                  45

Ala Ala Ile Trp Tyr Asp Gly His Asp Lys Tyr Tyr Ala Tyr Tyr Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Arg Asp Ser Ser Ser Trp Tyr Arg Tyr Phe Asp Tyr Trp Gly Gln
            100                 105                 110

Gly Thr Leu Val Thr Val Ser Ser
        115                 120

<210> SEQ ID NO 220
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 220

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Phe
            20                  25                  30

Gly Met His Trp Val Arg Gln Ala Pro Gly Lys Gly Leu Glu Trp Val
        35                  40                  45

Ala Ala Ile Trp Tyr Asp Gly His Asp Lys Tyr Tyr Ser Tyr Tyr Val
    50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Arg Asp Ser Ser Ser Trp Tyr Arg Tyr Phe Asp Tyr Trp Gly Gln
            100                 105                 110

Gly Thr Leu Val Thr Val Ser Ser
        115                 120

<210> SEQ ID NO 221
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 221

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Ala Val Ile Trp Tyr Asp Gly Ser Asn Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Lys Asn Trp Ser Phe Asp Phe Trp Gly Gln Gly Thr Leu Val
            100                 105                 110

Thr Val Ser Ser
        115

<210> SEQ ID NO 222
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 222

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Gly Val Ser Arg Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Val Ser Gly
    50                  55                  60

Ser Gly Pro Gly Thr Asp Phe Thr Leu Thr Ile Ser Ser Leu Glu Pro
65                  70                  75                  80

Glu Asp Phe Ala Val Asp Tyr Cys Gln Gln Arg Ser Asn Trp Gln Tyr
                85                  90                  95

Thr Phe Gly Gln Gly Thr Lys Leu Glu Ile
            100                 105

<210> SEQ ID NO 223
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 223

Gln Lys Gln Leu Val Glu Phe Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Trp Asn Asp Gly Ser Asn Lys Tyr Tyr Val Asp Ser Val

```
                    50                  55                  60
Lys Gly Arg Phe Ile Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Met Gly Ile Tyr Tyr Tyr Gly Met Asp Val Trp Gly
                100                 105                 110

Gln Gly Thr Thr Val Thr Val Ser Ser
            115                 120
```

<210> SEQ ID NO 224
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 224

```
Glu Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Val Ser Ser Tyr
                 20                  25                  30

Leu Ala Trp Tyr Gln Gln Lys Pro Gly Gln Ala Pro Arg Leu Leu Ile
             35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Thr Phe
                 85                  90                  95

Gly Gln Gly Thr Lys Val Glu Ile
                100
```

<210> SEQ ID NO 225
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 225

```
Glu Val Gln Leu Leu Glu Ser Gly Gly Gly Leu Val Gln Pro Gly Gly
  1               5                  10                  15

Ser Leu Arg Leu Ser Cys Ala Ala Ser Gly Phe Thr Phe Asn Ser Tyr
                 20                  25                  30

Ala Met Ser Trp Val Arg Gln Ala Pro Gly Lys Gly Leu Glu Trp Val
             35                  40                  45

Ser Ile Ile Ser Gly Ser Gly Phe Thr Tyr Tyr Ala Asp Ser Val
 50                  55                  60

Lys Gly Arg Phe Thr Ile Ser Arg Asp Asn Ser Arg Thr Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Arg Leu Val Ala Pro Gly Thr Phe Asp Tyr Trp Gly Gln
                100                 105                 110

Gly Ala Leu Val Thr Val Ser Ser
```

<210> SEQ ID NO 226
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 226

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Asn
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Phe
                85                  90                  95

Thr Phe Gly Pro Gly Thr Lys Val Asp Ile Lys
            100                 105

<210> SEQ ID NO 227
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 227

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ile Ile Ser Gly Ser Gly Gly Phe Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Arg Leu Arg Ala Glu Asp Thr Ala Ile Tyr Phe Cys
                85                  90                  95

Ala Lys Asp Asp Ile Pro Ala Ala Gly Thr Phe Asp Pro Trp Gly Gln
            100                 105                 110

Gly Thr Leu Val Thr Val Ser Ser
        115                 120

<210> SEQ ID NO 228
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 228

```
Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Lys Pro Gly Lys Ala Pro Lys Leu Leu Ile
        35                  40                  45

Tyr Asp Val Ser Ser Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Phe Asn Ser Tyr Trp Thr
                85                  90                  95

Phe Gly Gln Gly Thr Lys Val Glu Ile Lys
            100                 105

<210> SEQ ID NO 229
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 229

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Leu Ile Ser Gly Ser Gly Gly Leu Thr Tyr Ala Asp Ser Val
50                  55                  60

Lys Gly Arg Phe Thr Ile Ser Arg Asp Asn Ser Lys Arg Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Leu Val Thr Gly Ala Leu Asp Tyr Trp Gly Gln Gly
            100                 105                 110

Thr Leu Val Thr Val Ser Ser
        115

<210> SEQ ID NO 230
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 230

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ile Ile Ser Gly Ser Gly Gly Phe Thr Tyr Tyr Ala Asp Ser Val
50                  55                  60
```

```
Lys Gly Arg Phe Thr Ile Ser Arg Asp Asn Ser Lys Lys Thr Leu Tyr
 65                  70                  75                  80

Leu Gln Met Ser Arg Leu Arg Ala Glu Asp Thr Ala Ile Tyr Phe Cys
                 85                  90                  95

Ala Lys Asp Asp Ile Pro Ala Ala Gly Thr Phe Asp Pro Trp Gly Gln
            100                 105                 110

Gly Thr Leu Val Thr Val Ser Ser
            115                 120

<210> SEQ ID NO 231
<211> LENGTH: 113
<212> TYPE: PRT
<213> ORGANISM: Mus musculus

<400> SEQUENCE: 231

Asp Ile Leu Met Thr Gln Thr Pro Leu Ser Leu Pro Val Ser Leu Gly
  1               5                  10                  15

Asp Gln Ala Ser Ile Ser Cys Arg Ser Ser Gln Ser Ile Val His Gly
                 20                  25                  30

Asn Gly Asn Thr Tyr Leu Glu Trp His Leu Gln Lys Pro Gly Gln Ser
             35                  40                  45

Pro Lys Leu Leu Ile Tyr Arg Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Asn Arg Val Glu Ala Glu Asp Leu Gly Val Tyr Tyr Cys Phe Gln Gly
                 85                  90                  95

Ser His Val Pro Tyr Thr Phe Gly Gly Gly Thr Lys Val Glu Ile Lys
            100                 105                 110

Arg

<210> SEQ ID NO 232
<211> LENGTH: 113
<212> TYPE: PRT
<213> ORGANISM: Mus musculus

<400> SEQUENCE: 232

Asp Ile Val Met Thr Gln Thr Pro Leu Ser Leu Pro Val Ser Leu Gly
  1               5                  10                  15

Asp Gln Ala Ser Met Tyr Cys Arg Ser Ser Gln Ser Pro Val His Ser
                 20                  25                  30

Asn Gly Asn Thr Tyr Leu His Trp Tyr Leu Gln Lys Pro Gly Gln Ser
             35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                 85                  90                  95

Thr His Ile Pro Trp Thr Phe Gly Gly Gly Thr Lys Val Glu Ile Lys
            100                 105                 110

Arg

<210> SEQ ID NO 233
<211> LENGTH: 123
<212> TYPE: PRT
```

```
<213> ORGANISM: Mus musculus

<400> SEQUENCE: 233

Gln Val Gln Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Tyr
            20                  25                  30

Trp Leu Asn Trp Val Lys Gln Arg Pro Gly Gln Gly Leu Glu Trp Ile
        35                  40                  45

Val Met Ile Asp Pro Ser Asp Ser Glu Thr His Tyr Asn Gln Val Phe
    50                  55                  60

Lys Asp Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ile Arg Gly Arg Gly Asn Phe Tyr Gly Gly Ser His Ala Met Glu Tyr
                100                 105                 110

Trp Gly Gln Gly Thr Leu Leu Thr Val Ser Ser
            115                 120

<210> SEQ ID NO 234
<211> LENGTH: 118
<212> TYPE: PRT
<213> ORGANISM: Mus musculus

<400> SEQUENCE: 234

Gln Val Gln Leu Gln Gln Pro Gly Ala Glu Leu Val Lys Pro Gly Thr
1               5                   10                  15

Ser Val Lys Leu Ser Cys Lys Ala Ser Gly Tyr Ser Phe Thr Ser Tyr
            20                  25                  30

Trp Met His Gly Val Arg Gln Arg Pro Gly Gln Gly Leu Glu Trp Ile
        35                  40                  45

Gly Glu Ile Asp Pro Ser Asn Gly Arg Thr Asn Tyr Asn Glu Lys Phe
    50                  55                  60

Lys Ser Lys Ala Thr Leu Thr Val Asp Lys Ser Ser Ser Thr Ala Tyr
65                  70                  75                  80

Ile Gln Leu Ser Ser Leu Thr Ser Glu Asp Ser Ala Val Tyr Tyr Cys
                85                  90                  95

Thr Arg Glu Arg Ser Pro Arg Tyr Phe Asp Val Trp Gly Ala Gly Thr
                100                 105                 110

Thr Leu Thr Val Ser Ser
            115
```

SYNERGISTIC COMBINATIONS OF OX40L ANTIBODIES FOR THE TREATMENT OF GVHD

CROSS REFERENCE TO RELATED APPLICATIONS

This application is a continuation application under 35 U.S.C. § 120 of co-pending U.S. application Ser. No. 15/604,495, filed on May 24, 2017, which is a continuation application of co-pending U.S. application Ser. No. 15/333, 517, filed on Oct. 25, 2016, which is a continuation application of U.S. application Ser. No. 15/142,538 filed on Apr. 29, 2016, the contents of all of which are incorporated herein by reference in their entireties.

U.S. application Ser. No. 15/142,538 filed on Apr. 29, 2016, is a continuation application under 35 U.S.C. § 120 of co-pending International Application No. PCT/GB2016/050565 filed Mar. 3, 2016, which designated the U.S., and which claims priority of PCT/GB2015/050614 filed on Mar. 3, 2015, which claims priority to GB Patent Application No. GB1516008.8 filed on Sep. 9, 2015 the contents of each of which are incorporated herein by reference in their entireties.

U.S. application Ser. No. 15/142,538 filed on Apr. 29, 2016, is a Continuation-in-Part of co-pending application under 35 U.S.C. § 120 of co-pending International Application No. PCT/GB2015/050614 filed on Mar. 3, 2015, which claims priority to GB Patent Application No. GB1516008.8 filed on Sep. 9, 2015 the contents of each of which are incorporated herein by reference in their entireties.

U.S. application Ser. No. 15/142,538 filed on Apr. 29, 2016, is a Continuation-in-Part application of U.S. application Ser. No. 14/935,937 filed on Nov. 9, 2015, now U.S. Pat. No. 9,434,785 issued Sep. 6, 2016, which is a Continuation-in-Part application of U.S. application Ser. No. 14/811,163 filed on Jul. 28, 2015, now U.S. Pat. No. 9,234,043 issued Jan. 12, 2016, which is a continuation of U.S. application Ser. No. 14/700,896, filed on Apr. 30, 2015, now U.S. Pat. No. 9,139,653, issued on Sep. 22, 2015. This application also claims priority to GB Patent Application No. GB1516008.8 filed on Sep. 9, 2015 the contents of each of which are incorporated herein by reference in their entireties.

U.S. application Ser. No. 15/142,538 filed on Apr. 29, 2016, is a Continuation-in-Part application under 35 U.S.C. § 120 of U.S. application Ser. No. 14/955,843 filed on Dec. 1, 2015, now abandoned, which is a Continuation application of U.S. application Ser. No. 14/811,163 filed on Jul. 28, 2015, now U.S. Pat. No. 9,234,043 issued Jan. 12, 2016, which is a continuation of U.S. application Ser. No. 14/700, 896, filed on Apr. 30, 2015, now U.S. Pat. No. 9,139,653, issued on Sep. 22, 2015. This application also claims priority to GB Patent Application No. GB1516008.8 filed on Sep. 9, 2015 the contents of each of which are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Oct. 25, 2016, is named Sequence_listing-069496-087031.txt and is 184,690 bytes in size.

TECHNICAL FIELD

The present invention relates to anti-human OX40L antibodies, new medical uses and methods.

BACKGROUND

OX40 ligand (OX40L) is a TNF family member; a 34 kDa type II transmembrane protein. The crystallized complex of human OX40 and OX40L is a trimeric configuration of one OX40L (trimer) and three OX40 monomers. The human extracellular domain is 42% homologous to mouse OX40L.

OX40L is not constitutively expressed but can be induced on professional APCs such as B-cells, dendritic cells (DCs) and macrophages. Other cell types such as Langerhans cells, endothelial cells, smooth muscle cells, mast cells and natural killer (NK) cells can be induced to express OX40L. T-cells can also express OX40L. The OX40L receptor, OX40, is expressed on activated T-cells (CD4 and CD8 T-cells, Th2, Th1 and Th17 cells) and $CD4^+Foxp3^+$ cells, even in the absence of activation.

The interaction between OX40 and OX40L occurs during the T-cell-DC interaction 2 or 3 days after antigen recognition. After leaving DCs, the OX40-expressing T-cell may interact with an OX40L-expressing cell other than a DC and receive an OX40 signal from this cell, which may provide essential signals for the generation of memory T-cells, the enhancement of Th2 response and the prolongation of the inflammatory responses. OX40 signals into responder T-cells render them resistant to Treg mediated suppression.

Graft versus host disease is a major cause of mortality following allogeneic bone marrow treatment. In the acute version of the disease, mature T-cells present in the bone marrow graft recognise the donor tissue as foreign in an environment of damaged tissue, which, via host APC's cause the activation and proliferation of the donor T-cells, with subsequent T-cell migration into the liver, spleen, gut, skin and lungs, causing tissue damage by the CTL effector response and inflammatory cytokine/chemokine release. Onset for acute disease is usually within the first 100 days post transplantation (Hill-Ferrara, Blood May 1, 2000 vol. 95 no. 9 2754-275, Reddy-Ferrara Blood, Volume 17, Issue 4, December 2003).

Chronic GvHD usually appears 100 days post transplantation and several factors are thought to be involved, including thymic damage caused by prior acute GvHD which results in a reduced clearance of pathogenic T-cells (Zhang et al, Sep. 1, 2007 vol. 179 no. 5 3305-3314), up-regulation of TGF-β, which causes fibrosis (McCormick et al J Immuno, Nov. 15, 1999 vol. 163 no. 10 5693-5699), and a B-cell component driven by elevated B-Cell activating factor (BAFF) (Sarantopoulos et al, Clin Cancer Res Oct. 15, 2007 13; 6107) as well as auto-antibodies against platelet derived growth factor receptor (Svegliati et al, Blood Jul. 1, 2007 vol. 110 no. 1 237-241).

Clinical studies have shown that OX40 is up-regulated in both acute (Morante et al, Clinical and Experimental Immunology, 145:36-43) and chronic (Kotani et al, Blood Nov. 15, 2001 vol. 98 no. 10 3162-3164) GvHD. Administration of an antagonistic anti-OX40L enhanced survival in a lethal acute mouse model of GvHD, with a 70% survival in the treated group compared to the untreated who all died by day 43 (Tsukada et al, Blood, 1 Apr. 2000, Volume 95, Number 7) whereas treatment with an agonistic anti-OX40 Ab accelerated the disease and mortality (Blazar et al Blood May 1, 2003 vol. 101 no. 9 3741-3748). Blockade of the OX40-OX40L interaction has been shown to be efficacious in several other inflammatory disease, with anti-OX40L Ab being used to treat a mouse model of colitis (Totsuka et al., AJP-GI Apr. 1, 2003 vol. 284 no. 4 G595-G603), and that an anti-OX40L Ab could block the development of diabetes in NOD mice (Pakala et al European Journal of Immunology Volume 34, Issue 11, pages 3039-3046, November 2004).

REFERENCES

Lamb, L. S., Abhyankar, S. A., Hazlett, L., O'Neal, W., Folk, R. S., Vogt, S., Parrish, R. S., Bridges, K., Henslee-Downey, P. J. and Gee, A. P. (1999), Expression of CD134 (OX-40) on T-cells during the first 100 days following allogeneic bone marrow transplantation as a marker for lymphocyte activation and therapy-resistant graft-versus-host disease. Cytometry, 38: 238-243.

Xupeng Ge, Julia Brown, Megan Sykes, Vassiliki A. Boussiotis, CD134-Allodepletion Allows Selective Elimination of Alloreactive Human T-cells without Loss of Virus-Specific and Leukemia-Specific Effectors, Biology of Blood and Marrow Transplantation, Volume 14, Issue 5, May 2008, Pages 518-530.

Naoto Ishii, Takeshi Takahashi, Pejman Soroosh, Kazuo Sugamura, Chapter 3-OX40-OX40 Ligand Interaction in T-Cell-Mediated Immunity and Immunopathology, In: Frederick W. Alt, Editor(s), Advances in Immunology, Academic Press, 2010, Volume 105, Pages 63-98.

Croft, M., So, T., Duan, W. and Soroosh, P. (2009), The significance of OX40 and OX40L to T-cell biology and immune disease. Immunological Reviews, 229: 173-191.

SUMMARY OF THE INVENTION

The invention provides anti-human OX40L (hOX40L) antibodies and fragments and novel medical applications for treating or preventing hOX40L-mediated diseases or conditions in humans. To this end, the invention provides:—

In a First Configuration

An antibody or a fragment thereof that specifically binds to hOX40L for treating or preventing a hOX40L-mediated disease or condition in a human in a method wherein the antibody or fragment is administered to said human, wherein the antibody or fragment is for treating or preventing said hOX40L-mediated disease or condition by decreasing one, more or all of
  a. secretion of a cytokine selected from TNF alpha, IL-2, IL-3, IL-4, IL-5, IL-6, IL-8, IL-9, IL-10, IL-13, IL-17, RANTES and interferon gamma in the human;
  b. the proliferation of leukocytes of the human; and
  c. binding of hOX40 receptor expressed by human T-cells with endothelial cell expressed hOX40L.

In a Second Configuration

An antibody or a fragment thereof, that specifically binds to hOX40L and competes for binding to said hOX40L with an antibody selected from the group consisting of 02D10, 10A07, 09H04 and 19H01.

In a Third Configuration

Use of an antibody or a fragment thereof, that specifically binds to hOX40L in the manufacture of a medicament for administration to a human, for treating or preventing a hOX40L-mediated disease or condition in the human by decreasing one, more or all of
  a. secretion of a cytokine selected from TNF alpha, IL-2, IL-3, IL-4, IL-5, IL-6, IL-8, IL-9, IL-10, IL-13, IL-17, RANTES and interferon gamma in the human;
  b. the proliferation of leukocytes of the human; and
  c. binding of hOX40 receptor expressed by human T-cells with endothelial cell expressed hOX40L.

In a Fourth Configuration

A method of treating or preventing a hOX40L-mediated disease or condition in a human by decreasing one, more or all of
  a. secretion of a cytokine selected from TNF alpha, IL-2, IL-3, IL-4, IL-5, IL-6, IL-8, IL-9, IL-10, IL-13, IL-17, RANTES and interferon gamma in the human;
  b. the proliferation of leukocytes of the human; and
  c. binding of hOX40 receptor expressed by human T-cells with endothelial cell expressed hOX40L;
wherein the method comprises administering to said human a therapeutically effective amount of an antibody or fragment that specifically binds to hOX40L.

In a Fifth Configuration

An antibody or a fragment thereof, that specifically binds to hOX40L and competes for binding to said hOX40L with the antibody 02D10, wherein the antibody or fragment comprises a VH domain which comprises a HCDR3 comprising the motif VRGXYYY, wherein X is any amino acid.

In a Sixth Configuration

An antibody or a fragment thereof, that specifically binds to hOX40L and competes for binding to said hOX40L with the antibody 02D10, wherein the antibody or fragment comprises a VH domain which comprises the HCDR3 sequence of SEQ ID NO:40 or 46 or the HCDR3 sequence of SEQ ID NO:40 or 46 comprising less than 5 amino acid substitutions.

In a Seventh Configuration

A human antibody or fragment thereof comprising a HCDR3 of from 16 to 27 amino acids and derived from the recombination of a human VH gene segment, a human D gene segment and a human JH gene segment, wherein the human JH gene segment is IGHJ6, which specifically binds to hOX40L for treating or preventing an autoimmune disease selected from an autoimmune disease or condition, a systemic inflammatory disease or condition, or transplant rejection.

In an Eighth Configuration

Use of a human antibody or fragment thereof comprising a HCDR3 of from 16 to 27 amino acids and derived from the recombination of a human VH gene segment, a human D gene segment and a human JH gene segment, wherein the human JH gene segment is IGHJ6, which specifically binds to hOX40L in the manufacture of a medicament for administration to a human for treating or preventing a hOX40L mediated disease or condition in the human selected from an autoimmune disease or condition, a systemic inflammatory disease or condition, or transplant rejection.

In a Ninth Configuration

A method of treating or preventing a hOX40L mediated disease or condition selected from an autoimmune disease or condition, a systemic inflammatory disease or condition, or transplant rejection, comprising administering to said human a therapeutically effective amount of a human antibody or fragment thereof comprising a HCDR3 of from 16 to 27 amino acids and derived from the recombination of a human VH gene segment, a human D gene segment and a human JH gene segment, wherein the human JH gene segment is IGHJ6, which specifically binds to hOX40L, wherein the hOX40L mediated disease or condition is thereby treated or prevented.

The invention also provides pharmaceutical compositions, kits, nucleic acids, vectors and hosts.

BRIEF DESCRIPTION OF THE FIGURES

FIG. 2A shows the effect of anti-OX40L antibodies in PBMC/T MLR percentage inhibition relative to no IgG wells for donor pairing 1; FIG. 2B shows the same for donor pairing 2; and FIG. 2C for donor pairing 3. FIG. 2D shows the effect of anti-OX40L antibodies in PBMC/T MLR IFN gamma relative to no IgG wells for donor pairing 1; FIG. 2E shows the same for donor pairing 2 and FIG. 2F shows the same for donor pairing 3.

FIG. 3A shows pre-HCT and FIG. 3B shows post-HCT cell distribution.

FIGS. 4A-4B show OX40L blockade controls expansion of CD4+ Tscm cells while preserving CD4+ T naïve cells following allogeneic HCT. Absolute numbers of peripheral blood CD4+ Tscm (FIG. 4A) and T naïve (FIG. 4B) following allogeneic HCT in control animal and 2D10 IgG4PE treated animals.

FIGS. 5A-5C show OX40 expression on naïve CD4+ T and memory stem T-cells in a representative animal following allogeneic HCT. FIGS. 5A and 5B show FACS plots were gated on CD3+CD4+CD45RA+CCR7+. The histogram of FIG. 5C shows OX40 expression in different T-cell subsets of CD4+ T-cells: Naïve (CD45RA+CCR7+CD95−), memory stem (SCM: CD45RA+CCR7+CD95+), central memory (CM: CD45RA-CCR7+), effector memory (EM: CD45RA-CCR7−) and terminally differentiated effector-memory cells re-expressing CD45RA (TEMRA: CD45RA+CCR7−).

DETAILED DESCRIPTION OF THE INVENTION

Figure 1:
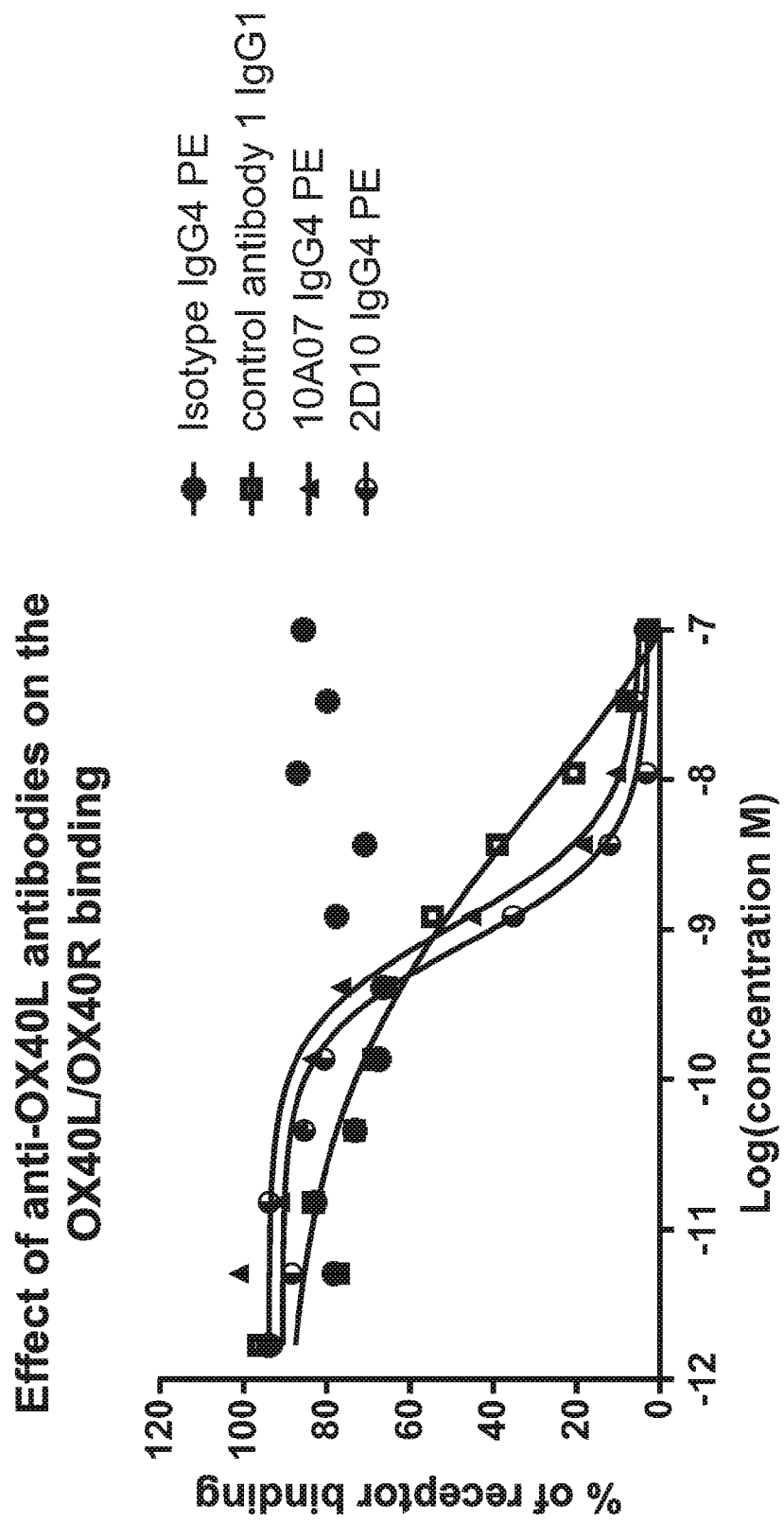
FIG. 1 shows profiling of fully human recombinant anti-OX40L antibodies in HTRF Ligand/Receptor Neutralisation assay. Data shown is representative of three repeat experiments.
Figure 2A:
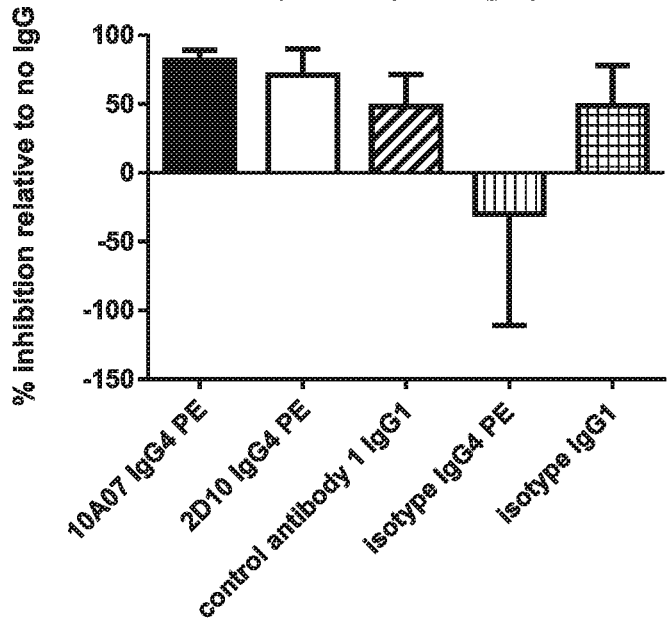
FIGS. 2A-2F show determining effect of anti-OX40L antibodies in allogeneic PBMC/T Mixed Lymphocyte Reaction. Data shown is from three independent donor pairings where it is assumed each donor is a different individual.
Figure 2B:
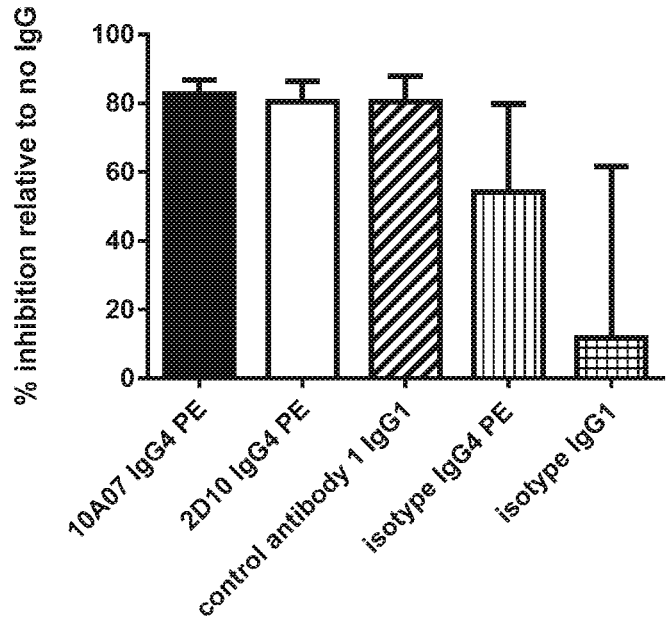
Figure 2C:
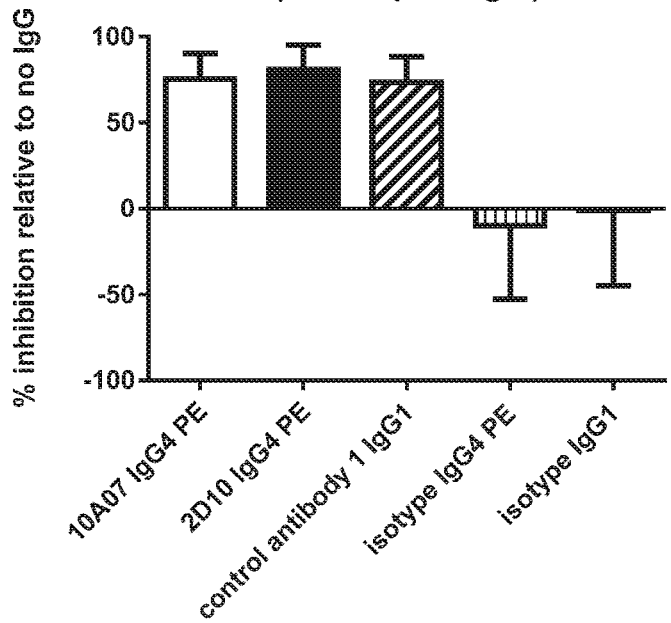
Figure 2D:
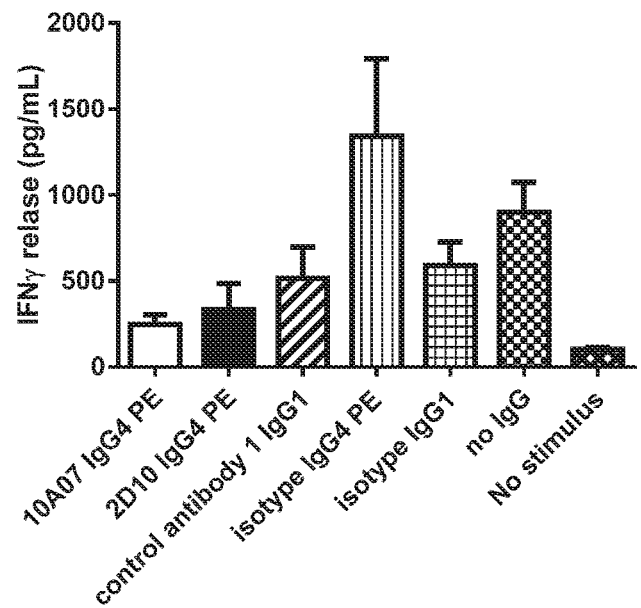
Figure 2E:
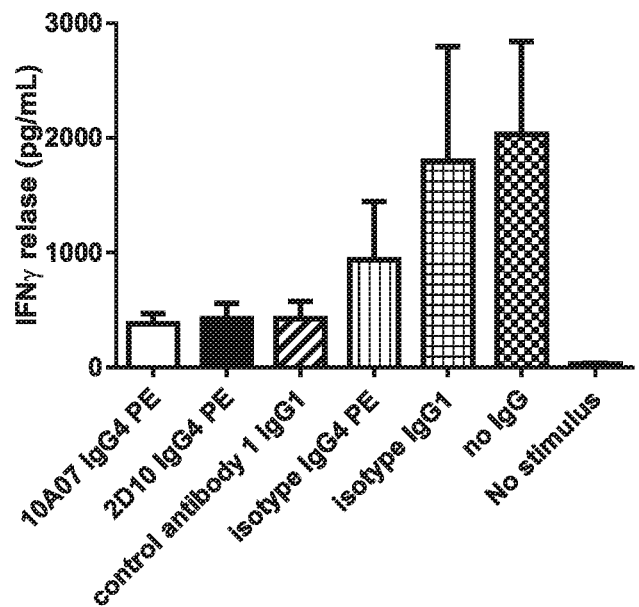
Figure 2F:
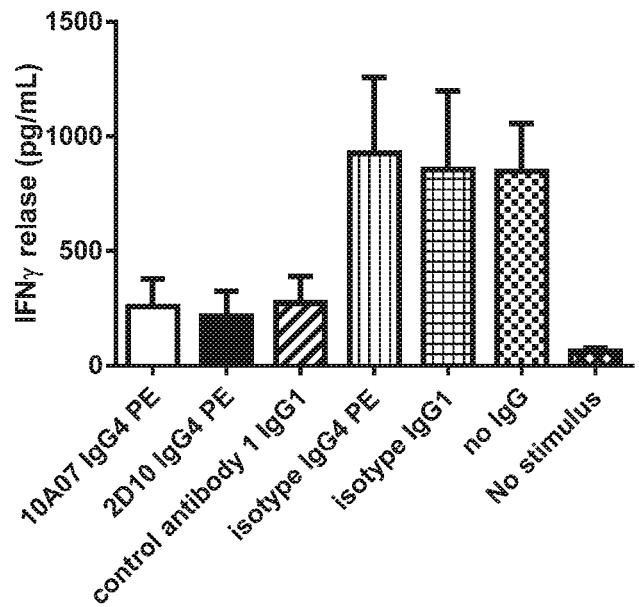

The invention provides the following aspects 1 to 113.

The invention is useful, for example, for treating or preventing transplant rejection, e.g., graft versus host disease (GvHD) or allogeneic transplant rejection. The invention is also useful, for example, for treating or preventing an inflammatory bowel disease, e.g., UC or CD, or for treating or preventing an airway inflammatory disease or condition. In an example this aspect is useful for treating or preventing asthma. The invention is also useful, for example, for treating or preventing fibrosis. The invention is also useful, for example, for treating or preventing diabetes. The invention is also useful, for example, for treating or preventing uveitis. The invention is also useful, for example, for treating or preventing pyoderma gangrenosum. The invention is also useful, for example, for treating or preventing giant cell arteritis. The invention is also useful, for example, for treating or preventing Schnitzler syndrome. The invention is also useful, for example, for treating or preventing non-infectious scleritis.

1. An antibody or a fragment thereof that specifically binds to hOX40L for treating or preventing a hOX40L-mediated disease or condition in a human in a method wherein the antibody or fragment is administered to said human, wherein the antibody or fragment is for treating or preventing said hOX40L-mediated disease or condition by decreasing one, more or all of
   a. secretion of a cytokine selected from TNF alpha, IL-2, IL-3, IL-4, IL-5, IL-6, IL-8, IL-9, IL-10, IL-13, IL-17, RANTES and interferon gamma in the human;
   b. the proliferation of leukocytes of the human; and
   c. binding of hOX40 receptor expressed by human T-cells with endothelial cell expressed hOX40L.

The inventors, thus identified for the first time decreases of (a), (b) and (c) as ways of treating and/or preventing OX40L-mediated disease and conditions in humans and they provide antibodies and antibody fragments for this purpose.

In an example, the secretion is leukocyte secretion. In an example, (a) is indicated by a significantly elevated level of the cytokine(s) in human blood, plasma or serum.

In an example, the cytokine is selected from (i) TNF alpha, (ii) IL-2 and (iii) interferon gamma. In example, the cytokine TNF alpha. In example, the cytokine is IL-2. In an example, the cytokine is interferon gamma. In an example, the cytokines are (i) and (ii); or (i) and (iii); or (ii) and (iii); or (i)-(iii).

In an example, the decrease of (a), (b) or (c) or any other decrease disclosed herein is a decrease of at least 10 or 20% compared to the level in a human at risk of or suffering from the hOX40L-mediated disease or condition. In an example, the latter is the human recited in aspect 1 prior to administration of the antibody or fragment; in another example the latter human is a different human. In an example, said decrease is at least 10, 20, 30, 40, 50 or 60%.

(i) In an example, the antibody or fragment is capable of effecting a decrease of secretion of the relevant cytokine from leukocytes (eg, human T-cells) in an in vitro assay (as explained further below), and thus administration of such antibody or fragment to the human leads to decrease of (a).

(ii) In an example, the antibody or fragment is capable of effecting a decrease of the proliferation of leukocytes (eg, human PBMCs and/or human T-cells) in an in vitro assay (as explained further below), and thus administration of such antibody or fragment to the human leads to decrease of (b).

(iii) In an example, the antibody or fragment is capable of effecting a decrease of the binding of hOX40 receptor expressed by human T-cells with endothelial cell expressed hOX40L in an in vitro assay (as explained further below), and thus administration of such antibody or fragment to the human leads to decrease of (c).

In an example, (i) and (ii); or (i) and (iii); or (ii) and (iii); or (i)-(iii) apply.

Additionally or alternatively, assessment of said decreases can be performed using samples from the treated human. For example, reference is made to J. Clin. Immunol., 2004 January, 24(1):74-85; "*Increased expression of CCL20 in human inflammatory bowel disease*"; Kaser A et al. This publication provides an example of a generally-applicable technique of using tissue biopsies and reading out decreased cytokine levels indicative of decreased cytokine secretion after treatment with an antibody in vivo. Similar methods can be used to determine decrease of the secretion of one or more cytokines in a human having received an antibody of the invention. The skilled person will be familiar with techniques for assessing cytokine levels in patients and patient samples, for example, by use of one or more of tissue biopsy, immunohistochemistry, immunofluorescence, tissue staining, cytokine mRNA quantification (e.g., using PCR, such as Taqman™ PCR), cytokine protein detection and quantification (e.g., using cytokine-specific tool antibody and quantification, such as by ELISA or another standard protein quantification technique). For example, where the disease or condition is one of the GI tract (e.g., IBD), one can perform biopsy of relevant gut tissue from a patient that has received an antibody of the invention, followed by quantification of cytokine mRNA and/or cytokine protein (e.g., using quantitative PCR). The result can be compared with a cytokine quantification in biopsied relevant tissue from the same patient prior to antibody administration or compared to another human patient suffering from the same disease or condition but receiving no anti-OX40L treatment or no treatment for the disease or condition. In this way, the skilled person can determine that the antibody of the invention decreases secretion of the cytokine in the human recipient. Instead of assessing gut tissue levels, one can instead use a different tissue or sample from the human patient dependent upon the nature and location of the disease or condition. For example, where the disease or condition is one of the airways (e.g., lung), it is possible to take a lung or other airway tissue sample for cytokine assessment. Alternatively, one can use a Bronchoalveolar lavage (BAL) sample, as will be apparent to the skilled person. In another example, for some disease or conditions one can assess the decrease in cytokine in a blood, serum or plasma sample taken from a human that has received an antibody of the invention, and then comparing to the level before receiving the antibody or comparing to the level in an untreated human, as discussed above.

As is known in the art, the term "leukocytes" includes, for example, one or more of lymphocytes, polymorphonuclear leukocyte and monocytes. As is also readily apparent to the skilled person the term "monocytes" includes, for example, peripheral blood mononuclear cells (PBMCs) or monocyte derived cells, e.g., dendritic cells (DCs). See, for example, Immunobiology, 2013 November, 218(11):1392-401. doi: 10.1016/j.imbio.2013.07.005. Epub 2013 Jul. 25; "Leukoreduction system chambers are an efficient, valid, and economic source of functional monocyte-derived dendritic cells and lymphocytes", Pfeiffer I A et al.

The proliferation of leukocytes, e.g., lamina propria lymphocytes (LPLs), can be assessed using tissue biopsy, staining and histology, as will be apparent to the skilled person. Hematoxylin and eosin stain (H&E stain or HE stain) is, for example, commonly used in histology to look for infiltrating lymphocytes a whole range of human tissue and is one of the principal stains in histology. It is the most widely used stain in medical diagnosis and is often the gold standard, and as such can be used to assess proliferation of leukocytes as per the invention. For example, GI tract tissue (e.g., gut tissue) from a human that is suffering from or at risk of a hOX40L-mediated disease or condition can be obtained, stained and assessed for the extent of infiltration of LPLs. Comparison can be made between such tissue from a human that has received an antibody of the invention compared to the extent of infiltration in tissue obtained from the same human prior to administration of antibody or from another human that has not received treatment and is at risk of or suffering from the disease or condition. For example, the comparison is between human gut tissues taken from the same (or different) humans suffering from IBD.

One can, for example, determine if the antibody or fragment is capable of decreasing binding of hOX40 receptor expressed by human T-cells with endothelial cell expressed hOX40L using standard binding assays are familiar to the skilled person, e.g., using ELISA or SPR.

Inflammatory bowel disease (IBD) is a chronic inflammatory disorder affecting the gastrointestinal tract with an apparently ever-increasing incidence and tendency to more severe clinical phenotypes. The disease is characterised by an exaggerated immune response to the luminal flora, suggesting that deficiencies in barrier function of intestinal flora may be involved, and studies support this notion (Cucchiara et al., 2012; Jostins et al., 2012; Manichanh et al., 2012; Salzman et al., 2007, all cited in Deuring et al., "*The cell biology of the intestinal epithelium and its relation to inflammatory bowel disease*", The International Journal of Biochemistry & Cell Biology 45 (2013) 798-806). IBD includes two main groups: Crohn's disease (CD) and ulcerative colitis (UC). CD patients can have inflammatory lesions in their entire gastrointestinal tract, whereas the inflammation in UC patients is restricted to the colon. Reference is also made to Hisamatsu et al. ("*Immune aspects of the pathogenesis of inflammatory bowel disease*", Pharmacology & Therapeutics 137 (2013) 283-297) and the documents cited therein.

Granuloma formation is the one of the most important pathological characteristics of human Crohn's disease. Mizoguchi et al demonstrated that F4/80-positive immature CD11c$^+$ dendritic cells (DCs) produce IL-23 and contribute to granuloma formation in a murine colitis model (Mizoguchi et al., 2007). A Th1 immune response is predominant in Crohn's disease. Indeed, CD4$^+$ T-cells in the LP of Crohn's disease expressed T-bet and produced large amounts of interferon (IFN)-γ (Matsuoka et al., 2004). Sakuraba et al demonstrated that DCs in the mesentric lymph nodes of patients with Crohn's disease strongly promoted a Th1 and Th17 immune response (Sakuraba et al., 2009). Mesentric lymph node DCs contribute to IBD pathogenesis, particularly that of Crohn's disease.

Role of Cytokines in Disease and Conditions

Reference is made to Muzes et al, *World J Gastroenterol* 2012 Nov. 7; 18(41): 5848-5861 ISSN 1007-9327 (print) ISSN 2219-2840 (online), "*Changes of the cytokine profile in inflammatory bowel Diseases*".

Cytokines are indispensable signals of the mucosa-associated immune system for maintaining normal gut homeostasis. An imbalance of their profile in favour of inflammation initiation may lead to disease states, such as that is observed in inflammatory bowel diseases (IBD), e.g., Crohn's disease (CD) and ulcerative colitis (UC). The role of pro-inflammatory cytokines such as IL-1α, IL-1β, IL-2, -6, -8, -12, -17, -23, IFN-gamma, or TNF alpha in IBD is associated with the initiation and progression of UC and CD. CD is often described as a prototype of T-helper (Th) 1-mediated diseases because the primary inflammatory mediators are the Th1 cytokines such as interleukin (IL)-12, interferon (IFN)-γ, and tumour necrosis factor (TNF)-α.

Binding of TNF-like ligands to their receptors triggers intracellular pathways that are directly involved in cell proliferation, differentiation, and survival. Most members of the TNF/TNF-receptor protein superfamilies are expressed on immune cells and play a critical role in multiple components of the immune response. TNF-α is a master cytokine in the pathogenesis of IBD. It exerts its pleiotropic effects through the expression of adhesion molecules, fibroblast proliferation, procoagulant factors, as well as the initiation of cytotoxic, apoptotic and acute-phase responses. The source of TNF-α in IBD is partly the innate immune cells, such as macrophages or monocytes, and also differentiated Th1 cells. The serum levels of TNF-α correlate with the clinical activity of UC and CD[31]. It plays an orchestrating role in colonic inflammation in IBD. The role of TNF-α in CD has been widely investigated. Binding TNF-α to serum soluble TNF receptor 1 and 2 (sTNFR1 and 2) initiates pro-inflammatory signalling. The levels of sTNFR1 and 2 are elevated in CD.

Tumour necrosis factor-like factor (TL1A), another member of the TNF family, stimulates IFN-γ secretion by binding to death receptor 3 (DR3). DR3 is expressed by a high percentage of cells from mucosal biopsies of UC and CD, and an increase of IFN-γ level has been observed with disease activity in IBD patients. The TL1A/DR3 system is involved in the pathogenesis of CD. The macrophages of the lamina propria are a major producer of TL1A, which expression is markedly enhanced in CD. It has been found that TL1A and IL-23 synergistically promotes the production of IFN-γ by mucosal T-cells. FN-Y: is produced by TH1 T-cells. Once inflammation is initiated, IFN-γ is produced and subsequently acts through various molecules and pathways of the immune system to intensify the inflammatory process. There is an overwhelming body of literature extensively documenting the proinflammatory nature of IFN-γ which has led to the mainstream opinion that IFN-γ is a prime proinflammatory cytokine in inflammation and autoimmune disease. Interferon-gamma is causatively involved in experimental inflammatory bowel disease in mice (Ito et al, *Clinical and Experimental Immunology* (2006), 146:330-338). The study clearly demonstrated that IFN-γ$^{-/-}$ mice manifested attenuated colitis after stimulation with DSS, in terms of the degree of body weight loss, DAI, histological score and MPO activity. IFN-γ was increasingly produced in the colon of DSS-treated WT mice that showed severe IBD-like symptoms.

Interleukin-2 (IL-2) is produced by T-cells and is mostly important for T-cells to differentiate into effector T-cells. IL-2 is also important for T-cell proliferation. This is important for IBD because effector T-cells are thought to be a major cell type to cause damage in IBD.

IL-8 (interleukin-8; aka CXCL8) primarily mediates the activation and migration of neutrophils into tissue from peripheral blood and to sites of inflammation. The tissue level of IL-8 has been found to be higher in active UC compared to normal colonic tissue, and its serum concentration has been related to endoscopic and histological severity of UC. IL-8 is important for inflammatory settings and cancer (see, e.g., "*The Chemokine CXCL8 in Carcinogenesis and Drug Response*", ISRN Oncol. 2013 Oct. 9; 2013: 859154; Gales D et al., and Future Oncol., 2010 January; 6(1):111-6. doi: 10.2217/fon.09.128; "*CXCL8 and its cognate receptors in melanoma progression and metastasis*", Singh S et al.). In cancer particularly, IL-8 is thought to contribute also by supporting angiogenesis.

In any configuration, aspect, concept or example herein the antibody or fragment antagonises the binding of hOX40L to an OX40 receptor.

In any configuration, aspect, concept or example herein, the antibody or fragment antagonises the binding of hOX40L to OX40.

In any configuration, aspect, concept or example herein, the OX40L receptor can be human OX40.

In any configuration, aspect, concept or example herein the human is suffering from or at risk of asthma and the antibody or fragment decreases IgE in a human.

In any configuration, aspect, concept or example herein the human is suffering from or at risk of asthma and the antibody or fragment is for decreasing IgE in a human.

2. The antibody or fragment of aspect 1, wherein the antibody or fragment decreases the binding of hOX40 receptor expressed by human T-cells with endothelial cell expressed hOX40L and decreases the proliferation of human T-cells; wherein the antibody or fragment is for treating or preventing said hOX40L-mediated disease or condition by decreasing the secretion of a cytokine selected from TNF alpha, IL-2, IL-3, IL-4, IL-5, IL-6, IL-8, IL-9, IL-10, IL-13, IL-17, RANTES and interferon gamma.

In an example, the cytokine is selected from (i) TNF alpha, (ii) IL-2 and (iii) interferon gamma. In an example, the cytokine is TNF alpha. In an example, the cytokine is IL-2. In an example, the cytokine is interferon gamma. In an example, the cytokines are (i) and (ii); or (i) and (iii); or (ii) and (iii); or (i)-(iii).

3. The antibody or fragment of aspect 1, wherein the leukocytes are selected from the group consisting of polymorphonuclear leukocytes, monocytes, peripheral blood mononuclear cells (PBMCs), lymphocytes, T-cells, antigen presenting cells (APCs), dendritic cells (DC cells) and natural killer cells (NK cells).

In one embodiment, the leukocytes are peripheral blood mononuclear cells (PBMCs) and T-cells (e.g. PBMCs).

4. The antibody or fragment of aspect 3, wherein the leukocytes comprise lamina propria lymphocytes (LPLs) and the disease or condition is a disease or condition of the gastrointestinal tract (GI tract).

5. The antibody or fragment of any preceding aspect, wherein the epithelial cells comprise cells selected from the group consisting of gastrointestinal cells, colon cells, intestinal cells and airway (e.g., lung) epithelial cells.

In another embodiment, the epithelial cells comprise cells selected from the group consisting of gastrointestinal cells, colon cells, intestinal cells, ocular cells and airway (e.g., lung) epithelial cells. In another embodiment, the epithelial cells comprise cells selected from the group consisting of gastrointestinal cells, colon cells, intestinal cells and ocular cells. In a further embodiment, the epithelial cells comprise ocular cells.

6. The antibody or fragment of any preceding aspect, for treating or preventing said hOX40L-mediated disease or condition in said human by decreasing the proliferation of T-cells in said human.

In an example, the antibody or fragment is capable of effecting a decrease of the proliferation of T-cells in an in vitro assay (e.g., in a human DC cell/T-cell in vitro assay, for example as explained further below), and thus administration of such antibody or fragment to the human leads to decrease of the proliferation of T-cells in said human.

7. The antibody or fragment of any preceding aspect, for treating or preventing said hOX40L-mediated disease or condition in said human by antagonising the interaction between hOX40L and leukocytes of the human, wherein the proliferation of leukocytes is decreased.

In an example, the antibody or fragment is capable of effecting a decrease of the proliferation of leukocytes (e.g., mononuclear cells) in an in vitro assay (e.g., in a MLR in vitro assay, for example as explained further below), and thus administration of such antibody or fragment to the human leads to decrease of the proliferation of leukocytes in said human.

8. The antibody or fragment of any preceding aspect, for treating or preventing said hOX40L-mediated disease or condition in said human by decreasing the proliferation of leukocytes of the human by antagonising the OX40L/OX40L receptor interaction mediated by T-cells in said human.

In an example, the antibody or fragment is capable of effecting a decrease of the proliferation of leukocytes (e.g., mononuclear cells) in an in vitro assay wherein the antibody or fragment antagonises OX40L/OX40L receptor interaction mediated by T-cells in said assay, and thus administration of such antibody or fragment to the human leads to decrease of the proliferation of leukocytes in said human.

9. The antibody or fragment of any preceding aspect, for treating or preventing said hOX40L-mediated disease or condition in said human by decreasing the secretion of a cytokine selected from TNF alpha, IL-2 and interferon gamma in the human.

In an example, the antibody or fragment is for treating or preventing said hOX40L-mediated disease, condition or epithelial cell damage in said human by decreasing the secretion of (i) IL-2 and interferon gamma, (ii) IL-2 and TNF alpha or (iii) interferon gamma and TNF alpha in the human.

In an example, the antibody or fragment is capable of effecting a decrease of the secretion of a cytokine selected from IL-2, TNF alpha and interferon gamma in an in vitro assay (e.g., in a MLR in vitro assay, for example as explained further below), and thus administration of such antibody or fragment to the human leads to decrease of the secretion of said selected cytokine(s) in said human.

In an example, the antibody or fragment is capable of effecting a decrease of the secretion of IL-8 in an in vitro assay (e.g., in a MLR in vitro assay, for example as explained further below), and thus administration of such antibody or fragment to the human leads to decrease of the secretion of IL-8 in said human.

10. The antibody or fragment of aspect 9, for treating or preventing said disease or condition by decreasing the secretion of said cytokine mediated by the interaction of dendritic cells (DC cells) with T-cells in the human.

In an example, the antibody or fragment is capable of effecting a decrease of said cytokine(s) secretion in a DC cell/T-cell in vitro assay (for example as explained further below), and thus administration of such antibody or fragment to the human leads to decrease of the secretion of said cytokine(s) in said human.

11. The antibody or fragment of any preceding aspect, wherein gastrointestinal cell, colon cell, intestinal cell or airway (e.g., lung) cell damage is a symptom or cause of said disease or condition in humans.

In another embodiment, the epithelial cells comprise cells selected from the group consisting of gastrointestinal cells, colon cells, intestinal cells, ocular cells and airway (e.g., lung) epithelial cells. In another embodiment, the epithelial cells comprise cells selected from the group consisting of gastrointestinal cells, colon cells, intestinal cells and ocular cells. In a further embodiment, the epithelial cells comprise ocular cells.

12. The antibody or fragment of any preceding aspect, wherein the human is suffering from or at risk of an inflammatory bowel disease (IBD), allogeneic transplant rejection, graft-versus-host disease (GvHD), diabetes or airway inflammation and said method treats or prevents IBD, allogeneic transplant rejection, GvHD, diabetes or airway inflammation in the human.

12a. The antibody or fragment of any preceding aspect, wherein the human is suffering from or at risk of an inflammatory bowel disease (IBD), allogeneic transplant rejection, graft-versus-host disease (GvHD), uveitis, pyoderma gangrenosum, giant cell arteritis, Schnitzler syndrome, non-infectious scleritis, diabetes or airway inflammation and said method treats or prevents IBD, allogeneic transplant rejection, GvHD, uveitis, pyoderma gangrenosum, giant cell arteritis, Schnitzler syndrome, non-infectious scleritis, diabetes or airway inflammation in the human.

In an example of any preceding aspect the human is suffering from or at risk of an inflammatory or autoimmune disease or condition or has been diagnosed as such.

In an example, the autoimmune disease or condition is selected from the following:—

Acute disseminated encephalomyelitis (ADEM)
Addison's disease
Allergic granulomatosis and angiitis or Churg-Strauss syndrome (CSS)
Alopecia or Alopecia Areata (AA)
Anklosing spondylitis
Autoimmune chronic active hepatitis (CAH)
Autoimmune hemolytic anemia
Autoimmune pancreatitis (AIP)
Autoimmune retinopathy (AR) see Retinopathy
Autoimmune thrombocytopenic purpura
Autoimmune neutropenia
Autoimmune Inner Ear Disease (AIED)
Antiphospholipid Syndrome (APS)
Autoimmune Lymphoproliferative Syndrome (ALPS)
Behcet's syndrome
Bullus pemphigoid
Celiac disease
Churg-Strauss Syndrome (CSS) or Allergic Granulomatosis Angiitis
Chronic bullous disease of childhood
Chronic inflammatory demyelinating Polyradiculoneuropathy (CIDP)
Cietricial pemphigoid (CP)
Central Nervous System Vasculitis
Crohn's Disease
Cryoglobulinemia
Dermatitis herpetiformis (DH)
Discoid lupus erythematosus (DLE)

Encephalomyelitis
Epidermolysis bullosa acquisita (EBA)
Giant Cell Arteritis sec Temporal arteritis
Graft-versus-host disease
Graves' Disease
Gullain-Barre syndrome
Hanot Syndrome see Primary biliary Cirrhosis
Hashimoto's thyroiditis also called autoimmune thyroiditis and chronic lymphocytic thyroiditis
Hypersensitivity Vasculitis (HV) or small vessel vasculitis
Immune-mediated infertility
Inflammatory bowel disease
Insulin-dependent diabetes mellitus
Isolated vasculitis of the Central nervous system or CNS Vasculitis
Isaacs' Syndrome: Neuromyotonia
Kawasaki disease (KD)
Lambert-Eaton myasthenic syndrome (LEMS)
Linear IgA disease
Lupus—see Systemic lupus erythematosus
Meniere's Disease
Microscopic Polyangiitis (MPA)
Mixed connective tissue disease or MCTD
Monoclonal Gammopathy
Myasthenia Gravis
Multiple Sclerosis
Multifocal motor neuropathy
Neuromyotonia or Isaac's syndrome
Neutropenia see Autoimmune Neutropenia
Oophoritis
Opsoclonus-myoclonus syndrome
orchitis
Paraneoplastic neurologic disorders
Pemphigus vulgaris
Pemphigus follaceus PF)
Pemphigoid gestationis (PG)
Pernicious anemia
Paraneoplastic pemphigus (PNP)
Polyangiitis—see Microscopic polyangiitis
Polyarteritis nodosa (PAN)
Polymyositis/Dermatomyositis
Polymyalgia Rheumatica
Primary biliary Cirrhosis (PBC) also called Hanot Syndrome
Primary sclerosing cholangitis (PSC)
Raynaud's phenomenon
Recoverin-associated retinopathy (RAR) see Retinopathy
Reactive Arthritis formerly known as Reiter's syndrome,
Retinopathy
Rheumatoid arthritis (RA)
Sarcoidosis
Sclerosing cholangitis see Primary Sclerosing Cholangitis
Sjogren's syndrome
Systemic necrotizing vascolitides
Stiff man syndrome or Moersch-Woltmann syndrome
Systemic lupus erythematosus
Systemic sclerosis (scleroderma)
Temporal arteritis or giant cell arteritis (GCV)
Takayasu's arteritis
Thromboangiitis obliterans or Buerger's disease
Thyroiditis with hypothyroidism
Thyroiditis with hyperthyroidism
Type I autoimmune polyglandular syndrome (PAS)
Type II autoimmune polyglandular syndrome
Vasculitis
Wegener's granulomatosis In an example of any aspect, configuration, concept or embodiment, the human is suffering from uveitis. For example, the uveitis is non-infectious and/or autoimmune in nature, i.e. is non-infectious uveitis or is autoimmune uveitis. For example, the non-infectious/autoimmune uveitis is caused by and/or is associated with Behçet disease, Fuchs heterochromic iridocyclitis, granulomatosis with polyangiitis, HLA-B27 related uveitis, juvenile idiopathic arthritis, sarcoidosis, spondyloarthritis, sympathetic ophthalmia, tubulointerstitial nephritis or uveitis syndrome. In an example, the uveitis is systemic in nature, i.e. is systemic uveitis. For example, the systemic uveitis is caused by and/or is associated with ankylosing spondylitis, Behçet's disease, chronic granulomatous disease, enthesitis, inflammatory bowel disease, juvenile rheumatoid arthritis, Kawasaki's disease, multiple sclerosis, polyarteritis nodosa, psoriatic arthritis, reactive arthritis, sarcoidosis, systemic lupus erythematosus, Vogt-Koyanagi-Harada syndrome or Whipple's disease.

In an example of any aspect, configuration, concept or embodiment, the human is suffering from pyoderma gangrenosum, giant cell arteritis, Schnitzler syndrome or non-infectious scleritis. In an example, the human is suffering from pyoderma gangrenosum. In an example, the human is suffering from giant cell arteritis. In an example, the human is suffering from Schnitzler syndrome. In an example, the human is suffering from non-infectious scleritis.

In an example of any aspect, configuration, concept or embodiment, the human is suffering from a hOX40L mediated disease or condition selected from an autoimmune disease or condition, a systemic inflammatory disease or condition, or transplant rejection; for example inflammatory bowel disease (IBD), Crohn's disease, rheumatoid arthritis, transplant rejection, allogeneic transplant rejection, graft-versus-host disease (GvHD), ulcerative colitis, systemic lupus erythematosus (SLE), diabetes, uveitis, ankylosing spondylitis, contact hypersensitivity, multiple sclerosis and atherosclerosis, in particular GvHD. In another embodiment, the human is suffering from or is at risk from multivisceral organ transplant rejection.

13. An antibody or a fragment thereof, that specifically binds to hOX40L and competes for binding to said hOX40L with an antibody selected from the group consisting of 02D10, 10A07, 09H04 and 19H01.

In an example of any aspect, configuration, concept or embodiment, competition is determined by surface plasmon resonance (SPR), such techniques being readily apparent to the skilled person. SPR can be carried out using Biacore™, Proteon™ or another standard SPR technique. Such competition may be due, for example, to the antibodies/fragments binding to identical or overlapping epitopes of hOX40L. In an example of any aspect, configuration, concept or embodiment, competition is determined by ELISA, such techniques being readily apparent to the skilled person. In an example of any aspect, configuration, concept or embodiment, competition is determined by homogenous time resolved fluorescence (HTRF), such techniques being readily apparent to the skilled person. In an example of any aspect, configuration, concept or embodiment, competition is determined by fluorescence activated cell sorting (FACS), such techniques being readily apparent to the skilled person. In one aspect, the HTRF, ELISA and/or FACS methods are carried out as described in the Examples hereinbelow.

14. The antibody or fragment of aspect 13, wherein the antibody or fragment is according to any one of aspects 1 to 12.

15. The antibody or fragment of any preceding aspect, comprising lambda light chain variable domains (optionally which are human).

In an example of any aspect, configuration, concept or embodiment of the present invention, the variable domains of the antibody or fragment are human or humanised. Additionally, optionally the antibody or fragment further comprises human or humanised constant regions (e.g., human Fc and/or human CL). In an example of any aspect of the present invention, the variable domains of the antibody or fragment are produced by a transgenic animal (e.g., a rodent, mouse, rat, rabbit, chicken, sheep, Camelid or shark). In an example of any aspect of the present invention, the variable domains of the antibody or fragment are produced or identified by phage display, ribosome display or yeast display.

In an example of any aspect, configuration, concept or embodiment of the present invention, the antibody or fragment is recombinant.

In an example of any aspect, configuration, concept or embodiment of the present invention, the antibody or fragment is produced by a recombinant mammalian, bacterial, insect, plant or yeast cell. In an example, the mammalian cell is a CHO or HEK293 cell and the antibody or fragment comprises CHO or HEK293 cell glycosylation.

In an example of any aspect, configuration, concept or embodiment of the present invention, the antibody or fragment is isolated.

16. The antibody or fragment of any preceding aspect, comprising a VH domain which comprises a HCDR1 sequence selected from the group consisting of the HCDR1 of:
    a. 02D10, and wherein the antibody or fragment competes with 02D10 for binding to said hOX40L;
    b. 10A07, and wherein the antibody or fragment competes with 10A07 for binding to said hOX40L;
    c. 09H04, and wherein the antibody or fragment competes with 09H04 for binding to said hOX40L; and
    d. 19H01, and wherein the antibody or fragment competes with 19H01 for binding to said hOX40L.

17. The antibody or fragment of any preceding aspect, comprising a VH domain which comprises a HCDR2 sequence selected from the group consisting of the HCDR2 of:
    a. 02D10, and wherein the antibody or fragment competes with 02D10 for binding to said hOX40L;
    b. 10A07, and wherein the antibody or fragment competes with 10A07 for binding to said hOX40L;
    c. 09H04, and wherein the antibody or fragment competes with 09H04 for binding to said hOX40L; and
    d. 19H01, and wherein the antibody or fragment competes with 19H01 for binding to said hOX40L.

18. The antibody or fragment of any preceding aspect, comprising a VH domain which comprises a HCDR3 sequence selected from the group consisting of the HCDR3 of:
    a. 02D10, and wherein the antibody or fragment competes with 02D10 for binding to said hOX40L;
    b. 10A07, and wherein the antibody or fragment competes with 10A07 for binding to said hOX40L;
    c. 09H04, and wherein the antibody or fragment competes with 09H04 for binding to said hOX40L; and
    d. 19H01, and wherein the antibody or fragment competes with 19H01 for binding to said hOX40L.

19. The antibody or fragment of any preceding aspect, comprising a VH domain which comprises (i) the CDR1 and 2, (ii) CDR1 and 3, (iii) CDR2 and 3 or (iv) CDR1, 2 and 3 sequences:
    a. recited in (a) of aspects 16-18, and wherein the antibody or fragment competes with 02D10 for binding to said hOX40L;
    b. recited in (b) of aspects 16-18, and wherein the antibody or fragment competes with 10A07 for binding to said hOX40L;
    c. recited in (c) of aspects 16-18, and wherein the antibody or fragment competes with 09H04 for binding to said hOX40L; or
    d. recited in (d) of aspects 16-18, and wherein the antibody or fragment competes with 19H01 for binding to said hOX40L.

20. The antibody or fragment of any preceding aspect, comprising a VH domain which comprises an amino acid sequence selected from the group consisting of the VH amino acid sequences in the sequence listing.

In an aspect, the invention provides an anti-hOX40L antibody or fragment (optionally according to any other aspect recited herein) comprising a VH domain which comprises an amino acid sequence selected from the group consisting of the VH amino acid sequences in the sequence listing. In an aspect, the VH domain comprises an amino acid sequence selected from Seq ID No:2, Seq ID No:34, Seq ID No:66, Seq ID No:94, Seq ID No: 122, Seq ID No: 124, Seq ID NO: 126, Seq ID No: 128, Seq ID No: 132 or Seq ID No: 134.

In another example of the invention, the antibody or fragment comprises a VH domain amino acid sequence set out in the sequence listing below. Additionally or alternatively, the antibody or fragment comprises a HCDR1 domain amino acid sequence set out in the sequence listing below (i.e. Seq ID No:4, Seq ID No: 10, Seq ID No:36, Seq ID No:42, Seq ID No:68, Seq ID No:74, Seq ID No:96 or Seq ID No: 102, in particular, Seq ID No:36 or Seq ID No:42). Additionally or alternatively, the antibody or fragment comprises a HCDR2 domain amino acid sequence set out in the sequence listing below (i.e. Seq ID No:6, Seq ID No: 12, Seq ID No:38, Seq ID No:44, Seq ID No:70, Seq ID No:76, Seq ID No:98 or Seq ID No: 104, in particular Seq ID No:38 or Seq ID No:44). Additionally or alternatively, the antibody or fragment comprises a HCDR3 domain amino acid sequence set out in the sequence listing below (i.e. Seq ID No:8, Seq ID No: 14, Seq ID No:40, Seq ID No:46, Seq ID No:72, Seq ID No:78, Seq ID No:100 or Seq ID No: 106, in particular Seq ID No:40 or Seq ID No:46).

In an example of the invention, the antibody or fragment comprises a VL domain amino acid sequence set out in the sequence listing below. Additionally or alternatively, the antibody or fragment comprises a LCDR1 domain amino acid sequence set out in the sequence listing below (i.e. Seq ID No: 18, Seq ID No:24, Seq ID No:50, Seq ID No:56, Seq ID No:82, Seq ID No:88, Seq ID No: 110 or Seq ID No: 116, in particular Seq ID No:50 or Seq ID No:56). Additionally or alternatively, the antibody or fragment comprises a LCDR2 domain amino acid sequence set out in the sequence listing below (i.e. Seq ID No:20, Seq ID No:26, Seq ID No:52, Seq ID No:58, Seq ID No:84, Seq ID No:90, Seq ID No: 112 or Seq ID No: 118, in particular Seq ID No:52 or Seq ID No:58). Additionally or alternatively, the antibody or fragment comprises a LCDR3 domain amino acid sequence set out in the sequence listing below (i.e. Seq ID No:22, Seq ID No:28, Seq ID No:54, Seq ID No:60, Seq ID No:86, Seq ID No:92, Seq ID No: 114 or Seq ID No: 120, in particular Seq ID No:54 or Seq ID No:60).

In an example of any aspect herein, the antibody or fragment comprises a heavy chain comprising a constant region selected from the group consisting of the heavy chain constant region SEQ ID NOs in the sequence listing (i.e. any of Seq ID Nos: 126, 128, 132, or 134, in particular the constant region of Seq ID No: 128); and optionally a VH domain as recited in aspect 19 or 20. In an example, the antibody or fragment comprises two copies of such a heavy chain. In another example, the heavy chain comprise a rodent, rat, mouse, human, rabbit, chicken, Camelid, sheep, bovine, non-human primate or shark constant region (e.g., Fc), in particular a mouse constant region.

In an example of any aspect herein, the antibody or fragment comprises a heavy chain comprising a gamma (e.g., human gamma) constant region, e.g., a human gamma1 constant region. In another example of any aspect herein, the antibody of fragment comprises a human gamma 4 constant region. In another embodiment, the heavy chain constant region does not bind Fc-γ receptors, and e.g. comprises a Leu235Glu mutation (i.e. where the wild type leucine residue is mutated to a glutamic acid residue). In another embodiment, the heavy chain constant region comprises a Ser228Pro mutation to increase stability. In another embodiment, the heavy chain constant region is IgG4 comprising both the Leu235Glu mutation and the Ser228Pro mutation. This heavy chain constant region is referred to as "IgG4-PE" herein.

In an example of any aspect herein, the antibody or fragment is chimaeric, e.g., it comprises human variable domains and non-human (e.g., rodent, mouse or rat, such as mouse) constant regions.

21. The antibody or fragment of any one of aspects 16 to 20, comprising first and second copies of said VH domain.
22. The antibody or fragment of any preceding aspect, comprising a VL domain which comprises a LCDR1 sequence selected from the group consisting of the LCDR1 of:
   a. 02D10, and wherein the antibody or fragment competes with 02D10 for binding to said hOX40L;
   b. 10A07, and wherein the antibody or fragment competes with 10A07 for binding to said hOX40L;
   c. 09H04, and wherein the antibody or fragment competes with 09H04 for binding to said hOX40L; and
   d. 19H01, and wherein the antibody or fragment competes with 19H01 for binding to said hOX40L.
23. The antibody or fragment of any preceding aspect, comprising a VL domain which comprises a LCDR2 sequence selected from the group consisting of the LCDR2 of:
   a. 02D10, and wherein the antibody or fragment competes with 02D10 for binding to said hOX40L;
   b. 10A07, and wherein the antibody or fragment competes with 10A07 for binding to said hOX40L;
   c. 09H04, and wherein the antibody or fragment competes with 09H04 for binding to said hOX40L; and
   d. 19H01, and wherein the antibody or fragment competes with 19H01 for binding to said hOX40L.
24. The antibody or fragment of any preceding aspect, comprising a VL domain which comprises a LCDR3 sequence selected from the group consisting of the LCDR3 of:
   a. 02D10, and wherein the antibody or fragment competes with 02D10 for binding to said hOX40L;
   b. 10A07, and wherein the antibody or fragment competes with 10A07 for binding to said hOX40L;
   c. 09H04, and wherein the antibody or fragment competes with 09H04 for binding to said hOX40L; and
   d. 19H01, and wherein the antibody or fragment competes with 19H01 for binding to said hOX40L.
25. The antibody or fragment of any preceding aspect, comprising a VL domain which comprises (i) the CDR1 and 2, (ii) CDR1 and 3, (iii) CDR2 and 3 or (iv) CDR1, 2 and 3 sequences:
   a. recited in (a) of aspects 22-24, and wherein the antibody or fragment competes with 02D10 for binding to said hOX40L;
   b. recited in (b) of aspects 22-24, and wherein the antibody or fragment competes with 10A07 for binding to said hOX40L;
   c. recited in (c) of aspects 22-24, and wherein the antibody or fragment competes with 09H04 for binding to said hOX40L; or
   d. recited in (d) of aspects 22-24, and wherein the antibody or fragment competes with 19H01 for binding to said hOX40L.
26. The antibody or fragment of any preceding aspect, comprising a VL domain which comprises an amino acid sequence selected from the group consisting of the VL amino acid sequences in the sequence listing.

In an aspect of the invention, there is provided an anti-hOX40L antibody or fragment (optionally according to any other aspect herein), comprising a VL domain which comprises an amino acid sequence selected from the group consisting of the VL amino acid sequences in the sequence listing (i.e. Seq ID No: 16, Seq ID No:48, Seq ID No:80 or Seq ID No: 108, in particular Seq ID No:48).

In an example of any aspect herein, the antibody or fragment comprises a light chain (e.g., lambda light chain) comprising a constant region selected from the group consisting of the light chain constant region sequences in the sequence listing (i.e. Seq ID No: 136, Seq ID No: 138, Seq ID No: 140, Seq ID No: 142, Seq ID No: 144, Seq ID No: 146, Seq ID No: 148, Seq ID No: 152, Seq ID No: 154, Seq ID No: 156, Seq ID No: 158, Seq ID No: 160, Seq ID No: 162, Seq ID No: 164 or Seq ID No: 166); and optionally a VL domain (e.g., lambda VL) as recited in aspect 25 or 26. In an example, the antibody or fragment comprises two copies of such a light chain (optionally also two copies of the heavy chain described above). In another example, the light chain comprise a rodent, rat, mouse, human, rabbit, chicken, Camelid, sheep, bovine, non-human primate or shark constant region.

In an example of any aspect herein, the antibody or fragment comprises a light chain (e.g., kappa light chain) comprising a constant region selected from the group consisting of the light chain constant region sequences in the sequence listing (i.e. Seq ID No: 136, Seq ID No: 138, Seq ID No: 140, Seq ID No: 142, Seq ID No: 144, Seq ID No: 146, Seq ID No: 148, Seq ID No: 152, Seq ID No: 154, Seq ID No: 156, Seq ID No: 158, Seq ID No: 160, Seq ID No: 162, Seq ID No: 164 or Seq ID No: 166); and optionally a VL domain (e.g., kappa VL) as recited in aspect 25 or 26. In an example, the antibody or fragment comprises two copies of such a light chain (optionally also two copies of the heavy chain described above). In another example, the light chain comprise a rodent, rat, mouse, human, rabbit, chicken, Camelid, sheep, bovine, non-human primate or shark constant region.

In an example, the antibody or fragment comprises a lambda light chain comprising a constant region selected from the group consisting of the light chain constant region sequences in the sequence listing (i.e. Seq ID No: 146, Seq ID No: 148, Seq ID No:152, Seq ID No: 154, Seq ID No: 156, Seq ID No: 158, Seq ID No: 160, Seq ID No: 162, Seq ID No: 164 or Seq ID No: 166); and optionally a lambda VL domain.

In an example, the antibody or fragment comprises a kappa light chain comprising a constant region selected from the group consisting of the light chain constant region sequences in the sequence listing (i.e. i.e. Seq ID No: 136, Seq ID No: 138, Seq ID No: 140, Seq ID No: 142 or Seq ID No: 144); and optionally a kappa VL domain.

In an example, the VL domains of the antibody or fragment are lambda Light chain variable domains. In an example, the VL domains of the antibody or fragment are kappa Light chain variable domains.

27. The antibody or fragment of any one of aspects 22 to 26, comprising first and second copies of said VL domain.

28. The antibody or fragment of any preceding aspect, wherein the hOX40L is human cell surface-expressed hOX40L, e.g., on endothelial cells (e.g., an airway or GI tract endothelial cell).

In another embodiment, the epithelial cells comprise cells selected from the group consisting of gastrointestinal cells, colon cells, intestinal cells, ocular cells and airway (e.g., lung) epithelial cells. In another embodiment, the epithelial cells comprise cells selected from the group consisting of gastrointestinal cells, colon cells, intestinal cells and ocular cells. In a further embodiment, the epithelial cells comprise ocular cells.

29. The antibody or fragment of any preceding aspect, wherein the antibody or fragment decreases the proliferation of human PBMCs or T-cells in the presence of hOX40L in an in vitro mixed lymphocyte reaction (MLR) assay by at least 20, 30, 40, 50 or 60% compared to the proliferation of human PBMCs or T-cells in the presence of hOX40L in an in vitro control MLR assay in the absence of an antibody that is specific for hOX40L. An illustration of a suitable assay is provided in the examples below.

30. The antibody or fragment of aspect 29, wherein the hOX40L in the assay is surface-expressed on human dendritic cells (DC cells).

An illustration of a suitable assay is provided in the examples below.

31. The antibody or fragment of any preceding aspect, wherein the antibody or fragment decreases NF-κB activity in human HT-1080 cells expressing hOX40 receptor in vitro in the presence of hOX40L.

In an example, the antibody or fragment the decrease in NF-κB activity is determined by detecting a decrease in IL-8 secretion by HT-1080 cells (ATCC® CCL-121) (optionally transfected with hOX40 Receptor, in the presence of hOX40) in vitro.

32. The antibody or fragment of any preceding aspect, wherein the antibody or fragment decreases IL-8 secretion from human HT-1080 cells expressing hOX40 receptor in vitro in the presence of hOX40L.

33. The antibody or fragment of aspect 32, wherein the antibody or fragment decreases IL-8 secretion by at least 20, 30, 40, 50 or 60% compared to the IL-8 production by HT-1080 cells expressing hOX40 receptor in vitro in the presence of hOX40L in the absence of an antibody that is specific for hOX40L.

34. The antibody or fragment of any preceding aspect, wherein the antibody or fragment decreases hOX40L-stimulated human T-cell proliferation in vitro.

35. The antibody or fragment of any preceding aspect, wherein the antibody or fragment decreases hOX40L-stimulated IL-2 secretion from human T-cells in vitro.

36. The antibody or fragment of any preceding aspect, wherein the antibody or fragment decreases cytokine secretion mediated by the interaction of human dendritic cells (DC cells) with human T-cells, wherein the cytokine is selected from one, two, more or all of TNF alpha, IL-2, IL-3, IL-4, IL-5, IL-6, IL-8, IL-9, IL-10, IL-13, IL-17, RANTES and interferon gamma.

This can be assessed, for example, using a MLR in vitro assay (e.g., a DC/T-cell MLR in vitro assay). An illustration of a suitable assay is provided in the examples below.

In an example, the DC cells are mismatched to the T-cells, e.g., MHC mis-matched, as is possible for example when the DC cells are from a human that is different from the T-cell human source. In an example, the DC cells are produced by in vitro induction of human monocytes with GMCSF and IL-4.

37. The antibody or fragment of any preceding aspect, wherein the antibody or fragment decreases interferon gamma secretion by at least 20, 30, 40, 50 or 60% compared to the production of interferon gamma mediated by the interaction of human dendritic cells (DC cells) with human T-cells in the absence of an antibody that is specific for hOX40L.

38. The antibody or fragment of any preceding aspect, wherein the antibody or fragment decreases TNF alpha secretion by at least 20, 30, 40, 50 or 60% compared to the production of TNF alpha mediated by the interaction of human dendritic cells (DC cells) with human T-cells in the absence of an antibody that is specific for hOX40L.

39. The antibody or fragment of any preceding aspect, wherein the antibody or fragment decreases IL-2 secretion by at least 10, 20, 30, 40, 50 or 60% compared to the production of IL-2 mediated by the interaction of human dendritic cells (DC cells) with human T-cells in the absence of an antibody that is specific for hOX40L.

40. The antibody or fragment of any preceding aspect, wherein the antibody or fragment decreases cytokine secretion (e.g., leukocyte cytokine secretion) in a human peripheral blood mononuclear cell (PBMC) mixed lymphocyte (MLR) assay, wherein the cytokine is selected from one, two, more or all of TNF alpha, IL-2, IL-4, IL-3, IL-6, IL-8, IL-10, IL-17, RANTES and interferon gamma.

41. The antibody or fragment of any preceding aspect, wherein the antibody or fragment decreases interferon gamma secretion by at least 20, 30, 40, 50 or 60% compared to the production of interferon gamma in a human PBMC MLR assay in the absence of an antibody that is specific for hOX40L.

In one embodiment, the comparison is to the production of interferon gamma in a human PBMC MLR assay in the absence of antibody.

42. The antibody or fragment of any preceding aspect, wherein the antibody or fragment decreases TNF alpha secretion by at least 20, 30, 40, 50 or 60% compared to the production of TNF alpha in a human PBMC MLR assay in the absence of an antibody that is specific for hOX40L.

43. The antibody or fragment of any preceding aspect, wherein the antibody or fragment decreases IL-2 secretion by at least 10, 20, 30, 40, 50 or 60% compared to the production of IL-2 in a human PBMC MLR assay in the absence of an antibody that is specific for hOX40L.

44. The antibody or fragment of any one of aspects 36 to 43, wherein the cells are primary cells.

A "primary cell" refers to a cell in a human or such a cell that has been taken from the patient for binding to the antibody or fragment of the invention in vitro (as may be useful, for example, in a method of diagnosis of OX40L status or disease/condition status in the human). Primary cells as used herein are not cells of human cell lines, which typically have undergone many cultures in vitro. The ability of the antibody or fragment of the invention to specifically inhibit hOX40L binding to receptor in this embodiment is advantageous since it provides a direct indication of the utility for addressing cells in human patients suffering or at risk of a hOX40L-mediated disease or condition.

45. The antibody or fragment of any preceding aspect, wherein the antibody or fragment inhibits binding of hOX40L to a hOX40L receptor (e.g., hOX40) with an $IC_{50}$ of $1\times10^{-8}$ or less in a HTRF (homogenous time resolved fluorescence) assay.

In an example, the $IC_{50}$ is in the range from $1\times10^{-8}$ to $1\times10^{-11}$ or in the range from $1\times10^{-9}$ to $1\times10^{-10}$.

46. A pharmaceutical composition for treating and/or preventing a OX40L-mediated condition or disease, the composition comprising an antibody or fragment of any preceding aspect and a diluent, excipient or carrier; and optionally further comprising an anti-inflammatory drug.

In an example, the anti-inflammatory drug is independently selected from the group consisting of corticosteroids (e.g. methylprednisolone), anti-IL12/IL-23 antibodies (e.g. ustekinumab), anti-VLA4 antibodies (e.g. natalizumab), anti-LFA1 antibodies, anti-complement C5 antibodies (e.g. eculizumab), anti-a4b7 integrin antibodies (e.g. vedolizumab), anti-IL6 antibodies (e.g. tocilizumab), anti-IL2R antibodies (e.g. basilixumab) or anti-TNFa antibodies/ TNFa-Fc molecules (e.g. etanercept, adalimumab, infliximab, golimumab, certolizumab pegol). In an example, the anti-inflammatory drug is independently selected from the group consisting of corticosteroids (e.g. methylprednisolone) and anti-LFA1 antibodies.

47. A pharmaceutical composition or kit for treating and/or preventing a OX40L-mediated condition or disease, the composition or kit comprising an antibody or fragment of the invention (and optionally an anti-inflammatory drug) optionally in combination with a label or instructions for use to treat and/or prevent said disease or condition in a human; optionally wherein the label or instructions comprise a marketing authorisation number (e.g., an FDA or EMA authorisation number); optionally wherein the kit comprises an IV or injection device that comprises the antibody or fragment.

48. A nucleic acid that encodes the HCDR3 of an antibody recited in any one of aspects 1 to 45.

In one embodiment, the HCDRs herein are according to Kabat nomenclature. In another embodiment, the HCDRs herein are according to the IMGT nomenclature.

49. The nucleic acid of aspect 48 comprising a nucleotide sequence that is at least 80, 85, 90, 95, 96, 97, 98 or 99% identical or is 100% identical to a HCDR3 sequence in the sequence listing.

In an aspect, the invention provides a nucleic acid comprising a nucleotide sequence that encodes a VH domain of an anti-hOX40L antibody, wherein the nucleotide sequence comprises a HCDR3 sequence that is at least 80, 85, 90, 95, 96, 97, 98 or 99% identical or is 100% identical to a HCDR3 sequence in the sequence listing. Optionally, the antibody is according to any other aspect herein.

In another embodiment, there is provided the nucleic acid of aspect 48 comprising a nucleotide sequence that is 100% identical to a HCDR3 sequence in the sequence listing, except for 1, 2 or 3 nucleotide substitutions, wherein each substitution produces no amino acid change or produces a conservative amino acid change (i.e., the nucleotide substitution is a synonymous substitution) in the corresponding protein sequence. The skilled person will be familiar with conservative amino acid changes.

Amino acid substitutions include alterations in which an amino acid is replaced with a different naturally-occurring amino acid residue. Such substitutions may be classified as "conservative", in which case an amino acid residue contained in a polypeptide is replaced with another naturally occurring amino acid of similar character either in relation to polarity, side chain functionality or size. Such conservative substitutions are well known in the art. Substitutions encompassed by the present invention may also be "non-conservative", in which an amino acid residue which is present in a peptide is substituted with an amino acid having different properties, such as naturally-occurring amino acid from a different group (e.g., substituting a charged or hydrophobic amino; acid with alanine), or alternatively, in which a naturally-occurring amino acid is substituted with a non-conventional amino acid.

Additionally or alternatively, there is provided the nucleic acid of aspect 49 comprising a nucleotide sequence that is 100% identical to a HCDR3 sequence in the sequence listing, except for 1, 2, 3, 4, 5, 6 or 7 synonymous nucleotide substitutions and no, 1, 2 or 3 nucleotide substitutions that produce conservative amino acid changes in the corresponding protein sequence.

50. A nucleic acid that encodes the HCDR2 of an antibody recited in any one of aspects 1 to 45; optionally wherein the nucleic acid is according to aspect 48 or 49.

51. The nucleic acid of aspect 50 comprising a nucleotide sequence that is at least 80, 85, 90, 95, 96, 97, 98 or 99% identical or is 100% identical to a HCDR2 sequence in the sequence listing.

In an aspect, the invention provides a nucleic acid comprising a nucleotide sequence that encodes a VH domain of an anti-hOX40L antibody, wherein the nucleotide sequence comprises a HCDR2 sequence that is at least 80, 85, 90, 95, 96, 97, 98 or 99% identical or is 100% identical to a HCDR2 sequence in the sequence listing. Optionally, the antibody is according to any other aspect herein.

In another embodiment, there is provided the nucleic acid of aspect 51 comprising a nucleotide sequence that is 100% identical to a HCDR2 sequence in the sequence listing, except for 1, 2 or 3 nucleotide substitutions, wherein each substitution produces no amino acid change or produces a conservative amino acid change (i.e., the nucleotide substitution is a synonymous substitution) in the corresponding protein sequence. The skilled person will be familiar with conservative amino acid changes.

Additionally or alternatively, there is provided the nucleic acid of aspect 50 comprising a nucleotide sequence that is 100% identical to a HCDR2 sequence in the sequence listing, except for 1, 2, 3, 4, 5, 6 or 7 synonymous nucleotide substitutions and no, 1, 2 or 3 nucleotide substitutions that produce conservative amino acid changes in the corresponding protein sequence.

52. A nucleic acid that encodes the HCDR1 of an antibody recited in any one of aspects 1 to 45; optionally wherein the nucleic acid is according to any one of aspects 48 to 51.

53. The nucleic acid of aspect 52 comprising a nucleotide sequence that is at least 80, 85, 90, 95, 96, 97, 98 or 99% identical to or is 100% identical to a HCDR1 sequence in the sequence listing.

In an aspect, the invention provides a nucleic acid comprising a nucleotide sequence that encodes a VH domain of an anti-hOX40L antibody, wherein the nucleotide sequence comprises a HCDR1 sequence that is at least 80, 85, 90, 95, 96, 97, 98 or 99% identical or is 100% identical to a HCDR1 sequence in the sequence listing. Optionally, the antibody is according to any other aspect herein.

In another embodiment, there is provided the nucleic acid of aspect 52 comprising a nucleotide sequence that is 100% identical to a HCDR1 sequence in the sequence listing, except for 1, 2 or 3 nucleotide substitutions, wherein each substitution produces no amino acid change or produces a conservative amino acid change (i.e., the nucleotide substitution is a synonymous substitution) in the corresponding protein sequence. The skilled person will be familiar with conservative amino acid changes.

Additionally or alternatively, there is provided the nucleic acid of aspect 52 comprising a nucleotide sequence that is 100% identical to a HCDR1 sequence in the sequence listing, except for 1, 2, 3, 4, 5, 6 or 7 synonymous nucleotide substitutions and no, 1, 2 or 3 nucleotide substitutions that produce conservative amino acid changes in the corresponding protein sequence.

54. A nucleic acid that encodes a VH domain and/or a VL domain of an antibody recited in any one of aspects 1 to 45.

55. The nucleic acid of aspect 54 comprising a nucleotide sequence that is at least 80, 85, 90, 95, 96, 97, 98 or 99% identical to or is 100% identical to a VH domain nucleotide sequence in the sequence listing.

In another embodiment, there is provided the nucleic acid of aspect 54 comprising a nucleotide sequence that is 100% identical to a VH domain nucleotide sequence in the sequence listing, except for 1, 2 or 3 nucleotide substitutions, wherein each substitution produces no amino acid change or produces a conservative amino acid change (i.e., the nucleotide substitution is a synonymous substitution) in the corresponding protein sequence. The skilled person will be familiar with conservative amino acid changes.

Additionally or alternatively, there is provided the nucleic acid of aspect 54 comprising a nucleotide sequence that is 100% identical to a VH domain nucleotide sequence in the sequence listing, except for 1, 2, 3, 4, 5, 6 or 7 synonymous nucleotide substitutions and no, 1, 2 or 3 nucleotide substitutions that produce conservative amino acid changes in the corresponding protein sequence.

56. The nucleic acid of aspect 54 or 55 comprising a nucleotide sequence that is at least 80, 85, 90, 95, 96, 97, 98 or 99% identical to or is 100% identical to a VL domain nucleotide sequence in the sequence listing.

In another embodiment, there is provided the nucleic acid of aspect 54 or 55 comprising a nucleotide sequence that is 100% identical to a VL domain nucleotide sequence in the sequence listing, except for 1, 2 or 3 nucleotide substitutions, wherein each substitution produces no amino acid change or produces a conservative amino acid change (i.e., the nucleotide substitution is a synonymous substitution) in the corresponding protein sequence. The skilled person will be familiar with conservative amino acid changes.

Additionally or alternatively, there is provided the nucleic acid of aspect 54 or 55 comprising a nucleotide sequence that is 100% identical to a VL domain nucleotide sequence in the sequence listing, except for 1, 2, 3, 4, 5, 6 or 7 synonymous nucleotide substitutions and no, 1, 2 or 3 nucleotide substitutions that produce conservative amino acid changes in the corresponding protein sequence.

57. A nucleic acid that encodes a heavy chain or a light chain of an antibody recited in any one of aspects 1 to 45.

58. The nucleic acid of aspect 57, comprising a nucleotide sequence as recited in any one of aspects 48 to 56.

59. A vector (e.g., a mammalian expression vector) comprising the nucleic acid of any one of aspects 48 to 58; optionally wherein the vector is a CHO or HEK293 vector. In an example, the vector is a yeast vector, e.g., a *Saccharomyces* or *Pichia* vector.

60. A host comprising the nucleic acid of any one of aspects 48 to 58 or the vector of aspect 59. In an example, the host is a mammalian (e.g., human, e.g., CHO or HEK293) cell line or a yeast or bacterial cell line.

61. Use of an antibody or a fragment thereof, that specifically binds to hOX40L in the manufacture of a medicament for administration to a human, for treating or preventing a hOX40L-mediated disease or condition in the human by decreasing one, more or all of
  a. secretion of a cytokine selected from TNF alpha, IL-2, IL-3, IL-4, IL-5, IL-6, IL-8, IL-9, IL-10, IL-13, IL-17, RANTES and interferon gamma in the human;
  b. the proliferation of leukocytes of the human; and
  c. binding of hOX40 receptor expressed by human T-cells with endothelial cell expressed hOX40L.

The features of any of the previous aspects, configurations, concepts, examples or embodiments optionally apply mutatis mutandis to this use.

In an example, the human is suffering from or at risk of asthma and the antibody or fragment is for decreasing IgE in the human, thereby treating, preventing or reducing asthma in the human.

62. A method of treating or preventing a hOX40L-mediated disease or condition in a human by decreasing one, more or all of
  a. secretion of a cytokine selected from TNF alpha, IL-2, IL-3, IL-4, IL-5, IL-6, IL-8, IL-9, IL-10, IL-13, IL-17, RANTES and interferon gamma in the human;
  b. the proliferation of leukocytes of the human; and
  c. binding of hOX40 receptor expressed by human T-cells with endothelial cell expressed hOX40L;
    wherein the method comprises administering to said human a therapeutically effective amount of an antibody or fragment that specifically binds to hOX40L.

The features of any of the previous aspects, examples or embodiments optionally apply mutatis mutandis to this method.

The method of the invention treats or prevents said disease or condition in the human. A "therapeutically effective amount" of the antibody or fragment is that amount (administered in one or several doses, which may be spaced in time, e.g., substantially monthly administration) that is effective to bring about said treatment or prevention. This will be readily apparent to the skilled person and may vary according to the particular human patient and disease or condition being addressed.

In an example, the human is suffering from or at risk of asthma and the antibody or fragment decreases IgE in the human, thereby treating, preventing or reducing asthma in the human.

63. The method or use of aspect 61 or 62, for treating or preventing said hOX40L-mediated disease, condition or epithelial cell damage in said human by decreasing the proliferation of T-cells in said human.

64. The method or use of any one of aspects 61 to 63, for treating or preventing said hOX40L-mediated disease, condition or epithelial cell damage in said human by antagonising the interaction between hOX40L and leukocytes of the human, wherein the proliferation of leukocytes is decreased.

65. The method or use of any one of aspects 61 to 64, for treating or preventing said hOX40L-mediated disease, condition or epithelial cell damage in said human by decreasing the proliferation of leukocytes of the human by antagonising the OX40L/OX40L receptor interaction mediated by T-cells in said human.

66. The method or use of any one of aspects 61 to 65, for treating or preventing said hOX40L-mediated disease, condition or epithelial cell damage in said human by decreasing the secretion of IL-8 cytokine in the human.

67. The method of aspect 66, for treating or preventing said disease, condition or epithelial cell damage by decreasing the secretion of said IL-8 mediated by the interaction of dendritic cells (DC cells) with T-cells in the human.

68. The method or use of any one of aspects 61 to 67, wherein gastrointestinal cell, colon cell, intestinal cell or airway (e.g., lung) cell damage is a symptom or cause of said disease or condition in humans.

In another embodiment, the epithelial cells comprise cells selected from the group consisting of gastrointestinal cells, colon cells, intestinal cells, ocular cells and airway (e.g., lung) epithelial cells. In another embodiment, the epithelial cells comprise cells selected from the group consisting of gastrointestinal cells, colon cells, intestinal cells and ocular cells. In a further embodiment, the epithelial cells comprise ocular cells.

69. The method or use of any one of aspects 61 to 68, wherein the human is suffering from or at risk of an inflammatory bowel disease (IBD), allogeneic transplant rejection, graft-versus-host disease (GvHD), diabetes or airway inflammation and said method treats or prevents IBD, allogeneic transplant rejection, GvHD, diabetes or airway inflammation in the human.

69a. The method or use of any one of aspects 61 to 68, wherein the human is suffering from or at risk of an inflammatory bowel disease (IBD), allogeneic transplant rejection, graft-versus-host disease (GvHD), uveitis, pyoderma gangrenosum, giant cell arteritis, Schnitzler syndrome, non-infectious scleritis, diabetes or airway inflammation and said method treats or prevents IBD, allogeneic transplant rejection, GvHD, uveitis, pyoderma gangrenosum, giant cell arteritis, Schnitzler syndrome, non-infectious scleritis, diabetes or airway inflammation in the human.

In any aspect, configuration, concept or embodiment, the human is suffering from or at risk of a hOX40L-mediated disease or condition selected from an autoimmune disease or condition, a systemic inflammatory disease or condition, or transplant rejection; for example inflammatory bowel disease (IBD), Crohn's disease, rheumatoid arthritis, transplant rejection, allogeneic transplant rejection, graft-versus-host disease (GvHD), ulcerative colitis, systemic lupus erythematosus (SLE), diabetes, uveitis, ankylosing spondylitis, contact hypersensitivity, multiple sclerosis and atherosclerosis, in particular GvHD.

70. The method or use of any one of aspects 61 to 69a, wherein the antibody or fragment is according to any one of aspects 1 to 45 or any example, configuration, concept, aspect or embodiment described herein.

71. The antibody, fragment, composition, kit, method or use of any preceding aspect, for treating or preventing an inflammatory or autoimmune disease or condition in a human or for reducing or preventing angiogenesis in a human.

72. The antibody, fragment, composition, kit, method or use of any preceding aspect, wherein the disease or condition is selected from the group consisting of an inflammatory bowel disease (IBD), Chrohn's disease, rheumatoid arthritis, psoriasis, bronchiolitis, gingivitis, transplant rejection, allogeneic transplant rejection, graft-versus-host disease (GvHD), asthma, adult respiratory distress syndrome (ARDS), septic shock, ulcerative colitis, Sjorgen's syndrome, airway inflammation, systemic lupus erythematosus (SLE), diabetes, contact hypersensitivity, multiple sclerosis and atherosclerosis.

72a. The antibody, fragment, composition, kit, method or use of any preceding aspect, wherein the disease or condition is selected from the group consisting of an inflammatory bowel disease (IBD), Chrohn's disease, rheumatoid arthritis, psoriasis, bronchiolitis, gingivitis, transplant rejection, allogeneic transplant rejection, graft-versus-host disease (GvHD), asthma, adult respiratory distress syndrome (ARDS), septic shock, ulcerative colitis, Sjorgen's syndrome, airway inflammation, systemic lupus erythematosus (SLE), uveitis, pyoderma gangrenosum, giant cell arteritis, Schnitzler syndrome, non-infectious scleritis, diabetes, contact hypersensitivity, multiple sclerosis and atherosclerosis.

In any aspect, configuration, concept or embodiment, the human is suffering from or at risk of a hOX40L-mediated disease or condition selected from an autoimmune disease or condition, a systemic inflammatory disease or condition, or transplant rejection; for example inflammatory bowel disease (IBD), Crohn's disease, rheumatoid arthritis, transplant rejection, allogeneic transplant rejection, graft-versus-host disease (GvHD), ulcerative colitis, systemic lupus erythematosus (SLE), diabetes, uveitis, ankylosing spondylitis, contact hypersensitivity, multiple sclerosis and atherosclerosis, in particular GvHD.

In an example, the disease or condition is an OX40L-mediated disease or condition disclosed in U.S. Pat. No. 7,812,133 or EP1791869.

In an example, the disease or condition is an inflammatory or autoimmune disease or condition. In an example, the disease or condition is transplant rejection.

As used herein, inflammatory disease or condition refers to pathological states resulting in inflammation, for example caused by neutrophil chemotaxis. Examples of such disorders include inflammatory skin diseases including psoriasis; responses associated with inflammatory bowel disease (such as Crohn's disease and ulcerative colitis); ischemic reperfusion; adult respiratory distress syndrome; dermatitis; meningitis; encephalitis; uveitis; autoimmune diseases such as rheumatoid arthritis, Sjorgen's syndrome, vasculitis; diseases involving leukocyte diapedesis; central nervous system (CNS) inflammatory disorder, multiple organ injury syndrome secondary to septicaemia or trauma; alcoholic hepatitis, bacterial pneumonia, antigen-antibody complex mediated diseases; inflammations of the lung, including pleurisy, alveolitis, vasculitis, pneumonia, chronic bronchitis, bronchiectasis, and cystic fibrosis; etc. The preferred indications are bacterial pneumonia and inflammatory bowel disease such as ulcerative colitis. The invention is thus in an example provided for treating or preventing any one or more of such conditions.

In an example, the disease or condition is cancer.

In an example, the disease is uveitis, such as systemic uveitis or autoimmune/non-infectious uveitis.

73. An antibody or a fragment thereof, that specifically binds to hOX40L and competes for binding to said hOX40L with the antibody 02D10, wherein the antibody or fragment comprises a VH domain which comprises a HCDR3 comprising the motif VRGXYYY, wherein X is any amino acid.

The features of the antibodies of any of the aspects, configurations, concepts, examples or embodiments described herein optionally apply mutatis mutandis to these antibodies, e.g the antibody may be a human antibody or chimeric antibody having functional features as described herein. Competition may be determined as described in any aspect, embodiment, example, concept or configuration described herein, e.g. as determined by SPR, ELISA, HTRF or FACS.

In one embodiment, the antibody or fragment competes with the variable regions of 02D10 (e.g. competes with an antibody comprising the heavy chain variable region of SEQ ID No: 34 and the light chain variable region of SEQ ID No:48). In another embodiment, the antibody or fragment competes with 02D10 IgG4-PE having a heavy chain amino acid sequence of SEQ ID No:62 and a light chain amino acid sequence of SEQ ID No:64.

In another embodiment, the antibody or fragment additionally or alternatively competes with 10A7. In one embodiment, the antibody or fragment competes with the variable regions of 10A7 (e.g. competes with an antibody comprising the heavy chain variable region of SEQ ID No: 2 and the light chain variable region of SEQ ID No: 16). In another embodiment, the antibody or fragment competes with 02D10 IgG4-PE having a heavy chain amino acid sequence of SEQ ID No:30 and a light chain amino acid sequence of SEQ ID No:32.

In one embodiment, the amino acid is any naturally-occurring amino acid.

74. The antibody or fragment according to aspect 73, where X is a neutral amino acid, optionally P or G.

In an embodiment, X is P or G. In an embodiment, X is selected from P, N, A or G. In another embodiment, X is selected from P, G or N. In another embodiment, X is selected from P, G or A.

75. An antibody or a fragment thereof, optionally according to aspect 73 or 74, that specifically binds to hOX40L and competes for binding to said hOX40L with the antibody 02D10, wherein the antibody or fragment comprises a VH domain which comprises the HCDR3 sequence of SEQ ID NO:40 or 46 or the HCDR3 sequence of SEQ ID NO:40 or 46 comprising less than 5 amino acid substitutions.

The features of the antibodies of any of the aspects, configurations, concepts, examples or embodiments described herein optionally apply mutatis mutandis to these antibodies, e.g the antibody may be a human antibody or chimeric antibody having functional features as described herein. Competition may be determined as described in any aspect, embodiment, concept, example or configuration described herein, e.g. as determined by SPR, ELISA, HTRF or FACS.

In an embodiment, the HCDR3 sequence of SEQ ID NO:40 or 46 comprises less than 4 amino acid substitutions (i.e. 3 or fewer). In an embodiment, the HCDR3 sequence of SEQ ID NO:40 or 46 comprises less than 3 amino acid substitutions (i.e. 2 or 1 substitutions). In an embodiment, the HCDR3 sequence of SEQ ID NO:40 or 46 comprises less than 2 amino acid substitutions (i.e. one substitution).

In one embodiment, the antibody or fragment competes with the variable regions of 02D10 (e.g. competes with an antibody comprising the heavy chain variable region of SEQ ID No: 34 and the light chain variable region of SEQ ID No:48). In another embodiment, the antibody or fragment competes with 02D10 IgG4-PE having a heavy chain amino acid sequence of SEQ ID No:62 and a light chain amino acid sequence of SEQ ID No:64.

In another embodiment, the antibody or fragment additionally or alternatively competes with 10A7. In one embodiment, the antibody or fragment competes with the variable regions of 10A7 (e.g. competes with an antibody comprising the heavy chain variable region of SEQ ID No: 2 and the light chain variable region of SEQ ID No: 16). In another embodiment, the antibody or fragment competes with 02D10 IgG4-PE having a heavy chain amino acid sequence of SEQ ID No:30 and a light chain amino acid sequence of SEQ ID No:32.

76. An antibody or fragment according to any one of aspects 73 to 75, the VH domain comprising a HCDR3 of from 16 to 27 amino acids and which is derived from the recombination of a human VH gene segment, a human D gene segment and a human JH gene segment, wherein the human JH gene segment is IGHJ6 (e.g. IGHJ6*02).

In an embodiment, the human JH gene segment is selected from IGHJ6*01, IGHJ6*02, IGHJ6*03 and IGHJ6*04. In another embodiment, the human JH gene segment is selected from IGHJ6*01, IGHJ6*02 and IGHJ6*04. In another embodiment, the JH gene segment is IGHJ6*02.

In a further embodiment, the human VH gene segment is IGHV3-23, for example selected from IGHV3-23*01, IGHV3-23*02, IGHV3-23*03, IGHV3-23*04 or IGHV3-23*05. In another embodiment, the human VH gene segment is IGHV3-23*01 or IGHV3-23*04, in particular IGHV3-23*04.

In a further embodiment, the human DH gene segment is IGHD3-10, for example selected from IGHD3-10*01 or IGHD3-10*02. In one embodiment, the human DH gene segment is IGHD3-10*01. In one embodiment, the human DH gene segment is IGHD3-10*02.

77. The antibody or fragment according to any one of aspects 73 to 76, the VH domain comprising the HCDR1 sequence of SEQ ID NO:36 or 42 or the HCDR1 sequence of SEQ ID NO:36 or 42 comprising less than 4 amino acid substitutions.

In an embodiment, the HCDR1 sequence of SEQ ID NO:36 or 42 comprises less than 3 amino acid substitutions (i.e. 2 or 1 substitutions). In an embodiment, the HCDR1 sequence of SEQ ID NO:36 or 42 comprises less than 2 amino acid substitutions (i.e. one substitution).

78. The antibody or fragment according to any one of aspects 73 to 77, the VH domain comprising the HCDR2 sequence of SEQ ID NO:38 or 44, or the HCDR2 sequence of SEQ ID NO:38 or 44 comprising less than 5 amino acid substitutions.

In an embodiment, the HCDR2 sequence of SEQ ID NO:38 or 44 comprises less than 4 amino acid substitutions (i.e. 3 or fewer). In an embodiment, the HCDR2 sequence of SEQ ID NO:38 or 44 comprises less than 3 amino acid substitutions (i.e. 2 or 1 substitutions). In an embodiment, the HCDR2 sequence of SEQ ID NO:38 or 44 comprises less than 2 amino acid substitutions (i.e. one substitution).

79. The antibody or fragment according to any one of aspects 73 to 78, the VH domain comprising an amino acid sequence of SEQ ID NO: 34, or a heavy chain variable domain amino acid sequence that is at least 80% (e.g. at least 85%) identical to SEQ ID NO:34.

In an embodiment, the heavy chain variable domain amino acid sequence is at least 85%, at least 90%, at least 95%, least 96% at least 97% at least 98% or at least 99% identical to SEQ ID NO:34.

80. The antibody or fragment according to any one of aspects 73 to 79 comprising first and second copies of said VH domain.

81. The antibody or fragment according to any one of aspects 73 to 80, comprising a VL domain which comprises the LCDR1 sequence of SEQ ID NO:54 or 60, or the LCRD3 sequence of SEQ ID NO:54 or 60 comprising less than 5 amino acid substitutions.

In an embodiment, the LCRD3 sequence of SEQ ID NO:54 or 60 comprises less than 4 amino acid substitutions (i.e. 3 or fewer). In an embodiment, the LCRD3 sequence of SEQ ID NO:54 or 60 comprises less than 3 amino acid substitutions (i.e. 2 or 1 substitutions). In an embodiment, the LCRD3 sequence of SEQ ID NO:54 or 60 comprises less than 2 amino acid substitutions (i.e. one substitution).

82. The antibody or fragment according to any one of aspects 73 to 81, comprising a or said VL domain, which VL domain comprises the LCDR2 sequence of SEQ ID NO:52 or 58, or the LCRD2 sequence of SEQ ID NO:52 or 58 comprising less than 2 amino acid substitutions.

83. The antibody or fragment according to any one of aspects 73 to 82, comprising a or said VL domain, which VL domain comprises the LCDR1 sequence of SEQ ID NO:54 or 60, or the LCRD1 sequence of SEQ ID NO:54 or 60 comprising less than 4 amino acid substitutions.

In an embodiment, the LCDR1 sequence of SEQ ID NO:54 or 60 comprises less than 3 amino acid substitutions (i.e. 2 or 1 substitutions). In an embodiment, the LCDR1 sequence of SEQ ID NO:54 or 60 comprises less than 2 amino acid substitutions (i.e. one substitution).

84. The antibody or fragment according to any one of aspects 73 to 83, comprising a or said VL domain, which VL domain comprises an amino acid sequence of SEQ ID NOs: 48, or a light chain variable domain amino acid sequence that is at least 80% (e.g. at least 85%) identical to SEQ ID NO:48.

In an embodiment, the light chain variable domain amino acid sequence is at least 85%, at least 90%, at least 95%, least 96% at least 97% at least 98% or at least 99% identical to SEQ ID NO:48.

85. The antibody or fragment according to any one of aspects 81 to 84, comprising first and second copies of said VL domain.

86. The antibody or fragment according to any one of aspects 81 to 85, wherein the antibody or fragment comprises a kappa light chain.

In another embodiment, the VL domain is a kappa VL domain. In an embodiment, the kappa VL domain is derived from the recombination of a human VL gene segment, and a human JL gene segment, wherein the human VL gene segment is IGKV1D-39. In another embodiment, the VL gene segment is IGKV1D-39*01.

In a further embodiment, the human JL gene segment is IGKJ1 or IGKJ3. In another embodiment, the JL gene segment is IGKJ1*01. In another embodiment, the JL gene segment is IGKJ3*01.

87. The antibody or fragment according to any one of aspects 75 to 86 wherein the amino acid substitutions are conservative amino acid substitutions, optionally wherein the conservative substitutions are from one of six groups (each group containing amino acids that are conservative substitutions for one another) selected from:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W)

In an embodiment, the conservative amino acid substitutions are as described herein. For example, the substitution may be of Y with F, T with S or K, P with A, E with D or Q, N with D or G, R with K, G with N or A, T with S or K, D with N or E, I with L or V, F with Y, S with T or A, R with K, G with N or A, K with R, A with S, K or P. In another embodiment, the conservative amino acid substitutions may be wherein Y is substituted with F, T with A or S, I with L or V, W with Y, M with L, N with D, G with A, T with A or S, D with N, I with L or V, F with Y or L, S with A or T and A with S, G, T or V.

88. The antibody or fragment according to any one of aspects 73 to 87, wherein the antibody or fragment comprises a constant region, e.g. an IgG4 constant region, optionally wherein the constant region is IgG4-PE (Seq ID No: 128).

In another example of any aspect herein, the antibody of fragment comprises a human gamma 4 constant region. In another embodiment, the heavy chain constant region does not bind Fc-γ receptors, and e.g. comprises a Leu235Glu mutation (i.e. where the wild type leucine residue is mutated to a glutamic acid residue). In another embodiment, the heavy chain constant region comprises a Ser228Pro mutation to increase stability.

89. The antibody according to any one of aspects 73 to 88, wherein the antibody comprises a heavy chain and a light chain, the heavy chain amino acid sequence consisting of the sequence of SEQ ID No:62 and the light chain amino acid sequence consisting of the sequence of SEQ ID No:64.

90. An antibody or fragment as defined in any one of aspects 73 to 89, 98, 99, 101 or 102 for use in treating or preventing a hOX40L-mediated disease or condition selected from an autoimmune disease or condition, a systemic inflammatory disease or condition, or transplant rejection; for example inflammatory bowel disease (IBD), Crohn's disease, rheumatoid arthritis, transplant rejection, allogeneic transplant rejection, graft-versus-host disease (GvHD), ulcerative colitis, systemic lupus erythematosus (SLE), diabetes, uveitis, ankylosing spondylitis, contact hypersensitivity, multiple sclerosis or atherosclerosis, in particular GvHD.

The features of the antibodies, and the hOX40L-mediated disease of any of the aspects, configurations, concepts, examples or embodiments as described herein optionally apply mutatis mutandis to this use. Any of the compositions, dosing schedules or modes of administration as described in any aspect, configuration, concept, example or embodiment herein optionally apply mutatis mutandis to this use.

91. Use of an antibody or fragment as defined in any one of aspects 73 to 89, 98, 99, 101 or 102 in the manufacture of a medicament for administration to a human for treating or preventing a hOX40L mediated disease or condition in the human selected from an autoimmune disease or condition, a systemic inflammatory disease or condition, or transplant/host rejection; for example inflammatory bowel disease (IBD), Crohn's disease, rheumatoid arthritis, transplant rejection, allogeneic transplant rejection, graft-versus-host disease (GvHD), ulcerative colitis, systemic lupus erythematosus (SLE), diabetes, uveitis, ankylosing spondylitis, contact hypersensitivity, multiple sclerosis or atherosclerosis, in particular GvHD.

The features of the antibodies, and the hOX40L-mediated disease of any of the aspects, configurations, concepts, examples or embodiments as described herein optionally apply mutatis mutandis to this use. Any of the compositions, dosing schedules or modes of administration as described in any aspect, configuration, concept, example or embodiment herein optionally apply mutatis mutandis to this use.

92. A method of treating or preventing a hOX40L mediated disease or condition selected from an autoimmune disease or condition, a systemic inflammatory disease or condition, or transplant rejection; for example inflammatory bowel disease (IBD), Crohn's disease, rheumatoid arthritis, transplant rejection, allogeneic transplant rejection, graft-versus-host disease (GvHD), ulcerative colitis, systemic lupus erythematosus (SLE), diabetes, uveitis, ankylosing spondylitis, contact hypersensitivity, multiple sclerosis or atherosclerosis, in particular GvHD in a human, comprising administering to said human a therapeutically effective amount of an antibody or fragment as defined in any one of aspects 73 to 89, 98, 99, 101 or 102, wherein the hOX40L mediated disease or condition is thereby treated or prevented.

The features of the antibodies, and the hOX40L-mediated disease of any of the aspects, configurations, concepts, examples or embodiments as described herein optionally apply mutatis mutandis to this method. Any of the compositions, dosing schedules or modes of administration as described in any aspect, configuration, concept, example or embodiment herein optionally apply mutatis mutandis to this method.

93. The antibody or fragment according to aspect 90, the use according to aspect 91, or the method according to aspect 92, wherein the hOX40L-mediated disease or condition is GvHD.

In another embodiment, the antibody or fragment is capable of treating or preventing GvHD.

94. The antibody or fragment, the use or the method according to any one of aspects 90 to 93, wherein the antibody is administered prophylactically.

In an embodiment, the prophylaxis prevents the onset of the disease or condition or of the symptoms of the disease or condition. In one embodiment, the prophylactic treatment prevents the worsening, or onset, of the disease or condition. In one embodiment, the prophylactic treatment prevents the worsening of the disease or condition.

In another embodiment, said antibody is administered intravenously. In another embodiment, said antibody is administered at a dose of about 5-10 mg/kg (e.g. at about 8 mg/kg). In another embodiment, said antibody is administered at a dose selected from about 0.1 mg/kg, about 0.5 mg/kg, about 1 mg/kg, 3 mg/kg, 5 mg/kg, about 10 mg/kg, about 15 mg/kg, about 20 mg/kg, about 25 mg/kg, about 30 mg/kg, about 40 mg/kg, about 50 mg/kg, about 60 mg/kg, about 70 mg/kg, about 80 mg/kg about 90 mg/kg or about 100 mg/kg, in particular about 1 mg/kg, or about 3 mg/kg.

In another embodiment, said antibody is administered 1-4 days before transplant, e.g. 1-3 days before transplant or 1-2 days before transplant. In another embodiment, said antibody is administered weekly, bi-weekly or monthly following transplant, e.g. bi-weekly. In a further embodiment, said antibody is administered intravenously prophylactically 1-3 days before transplant at a dose of about 5-10 mg/kg (e.g. about 8 mg/kg) and then intravenously, bi-weekly at a dose of about 5-10 mg/kg (e.g. about 8 mg/kg).

In another embodiment, the patient is monitored periodically post-transplant, for the presence of a biomarker predictive for the development of GvHD (e.g. acute GvHD), and the anti-OX40L antibody of the invention is administered once the biomarker levels are such that the patient is determined to be at risk of developing GvHD (e.g. acute GvHD). This strategy would avoid unnecessary dosing of drug and unnecessary suppression of the immune system. Examples of biomarkers which may be useful as predictive biomarkers of acute GvHD may be those identified in Levine et al., "*A prognostic score for acute graft-versus-host disease based on biomarkers: a multicentre study*", Lancet Haematol 2015; 2:e21-29. These biomarkers include, but are not limited to TNFR1, ST-2, elafin and IL2Rα and Reg3α.

95. A human antibody or fragment thereof comprising a HCDR3 of from 16 to 27 amino acids and derived from the recombination of a human VH gene segment, a human D gene segment and a human JH gene segment, wherein the human JH gene segment is IGHJ6 (e.g. IGHJ6*02), which specifically binds to hOX40L for treating or preventing a hOX40L-mediated disease or condition selected from an autoimmune disease or condition, a systemic inflammatory disease or condition, or transplant rejection; for example inflammatory bowel disease (IBD), Crohn's disease, rheumatoid arthritis, transplant rejection, allogeneic transplant rejection, graft-versus-host disease (GvHD), ulcerative colitis, systemic lupus erythematosus (SLE), diabetes, uveitis, ankylosing spondylitis, contact hypersensitivity, multiple sclerosis or atherosclerosis, in particular GvHD (e.g. wherein the antibody is for the prevention of GvHD).

The features of the antibodies, and the hOX40L-mediated disease of any of the aspects, configurations, concepts, examples or embodiments optionally apply mutatis mutandis to this use. Any of the compositions, dosing schedules or modes of administration as described in any aspect, configuration, concept, example or embodiment herein optionally apply mutatis mutandis to this use.

96. Use of a human antibody or fragment thereof comprising a HCDR3 of from 16 to 27 amino acids and derived from the recombination of a human VH gene segment, a human D gene segment and a human JH gene segment, wherein the human JH gene segment is IGHJ6 (e.g. IGHJ6*02), which specifically binds to hOX40L in the manufacture of a medicament for administration to a human for treating or preventing a hOX40L mediated disease or condition in the human selected from an autoimmune disease or condition, a systemic inflammatory disease or condition, or transplant rejection; for example inflammatory bowel disease (IBD), Crohn's disease, rheumatoid arthritis, transplant rejection, allogeneic transplant rejection, graft-versus-host disease (GvHD), ulcerative colitis, systemic lupus erythematosus (SLE), diabetes, uveitis, ankylosing spondylitis, contact hypersensitivity, multiple sclerosis or atherosclerosis, in particular GvHD.

The features of the antibodies, and the hOX40L-mediated disease of any of the aspects, configurations, concepts, examples or embodiments optionally apply mutatis mutandis to this use. Any of the compositions, dosing schedules or modes of administration as described in any aspect, configuration, concept, example or embodiment herein optionally apply mutatis mutandis to this use.

97. A method of treating or preventing a hOX40L mediated disease or condition selected from an autoimmune disease or condition, a systemic inflammatory disease or condition, or transplant rejection; for example inflammatory bowel disease (IBD), Crohn's disease, rheumatoid arthritis, transplant rejection, allogeneic transplant rejection, graft-versus-host disease (GvHD), ulcerative colitis, systemic lupus erythematosus (SLE), diabetes, uveitis, ankylosing spondylitis, contact hypersensitivity, multiple sclerosis or atherosclerosis, in particular GvHD in a human, comprising administering to said human a therapeutically effective amount of a human antibody or fragment thereof comprising a HCDR3 of from 16 to 27 amino acids and derived from the recombination of a human VH gene segment, a human D gene segment and a human JH gene segment, wherein the human JH gene segment is IGHJ6 (e.g. IGHJ6*02), which specifically binds to hOX40L, wherein the hOX40L mediated disease or condition is thereby treated or prevented.

The features of the antibodies, and the hOX40L-mediated disease of any of the aspects, configurations, concepts, examples or embodiments optionally apply mutatis mutandis to this method. Any of the compositions, dosing schedules or modes of administration as described in any aspect, configuration, concept, example or embodiment herein optionally apply mutatis mutandis to this method.

In an embodiment of any one of aspects 95 to 97, the human JH gene segment is selected from IGHJ6*01, IGHJ6*02, IGHJ6*03 and IGHJ6*04. In another embodiment of any one of aspects 95 to 97, the human JH gene segment is selected from IGHJ6*01, IGHJ6*02 and IGHJ6*04. In another embodiment of any one of aspects 95 to 97, the JH gene segment is IGHJ6*02.

In a further embodiment of any one of aspects 95 to 97, the human VH gene segment is IGHV3-23, for example selected from IGHV3-23*01, IGHV3-23*02, IGHV3-23*03, IGHV3-23*04 or IGHV3-23*05. In another embodiment of any one of aspects 95 to 97 the human VH gene segment is IGHV3-23*01 or IGHV3-23*04, in particular IGHV3-23*04.

In a further embodiment of any one of aspects 95 to 97, the human DH gene segment is IGHD3-10, for example selected from IGHD3-10*01 or IGHD3-10*02. In one embodiment of any one of aspects 95 to 97, the human DH gene segment is IGHD3-10*01. In one embodiment of any one of aspects 95 to 97, the human DH gene segment is IGHD3-10*02.

In an embodiment of any one of aspects 90 to 97, the antibody is capable of treating or preventing GvHD. In another embodiment of any one of aspects 90 to 97, the antibody or fragment is used for the treatment or prevention of a disease other than GvD, but the antibody or fragment is capable of treating or preventing GvHD.

98. The antibody or fragment according to aspect 86, or the antibody or fragment according to aspect 95, the use according to aspect 96, or the method according to aspect 97, wherein the antibody or fragment comprises a kappa light chain, e.g. wherein the VL domain of the light chain is derived from the recombination of a human VL gene segment, and a human JL gene segment, wherein the human VL gene segment is IGKV1D-39 (e.g. IGKV1D-39*01), and optionally the human JL gene segment is IGKJ1 (e.g. IGKJ1*01) or IGKJ3 (e.g. IGKJ3*01).

In another embodiment, the VL domain is a kappa VL domain. In an embodiment, the kappa VL domain is derived from the recombination of a human VL gene segment, and a human JL gene segment, wherein the human VL gene segment is IGKV1D-39. In another embodiment, the VL gene segment is IGKV1D-39*01.

In a further embodiment, the human JL gene segment is IGKJ1. In another embodiment, the JL gene segment is IGKJ1*01. In a further embodiment, the human JL gene segment is IGKJ3. In another embodiment, the JL gene segment is IGKJ3*01

99. The antibody or fragment according to any one of aspects 73 to 89, 98, 101 or 102, or the antibody or fragment use or method according to any one of aspects 90 to 98, wherein the antibody or fragment enables greater than 80% stem cell donor chimerism by day 12 in a Rhesus macaque model of haploidentical hematopoietic stem cell transplantation, optionally wherein the antibody is for the prevention of GvHD.

In another aspect, there is provided an antibody or fragment, use or method according to any one of aspects 95 to 98, wherein the antibody or fragment is for treating or preventing transplant rejection (e.g. GvHD) in a human by enabling greater than 80% stem cell donor chimerism by day 12 in said human following donor human hematopoietic stem cell transplantation.

In another embodiment, there is provided an antibody or fragment according to any one of aspects 73 to 89, 98, 101 or 102, wherein the antibody or fragment enables greater than 80% stem cell donor chimerism by day 12 in a Rhesus macaque model of haploidentical hematopoietic stem cell transplantation.

In one embodiment, the chimerism is T cell (CD3$^+$/CD20$^-$) chimerism. In another embodiment, the chimerism is peripheral blood chimerism. In another embodiment, the chimerism is peripheral blood or T cell (CD3$^+$/CD20$^-$) chimerism.

In one embodiment, the stem cell donor chimerism (e.g. the peripheral blood or T cell (CD3$^+$/CD20$^-$) chimerism) is determined using divergent donor- and recipient-specific MHC-linked microsatellite markers, by comparing peak heights of the donor- and recipient-specific amplicons. In another embodiment, stem cell donor chimerism is determined as described in Kean, L S, et al., "*Induction of chimerism in rhesus macaques through stem cell transplant and costimulation blockade-based immunosuppression*", Am J Transplant. 2007 February; 7(2):320-35. In another embodiment, stem cell donor chimerism is determined as described in Example 7.

In one embodiment, the Rhesus macaque model of haploidentical haematopoietic stem cell is performed by the transplant (HSCT) recipient animals undergoing a conditioning procedure together with anti-OX40L antibody administration, followed by infusion of a peripheral blood product isolated from a half-sibling donor animal, following which animals continue to receive weekly doses of the anti-OX40L antibody of the invention, and blood samples are taken and analysed for chimerism.

In another embodiment, in the HSCT model, recipient animals receive a conditioning radiation dose of 1020 cGy in 4 dose fractions over 2 days (experimental Day−2 and Day−1) to ablate the host haematopoietic system before intravenous administration of an anti-OX40L antibody of the invention (Day−2, with subsequent intravenous doses on Days 5, 12, 19, 26, 33, 40, 47) and transplant of white blood cell- and stem cell-enriched peripheral blood from an MHC half-matched (half-sibling) donor animal to reconstitute the recipient's immune system, together with provision of continuous supportive care, blood sampling and monitoring for signs of GVHD.

In one embodiment, the antibody or fragment, use or method is for the prevention of GvHD.

In an embodiment, the anti-hOX40L antibody of the invention is administered prophylactically. In one embodiment, the prophylactic treatment prevents the worsening or onset of the disease or condition.

In another embodiment, said antibody is administered intravenously. In another embodiment, said antibody is administered at a dose of about 5-10 mg/kg (e.g. at about 8 mg/kg). In another embodiment, said antibody is administered intravenously. In another embodiment, said antibody is administered at a dose of about 5-10 mg/kg (e.g. at about 8 mg/kg). In another embodiment, said antibody is administered at a dose selected from about 0.1 mg/kg, about 0.5 mg/kg, about 1 mg/kg, 3 mg/kg, 5 mg/kg, about 10 mg/kg, about 15 mg/kg, about 20 mg/kg, about 25 mg/kg, about 30 mg/kg, about 40 mg/kg, about 50 mg/kg, about 60 mg/kg, about 70 mg/kg, about 80 mg/kg about 90 mg/kg or about 100 mg/kg, in particular about 1 mg/kg, or about 3 mg/kg.

In another embodiment, said antibody is administered 1-4 days before transplant, e.g. 1-3 days before transplant or 1-2 days before transplant. In another embodiment, said antibody is administered weekly, bi-weekly or monthly following transplant, e.g. bi-weekly. In a further embodiment, said antibody is administered intravenously prophylactically 1-3 days before transplant at a dose of about 5-10 mg/kg (e.g. about 8 mg/kg) and then intravenously, bi-weekly at a dose of about 5-10 mg/kg (e.g. about 8 mg/kg).

In another embodiment, the patient is monitored periodically post-transplant, for the presence of a biomarker predictive for the development of GvHD (e.g. acute GvHD), and the anti-OX40L antibody of the invention is administered once the biomarker levels are such that the patient is determined to be at risk of developing GvHD (e.g. acute GvHD). This strategy would avoid unnecessary dosing of drug and unnecessary suppression of the immune system. Examples of biomarkers which may be useful as predictive biomarkers of acute GvHD may be those identified in Levine et al., "A prognostic score for acute graft-versus-host disease based on biomarkers: a multicentre study", Lancet Haematol 2015; 2:e21-29. These biomarkers include, but are not limited to TNFR1, ST-2, elafin and IL2Rα and Reg3α.

In a further embodiment, the HSCT model is conducted as described in Miller, Weston P., et al. "*GVHD after haploidentical transplantation: a novel, MHC-defined rhesus macaque model identifies CD28⁻ CD8⁺ T cells as a reservoir of breakthrough T-cell proliferation during costimulation blockade and sirolimus-based immunosuppression.*" Blood, 116, 24(2010):5403-5418. In a further embodiment, the HSCT model is carried out as described in Example 7.

100. The antibody or fragment, use or method according to any one of aspects 95 to 99, wherein the antibody is as defined in any one of aspects 73 to 89, 98, 99, 101 or 102.
101. The antibody or fragment according to any one of aspects 73 to 89, 98, 99 or 102, or the antibody or fragment, use or method according to any one of aspects 90 to 100, wherein the antibody or fragment expresses as a stably transfected pool in Lonza GS-Xceed™ at level greater than 1.5 g/L in a fed batch overgrow culture using Lonza version 8 feed system with an overgrow period of 14 days.

In one embodiment, the expression level is greater than 1.0 g/L, greater than 1.1 g/L, greater than 1.2 g/L, greater than 1.3 g/L or greater than 1.4 g/L.
102. An antibody or fragment according to any one of aspects 73 to 89, 98, 99 or 101, or the antibody or fragment, use or method according to any one of aspects 90 to 101, wherein the antibody or fragment maintains a naïve population of CD4⁺ T-cells of >20% of total CD4⁺ T cell population at day 12 in a Rhesus macaque model of haploidentical hematopoietic stem cell transplantation.

In another aspect, there is provided an antibody or fragment according to any one of aspects 73 to 89, 98, 99 or 101, or an antibody or fragment, use or method according to any one of aspects 90 to 101, wherein the antibody or fragment is for treating or preventing transplant rejection in a human by maintaining a naïve population of donor CD4⁺ T-cells of >20% of total CD4⁺ T cell population at day 12 in said human following donor human hematopoietic stem cell transplantation In one embodiment, the HSCT model is as described in any embodiment contemplated hereinabove, e.g. as described in connection with aspect 99.

In another embodiment, the naïve population is measured by evaluating the relative proportion of specific T cell phenotypes using flow cytometry where cell subsets are identified by labelling with fluorescent antibody probes and whereby naïve CD4 or CD8 T-cells are labelled CD4⁺/CD28⁺/CD95⁻ or CD8⁺/CD28⁺/CD95⁻, respectively, central memory CD4 or CD8 T-cells are labelled CD4⁺/CD28⁺/CD95⁺ or CD8⁺/CD28⁺/CD95⁺, respectively, and effector memory CD4 or CD8 T-cells are labelled CD4⁺/CD28⁻/CD95⁺ or CD8⁺/CD28⁻/CD95⁺, respectively.

103. The antibody or fragment, use or the method according to any one of aspects 90 to 102, further comprising administering to the human a further therapeutic agent, optionally wherein the further therapeutic agent is independently selected from the group consisting of rapamycin (sirolimus), tacrolimus, ciclosporin, corticosteroids (e.g. methylprednisolone), methotrexate, mycophenolate mofetil, anti-CD28 antibodies, anti-IL12/IL-23 antibodies (e.g. ustekinumab), anti-CD20 antibodies (e.g. rituximab), anti-CD30 antibodies (e.g. brentuximab), CTLA4-Fc molecules (e.g. abatacept), CCR5 receptor antagonists (e.g. maraviroc), anti-CD40L antibodies, anti-VLA4 antibodies (e.g. natalizumab), anti-LFA1 antibodies, fludarabine, anti-CD52 antibodies (e.g. alemtuzumab), anti-CD45 antibodies, cyclophosphamide, anti-thymocyte globulins, anti-complement C5 antibodies (e.g. eculizumab), anti-a4b7 integrin antibodies (e.g. vedolizumab), anti-IL6 antibodies (e.g. tocilizumab), anti-IL2R antibodies (e.g. basilixumab), anti-CD25 antibodies (e.g. daclizumab), anti-TNFa/TNFa-Fc molecules (e.g. etanercept, adalimumab, infliximab, golimumab or certolizumab pegol) and Vorinostat, in particular rapamycin (sirolimus), tacrolimus, ciclosporin, corticosteroids (e.g. methylprednisolone), methotrexate, mycophenolate mofetil, anti-CD28 antibodies, CTLA4-Fc molecules (e.g. abatacept), anti-CD40L antibodies, anti-LFA1 antibodies, anti-CD52 antibodies (e.g. alemtuzumab), cyclophosphamide and anti-thymocyte globulins.

In one embodiment, the further therapeutic agent is an anti-inflammatory drug. In another embodiment, the anti-inflammatory drug is independently selected from the group consisting of corticosteroids (e.g. methylprednisolone), anti-IL12/IL-23 antibodies (e.g. ustckinumab), anti-VLA4 antibodies (e.g. natalizumab), anti-LFA1 antibodies, anti-complement C5 antibodies (e.g. eculizumab), anti-a4b7 integrin antibodies (e.g. vedolizumab), anti-IL6 antibodies (e.g. tocilizunmab), anti-IL2R antibodies (e.g. basilixumab) or anti-TNFa antibodics/TNFa-Fc molecules (e.g. ctanercept, adalimumab, infliximab, golimumab, certolizumab pegol). In an example, the anti-inflammatory drug is independently selected from the group consisting of corticosteroids (e.g. methylprednisolone) and anti-LFA1 antibodies.

In one embodiment, the combination comprises an anti-OX40L antibody of the invention and further therapeutic agents independently selected from the group consisting of calcineurin inhibitors (e.g. tacrolimus, ciclosporin), mTOR inhibitors (e.g. rapamycin (sirolimus)), and antiproliferative agents (e.g. mycophenolate mofetil, cyclophosphamide).

In one embodiment, the combination comprises an anti-OX40L antibody of the invention and further therapeutic agents independently selected from the group consisting of immunosuppressants that modulate IL-2 signalling (e.g. tacrolimus, ciclosporin, rapamycin (sirolimus), and anti-CD25 antibodies (e.g. basilixumab, daclizumab).

In one embodiment, the combination comprises an anti-OX40L antibody of the invention and rapamycin (sirolimus). In another embodiment, the combination comprises an anti-OX40L antibody of the invention and tacrolimus. In another embodiment, the combination comprises an anti-OX40L antibody of the invention and tacrolimus and methotrexate. In another embodiment, the combination comprises an anti-OX40L antibody of the invention and ciclosporin. In another embodiment, the combination comprises an anti-OX40L antibody of the invention and ciclosporin and methotrexate. In another embodiment, the combination comprises an anti-OX40L antibody of the invention and cyclophosphamide. In another embodiment, the combination comprises an anti-OX40L antibody of the invention and mycophenolate mofetil.

104. The antibody or fragment, use or the method according to aspect 103, wherein the further therapeutic agent is administered sequentially or simultaneously with the anti-hOX40L antibody or fragment.

105. A pharmaceutical composition comprising an antibody of fragment as defined in any one of aspects 73 to 89, 98, 99, 101 or 102 and a pharmaceutically acceptable excipient, diluent or carrier and optionally further comprising a further therapeutic agent independently selected from the group consisting of rapamycin (sirolimus), tacrolimus, ciclosporin, corticosteroids (e.g. methylprednisolone), methotrexate, mycophenolate mofetil, anti-CD28 antibodies, anti-IL12/IL-23 antibodies (e.g. ustekinumab), anti-CD20 antibodies (e.g. rituximab), anti-CD30 antibodies (e.g. brentuximab), CTLA4-Fc molecules (e.g. abatacept), CCR5 receptor antagonists (e.g. maraviroc), anti-CD40L antibodies, anti-VLA4 antibodies (e.g. natalizumab), anti-LFA1 antibodies, fludarabine, anti-CD52 antibodies (e.g. alemtuzumab), anti-CD45 antibodies, cyclophosphamide, anti-thymocyte globulins, anti-complement C5 antibodies (e.g. eculizumab), anti-a4b7 integrin antibodies (e.g. vedolizumab), anti-IL6 antibodies (e.g. tocilizumab), anti-IL2R antibodies (e.g. basilixumab), anti-CD25 antibodies (e.g. daclizumab), anti-TNFa/TNFa-Fc molecules (e.g. etanercept, adalimumab, infliximab, golimumab or certolizumab pegol) and Vorinostat, in particular rapamycin (sirolimus), tacrolimus, ciclosporin, corticosteroids (e.g. methylprednisolone), methotroxate, mycophenolate mofetil, anti-CD28 antibodies, CTLA4-Fc molecules (e.g. abatacept), anti-CD40L antibodies, anti-LFA1 antibodies, anti-CD52 antibodies (e.g. alemtuzumab), cyclophosphamide and anti-thymocyte globulins.

The pharmaceutically acceptable excipients, diluents or carriers as described herein apply mutatis mutandis to these compositions.

In one embodiment, the further therapeutic agent is an anti-inflammatory drug. In another embodiment, the anti-inflammatory drug is independently selected from the group consisting of corticosteroids (e.g. methylprednisolone), anti-IL12/IL-23 antibodies (e.g. ustekinumab), anti-VLA4 antibodies (e.g. natalizumab), anti-LFA1 antibodies, anti-complement C5 antibodies (e.g. eculizumab), anti-a4b7 integrin antibodies (e.g. vedolizumab), anti-IL6 antibodies (e.g. tocilizumab), anti-IL2R antibodies (e.g. basilixumab) or anti-TNFa antibodies/TNFa-Fc molecules (e.g. etanercept, adalimumab, infliximab, golimumab, certolizumab pegol). In an example, the anti-inflammatory drug is independently selected from the group consisting of corticosteroids (e.g. methylprednisolone) and anti-LFA1 antibodies.

In one embodiment, the further therapeutic agent is independently selected from the group consisting of calcineurin inhibitors (e.g. tacrolimus, ciclosporin), mTOR inhibitors (e.g. rapamycin (sirolimus)), and antiproliferative agents (e.g. mycophenolate mofetil, cyclophosphamide).

In one embodiment, the further therapeutic agent is independently selected from the group consisting of immunosuppressants that modulate IL-2 signalling (e.g. tacrolimus, ciclosporin, rapamycin (sirolimus), and anti-CD25 antibodies (e.g. basilixumab, daclizumab).

In one embodiment, the further therapeutic agent is rapamycin (sirolimus). In another embodiment, the further therapeutic agent is tacrolimus. In another embodiment, the further therapeutic agent is a combination of tacrolimus and methotrexate. In another embodiment, the further therapeutic agent is ciclosporin. In another embodiment, the further therapeutic agent is a combination of ciclosporin and methotrexate. In another embodiment, the further therapeutic agent is cyclophosphamide. In another embodiment, the further therapeutic agent is mycophenolate mofetil 106. A pharmaceutical composition according to aspect 105, or a kit comprising a pharmaceutical composition as defined in aspect 105, wherein the composition is for treating and/or preventing a hOX40L-mediated condition or disease selected from an autoimmune disease or condition, a systemic inflammatory disease or condition, or transplant rejection; for example inflammatory bowel disease (IBD), Crohn's disease, rheumatoid arthritis, transplant rejection, allogeneic transplant rejection, graft-versus-host disease (GvHD), ulcerative colitis, systemic lupus erythematosus (SLE), diabetes, uveitis, ankylosing spondylitis, contact hypersensitivity, multiple sclerosis and atherosclerosis, in particular GvHD.

The hOX40L-mediated diseases of any of the aspects, configurations, concepts, examples or embodiments described herein optionally apply mutatis mutandis to this combination.

107. A pharmaceutical composition according to aspect 105 or aspect 106 in combination with, or kit according to aspect 106 comprising a label or instructions for use to treat and/or prevent said disease or condition in a human; optionally wherein the label or instructions comprise a marketing authorisation number (e.g., an FDA or EMA authorisation number); optionally wherein the kit comprises an IV or injection device that comprises the antibody or fragment.

The labels, instructions, hOX40L-mediated diseases and conditions of any of the aspects, configurations, concepts, examples or embodiments described herein optionally apply mutatis mutandis to this combination.

108. A nucleic acid that encodes the HCDR3 of an antibody or fragment as defined in any one of aspects 73 to 89, 98, 99, 101 or 102.

109. A nucleic acid that encodes a VH domain and/or a VL domain of an antibody or fragment as defined in any one of aspects 73 to 89, 98, 99, 101 or 102.

110. A nucleic acid according to aspect 109 comprising a nucleotide sequence that is at least 80% identical to the sequence of SEQ ID NO: 33 and/or SEQ ID NO: 47.

In an example, the nucleotide sequence is at least 85% identical, at least 90% identical, at least 95% identical, at least 96% identical, at least 97% identical, at least 98% identical or at least 99% identical to the sequence of SEQ ID NO: 33 and/or SEQ ID NO: 47.

111. A nucleic acid that encodes a heavy chain or a light chain of an antibody recited in any one of aspects 73 to 89, 98, 99, 101 or 102.
112. A vector comprising the nucleic acid of any one of aspects 108 to 111; optionally wherein the vector is a CHO or HEK293 vector.
113. A host comprising the nucleic acid of any one of aspects 108 to 111 or the vector of aspect 112.

The present invention furthermore relates to the following concepts:

Concept 1. A method of reducing the proportion of (e.g. of depleting or decreasing the level of) CD45RA+CCR7+CD95+OX40+ memory stem T-cells (Tscm) comprising combining said cells with an agent (such as an anti-OX40 or an anti-OX40L antibody or fragment thereof) which reduces the proportion of Tscm cells (e.g. which depletes or decreases the level of said Tscm cells), and whereby the proportion of said Tscm cells is reduced (e.g. whereby the level of said Tscm cells is decreased or depleted).

CD45RA+CCR7+CD95+OX40+ memory stem T-cells (Tscm) are thought to be a newly-defined subset of stem cell memory T-cells which are long-lived and have the capacity for self-renewal. Therefore, these cells may be detrimental in various diseases, such as GvHD and autoimmune disorders, because they are the source of a persistent and multi-potent population of potentially self-reactive effector T-cells. It is known that T-cells develop through a pathway beginning with naïve T-cells (Tn), through stem cell memory T-cells (Tscm), through central memory T-cells (Tcm) and effector memory T-cells (Tem), before developing into short-lived effector T-cells (Teff), as described in Gattinoni and Restifo (2013), Inside Blood, 121(4), 567-568. At these various stages, different markers are expressed on the surface of the T-cells, which reflect the activation status of the T-cells, their tissue localisation and their responsiveness to various stimuli such as inflammatory cytokines.

Tscm cells as defined herein are characterised as CD45RA+CCR7+CD95+OX40+. For alternative prior art classifications of different T-cell types, see the figure in Gattinoni and Restifo (2013). Further markers may be present or absent, but Tscm cells must at a minimum be CD45RA+CCR7+CD95+OX40+. The various cell-surface markers are, in one embodiment, identified using flow cytometry using methods which are well-known to those of skill in the art. In one embodiment, the Tscm cells may additionally be CD8+. In another embodiment, the Tscm cells may additionally be CD62L+. Flow cytometry techniques are well-known to those skilled in the art. Agents which may be used in flow cytometry techniques are defined in Example 7 below. In one embodiment, the flow cytometry is carried out as described in Example 7 below. In another embodiment, the flow cytometry is carried out as described in Baumgarth & Roederer (2000), Journal of Immunological Methods, 243, 77-97. (see concept 25 hereinbelow).

In a particular embodiment, the Tscm cells are characterised as being CD4+CD45RA+CCR7+CD95+OX40+.

Without being bound by theory, it is thought that reducing this Tscm population will have a number of benefits in various diseases, as set out herein. In one embodiment, the Tscm cells are active Tscm cells.

Throughout concepts 1 to 83 herein, the proportion or levels of Tscm cells may be reduced in a sample, or indeed in (a sample of) the blood of a subject. The proportion or levels of Tscm cells may be determined relative to the entire T-cell population in the sample. In one embodiment, the proportion or level of Tscm cells is determined relative to other T-cells in the sample. T-cells generally may be identified as being CD3+, and include Tn cells, Tscm cells, Tcm cells, Tem cells and Teff cells. In a particular embodiment, the proportion or level of Tscm cells is determined relative to Tn cells (as defined hereinbelow) in the sample. The proportion or level of Tscm cells may be altered by depletion or by a decrease. In one embodiment, a ratio of T-cell types may be the same as a proportion of Tscm cells (e.g. as for concept 2 hereinbelow). In another embodiment, a level of T-cell types may be the same as a proportion of Tscm cells. In one embodiment, the ratio or proportion of Tscm:Tn is greater than 50:50. Particular ratios and proportions are as described in concepts 23 and 24.

As used in concepts 1 to 83 herein "depleting" and "depletes" describes an active effect following combination with an agent (such as an antibody) on the desired target to kill or remove the target cells (e.g. Tscm cells). When the agent is an antibody, this is usually achieved through effector functions, such as ADC, ADCC or CDC. Alternatively, the target may be killed or removed by a toxin, which may be conjugated to a drug or targeting moiety (such as an anti-OX40 or an anti-OX40L antibody). Such toxins will selectively kill or remove the cell to which they are targeted. Suitable immunoconjugates are described on page 90, and on pages 114 to 118, and 134 (in particular pages 114 to 116) herein.

"Decreasing" or "decreases" as used in concepts 1 to 83 herein refers to a mechanism other than depletion, which reduces the absolute number of cells in a given population. This may be achieved indirectly, for example through a blocking or neutralising agent (such as an antibody) against a target which indirectly results in the killing of a target cell (such as a Tscm), or prevents the expansion or growth of the target cells, resulting in an apparent decrease in proportions relative to another type of cell (such as Tn cells).

As used in concepts 1 to 83 herein, a "level" of a T-cell population may refer to the absolute number, or to the relative proportion of a type of T-cell.

Throughout the various concepts 1 to 83 described herein, an agent which reduces the proportion of Tscm cells may be, for example, an antibody or fragment thereof, a short interfering RNA (SiRNA), a zinc finger, a DARPin, an aptamer, a Spiegelmer, an ant-calin, a receptor-Fc fusion, a ligand-Fc fusion or a small molecule. In one embodiment, the agent targets OX40 (e.g. human OX40), or ligands of OX40. In another embodiment, the agent targets OX40L (e.g. human OX40L), or receptors of OX40L. In one example, the agent may be an OX40-Fc fusion protein (e.g. hOX40-Fc fusion), or may be an OX40L-Fc fusion protein (e.g. hOX40L-Fc fusion), both including functional fragments of OX40 and OX40L. These types of constructs are known to those skilled in the art. In another embodiment, the agent targets OX40 (e.g. human OX40). In another embodiment, the agent targets OX40L (e.g. human OX40L).

In a particular embodiment, the agent is an antibody or fragment thereof. Formats and structures of antibodies and fragments are described elsewhere herein and may be applied to any of the cencepts disclosed herein. The antibody or fragment may be any of the constructs as described herein (for example, as in any one of concepts 52 to 64 herein). In a particular embodiment, the agent is an anti-human OX40 antibody or fragment thereof. In another particular embodiment, the agent is an anti-human OX40L antibody, such as an antibody comprising the amino acid sequence of 02D10 described herein or an antibody comprising the amino acid sequence of oxelumab.

Concept 2. A method of altering the ratio of cell types in a T-cell population in a sample, the method comprising:

a. providing said population, wherein the population comprises a mixture of different T-cell types, wherein the population comprises CD45RA+CCR7+CD95+OX40+ Tscm cells,
b. providing an agent which reduces the proportion of Tscm cells (or providing an anti-OX40 or an anti-OX40L antibody or fragment thereof); and
c. combining said cell population with an amount of said agent (e.g. antibody or fragment thereof) effective to alter the ratio (e.g. to reduce the proportion) of Tscm cells in said population.

Throughout concepts 1 to 83 herein, the ratio of T-cell types may be altered in a sample, for example by increasing the proportion of naïve T-cells (Tn, as defined hereinbelow). In another embodiment, the ratio of T-cell types may be altered by decreasing the proportion of Tscm cells. The ratio of Tscm cells may be determined relative to the entire sample. In one embodiment, the ratio of T-cells is determined by comparing the proportion of naïve T-cells or Tscm cells relative to other T-cells in the sample. T-cells generally may be identified as being CD3+, and include Tn cells, Tscm cells, Tcm cells, Tem cells and Teff cells. In a particular embodiment, the ratio of T-cells is determined as the ratio of Tscm cells relative to naïve T-cells in the sample. The ratio of T-cells may be altered by depletion or by a decrease of Tscm cells. The ratio of T-cells may be altered by an increase or expansion of naïve T-cells.

Concept 3. A method according to concept 2, wherein in step a), the population further comprises CD45RA+CCR7+CD95− naïve T-cells (Tn).

Naïve T-cells (Tn) as defined in concepts 1 to 83 herein are characterised as CD45RA+CCR7+CD95−. Further markers may be present or absent, but Tn cells must at a minimum be CD45RA+CCR7+CD95−. In one embodiment, Tn cells may additionally be CD8+ or CD4+, in particular CD4+. It is thought that Tn are beneficial because these represent the entire pool of T-cells from which adaptive T-cell immune responses can develop to protect an individual when exposed to potentially harmful pathogens and malignant cells.

Concept 4. A method according to concept 3 wherein the ratio of Tscm:Tn in the population of step a) is greater than 50:50.

Concept 5. A method according to any one of concepts 1 to 4, wherein the method is carried out ex vivo in a sample of blood extracted from a human donor subject.

Concept 6. A method according to concept 5, wherein blood produced by said method is reintroduced to a recipient human subject.

In one embodiment, the recipient human subject is the same donor human subject from whom the sample was removed. In another embodiment, the recipient human subject is different to the donor human subject. When the recipient is different to the donor, it is preferable that the donor is of the same gender as the recipient subject. In another embodiment, the donor may be of a similar age and ethnicity as the recipient subject. In another embodiment, the donor may have the same or similar allotype markers as the recipient subject.

In another embodiment, the recipient human donor may receive more than one transfusion of donor blood, according to the severity of the disease to be treated.

Concept 7. A method according to any one of concepts 1 to 4, wherein the method is carried out in vivo in a human subject.

Concept 8. A method according to concept 7, wherein the subject has or is at risk of a Tscm-mediated disease or condition.

As used herein, a subject may be identified as being "at risk of a Tscm-mediated disease or condition" when the cellular changes in their T-cell population have begun to take place, but the subject has not yet presented symptoms or would not be diagnosed as having such a disease by any conventional method. Thus, the methods and uses disclosed herein may aid in the early identification of patients who will develop such diseases. In one embodiment, the disease is prevented (i.e. the treatment is prophylactic).

In a particular embodiment, the subject is at risk of GvHD or transplant rejection when they are pre-operative for a transplant. Potential transplant therapies are envisaged in concept 78 hereinbelow.

In any of concepts 1 to 83 described herein, a Tscm-mediated disease may be as defined in any of concepts 71 to 80 hereinbelow.

Concept 9. A method of treating or reducing the risk of a Tscm-mediated disease or condition in a subject, the method comprising combining a population of T-cells with an agent (e.g. an anti-OX40 or an anti-OX40L antibody or fragment thereof) which reduces the proportion of Tscm cells (e.g. which depletes or decreases the level of said Tscm cells), and whereby the proportion of CD45RA+CCR7+CD95+OX40+ Tscm cells is reduced in the population (e.g. whereby the level of said Tscm cells is decreased or depleted in said population).

As used in concepts 1 to 83 herein, the "treatment" of a Tscm-mediated disease includes the reduction of one or more symptom(s) of said Tscm-mediated disease. The "prevention" of a Tscm-mediated disease includes the prevention of one or more symptom(s) of said Tscm-mediated disease.

Concept 10. A method according to any one of concepts 7 to 9, wherein the agent (e.g. antibody or fragment thereof) is combined by administering said agent (e.g. antibody or fragment) in a therapeutically effective amount to said subject, whereby said Tscm-mediated disease or condition is treated or the risk of said Tscm-mediated disease or condition is reduced in said subject.

In one embodiment, the administration is prophylactic to reduce the risk of a Tscm-mediated disease.

In any of the concepts described herein, a therapeutically effective or prophylactically effective amount of the antibody or fragment is as described elsewhere (see page 29, 73, 105 to 107 for therapy, and pages 72, and 102 to 103 for prophylaxis). In any of the concepts described herein, modes and compositions for administration may be as described elsewhere (see pages 118 to 142 herein). In one embodiment, the antibody or fragment is administered by bolus injection (e.g. intravenously).

Concept 11. A method of treating or reducing the risk of a Tscm-mediated disease or condition in a subject comprising administering to said subject a therapeutically effective amount of an agent (e.g. an anti-OX40 or an anti-OX40L antibody or fragment thereof) which reduces the proportion of Tscm cells (e.g. which depletes or decreases the level of said Tscm cells), and whereby the proportion of CD45RA+CCR7+CD95+OX40+ Tscm cells is reduced (e.g. whereby the level of said Tscm cells is decreased or depleted), wherein the Tscm-mediated disease or condition is thereby treated or the risk of said Tscm-mediated disease or condition is reduced.

Concept 12a. An agent (e.g. an anti-OX40 or an anti-OX40L antibody or fragment thereof) which reduces the proportion of Tscm cells (e.g. which depletes or decreases the level of said Tscm cells) for use in treating or reducing the risk of a Tscm-mediated disease or condition in a subject; or concept 12b. An anti-OX40 or an anti-OX40L antibody or fragment thereof for use in treating or reducing the risk of a Tscm-mediated disease or condition in a subject.

Concept 13a. Use of an agent (e.g. an anti-OX40 or an anti-OX40L antibody or fragment thereof) which reduces the proportion of Tscm cells (e.g. which depletes or decreases the level of said Tscm cells) for the treatment or prevention of a Tscm-mediated disease or condition in a subject; or concept 13b. Use of an anti-OX40 or an anti-OX40L antibody or fragment thereof for the treatment or prevention of a Tscm-mediated disease or condition in a subject.

Concept 14a. Use of an agent (e.g. an anti-OX40 or an anti-OX40L antibody or fragment thereof) which reduces the proportion of Tscm cells (e.g. which depletes or decreases the level of said Tscm cells) in the manufacture of a medicament for the treatment or prevention of a Tscm-mediated disease or condition in a subject; or concept 14b. The use of an anti-OX40 or an anti-OX40L antibody or fragment thereof in the manufacture of a medicament for the treatment or prevention of a Tscm-mediated disease or condition in a subject.

Concept 15a. A composition comprising an agent (e.g. an anti-OX40 or an anti-OX40L antibody or fragment thereof) which reduces the proportion of Tscm cells (e.g. which depletes or decreases the level of said Tscm cells) for the treatment or prevention of a Tscm-mediated disease or condition in a subject; or concept 15b. A composition comprising an anti-OX40 or an anti-OX40L antibody or fragment thereof for the treatment or prevention of a Tscm-mediated disease or condition in a subject.

Concept 16. A method of treating a disease or condition in a subject in need thereof, comprising:
   a. Performing an assay to measure the level of CD45RA+CCR7+CD95− Tn cells and the level of CD45RA+CCR7+CD95+OX40+ Tscm cells in a sample obtained from the subject; and
   b. Administering an agent (e.g. an anti-OX40 or an anti-OX40L antibody or fragment thereof) which reduces the proportion of Tscm cells (e.g. which depletes or decreases the level of said Tscm cells), such as an anti-OX40 or an anti-OX40L antibody or fragment thereof, to the subject when the ratio of Tscm:Tn cells in the sample is determined in the assay to be greater than 50:50.

Concept 17a. An agent (e.g. an anti-OX40 or an anti-OX40L antibody or fragment thereof) which reduces the proportion of Tscm cells (e.g. which depletes or decreases the level of said Tscm cells) for use in therapy of a subject, wherein the agent is to be administered to a subject who has, or has been determined to have, a ratio of CD45RA+CCR7+CD95+OX40+ Tscm cells:CD45RA+CCR7+CD95− Tn cells of greater than 50:50; or concept 17b. An anti-OX40 or an anti-OX40L antibody or fragment thereof for use in therapy of a subject, wherein the antibody or fragment thereof is to be administered to a subject who has, or has been determined to have, a ratio of CD45RA+CCR7+CD95+OX40+ Tscm cells:CD45RA+CCR7+CD95− Tn cells of greater than 50:50.

Concept 18a. Use of an agent (e.g. an anti-OX40 or an anti-OX40L antibody or fragment thereof) which reduces the proportion of Tscm cells (e.g. which depletes or decreases the level of said Tscm cells) for therapy of a subject who has, or has been determined to have, a ratio of CD45RA+CCR7+CD95+OX40+ Tscm cells: CD45RA+CCR7+CD95− Tn cells of greater than 50:50; or concept 18b. Use of an anti-OX40 or an anti-OX40L antibody or fragment thereof for therapy of a subject who has, or has been determined to have, a ratio of CD45RA+CCR7+CD95+OX40+ Tscm cells: CD45RA+CCR7+CD95− Tn cells of greater than 50:50.

Concept 19a. Use of an agent (e.g. an anti-OX40 or an anti-OX40L antibody or fragment thereof) which reduces the proportion of Tscm cells (e.g. which depletes or decreases the level of said Tscm cells) in the manufacture of a medicament for use in therapy of a subject, wherein the agent is to be administered to a subject who has, or has been determined to have, a ratio of CD45RA+CCR7+CD95+OX40+ Tscm cells:CD45RA+CCR7+CD95− Tn cells of greater than 50:50; or concept 19b. Use of an anti-OX40 or an anti-OX40L antibody or fragment thereof in the manufacture of a medicament for use in therapy of a subject, wherein the antibody or fragment thereof is to be administered to a subject who has, or has been determined to have, a ratio of CD45RA+CCR7+CD95+OX40+ Tscm cells: CD45RA+CCR7+CD95− Tn cells of greater than 50:50.

In any of concepts 17 to 19, the ratio is determined in a sample, for example, in a sample of blood obtained from said subject.

Concept 20. A method according to concept 16a or b, an agent or an antibody or fragment for the use according to concept 17a or b, or the use according to concept 18a or b or concept 19 a or b, wherein the therapy is the treatment or prevention of a Tscm-mediated disease or condition, preferably wherein the therapy is the treatment of a Tscm-mediated disease or condition.

In another embodiment, the subject has or is at risk of a Tscm-mediated disease or condition. The Tscm-mediated disease or condition may be as defined in any one of concepts 71 to 80 hereinbelow.

Concept 21. A method of classifying a subject as having or as being at risk of a Tscm-mediated disease or condition (e.g. which disease or condition is suitable for treatment with an anti-OX40 or an anti-OX40L antibody or fragment thereof), comprising:
   a. performing an assay that detects (i) CD45RA+CCR7+CD95+OX40+ Tscm cells, and (ii) CD45RA+CCR7+CD95− Tn cells in a sample obtained from said subject; and
   b. classifying the subject as having, or as being at risk of a Tscm-mediated disease or condition if the ratio of Tscm:Tn cells in the sample is greater than 50:50.

Concept 22. A method according to concept 21 further comprising the step of:
   c. administering to said subject an anti-OX40 or an anti-OX40L antibody or fragment thereof which reduces the proportion of said Tscm cells in the blood of said subject, (e.g. which depletes or decreases the level of said Tscm cells) if said subject has been classified as having or as being at risk of a Tscm-mediated disease or condition in step b).

Tscm-mediated diseases or conditions which may be suitable for treatment with an anti-OX40 or an anti-OX40L antibody or fragment thereof are as described in any one of concepts 71 to 80 herein below.

Concept 23. A method according to any one of concepts 4, 16, or 20 to 22, an agent or an antibody or fragment for the use according to concept 17 or 20, or the use according to any one of concepts 18 to 20, wherein the ratio of Tscm:Tn cells is (or is determined or classified to be) greater than 60:40, or is greater than 70:30, or is greater than 75:25, such as greater than 70:30.

In another embodiment, the ratio is (or is determined or classified to be) greater than 55:45. In another embodiment, the ratio is (or is determined or classified to be) greater than 65:35.

Concept 24. A method, agent or an antibody or fragment for the use, or the use according to concept 23, wherein the ratio of Tscm:Tn cells is (or is determined or classified to be) greater than 80:20, or is greater than 85:15, for example greater than 90:10, e.g. greater than 95:5.

Concept 25. A method according to any one of concepts 4, 16, or 20 to 24, an agent or an antibody or fragment for the use according to any one of concepts 17, 20, 23 or 24, or the use according to any one of concepts 18 to 20, 23 or 24, wherein the ratio of Tscm:Tn cells is determined (or is determinable) by flow cytometry.

Flow cytometry techniques are well-known to those skilled in the art, as discussed above. Agents which may be used in flow cytometry techniques are defined in Example 7 below. In one embodiment, the flow cytometry is carried out as described in Example 7 below. In another embodiment, the flow cytometry is carried out as described in Baumgarth & Roederer (2000).

Concept 26. A method for treating or reducing the risk of a Tscm-mediated disease or condition with an agent (e.g. an anti-OX40 or an anti-OX40L antibody or fragment thereof) which reduces the proportion of Tscm cells (e.g. which depletes or decreases the level of said Tscm cells), or with an anti-OX40 or an anti-OX40L antibody or fragment thereof, comprising the steps of:
  a. determining whether the subject is a candidate for treatment by detecting the presence of OX40 on the surface of CD45RA+CCR7+CD95+ Tscm cells obtained from a sample from the subject; and
  b. administering said agent, such as said antibody or fragment, to the subject if the subject is identified as a candidate for treatment.

Concept 27. A method according to concept 26, wherein the presence of OX40 on the surface of the Tscm cells is determined using flow cytometry.

In one embodiment, the subject is a human and the OX40 is human OX40.

Concept 28. A method, comprising:
  a. obtaining at least two T-cell samples derived from a subject who has or is at risk of a Tscm-mediated disease or condition, wherein said at least two samples comprise a first sample and a second sample,
  b. determining levels of CD45RA+CCR7+CD95+OX40+ Tscm cells in said first and second samples;
  c. treating said subject to reduce the proportion of CD45RA+CCR7+CD95+OX40+ Tscm cells (e.g. to deplete or decrease the level of Tscm cells) by administering an agent which reduces the proportion of Tscm cells (e.g. which depletes or decreases the level of said Tscm cells), or by administering an anti-OX40 or an anti-OX40L antibody or fragment thereof, if the levels of Tscm cells in said second sample are elevated as compared to said first sample, in order to treat or reduce the risk of said Tscm-mediated disease or condition.

The levels of Tscm in said first and second samples in step b. may be either the absolute number of Tscm cells, or may be the relative proportions of Tscm (e.g. the ratio of Tscm:Tn, or Tacm:total T-cell count). The levels of Tscm cells may be elevated in the second sample if they are statistically significantly higher than the levels in the first sample.

Concept 29. A method according to concept 28, wherein said first sample is collected:
  i. before the onset of said disease or condition; or
  ii. after the onset of said disease or condition; and
  optionally wherein said second sample is collected no longer than one month, e.g. no longer than one week after the first sample.

As used in the concepts herein, a subject may be determined to be "before the onset of a Tscm-mediated disease or condition" if the subject is presenting no symptoms which would conventionally be associated with said disease or condition or if the subject would not be diagnosed as having such a disease or condition by any conventional method. For example, the presence of signs and symptoms of acute GvHD may be staged and graded according to a standardised scale such as described in Przepiorka et al. (1995), 1994 Consensus Conference on Acute GvHD Grading Bone Marrow Transplant 1995; 15, 825-828. Similar disease grading scales are also in routine clinical use for other relevant diseases, such as rheumatoid arthritis and inflammatory bowel diseases.

Concept 30. A method according to concept 28 or concept 29, wherein the Tscm-mediated disease or condition is a transplant, and wherein in step c) the treatment is in order to reduce the risk of transplant rejection, optionally wherein the first sample is taken before the transplant, and the second sample is taken after the transplant.

The first sample may be taken pre-operatively, e.g. after the subject has been identified as a candidate for treatment. The second sample is taken after the transplant and may be used by physicians as a method of monitoring the acceptance of the transplant. Thus, it may be that the physician may take more than one sample after the transplant, e.g. a daily blood sample to monitor the subject for changes in the proportion of Tscm:Tn or the levels of Tscm in the sample. The samples may be taken every other day, weekly, monthly or longer (including yearly) according to the likelihood of transplant rejection. For example, if the transplant is autologous, then the likelihood of transplant rejection may be reduced as compared to an allogeneic transplant, and therefore the time period between sample collections post-transplant may be longer than with an allogeneic transplant, where the risk of rejection is higher.

Concept 31. A method according to concept 30, wherein in step a), the first sample is collected no longer than a week, e.g. no longer than 6 days, no longer than 5 days, no longer than 4 days, or no longer than 3 days, such as no longer than 2 days before said transplant.

Concept 32. A method according to any one of concepts 28 to 31, wherein the second sample is collected no longer than 6 days, no longer than 5 days, no longer than 4 days, or no longer than 3 days, such as no longer than 2 days after the first sample or after said transplant.

Concept 33. A method according to any one of concepts 28 to 32, wherein in step c), the levels of Tscm cells in said second sample are greater than double the levels as compared to said first sample, for example are greater than three times the level, or preferably are greater than 4 times the levels as compared to said first sample.

In one embodiment, in step c), the levels of Tscm cells in said second sample are greater than 4 times (e.g. greater than 4.5 times) the levels as compared to said first sample. In another embodiment, in step c), the levels of Tscm cells in said second sample are greater than 5 times the levels as compared to said first sample.

Concept 34. A method according to any one of concepts 30 to 33, wherein the subject is given a prophylactic dose of an agent which reduces the proportion of Tscm cells (e.g. which depletes or decreases the level of said Tscm cells), or is given a prophylactic dose of an anti-OX40 or an anti-OX40L antibody or fragment thereof, before said transplant, and the first sample is taken before administration of said agent, or antibody or fragment thereof, and wherein the second sample is taken after the transplant or after administration of the agent, or the antibody or fragment thereof (preferably, where in the second sample is taken after the transplant).

In one embodiment, the prophylactic dose is an effective prophylactic dose. By "effective", it is meant that the dose is effective to reduce the proportion or level of Tscm as described herein, or effective to prevent or reduce the risk of a Tscm-mediated disease or condition.

The methods as described herein may be used to correct an already-aberrant level of Tscm cells, by administration of an agent which reduces the proportion of Tscm cells (e.g. which depletes or decreases the level of said Tscm cells), or by administration of an anti-OX40 or an anti-OX40L antibody or fragment thereof, before a transplant, in order to reduce the risk of transplant rejection after the transplant. Therefore, multiple samples may be taken after administration of the agent (or of the anti-OX40 or an anti-OX40L antibody or fragment thereof), but before the transplant. Comparison may be made between the collected samples and a sample obtained from a healthy donor.

Concept 35. A method according to any one of concepts 30 to 33, wherein the subject is given a therapeutic dose of an agent which reduces the proportion of Tscm cells (e.g. which depletes or decreases the level of said Tscm cells), or is given a therapeutic dose of an anti-OX40 or an anti-OX40L antibody or fragment thereof, after the transplant, and wherein the first sample is taken before said transplant, and the second sample is taken after the transplant.

In one embodiment, the therapeutic dose is an effective therapeutic dose. By "effective", it is meant that the dose is effective to reduce the proportion or level of Tscm as described herein, or effective to treat a Tscm-mediated disease or condition.

In one embodiment, the second sample is taken after the administration of the agent, or antibody or fragment thereof. This would enable a physician to check that the levels or proportion of Tscm cells remain "normal", i.e. as compared to the first sample, or to a sample obtained from a healthy donor.

Concept 36. A method according to any one of concepts 30 to 33, wherein the subject is given a therapeutic dose of an agent which reduces the proportion of Tscm cells (e.g. which depletes or decreases the level of said Tscm cells), or is given a therapeutic dose of an anti-OX40 or an anti-OX40L antibody or fragment thereof, after the transplant, and wherein the first sample is taken before said transplant, and the second sample is taken after the administration of said agent, or of said antibody or fragment thereof.

Concept 37. A method according to any one of concepts 34 to 36, further comprising the steps of:
  d. obtaining a third sample derived from said subject;
  e. determining the levels of CD45RA+CCR7+CD95+OX40+ Tscm cells in said third sample;
  f. treating said subject to reduce the proportion of CD45RA+CCR7+CD95+OX40+ Tscm cells (e.g. to deplete or decrease the level) of Tscm cells by administering an agent which reduces the proportion of Tscm cells (e.g. which depletes or decreases the level of said Tscm cells), or by administering an anti-OX40 or an anti-OX40L antibody or fragment thereof, if the levels of Tscm cells in said third sample are elevated as compared to said second or said first sample.

The levels are considered to be "elevated" as described hereinabove (e.g. as for concept 28 or 33).

Concept 38. A method according to concept 37, wherein steps d) to f) are repeated as necessary until the levels of Tscm cells remain at a therapeutically-effective, or at a prophylactically-effective levels, e.g. at a substantially constant level in said subject.

As used in the concepts herein, a "substantially constant level" may be described as within 30% variance between samples. In one embodiment, a substantially constant level is within 20% variance between samples. In another embodiment, a substantially constant level is within 15% variance between samples, such as within 10% variance between samples, e.g. within 5% variance between samples.

Concept 39. A method according to any one of concepts 28 to 38, wherein the second sample is taken no longer than one month after the first sample, such as no longer than one week, no longer than 6 days, no longer than 5 days, no longer than 4 days, or no longer than 3 days, e.g. no longer than 2 days after the first sample, and optionally wherein the third sample is taken no longer than one month after the second sample, such as no longer than one week, no longer than 6 days, no longer than 5 days, no longer than 4 days, or no longer than 3 days, e.g. no longer than 2 days after the second sample.

Timepoints for taking any of the samples described in these concepts will depend on a number of factors, such as the likelihood of the subject having or being at risk of a Tscm-mediated disease (e.g. GvHD or transplant rejection), the level determined in the previous sample, the type of transplant, etc. A person skilled in the art will be able to determine appropriate time points as necessary or desired. The timepoints may be monthly, every other month, quarterly, half-yearly or yearly, if desired.

Concept 40. In vitro use of CD45RA+CCR7+CD95+OX40+ Tscm cells, as a diagnostic for a Tscm-mediated disease or condition in a subject (for example, which disease or condition can be treated or prevented with an agent which reduces the proportion of Tscm cells (e.g. which depletes or decreases the level of said Tscm cells), or with an anti-OX40 or an anti-OX40L antibody or fragment thereof in the subject).

In one embodiment, there is provided biomarker of an autoimmune disease, HIV-1, and a T-cell malignancy, wherein the biomarker is a CD45RA+CCR7+CD95+OX40+ Tscm cell. In another embodiment, the biomarker is of any of the diseases described in concepts 71 to 80 hereinbelow. In another embodiment, the Tscm cell is a CD4+CD45RA+CCR7+CD95+OX40+ Tscm cell.

Concept 41. Use of a biomarker of a Tscm-mediated disease or condition, wherein the biomarker is CD45RA+CCR7+CD95+OX40+ Tscm cells, in vitro as a diagnostic for a Tscm-mediated disease or condition (e.g. which disease or condition can be treated or prevented with an agent which reduces the proportion of Tscm cells (e.g. which depletes or decreases the level of said Tscm cells), or with an anti-OX40 or an anti-OX40L antibody or fragment thereof in the subject).

In one embodiment, the Tscm-mediated diseases are any of those described in concepts 71 to 80 hereinbelow.

Concept 42. A method of maintaining CD45RA+CCR7+CD95− Tn cells, whilst decreasing CD45RA+CCR7+CD95+OX40+ Tscm cells in a population of T-cells in a sample, said method comprising contacting said sample with an effective amount of an agent which reduces the proportion of Tscm cells (e.g. which depletes or decreases the level of said Tscm cells), or with an anti-OX40 or an anti-OX40L antibody or fragment thereof.

As used in concepts 1 to 83 herein, "maintains" or "maintaining" with respect to a level or a proportion may be described as substantially constant. A substantially constant level may be within 30% variance between samples. In one embodiment, a substantially constant level is within 20% variance between samples. In one embodiment, a substantially constant level is within 15% variance between samples, such as within 10% variance between samples, e.g. within 5% variance between samples. In another embodiment, a substantially constant level is one which does not show a statistically significant change in level. In one embodiment, a substantially constant level is one which reaches the 95% confidence level (e.g greater than 97% or greater than 99%). "Statistically significant" may be as defined above in concept 28 herein.

Concept 43. A method according to concept 42, wherein the level of said Tn cells are at least maintained, whilst the levels of said Tscm cells are decreased in said sample, optionally wherein the sample is from a subject.

Concept 44. A method according to any one of concepts 2 to 8, 10, 16, 20, 21, 23 to 39, 42 or 43, an agent or an antibody or fragment thereof for the use according to any one of concepts 12, 17, 20, 21 or 23 to 25, the use according to any one of concepts 13, 14, 18 to 20 or 23 to 25, or the composition according to concept 15, wherein agent (e.g. the antibody or fragment thereof) reduces the proportion of CD45RA+CCR7+CD95+OX40+ Tscm cells (e.g. depletes or decreases the level of Tscm cells).

Concept 45. A method or fragment thereof according to any one of concepts 1 to 8, 10, 16, 20, 21, 23 to 39 or 42 to 44, an agent or an antibody or fragment thereof for the use according to any one of concepts 12, 17, 20, 21, 23 to 25, or 44, the use according to any one of concepts 13, 14, 18 to 20 or 23 to 25 or 44, or the composition according to concept 15 or concept 44, wherein the agent (e.g. the antibody or fragment thereof) maintains CD45RA+CCR7+CD95– Tn cells.

Concept 46. A method according to concept 42 or 45, an agent or an antibody or fragment thereof for the use according to concept 45, the use according to concept 45, or the composition according to concept 45, wherein the Tn cells are maintained at a level of not below 50% of the level of said Tn cells in a sample from a healthy donor or from said subject before the onset of disease.

The healthy donor is preferably of the same species at the subject, for example, wherein the subject is a human, the donor is most preferably also a human. The donor is also preferably of the same gender as the subject. The donor is preferably of a similar age and ethnicity as the subject.

Concept 47. A method, an agent or an antibody or fragment for the use, a use or a composition according to concept 46, wherein the Tn cells are maintained at a level of not below 55% (such as not below 60%, for example not below 65%, e.g. not below 70%).

Concept 48. A method, an agent or an antibody or fragment for the use, a use or a composition according to concept 47, wherein the Tn cells are maintained at a level of not below 75% (such as not below 80%, for example not below 85%, e.g. not below 90%)

Concept 49. A method according to any one of concepts 1 to 8, or 42 to 48, an agent or an antibody or fragment thereof for the use according to any one of concepts 44 to 48, the use according to any one of concepts 38 to 41, or the composition according to any one of concepts 44 to 48, wherein the Tscm cells are depleted or decreased to a level of less than 50% of the level of said Tscm cells in a sample from a healthy donor or from said subject before the onset of disease.

Concept 50. A method, an antibody or fragment for the use, a use or a composition according to concept 49, wherein the Tscm cells are depleted or decreased to a level of less than 45% (such as less than 40%, for example less than 35%, e.g. less than 30% or less than 25%).

Concept 51. A method, an antibody or fragment for the use, a use or a composition according to concept 50, wherein the Tscm cells are depleted or decreased to a level of less than 20% (such as less than 15%, for example less than 10%.

Concept 52. A method, an antibody or fragment for the use, a use or a composition according to any preceding concept, wherein the antibody or fragment is a depleting antibody or fragment that specifically binds OX40 (in particular human OX40), optionally wherein the antibody is engineered for enhanced ADC, ADCC and/or CDC.

The potency of Fc-mediated effects may be enhanced by engineering the Fc domain by various established techniques. Such methods increase the affinity for certain Fc-receptors, thus creating potential diverse profiles of activation enhancement. This can achieved by modification of one or several amino acid residues (e.g. as described in Lazar et al., 2006, Proc. Natl. Acad. Sci. U.S.A., March 14; 103(11): 4005-10.) or by altering the natural glycosylation profile of the Fc domain by, for example, generating under fucosylated or de-fucosylated variants (as described in Natsume et al., 2009, Drug Des Devel Ther., 3:7-16). For example, to increase ADCC, residues in the hinge region can be altered to increase binding to Fc-gamma RIII (see, for example, Shields et al, 2001, J Biol Chem., March 2; 276(9):6591-604.).

Equally, the enhancement of CDC may be achieved by amino acid changes that increase affinity for C1q, the first component of the classic complement activation cascade (see Idusogie et al., J. Immunol., 2001; 166:2571-2575). Another approach is to create a chimeric Fc domain created from human IgG1 and human IgG3 segments that exploit the higher affinity if IgG3 for C1q (Natsume et al., 2008, Cancer Res., 68: 3863-3872).

The antibody may be a targeting antibody (such as an anti-OX40 or an anti-OX40L antibody) which exhibits its effects through a toxin, to which the antibody may be conjugated. Such toxins will selectively kill or remove the cell to which they are targeted. Suitable immunoconjugates are described on page 90, and on pages 114 to 118, and 134 (in particular pages 114 to 116) herein.

Thus, in one embodiment, the antibody or fragment thereof is de-fucosylated. In another embodiment, the antibody or fragment thereof contains one or more mutations in the hinge or Fc region which enhances the ADCC and/or the CDC functionality.

Methods for determining depletion and/or ADCC and/or CDC functionality may be as described herein, or as well-known by those skilled in the art.

The OX40 antibodies may be as described in WO2014/148895 (Biocerox Products & Janssen Pharmaceuticals; see claims on pages 138 to 139 for specific sequences which are incorporated herein by reference), WO2013/068563 (Biocerox Products & Janssen Pharmaceuticals; see claims on pages 138 to 139 for specific sequences which are incorporated herein by reference), WO2013/130102 and WO2013/119202 (Providence Health & Services—Oregon, see mAb 9B12 as described in Weinberg, A. D., et al., J. Immunother., 29, 575-585 (2006), and fusions with IL-2 which are incorporated herein by reference), WO2013/038191 (Bioceros B.V.; see claims 4 to 11 for specific antibody sequences which are incorporated herein by reference), WO2013/028231 (Board of Regents, the University of Texas System; see claims 1 to 12 for specific antibody sequences which are incorporated herein by reference), WO2013/008171 (Glenmark Pharmaceuticals S.A.; see claims 1, 2, 5 to 12, 16 to 21 and 28 to 29 for specific antibody sequences which are incorporated herein by reference), WO2012/027328 (Board of Regents, the University of Texas System; see claims 1 to 11 for specific antibody sequences which are incorporated herein by reference), WO2010/096418 (UCB Pharma S.A.; see claims 1 to 9 and 11 to 14 for specific antibody sequences which are incorporated herein by reference), WO2009/079335 (Medarex, Inc & Pfizer, Inc; see claims 1 to 9 and 14 to 17 for specific antibody sequences which are incorporated herein by reference), WO2008/106116 (Genentech, Inc; see claims 1 to 12 for specific antibody sequences which are incorporated herein by reference), WO2007/062245 (Kirin Beer Kabushiki Kaisha & La Jolla Institute for Allergy and Immunology; see claim 12 for specific antibody deposit numbers, and claim 16 for specific antibody sequences, which are incorporated herein by reference) WO03/106498 (Crucell Holland B.V.; see claims 3 and 4 for specific antibody sequences which are incorporated herein by reference).

More generally anti-OX40 antibodies are described in WO99/42585, WO95/21251, WO95/21915 and WO95/12673.

Concept 53. A method, an antibody or fragment for the use, a use or a composition according to any preceding concept, wherein the antibody is an antagonistic or blocking antibody.

Methods for determining antagonism or blocking functionality may be as described herein, or as well-known by those skilled in the art. For example, in vitro techniques include SPR and/or ELISA, which are described elsewhere herein.

Concept 54. A method, an antibody or fragment for the use, a use or a composition according to concept 53, wherein the antibody specifically binds to OX40L (in particular human OX40L).

The OX40L antibodies may be any antibody or fragment as described herein. In one embodiment, the OX40L antibody is the antagonist anti-human OX40L (gp34) antibody ik-1 described by Matsumura et al., J Immunol. (1999), 163:3007.

Concept 55. A method, an antibody or fragment for the use, a use or a composition according to concept 56, wherein the antibody antagonises specific binding of OX40 to OX40L, e.g. as determined using SPR or ELISA.

SPR and ELISA methods may be as described elsewhere herein.

Concept 56. A method, an antibody or fragment for the use, a use or a composition according to any preceding concept, wherein the antibody is a humanized, human or fully human antibody.

Other antibody constructs may be as described herein.

Concept 57. A method, an antibody or fragment for the use, a use or a composition according to any preceding concept, wherein the antibody is a fragment of an antibody selected from the list of multispecific antibodies (eg. bispecific antibodies), intrabodies, single-chain Fv antibodies (scFv), camelized antibodies, Fab fragments, F(ab') fragments, disulfide-linked Fvs (sdFv), anti-idiotypic (anti-Id) antibodies, and epitope-binding fragments thereof.

Concept 58. A method, an antibody or fragment for the use, a use or a composition according to any preceding concept, wherein the antibody or fragment enables greater than 80% stem cell donor chimerism by day 12 in a Rhesus macaque model of haploidentical hematopoietic stem cell transplantation.

Concept 59. A method, an antibody or fragment for the use, a use or a composition according to any preceding concept, wherein the antibody or fragment expresses as a stably transfected pool in Lonza GS-Xceed™ at level greater than 1.5 g/L in a fed batch overgrow culture using Lonza version 8 feed system with an overgrow period of 14 days.

Concept 60. A method, an antibody or fragment for the use, a use or a composition according to any preceding concept, wherein the antibody or fragment thereof comprises a HCDR3 of from 16 to 27 amino acids and derived from the recombination of a human VH gene segment, a human D gene segment and a human JH gene segment, wherein the human JH gene segment is IGHJ6 (e.g. IGHJ6*02).

Concept 61. A method, an antibody or fragment for the use, a use or a composition according to any preceding concept, wherein the antibody or fragment thereof comprises a HCDR3 selected from:
  a. the HCDR3 of antibody 2D10 (Seq ID No:40 or Seq ID No:46);
  b. the HCDR3 of antibody 10A7 (Seq ID No:8 or SEQ ID No:14);
  c. the HCDR3 of antibody 09H04 (Seq ID No:72 or Seq ID No:78);
  d. the HCDR3 of antibody 19H01 (Seq ID No:100 or Seq ID No:106);
  e. a CDR3 of any of the nanobodies disclosed in WO2011/073180 (Ablynx, Seq ID Nos: 161 to 167 therein, which are incorporated herein by reference);
  f. an HCDR3 of any of the antibodies disclosed in WO2006/029879 (Roche/Genentech, Seq ID Nos: 33 to 38 therein, which are incorporated herein by reference); or
  g. an HCDR3 of any of the antibodies disclosed in U.S. Pat. No. 7,812,133 (Genentech, Seq ID Nos: 11 or 12 therein, which are incorporated herein by reference).

Concept 62. A method, an antibody or fragment for the use, a use or a composition according to any preceding concept, wherein the antibody or fragment thereof comprises:
  a. the CDRs of antibody 2D10 (Seq ID No:40 or Seq ID No:46 for CDRH3, SEQ ID No:38 or SEQ ID No:44 for CDRH2, SEQ ID No:36 or SEQ ID No:42 for CDRH1, SEQ ID No:50 or SEQ ID No:56 for CDRL1, SEQ ID No:52 or SEQ ID No:58 for CDRL2 and SEQ ID No:54 or SEQ ID No:60 for CDRL3);
  b. the CDRs of antibody 10A7 (Seq ID No:8 or SEQ ID No:14 for CDRH3, SEQ ID No:6 or SEQ ID No:12 for CDRH2, SEQ ID No:4 or SEQ ID No:10 for CDRH1, SEQ ID No:18 or SEQ ID No:24 for CDRL1, SEQ ID No:20 or SEQ ID No:26 for CDRL2 and SEQ ID No:22 or SEQ ID No:28 for CDRL3);
  c. the CDRs of antibody 09H04 (Seq ID No:72 or Seq ID No:78 for CDRH3, SEQ ID No:70 or SEQ ID No:76 for CDRH2, SEQ ID No:68 or SEQ ID No:74 for CDRH1, SEQ ID No:82 or SEQ ID No:88 for CDRL1, SEQ ID No:84 or SEQ ID No:90 for CDRL2 and SEQ ID No:86 or SEQ ID No:92 for CDRL3);
  d. the CDRs of antibody 19H01 (Seq ID No:100 or Seq ID No: 106 for CDRH3, SEQ ID No:98 or SEQ ID No: 104 for CDRH2, SEQ ID No:96 or SEQ ID No: 102 for CDRH1, SEQ ID No:110 or SEQ ID No: 116 for CDRL1, SEQ ID No: 112 or SEQ ID No: 118 for CDRL2 and SEQ ID No: 114 or SEQ ID No: 120 for CDRL3);

c. the CDRs of any of the nanobodies disclosed in WO2011/073180 (Ablynx: Seq ID Nos: 161 to 167 therein for CDR3; Seq ID Nos: 147 to 153 therein for CDR2; and Seq ID Nos: 133 to 139 therein for CDR1, which sequences are incorporated herein by reference);

f. the CDRs of any of the antibodies disclosed in WO2006/029879 (Roche/Genentech: Seq ID Nos: 33 to 38 therein for CDRH3; Seq ID Nos: 21 to 25 therein for CDRH1 and Seq ID Nos: 26 to 32 therein for CDRH2; SEQ ID NOs: 39 to 44 therein for CDRL1; SEQ ID NOs: 45 to 50 therein for CDRL2; and SEQ ID NOs: 51 to 57 therein for CDRL3, which sequences are incorporated herein by reference); or g. the CDRs of any of the antibodies disclosed in U.S. Pat. No. 7,812,133 (Genentech: Seq ID Nos: 11 or 12 therein for CDRH3; Seq ID Nos: 7 or 8 therein for CDRH1 and Seq ID Nos: 9 or 10 therein for CDRH2; SEQ ID NOs: 1 or 2 therein for CDRL1; SEQ ID NOs: 3 or 4 therein for CDRL2; and SEQ ID NOs: 5 or 6 therein for CDRL3, which sequences are incorporated herein by reference).

Concept 63. A method, an antibody or fragment for the use, a use or a composition according to any preceding concept, wherein the antibody or fragment thereof comprises the VH and/or VL domains selected from the following:

a. the VH and/or VL domains of antibody 2D10 (Seq ID No:34 for VH and/or Seq ID No:48 for VL);

b. the VH and/or VL domains of antibody 10A7 (Seq ID No:2 for VH and/or Seq ID No: 16 for VL);

c. the VH and/or VL domains of antibody 09H04 (Seq ID No:66 for VH and/or Seq ID No:80 for VL);

d. the VH and/or VL domains of antibody 19H01 (Seq ID No:94 for VH and/or Seq ID No:108 for VL);

e. a VH domains of any of the nanobodies disclosed in WO2011/073180 (Ablynx, Seq ID Nos: 177 to 185, 199 to 226 therein, which sequences are incorporated herein by reference [reproduced herein as Seq ID Nos: 177 to 213]);

f. the VH and/or VL domains of any of the antibodies disclosed in WO2006/029879 (Roche/Genentech, Seq ID Nos: 2, 4, 6, 8, 10, 12, 17, 19 and 20 therein for VH domains; and Seq ID Nos: 1, 3, 5, 7, 9, 11, 16 and 18 therein for VL domains, which sequences are incorporated herein by reference [reproduced herein as Seq ID Nos: 214 to 230]); or g. the VH and/or VL domains of any of the antibodies disclosed in U.S. Pat. No. 7,812,133 (Genentech, Seq ID Nos: 15 and 16 therein for VH domains; and Seq ID Nos: 13 and 14 therein for VL domains, which sequences are incorporated herein by reference [reproduced herein as Seq ID Nos: 231 to 234]).

Concept 64. A method, an antibody or fragment for the use, a use or a composition according to any preceding concept, wherein the antibody is oxelumab.

Concept 65. A method, an agent or an antibody or fragment for the use, a use or a composition according to any preceding concept, where in the Tscm cells and/or the Tn cells are CD4+.

In another embodiment, the Tscm cells and/or the Tn cells are CD8+.

Concept 66. A method, an agent or an antibody or fragment for the use, a use or a composition according to concept 64, wherein the Tscm cells and/or the Tn cells are circulating T-cells.

Concept 67. A method, an agent or an antibody or fragment for the use, a use or a composition according to concept 65, wherein the Tscm cells and/or the Tn cells are in a sample of blood, e.g. peripheral blood.

Whereas T-cells present in blood are relatively straight-forward to isolate and characterise, T-cells which are present in the tissues of a subject are generally more difficult to isolate. That said, it may be possible to isolate T-cells from various tissues (such as skin, tissues of the GI tract, e.g. bowel, and from inflamed joints, e.g. synovium)

Concept 68. A method according to any one of concepts 9 to 11, 16, 20 to 39 or 43 to 67, an agent or an antibody or fragment for the use according to any one of concepts 12, 17, 20, 21, 23 to 25 or 44 to 67, a use according to any one of concepts 13, 14, 18 to 20 or 23 to 25 or 44 to 67, or a composition according to any one of concepts 15 or 44 to 67, wherein the subject is a human patient.

Concept 69. A method, an agent or an antibody or fragment for the use, a use or a composition according to concept 68, wherein the subject is at risk of a Tscm-mediated disease or condition.

Concept 70. A method, an agent or an antibody or fragment for the use, a use or a composition according to concept 68, wherein the subject has a Tscm-mediated disease or condition.

Concept 71. A method, an agent or an antibody or fragment for the use, a use or a composition according to any preceding concept, wherein the Tscm-mediated disease or condition is mediated by CD45RA+CCR7+CD95+OX40+ Tscm cells.

Concept 72. A method, an agent or an antibody or fragment for the use, a use or a composition according to any one of concept 68 to 70, wherein the Tscm-mediated disease or condition is characterised by having a ratio of CD45RA+CCR7+CD95+OX40+ Tscm cells:CD45RA+CCR7+CD95− Tn cells of greater than 50:50.

In another embodiment, the disease or condition is characterised by having a ratio of Tscm cells:Tn cells as set out in any of concepts 23 to 25.

Concept 73. A method, an agent or an antibody or fragment for the use, a use or a composition according to concept 72, wherein the Tscm-mediated disease or condition is characterised by having a ratio of Tscm:Tn of greater than 60:40, or greater than 70:30, or greater than 75:25, such as greater than 70:30.

Concept 74. A method, an agent or an antibody or fragment for the use, a use or a composition according to concept 73, wherein the Tscm-mediated disease or condition is characterised by having a ratio of Tscm:Tn of greater than 80:20, or greater than 85:15, for example greater than 90:10, e.g. greater than 95:5.

Concept 75. A method, an agent or an antibody or fragment for the use, a use or a composition according to any preceding concept, wherein the Tscm-mediated disease or condition is selected from an autoimmune disease, HIV-1, and a T-cell malignancy.

Concept 76. A method, an agent or an antibody or fragment for the use, a use or a composition according to concept 75, wherein the Tscm-mediated disease or condition is selected from GvHD, transplant rejection, psoriasis, rheumatoid arthritis, systemic lupus erythematosus, multiple sclerosis, juvenile dermatomyositis, T-cell lymphoma and T-cell leukemia.

Concept 77. A method, an agent or an antibody or fragment for the use, a use or a composition according to concept 76, wherein the Tscm-mediated disease or condition is GvHD or transplant rejection.

Concept 78. A method, an agent or an antibody or fragment for the use, a use or a composition according to concept 76, wherein the transplant is a cell, tissue or organ transplant (e.g. liver, lung, heart, kidney or bowel), or a blood transplant (e.g. autologous or allogeneic), for example where the blood is bone marrow-derived, is cord-blood derived (umbilical), or is peripheral-blood derived.

In one embodiment, the transplant is a CAR T-cell transplant (chimeric antigen receptor).

Concept 79. A method, an agent or an antibody or fragment for the use, a use or a composition according to concept 76, wherein the Tscm-mediated disease or condition is a T-cell lymphoma selected from T-cell non-Hodgkin's lymphoma, peripheral T-cell lymphoma (PTCL), anaplastic large cell lymphoma (ALCL), angioimmunoblastic lymphoma, cutaneous T-cell lymphoma, adult T-cell leukemia/lymphoma, blastic NK-cell lymphoma, enteropathy-type T-cell lymphoma, hematosplenic gamma-delta T-cell lymphoma, lymphoblastic lymphoma (T-LBL) and nasal NK/T-cell lymphoma.

Concept 80. A method, an agent or an antibody or fragment for the use, a use or a composition according to concept 76, wherein the Tscm-mediated disease or condition is a T-cell leukemia selected from large granular lymphocytic leukemia (LGLL), T-cell prolymphocytic leukemia (T-PLL), T-cell acute lymphoblastic leukemia (T-ALL) and Sezary syndrome.

Concept 81. A method, an agent or an antibody or fragment for the use, a use or a composition according to any preceding concept, further comprising administering to the human a further therapeutic agent, optionally wherein the further therapeutic agent is independently selected from the group consisting of rapamycin (sirolimus), tacrolimus, ciclosporin, corticosteroids (e.g. methylprednisolone), methotrexate, mycophenolate mofetil, anti-CD28 antibodies, anti-IL12/IL-23 antibodies (e.g. ustekinumab), anti-CD20 antibodies (e.g. rituximab), anti-CD30 antibodies (e.g. brentuximab), CTLA4-Fc molecules (e.g. abatacept), CCR5 receptor antagonists (e.g. maraviroc), anti-CD40L antibodies, anti-VLA4 antibodies (e.g. natalizumab), anti-LFA1 antibodies, fludarabine, anti-CD52 antibodies (e.g. alemtuzumab), anti-CD45 antibodies, cyclophosphamide, anti-thymocyte globulins, anti-complement C5 antibodies (e.g. eculizumab), anti-a4b7 integrin antibodies (e.g. vedolizumab), anti-IL6 antibodies (e.g. tocilizumab), anti-IL2R antibodies (e.g. basilixtumab), anti-CD25 antibodies (e.g. daclizumab), anti-TNFa/TNFa-Fc molecules (e.g. etancercept, adalimumab, infliximab, golimumab or certolizumab pegol) and Vorinostat, in particular rapamycin (sirolimus), tacrolimus, ciclosporin, corticosteroids (e.g. methylprednisolone), methotrexate, mycophenolate mofetil, anti-CD28 antibodies, CTLA4-Fc molecules (e.g. abatacept), anti-CD40L antibodies, anti-LFA1 antibodies, anti-CD52 antibodies (e.g. alemtuzumab), cyclophosphamide and anti-thymocyte globulins.

In one embodiment, the further therapeutic agent is independently selected from the group consisting of calcineurin inhibitors (e.g. tacrolimus, ciclosporin), mTOR inhibitors (e.g. rapamycin (sirolimus)), and antiproliferative agents (e.g. mycophenolate mofetil, cyclophosphamide).

In one embodiment, the further therapeutic agent is independently selected from the group consisting of immunosuppressants that modulate IL-2 signalling (e.g. tacrolimus, ciclosporin, rapamycin (sirolimus), and anti-CD25 antibodies (e.g. basilixumab, daclizumab).

In one embodiment, the further therapeutic agent is rapamycin (sirolimus). In another embodiment, the further therapeutic agent is tacrolimus. In another embodiment, the further therapeutic agent is a combination of tacrolimus and methotrexate. In another embodiment, the further therapeutic agent is ciclosporin. In another embodiment, the further therapeutic agent is a combination of ciclosporin and methotrexate. In another embodiment, the further therapeutic agent is cyclophosphamide. In another embodiment, the further therapeutic agent is mycophenolate mofetil.

Concept 82. A method, an agent or an antibody or fragment for the use, a use or a composition according to any preceding concept, further comprising administering to the human a therapeutically effective amount of rapamycin.

Concept 83. A method, an agent or an antibody or fragment for the use, a use or a composition according to any preceding concept, further comprising administering to the human a therapeutically effective amount of tacrolimus.

The inventors have surprisingly found that an anti-OX40L antibody may provide synergistic effects when administered as part of a combination therapy with a further therapeutic agent. To that end, further concepts are provided below:

Concept 101. An anti-OX40L antibody or fragment thereof for use in treating or reducing the risk of an OX40L-mediated disease or condition in a subject in combination with a further therapeutic agent independently selected from the group consisting of rapamycin (sirolimus), tacrolimus, ciclosporin, corticosteroids (e.g. methylprednisolone), methotrexate, mycophenolate mofetil, anti-CD28 antibodies, anti-IL12/IL-23 antibodies (e.g. ustekinumab), anti-CD20 antibodies (e.g. rituximab), anti-CD30 antibodies (e.g. brentuximab), CTLA4-Fc molecules (e.g. abatacept), CCR5 receptor antagonists (e.g. maraviroc), anti-CD40L antibodies, anti-VLA4 antibodies (e.g. natalizumab), anti-LFA1 antibodies, fludarabine, anti-CD52 antibodies (e.g. alemtuzumab), anti-CD45 antibodies, cyclophosphamide, anti-thymocyte globulins, anti-complement C5 antibodies (e.g. eculizumab), anti-a4b7 integrin antibodies (e.g. vedolizumab), anti-IL6 antibodies (e.g. tocilizumab), anti-IL2R antibodies (e.g. basilixumab), anti-CD25 antibodies (e.g. daclizumab), anti-TNFa/TNFa-Fc molecules (e.g. etanercept, adalimumab, infliximab, golimumab or certolizumab pegol) and Vorinostat.

Concept 102. Use of an anti-OX40L antibody or fragment thereof for the treatment or prevention of an OX40L-mediated disease or condition in a subject in combination with a further therapeutic agent independently selected from the group consisting of rapamycin (sirolimus), tacrolimus, ciclosporin, corticosteroids (e.g. methylprednisolone), methotrexate, mycophenolate mofetil, anti-CD28 antibodies, anti-IL12/IL-23 antibodies (e.g. ustekinumab), anti-CD20 antibodies (e.g. rituximab), anti-CD30 antibodies (e.g. brentuximab), CTLA4-Fc molecules (e.g. abatacept), CCR5 receptor antagonists (e.g. maraviroc), anti-CD40L antibodies, anti-VLA4 antibodies (e.g. natalizumab), anti-LFA1 antibodies, fludarabine, anti-CD52 antibodies (e.g. alemtuzumab), anti-CD45 antibodies, cyclophosphamide, anti-thymocyte globulins, anti-complement C5 antibodies (e.g. eculizumab), anti-a4b7 integrin antibodies (e.g. vedolizumab), anti-IL6 antibodies (e.g. tocilizumab), anti-IL2R antibodies (e.g. basilixumab), anti-CD25 antibodies (e.g. daclizumab), anti-TNFa/TNFa-Fc molecules (e.g. etanercept, adalimumab, infliximab, golimumab or certolizumab pegol) and Vorinostat.

Concept 103. Use of an anti-OX40L antibody or fragment thereof in the manufacture of a medicament for the treatment or prevention of an OX40L-mediated disease or condition in a subject in combination with a further therapeutic agent independently selected from the group consisting of rapamycin (sirolimus), tacrolimus, ciclosporin, corticosteroids (e.g. methylprednisolone), methotrexate, mycophenolate mofetil, anti-CD28 antibodies, anti-IL12/IL-23 antibodies (e.g. ustekinumab), anti-CD20 antibodies (e.g. rituximab), anti-CD30 antibodies (e.g. brentuximab), CTLA4-Fc molecules (e.g. abatacept), CCR5 receptor antagonists (e.g. maraviroc), anti-CD40L antibodies, anti-VLA4 antibodies (e.g. natalizumab), anti-LFA1 antibodies, fludarabine, anti-CD52 antibodies (e.g. alemtuzumab), anti-CD45 antibodies, cyclophosphamide, anti-thymocyte globulins, anti-complement C5 antibodies (e.g. eculizumab), anti-a4b7 integrin antibodies (e.g. vedolizumab), anti-IL6 antibodies (e.g. tocilizumab), anti-IL2R antibodies (e.g. basilixumab), anti-CD25 antibodies (e.g. daclizumab), anti-TNFa/TNFa-Fc molecules (e.g. etanercept, adalimumab, infliximab, golimumab or certolizumab pegol) and Vorinostat.

Concept 104. A composition comprising an anti-OX40L antibody or fragment thereof for the treatment or prevention of an OX40L-mediated disease or condition in a subject in combination with a further therapeutic agent independently selected from the group consisting of rapamycin (sirolimus), tacrolimus, ciclosporin, corticosteroids (e.g. methylprednisolone), methotrexate, mycophenolate mofetil, anti-CD28 antibodies, anti-IL12/IL-23 antibodies (e.g. ustekinumab), anti-CD20 antibodies (e.g. rituximab), anti-CD30 antibodies (e.g. brentuximab), CTLA4-Fc molecules (e.g. abatacept), CCR5 receptor antagonists (e.g. maraviroc), anti-CD40L antibodies, anti-VLA4 antibodies (e.g. natalizumab), anti-LFA1 antibodies, fludarabine, anti-CD52 antibodies (e.g. alemtuzumab), anti-CD45 antibodies, cyclophosphamide, anti-thymocyte globulins, anti-complement C5 antibodies (e.g. eculizumab), anti-a4b7 integrin antibodies (e.g. vedolizumab), anti-IL6 antibodies (e.g. tocilizumab), anti-IL2R antibodies (e.g. basilixumab), anti-CD25 antibodies (e.g. daclizumab), anti-TNFa/TNFa-Fc molecules (e.g. ctanercept, adalimumab, infliximab, golimumab or certolizumab pegol) and Vorinostat.

Concept 105. A method of treating or preventing an OX40L-mediated disease or condition in a subject comprising administering to said human a therapeutically effective amount of an anti-OX40L antibody or fragment thereof in combination with a further therapeutic agent independently selected from the group consisting of rapamycin (sirolimus), tacrolimus, ciclosporin, corticosteroids (e.g. methylprednisolone), methotrexate, mycophenolate mofetil, anti-CD28 antibodies, anti-IL12/IL-23 antibodies (e.g. ustekinumab), anti-CD20 antibodies (e.g. rituximab), anti-CD30 antibodies (e.g. brentuximab), CTLA4-Fc molecules (e.g. abatacept), CCR5 receptor antagonists (e.g. maraviroc), anti-CD40L antibodies, anti-VLA4 antibodies (e.g. natalizumab), anti-LFA1 antibodies, fludarabine, anti-CD52 antibodies (e.g. alemtuzumab), anti-CD45 antibodies, cyclophosphamide, anti-thymocyte globulins, anti-complement C5 antibodies (e.g. eculizumab), anti-a4b7 integrin antibodies (e.g. vedolizumab), anti-IL6 antibodies (e.g. tocilizumab), anti-IL2R antibodies (e.g. basilixumab), anti-CD25 antibodies (e.g. daclizumab), anti-TNFa/TNFa-Fc molecules (e.g. etanercept, adalimumab, infliximab, golimumab or certolizumab pegol) and Vorinostat, wherein the OX40L-mediated disease or condition is thereby treated or prevented.

In any of the concepts herein, the combination may be used in the prevention of an OX40L-mediated disease. In any of the concepts, the combination may be used to reduce the risk of an OX40L-mediated disease. In any of the concepts, the combination may be used in the treatment of an OX40L-mediated disease.

A "combination" as described here may be as defined elsewhere herein, for example on page 100, on pages 105 to 107, and on pages 119 to 120. In one embodiment, the disease is rheumatoid arthritis or psoriasis, and the further therapeutic agent is an anti-IL-17 antibody (such as brodalumab, secukinumab and ixekizumab). Combinations may be administered concomitantly or sequentially. Administration may be via any of the methods disclosed herein, for example, as discussed in the section entitled "Methods of Administration and Dosing" beginning on page 130 herein.

As used in any of the concepts herein, the "treatment" of an OX40L-mediated disease includes the reduction of one or more symptom(s) of said OX40L-mediated disease. Treatment may be interpreted as described elsewhere herein, for example on page 107, and in the section entitled "Kits" (beginning on page 149, in particular page 152)

Immunosuppressive drug intervention in the management of GvHD associated with hematopoietic stem cell transplant (HSCT) may be administered to treat patients with confirmed disease. GvHD grading may be determined as described below.

In one embodiment, the administration is prophylactic to reduce the risk of an OX40L-mediated disease. As used in the concepts herein, "prevention" (or "prevent" or "preventing" and the like) of an OX40L-mediated disease includes the prevention of one or more symptom(s) of said OX40L-mediated disease. Preventing may refer to the total or partial inhibition of the development, recurrence, onset or spread of an OX40L-mediated disease and/or symptom related thereto, resulting from the administration combination of therapies provided herein (e.g., a combination of prophylactic and/or therapeutic agents). Preventing may be interpreted as disclosed elsewhere herein.

Immunosuppressive drug intervention in the management of GvHD associated with hematopoietic stem cell transplant (HSCT) may be administered to prevent disease in patients known to be at risk.

Thus, in one embodiment, a prophylactically-effective dose is administered before the onset of an OX40L-mediated disease or condition. As used in the concepts herein, a subject may be determined to be "before the onset of an OX40L-mediated disease or condition" if the subject is presenting no symptoms which would conventionally be associated with said disease or condition or if the subject would not be diagnosed as having such a disease or condition by any conventional method. In another embodiment, administration which is before the onert of disease may be termed "pre-emptive treatment", which refers to the use of further therapeutic agents (such as immunosuppressant agents) and/or an anti-OX40L antibody of the invention in individuals at risk of developing disease and where there may be early signs that emergence of clinically-relevant GvHD is imminent. For example, an experimental or predictive serum or cellular biomarker may indicate the optimal time for initiation of pre-emptive GvHD treatment.

For example, the presence of signs and symptoms of acute GvHD in a human may be staged and graded according to a standardised scale such as described in Przepiorka et al. In a primate, such as a rhesus *macaque* monkey, the presence of signs and symptoms of acute GvHD may be staged and graded according to a standardised scale such as described herein in Example 7. Similar disease grading scales are also in routine clinical use for other relevant diseases, such as rheumatoid arthritis and inflammatory bowel diseases.

"Prevention" or "prophylaxis" may be as described in aspect 94 herein, with dosages and timings of administration of the anti-OX40L antibody as described. A prophylactic agent may be used in any of the methods described on page 102 to 103.

The OX40L-mediated diseases or conditions may be any of the diseases or conditions mentioned herein, including those which are defined elsewhere herein as Tscm-mediated diseases or conditions (see concepts 75 to 80 hereinabove). In one embodiment, the OX40L-mediated diseases or conditions are as described in any of aspects 12, 12a, 69, 69a, 71, 72, 72a, 90 to 93 as described herein. In one embodiment, the OX40L-mediated diseases or conditions are as described in any of aspects 12, 12a, 69, 69a, 71, 72, 72a, 90 to 93 as described herein. In one embodiment, the OX40L-mediated disease or condition is a hOX40L-mediated disease or condition as described herein, for example on pages 103 to 104, or on page 131. In another embodiment, the OX40L-mediated diseases or conditions are as described in the section entitled "Methods of Administration and Dosing" beginning on page 130 herein. In a preferred embodiment, the disease or condition is GvHD or transplant rejection, in particular, GvHD. In another embodiment, the OX40L-mediated disease of condition is Chron's disease. In another embodiment, the OX40L-mediated disease of condition is inflammatory bowel disease (IBD). In another embodiment, the OX40L-mediated disease of condition is ulcerative colitis. In another embodiment, the OX40L-mediated disease of condition is psoriasis.

In any of concepts described herein, the anti-OX40L antibody and/or the further therapeutic agent are administered to the subject. Administration may be by any method described herein, for example as described on page 93, or in the sections entitled "Pharmaceutical compositions" and "Methods of Administration" beginning on pages 118 and 130 respectively. In one embodiment, the anti-OX40L antibody of the invention is administered intravenously. In one embodiment, the anti-OX40L antibody of the invention is administered subcutaneously.

In one embodiment, the further therapeutic agent is rapamycin (sirolimus) and is administered orally. In one embodiment, the further therapeutic agent is tacrolimus and is administered orally. In one embodiment, the further therapeutic agent is methotrexate and is administered orally and/or intravenously. In one embodiment, the further therapeutic agent is ciclosporin and is administered intravenously and/or orally. In one embodiment, the further therapeutic agent is cyclophosphamide and is administered intravenously and/or orally. In one embodiment, the further therapeutic agent is methyl prednisolone and is administered orally and/or intravenously.

Concept 106. A method, an antibody or fragment for the use, a composition for the use, or the use according to any one of concepts 101 to 105, wherein the subject has a post-treatment or post-prophylaxis survival time of at least 14 days, or at least 21 days, or at least 28 days, or at least 40 days, or at least 50 days, or at least 60 days.

Concept 107. A method, an antibody or fragment for the use, a composition for the use, or the use according to any one of concepts 101 to 105, wherein post-prophylaxis, the subject has at least 7 days, or at least 14 days, or at least 21 days, or at least 28 days, or at least 40 days, or at least 50 days, or at least 60 days disease-free.

Concept 108. A method, an antibody or fragment for the use, a composition for the use, or the use according to any one of concepts 101 to 105, wherein post-treatment, the subject has at least 7 days, or at least 14 days, or at least 21 days, or at least 28 days, or at least 40 days, or at least 50 days, or at least 60 days disease progression-free.

Concept 109. A method, an antibody or fragment for the use, a composition for the use, or the use according to any one of concepts 106 to 108, wherein the number of days of survival, the number of disease free days, or the number of disease-progression free days is at least 2 months, or at least 3 months, or at least 4 months, e.g. at least 5 months, such as at least 6 months.

Concept 110. A method, an antibody or fragment for the use, a composition for the use, or the use according to concept 109, wherein the number of days of survival, the number of disease free days, or the number of disease-progression free days is at least 9 months, or at least one year.

Concept 111. A method of preventing the onset of an OX40L-mediated disease or condition in a subject by administering a prophylactically-effective amount of an anti-OX40L antibody and administering a prophylactically-effective amount of a further therapeutic agent independently selected from the group consisting of rapamycin (sirolimus), tacrolimus, ciclosporin, corticosteroids (e.g. methylprednisolone), methotrexate, mycophenolate mofetil, anti-CD28 antibodies, anti-IL12/IL-23 antibodies (e.g. ustekinumab), anti-CD20 antibodies (e.g. rituximab), anti-CD30 antibodies (e.g. brentuximab), CTLA4-Fc molecules (e.g. abatacept), CCR5 receptor antagonists (e.g. maraviroc), anti-CD40L antibodies, anti-VLA4 antibodies (e.g. natalizumab), anti-LFA1 antibodies, fludarabine, anti-CD52 antibodies (e.g. alemtuzumab), anti-CD45 antibodies, cyclophosphamide, anti-thymocyte globulins, anti-complement C5 antibodies (e.g. eculizumab), anti-a4b7 integrin antibodies (e.g. vedolizumab), anti-IL6 antibodies (e.g. tocilizumab), anti-IL2R antibodies (e.g. basilixumab), anti-CD25 antibodies (e.g. daclizumab), anti-TNFa/TNFa-Fc molecules (e.g. ctancrcept, adalimumab, infliximab, golimumab or certolizumab pegol) and Vorinostat, wherein the onset of the OX40L-mediated disease or condition is prevented.

By "prophylactically-effective", it is meant that the dose is effective to prevent or reduce the risk of an OX40L-mediated disease or condition.

In one embodiment, the combination may be used to reduce the risk of an OX40L-mediated disease or condition. In concept 111, the anti-OX40L antibody of the invention and the further therapeutic agent may be administered to the patient prophylactically, which administration may be sequential or simultaneous. The dosing regimens and modes of administration may be those which are normal or traditionally administered by physicians for the further therapeutic agent. The dosing regimens and modes of administration may be those which are normal or traditionally administered by physicians for the anti-OX40L antibody of the invention. However, the concurrent use of both agents is expected to result in an improved prophylaxis as compared to either agent alone.

Concept 112. A method of treating an OX40L-mediated disease or condition in a subject by administering a prophylactically-effective amount of an anti-OX40L antibody and administering a therapeutically-effective amount of a further therapeutic agent independently selected from the group consisting of rapamycin (sirolimus), tacrolimus, ciclosporin, corticosteroids (e.g. methylprednisolone), methotrexate, mycophenolate mofetil, anti-CD28 antibodies, anti-IL12/IL-23 antibodies (e.g. ustekinumab), anti-CD20 antibodies (e.g. rituximab), anti-CD30 antibodies (e.g. brentuximab), CTLA4-Fc molecules (e.g. abatacept), CCR5 receptor antagonists (e.g. maraviroc), anti-CD40L antibodies, anti-VLA4 antibodies (e.g. natalizumab), anti-LFA1 antibodies, fludarabine, anti-CD52 antibodies (e.g. alemtuzumab), anti-CD45 antibodies, cyclophosphamide, anti-thymocyte globulins, anti-complement C5 antibodies (e.g. eculizumab), anti-a4b7 integrin antibodies (e.g. vedolizumab), anti-IL6 antibodies (e.g. tocilizumab), anti-IL2R antibodies (e.g. basilixumab), anti-CD25 antibodies (e.g. daclizumab), anti-TNFa/TNFa-Fc molecules (e.g. etanercept, adalimumab, infliximab, golimumab or certolizumab pegol) and Vorinostat, wherein the onset of the OX40L-mediated disease or condition is treated.

By "therapeutically effective", it is meant that the dose is effective to treat an OX40L-mediated disease or condition. Effective may be as defined on pages 96 to 97, or pn page 152 herein, and may provide serum concentrations as described in the section entitled "Pharmaceutical Compositions" starting on page 118 herein.

In concept 112, the anti-OX40L antibody of the invention may be administered to the patient, but despite prophylaxis, the onset of the OX40L-mediated disease or condition occurs (the onset may be delayed by a number of days or weeks, as compared with a patient who had not been receiving the antibody of the invention). In this case, a therapeutically-effective amount of a further therapeutic agent may be administered to treat the disease or condition.

Concept 113. A method of treating an OX40L-mediated disease or condition in a subject by administering a therapeutically-effective amount of an anti-OX40L antibody and administering a prophylactically-effective amount of a further therapeutic agent independently selected from the group consisting of rapamycin (sirolimus), tacrolimus, ciclosporin, corticosteroids (e.g. methylprednisolone), methotrexate, mycophenolate mofetil, anti-CD28 antibodies, anti-IL12/IL-23 antibodies (e.g. ustekinumab), anti-CD20 antibodies (e.g. rituximab), anti-CD30 antibodies (e.g. brentuximab), CTLA4-Fc molecules (e.g. abatacept), CCR5 receptor antagonists (e.g. maraviroc), anti-CD40L antibodies, anti-VLA4 antibodies (e.g. natalizumab), anti-LFA1 antibodies, fludarabine, anti-CD52 antibodies (e.g. alemtuzumab), anti-CD45 antibodies, cyclophosphamide, anti-thymocyte globulins, anti-complement C5 antibodies (e.g. eculizumab), anti-a4b7 integrin antibodies (e.g. vedolizumab), anti-IL6 antibodies (e.g. tocilizumab), anti-IL2R antibodies (e.g. basilixumab), anti-CD25 antibodies (e.g. daclizumab), anti-TNFa/TNFa-Fc molecules (e.g. etanercept, adalimumab, infliximab, golimumab or certolizumab pegol) and Vorinostat, wherein the onset of the OX40L-mediated disease or condition is treated.

In concept 113, the further therapeutic agent may be administered to the patient, but despite prophylaxis, the onset of the OX40L-mediated disease or condition occurs (the onset may be delayed by a number of days or weeks, as compared with a patient who had not been receiving the further therapeutic agent). In this case, a therapeutically-effective amount of an anti-OX40L antibody of the invention may be administered to treat the disease or condition.

Concept 114. A method of treating an OX40L-mediated disease or condition in a subject by administering a therapeutically-effective amount of an anti-OX40L antibody and administering a therapeutically-effective amount of a further therapeutic agent independently selected from the group consisting of rapamycin (sirolimus), tacrolimus, ciclosporin, corticosteroids (e.g. methylprednisolone), methotrexate, mycophenolate mofetil, anti-CD28 antibodies, anti-IL12/IL-23 antibodies (e.g. ustekinumab), anti-CD20 antibodies (e.g. rituximab), anti-CD30 antibodies (e.g. brentuximab), CTLA4-Fc molecules (e.g. abatacept), CCR5 receptor antagonists (e.g. maraviroc), anti-CD40L antibodies, anti-VLA4 antibodies (e.g. natalizumab), anti-LFA1 antibodies, fludarabine, anti-CD52 antibodies (e.g. alemtuzumab), anti-CD45 antibodies, cyclophosphamide, anti-thymocyte globulins, anti-complement C5 antibodies (e.g. eculizumab), anti-a4b7 integrin antibodies (e.g. vedolizumab), anti-IL6 antibodies (e.g. tocilizumab), anti-IL2R antibodies (e.g. basilixumab), anti-CD25 antibodies (e.g. daclizumab), anti-TNFa/TNFa-Fc molecules (e.g. etanercept, adalimumab, infliximab, golimumab or certolizumab pegol) and Vorinostat, wherein the onset of the OX40L-mediated disease or condition is treated.

In concept 114, both the anti-OX40L antibody of the invention and the further therapeutic agent are not administered until there are clinical signs of the OX40L-mediated disease or condition. The combination treatment of both agents may provide further benefits as compared to either agent alone.

Concept 115. A method according to concept 111 or concept 113, wherein the further therapeutic agent is independently selected from rapamycin (sirolimus), tacrolimus, a combination of tacrolimus and methotrexate, cyclophosphamide, ciclosporin, and a combination of ciclosporin and methotrexate.

In one embodiment, the OX40L-mediated disease or condition is GvHD or transplant rejection, particularly GvHD. In one embodiment, the OX40L-mediated disease or condition is GvHD or transplant rejection, particularly GvHD, and the further therapeutic agent is rapamycin (sirolimus). In one embodiment, the OX40L-mediated disease or condition is GvHD or transplant rejection, particularly GvHD, and the further therapeutic agent is tacrolimus. In one embodiment, the OX40L-mediated disease or condition is GvHD or transplant rejection, particularly GvHD, and the further therapeutic agent is a combination of tacrolimus and methotrexate. In one embodiment, the OX40L-mediated disease or condition is GvHD or transplant rejection, particularly GvHD, and the further therapeutic agent is cyclophosphamide. In one embodiment, the OX40L-mediated disease or condition is GvHD or transplant rejection, particularly GvHD, and the further therapeutic agent is ciclosporin. In one embodiment, the OX40L-mediated disease or condition is GvHD or transplant rejection, particularly GvHD, and the further therapeutic agent is a combination of ciclosporin and methotrexate. In one embodiment, the OX40L-mediated disease or condition is GvHD or transplant rejection, particularly GvHD, and the further therapeutic agent is mycophenolate mofetil.

In one embodiment, the anti-OX40L antibody is administered to a patient who is already receiving rapamycin (sirolimus). In another embodiment, embodiment, the anti-OX40L antibody is administered to a patient who is already receiving tacrolimus. In another embodiment, the anti-OX40L antibody is administered to a patient who is already receiving a combination of tacrolimus and methotrexate. In another embodiment, the anti-OX40L antibody is administered to a patient who is already receiving a combination of ciclosporin and methotrexate. In another embodiment, the anti-OX40L antibody is administered to a patient who is already receiving ciclosporin. In another embodiment, the anti-OX40L antibody is administered to a patient who is already receiving cyclophophamide. In another embodiment, the anti-OX40L antibody is administered to a patient who is already receiving mycophenolate mofetil.

These further therapeutic agents may be used prophylactically in the treatment of OX40L-mediated diseases or conditions. For example, in GvHD, preventive therapy (prophylaxis) is typically administered around the time of HSCT and is continued for a period of time following transplant to maintain immunosuppression during the period of greatest risk of developing acute GvHD. Specific drug regimens differ between transplant centres, but as an example prophylaxis with calcineurin inhibitors such as ciclosporin or tacrolimus, or with rapamycin (sirolimus) may be initiated within the 7 day period preceding transplant (such as Day−3, or Day−1 pre-HSCT), or immediately following the HSCT procedure (e.g. on Day 0, or Day+1 after transplant). Prophylaxis with mycophenolate mofetil is typically dosed following HSCT, for example starting between Day+1 to Day+5 post-transplant. Prophylaxis with these agents may be continued, for example, between 28 to 180 days or longer following transplant, with daily dosages calculated to maintain serum levels in the range to achieve effective immunosuppression without limiting side effects. In addition to calcineurin inhibitors, methotrexate is often used as an adjunct to prophylaxis, typically being administered on Days+1, +3, +6, and +11 post-transplant.

An anti-OX40L antibody of the invention may be used as prophylaxis in combination with tacrolimus, ciclosporin, a combination of tacrolimus and methotrexate, a combination of ciclosporin and methotrexate, cyclophosphamide, mycophenolate mofetil or rapamycin, where prophylaxis with any of these agents is started before or around the time of HSCT, or immediately following the transplant procedure, for example within the period 7 days before, to 7 days after transplant. Tacrolimus, or ciclosporin, or rapamycin may then be administered at therapeutically effective dose and frequency, for example daily, for up to 180 days following the transplant. An anti-OX40L antibody of the invention may be administered concurrently, starting before or around the time of HSCT, or immediately following the transplant procedure, for example within the period 7 days before, to 7 days after transplant. The anti-OX40L antibody may then be dosed at a therapeutically effective dose and frequency, for example biweekly or monthly, for up to 180 days following the transplant. Under these circumstances the combined activity of the anti-OX40L antibody and the additional prophylactic agent would be expected to display a synergistic effect in preventing the onset and/or severity of GvHD.

Concept 116. A method according to concept 112 or concept 114, wherein the further therapeutic agent is a corticosteroid (e.g. methylprednisolone).

In one embodiment, the OX40L-mediated disease or condition is GvHD or transplant rejection, in particular GvHD. In one embodiment, the OX40L-mediated disease or condition is GvHD or transplant rejection, in particular GvHD, and the further therapeutic agent is methylprednisolone.

In cases where breakthrough GvHD occurs (for example, even despite prophylaxis), treatment may be initiated immediately upon confirmation of Grade II or higher GvHD disease. Systemic corticosteroids such as methylprednisolone are the first-line treatment of choice, administered concurrently with ongoing prophylaxis with, for example, a calcineurin inhibitor such as ciclosporin or tacrolimus.

Where first-line treatment or prophylaxis fails to control GvHD, "salvage therapy" may be attempted in which case additional previously unused immunosuppressants such as rapamycin or mycophenolate mofetil may be administered. Thus, in one embodiment, a therapeutically effective amount of an anti-OX40L antibody of the invention is administered to a patient who is refractory to prophylaxis or treatment with any of: rapamycin, tacrolimus, tacrolimus in combination with methotrexate, cyclophosphamide, ciclosporin, ciclosporin in combination with methotrexate, or corticosteroids (e.g. methylprednisolone). In another embodiment, a therapeutically effective amount of an anti-OX40L antibody of the invention is administered to a patient who is refractory to prophylaxis or treatment with any of the further therapeutic agents mentioned herein. In another embodiment, an anti-OX40L antibody of the invention is administered as a salvage therapy.

Concept 117. A method of prolonging survival in a subject having or at risk of an OX40L-mediated disease or condition by administering a therapeutic or prophylactic combination of an anti-OX40L antibody and a further therapeutic agent independently selected from the group consisting of rapamycin (sirolimus), tacrolimus, ciclosporin, corticosteroids (e.g. methylprednisolone), methotrexate, mycophenolate mofetil, anti-CD28 antibodies, anti-IL12/IL-23 antibodies (e.g. ustekinumab), anti-CD20 antibodies (e.g. rituximab), anti-CD30 antibodies (e.g. brentuximab), CTLA4-Fc molecules (e.g. abatacept), CCR5 receptor antagonists (e.g. maraviroc), anti-CD40L antibodies, anti-VLA4 antibodies (e.g. natalizumab), anti-LFA1 antibodies, fludarabine, anti-CD52 antibodies (e.g. alemtuzumab), anti-CD45 antibodies, cyclophosphamide, anti-thymocyte globulins, anti-complement C5 antibodies (e.g. eculizumab), anti-a4b7 integrin antibodies (e.g. vedolizumab), anti-IL6 antibodies (e.g. tocilizumab), anti-IL2R antibodies (e.g. basilixumab), anti-CD25 antibodies (e.g. daclizumab), anti-TNFa/TNFa-Fc molecules (e.g. etanercept, adalimumab, infliximab, golimumab or certolizumab pegol) and Vorinostat.

In one embodiment, then OX40L-mediated disease or condition is GvHD or transplant rejection, in particular GvHD. A number of factors affect the severity and disease progression in GvHD, such as the pre-transplant conditioning regimen (e.g. myeloablation by irradiation, preparative chemotherapy), degree of donor-recipient tissue matching (HLA matching, and/or relationship of donor-recipient), and therapeutic or prophylactic treatment regimens.

In general, however, in primates, such as rhesus macaque that have received haploidentical stem cell transplants, the mean survival time (MST) post-transplant and in the absence of therapy is 8 days.

Concept 118. A method according to concept 117, wherein survival is increased by at least 7 days, or by at least 14 days, or by at least 20 days, or by at least 30 days or by at least 40 days, or by at least 50 days, or by at least 60 days, or by at least 70 days.

Concept 119. A method of increasing the number of disease-free, or disease-progression free, days in a subject having or at risk of an OX40L-mediated disease or condition by administering a therapeutic or prophylactic combination of an anti-OX40L antibody and a further therapeutic agent independently selected from the group consisting of rapamycin (sirolimus), tacrolimus, ciclosporin, corticosteroids (e.g. methylprednisolone), methotrexate, mycophenolate mofetil, anti-CD28 antibodies, anti-IL12/IL-23 antibodies (e.g. ustekinumab), anti-CD20 antibodies (e.g. rituximab), anti-CD30 antibodies (e.g. brentuximab), CTLA4-Fc molecules (e.g. abatacept), CCR5 receptor antagonists (e.g. maraviroc), anti-CD40L antibodies, anti-VLA4 antibodies (e.g. natalizumab), anti-LFA1 antibodies, fludarabine, anti-CD52 antibodies (e.g. alemtuzumab), anti-CD45 antibodies, cyclophosphamide, anti-thymocyte globulins, anti-complement C5 antibodies (e.g. eculizumab), anti-a4b7 integrin antibodies (e.g. vedolizumab), anti-IL6 antibodies (e.g. tocilizumab), anti-IL2R antibodies (e.g. basilixumab), anti-CD25 antibodies (e.g. daclizumab), anti-TNFa/TNFa-Fc molecules (e.g. etanercept, adalimumab, infliximab, golimumab or certolizumab pegol) and Vorinostat.

In one embodiment, then OX40L-mediated disease or condition is GvHD or transplant rejection, in particular GvHD. In humans, the presence of signs and symptoms of acute GvHD may be staged and graded according to a standardised scale such as described in Przepiorka et al. In primates, such as rhesus macaques, the presence of signs and symptoms of acute GvHD may be staged and graded according to a standardised scale such as described herein in Example 7.

Thus, the number of disease free days may be measured by absence of clinical grading symptoms. The number of disease-progression free days may be measures as the number of days where the clinical grading score does not change.

Concept 120. A method according to concept 119, wherein the number of disease-free, or disease-progression free, days is at least 7 days, or at least 14 days, or at least 21 days, or at least 28 or at least 40 days, or at least 50 days, or by at least 60 days, or at least 70 days.

Concept 121. A method according to concept 120, wherein the number of disease free, or disease-progression free, days is at least 90 days, at least 180 days or at least 365 days.

Concept 122. A method of treating or reducing the risk of transplant rejection or GvHD in a subject by administering a therapeutic or prophylactic combination of an anti-OX40L antibody and a further therapeutic agent independently selected from the group consisting of rapamycin (sirolimus), tacrolimus, ciclosporin, corticosteroids (e.g. methylprednisolone), methotrexate, mycophenolate mofetil, anti-CD28 antibodies, anti-IL12/IL-23 antibodies (e.g. ustekinumab), anti-CD20 antibodies (e.g. rituximab), anti-CD30 antibodies (e.g. brentuximab), CTLA4-Fc molecules (e.g. abatacept), CCR5 receptor antagonists (e.g. maraviroc), anti-CD40L antibodies, anti-VLA4 antibodies (e.g. natalizumab), anti-LFA1 antibodies, fludarabine, anti-CD52 antibodies (e.g. alemtuzumab), anti-CD45 antibodies, cyclophosphamide, anti-thymocyte globulins, anti-complement C5 antibodies (e.g. eculizumab), anti-a4b7 integrin antibodies (e.g. vedolizumab), anti-IL6 antibodies (e.g. tocilizumab), anti-IL2R antibodies (e.g. basilixumab), anti-CD25 antibodies (e.g. daclizumab), anti-TNFa/TNFa-Fc molecules (e.g. etanercept, adalimumab, infliximab, golimumab or certolizumab pegol) and Vorinostat, wherein the combination results in an increased survival in a Rhesus macaque model of haploidentical hematopoietic stem cell transplantation as compared to either the antibody or the further therapeutic agent as a monotherapy.

In one embodiment, the method is a method of preventing an OX40L-mediated disease or condition.

In one embodiment, the OX40L-mediated disease or condition is GvHD or transplant rejection, in particular GvHD. In one embodiment, the OX40L-mediated disease or condition is GvHD or transplant rejection, in particular GvHD, and the further therapeutic agent is a rapamycin (sirolimus). In one embodiment, the OX40L-mediated disease or condition is GvHD or transplant rejection, in particular GvHD, and the further therapeutic agent is tacrolimus. In one embodiment, the OX40L-mediated disease or condition is GvHD or transplant rejection, in particular GvHD, and the further therapeutic agent is a combination of tacrolimus and methotrexate. In one embodiment, the OX40L-mediated disease or condition is GvHD or transplant rejection, in particular GvHD, and the further therapeutic agent is cyclophosphamide. In one embodiment, the OX40L-mediated disease or condition is GvHD or transplant rejection, in particular GvHD, and the further therapeutic agent is ciclosporin. In one embodiment, the OX40L-mediated disease or condition is GvHD or transplant rejection, in particular GvHD, and the further therapeutic agent is a combination of ciclosporin and methotrexate. In one embodiment, the OX40L-mediated disease or condition is GvHD or transplant rejection, in particular GvHD, and the further therapeutic agent is mycophenolate mofetil.

The Rhesus macaque model of haploidentical hematopoietic stem cell transplantation may be as described in aspect 99 herein.

Concept 123. A method according to any one of concepts 106, 109, 110, 117, 119, or 122, wherein the survival is increased by at least 7 days, or by at least 14 days, or by at least 21 days, or by at least 28 days, or by at least 40 days, or by at least 50 days, or by at least 60 days, or by at least 70 days as compared to either the antibody or the further therapeutic agent as a monotherapy.

Concept 124. A method according to any one of concepts 106, 109, 110, 117, 119, or 122, wherein survival is at least doubled, e.g tripled, as compared to either the antibody or the further therapeutic agent as a monotherapy.

Concept 125. A method, an antibody or fragment for the use, a composition for the use, or the use according to any preceding concept, wherein the antibody specifically binds to human OX40L (hOX40L).

The hOX40L may be as described in aspect 28 or aspect 30 described herein.

In any of the concepts provided herein, the anti-OX40L antibody may be as described elsewhere herein. In one embodiment, the anti-OX40L antibody is as described in any of aspects 1 to 11, 13 to 27, 29, 31 to 43 or 45 described herein. In another embodiment, the anti-OX40L antibody is as described in aspects 73 to 89, or as in any of aspects 95 to 102 described herein. In another embodiment, the anti-OX40L antibody is as described in any of concepts 53 to 64 hereinabove. Other properties of anti-OX40L antibodies are described on pages 86 to 89, in the section entitled "bispecifics" beginning on page 90 herein, in the section entitled "Antibodies" beginning on page 108 herein and in the section entitled "Methods of Administration and Dosing" beginning on page 130 herein.

Concept 126. A method, an antibody or fragment for the use, a composition for the use, or the use according to concept 125, which competes for binding to said hOX40L with an antibody selected from the group consisting of 02D10, 10A07, 09H04 and 19H01.

Competition between antibodies may be determined as described in aspect 13 or aspect 73, for example as determined by SPR, ELISA, HTRF or FACS. Methods related to the measurement methods are disclosed herein, including in the Examples.

Concept 127. A method, an antibody or fragment for the use, a composition for the use, or the use according to concept 126, which competes for binding to said hOX40L with the antibody 02D10, wherein the antibody or fragment comprises a VH domain which comprises a HCDR3 comprising the motif VRGXYYY, wherein X is any amino acid.

Concept 128. A method, an antibody or fragment for the use, a composition for the use, or the use according to any preceeding concept, wherein the antibody antagonises specific binding of OX40 to OX40L, e.g. as determined using SPR or ELISA.

Antagonism and inhibition may be carried out as defined on page 94 to 95.

Concept 129. A method, an antibody or fragment for the use, a composition for the use, or the use according to any preceding concept, wherein the antibody is a humanized, human or fully human antibody.

Concept 130. A method, an antibody or fragment for the use, a composition for the use, or the use according to any preceding concept, wherein the antibody is a fragment of an antibody selected from the list of multispecific antibodies (eg. bi-specific antibodies), intrabodies, single-chain Fv antibodies (scFv), camelized antibodies, Fab fragments, F(ab') fragments, disulfide-linked Fvs (sdFv), anti-idiotypic (anti-Id) antibodies, and epitope-binding fragments thereof.

Concept 131. A method, an antibody or fragment for the use, a composition for the use, or the use according to any preceding concept, wherein the antibody or fragment enables greater than 80% stem cell donor chimerism by day 12 in a Rhesus macaque model of haploidentical hematopoietic stem cell transplantation.

Concept 132. A method, an antibody or fragment for the use, a composition for the use, or the use according to any preceding concept, wherein the antibody or fragment expresses as a stably transfected pool in Lonza GS-Xceed™ at level greater than 1.5 g/L in a fed batch overgrow culture using Lonza version 8 feed system with an overgrow period of 14 days.

Concept 133. A method, an antibody or fragment for the use, a composition for the use, or the use according to any preceding concept, wherein the antibody or fragment thereof comprises a HCDR3 of from 16 to 27 amino acids and derived from the recombination of a human VH gene segment, a human D gene segment and a human JH gene segment, wherein the human JH gene segment is IGHJ6 (e.g. IGHJ6*02).

Concept 134. A method, an antibody or fragment for the use, a composition for the use, or the use according to any preceding concept, wherein the antibody or fragment thereof comprises a CDR selected from:
 a. the HCDR3 of antibody 2D10 (Seq ID No:40 or Seq ID No:46);
 b. the HCDR3 of antibody 10A7 (Seq ID No:8 or SEQ ID No:14);
 c. the HCDR3 of antibody 09H04 (Seq ID No:72 or Seq ID No:78);
 d. the HCDR3 of antibody 19H01 (Seq ID No:100 or Seq ID No:106);
 e. a CDR3 of any of the nanobodies having the variable region amino acid sequence of Seq ID Nos: 177 to 213;
 f. an HCDR3 of any of the antibodies having the variable region amino acid sequence of Seq ID Nos: 215, 217, 219, 221, 223, 225, 227, 229 or 230; or
 g. an HCDR3 of any of the antibodies having the variable region amino acid sequence of Seq ID Nos: 232 or 234.

Concept 135. A method, an antibody or fragment for the use, a composition for the use, or the use according to any preceding concept, wherein the antibody or fragment thereof comprises:
 a. the CDRs of antibody 2D10 (Seq ID No:40 or Seq ID No:46 for CDRH3, SEQ ID No:38 or SEQ ID No:44 for CDRH2, SEQ ID No:36 or SEQ ID No:42 for CDRH1, SEQ ID No:50 or SEQ ID No:56 for CDRL1, SEQ ID No:52 or SEQ ID No:58 for CDRL2 and SEQ ID No:54 or SEQ ID No:60 for CDRL3);
 b. the CDRs of antibody 10A7 (Seq ID No:8 or SEQ ID No:14 for CDRH3, SEQ ID No:6 or SEQ ID No:12 for CDRH2, SEQ ID No:4 or SEQ ID No:10 for CDRH1, SEQ ID No:18 or SEQ ID No:24 for CDRL1, SEQ ID No:20 or SEQ ID No:26 for CDRL2 and SEQ ID No:22 or SEQ ID No:28 for CDRL3);
 c. the CDRs of antibody 09H04 (Seq ID No:72 or Seq ID No:78 for CDRH3, SEQ ID No:70 or SEQ ID No:76 for CDRH2, SEQ ID No:68 or SEQ ID No:74 for CDRH1, SEQ ID No:82 or SEQ ID No:88 for CDRL1, SEQ ID No:84 or SEQ ID No:90 for CDRL2 and SEQ ID No:86 or SEQ ID No:92 for CDRL3);
 d. the CDRs of antibody 19H01 (Seq ID No:100 or Seq ID No: 106 for CDRH3, SEQ ID No:98 or SEQ ID No: 104 for CDRH2, SEQ ID No:96 or SEQ ID No: 102 for CDRH1, SEQ ID No:110 or SEQ ID No: 116 for CDRL1, SEQ ID No: 112 or SEQ ID No: 118 for CDRL2 and SEQ ID No: 114 or SEQ ID No: 120 for CDRL3);
 e. the CDRs of any of the nanobodies having the variable region amino acid sequence of Seq ID Nos: 177 to 213;
 f. the heavy chain CDRs of any of the antibodies having the heavy chain variable region amino acid sequence of Seq ID Nos: 215, 217, 219, 221, 223, 225, 227, 229 or 230, and the light chain CDRs of any of the antibodies having the light chain variable region amino acid sequence of Seq ID Nos: 214, 216, 218, 220, 222, 224, 226 or 228; or
 g. the heavy chain CDRs of any of the antibodies having the heavy chain variable region amino acid sequence of Seq ID Nos: 232 or 234, and the light chain CDRs of any of the antibodies having the light chain variable region amino acid sequence of Seq ID Nos:231 or 233.

Concept 136. A method, an antibody or fragment for the use, a composition for the use, or the use according to any preceding concept, wherein the antibody or fragment thereof comprises the VH and/or VL domains selected from the following:
 a. the VH and/or VL domains of antibody 2D10 (Seq ID No:34 for VH and/or Seq ID No:48 for VL);
 b. the VH and/or VL domains of antibody 10A7 (Seq ID No:2 for VH and/or Seq ID No: 16 for VL);
 c. the VH and/or VL domains of antibody 09H04 (Seq ID No:66 for VH and/or Seq ID No:80 for VL);
 d. the VH and/or VL domains of antibody 19H01 (Seq ID No:94 for VH and/or Seq ID No:108 for VL);
 e. a VH domain of any of the nanobodies having the variable region amino acid sequence of Seq ID Nos: 177 to 213;
 f. a VH domain of any of the antibodies having the heavy chain variable region amino acid sequence of Seq ID Nos: 215, 217, 219, 221, 223, 225, 227, 229 or 230, and a VL domain of any of the antibodies having the light chain variable region amino acid sequence of Seq ID Nos: 214, 216, 218, 220, 222, 224, 226 or 228; or
 g. a VH domain of any of the antibodies having the heavy chain variable region amino acid sequence of Seq ID Nos: 232 or 234, and a VL domain of any of the antibodies having the light chain variable region amino acid sequence of Seq ID Nos:231 or 233.

Concept 137. A method, an antibody or fragment for the use, a composition for the use, or the use according to any preceding concept, wherein the antibody is oxelumab.

Concept 138. A method, an antibody or fragment for the use, a composition for the use, or the use according to any preceding concept, wherein the subject is a primate.

The term "subject" may be other subjects as described herein, for example as described on page 104. In one embodiment, the primate is a rhesus macaque monkey.

Concept 139. A method, an antibody or fragment for the use, a composition for the use, or the use according to any preceding concept, wherein the subject is a human.

In one embodiment, the subject is a human patient.

Concept 140. A method, an antibody or fragment for the use, a composition for the use, or the use according to any preceding concept, wherein the subject is at risk of an OX40L-mediated disease or condition.

In one embodiment, a subject may be identified as being "at risk of an OX40L-mediated disease or condition" if the subject has been previously identified as having an increased risk, e.g. by genotyping and/or phenotyping, but the subject has not yet presented symptoms or would not be diagnosed as having such a disease or condition by any conventional method. Thus, the methods and uses disclosed herein may aid in the early identification of patients who will develop such diseases or conditions. In one embodiment, the disease or condition is prevented (i.e. the treatment is prophylactic).

In one embodiment, the OX40L-mediated disease or condition is GvHD or transplant rejection, in particular GvHD. In a particular embodiment, the subject is at risk of GvHD or transplant rejection when they are pre-operative for a transplant. In particular, a subject is at risk of GvHD or transplant rejection when they have commenced a pre-transplant conditioning regimen (e.g. myeloablation by irradiation, preparative chemotherapy), and when degree of donor-recipient tissue matching (HLA matching, and/or relationship of donor-recipient) is not 100%. Potential transplant therapies are envisaged in concept 78 hereinabove.

Concept 141. A method, an antibody or fragment for the use, a composition for the use, or the use according to concept 40, wherein the method, antibody or fragment for the use, the use or the composition is for the prevention of the OX40L-mediated disease or condition.

Concept 142. A method, an antibody or fragment for the use, a composition for the use, or the use according to any one of concepts 101 to 139, wherein the subject has an OX40L-mediated disease or condition.

A subject has an OX40L-mediated disease or condition if the subject is presenting symptoms which would conventionally be associated with said disease or condition or if the subject would be diagnosed as having such a disease or condition by any conventional method. In one embodiment, the OX40L-mediated disease or condition is GvHD or transplant rejection, particularly GvHD, and a subject may be determined to have the disease by any of the methods mentioned in concepts 101 to 105 and 119 hereinabove.

Concept 143. A method, an antibody or fragment for the use, a composition for the use, or the use according to concept 142, wherein the method, antibody or fragment for the use, the composition for the use, or the use is for the treatment of the OX40L-mediated disease or condition.

In one embodiment, treatment is commenced when the OX40L-mediated disease or condition has been diagnosed as a confirmed disease or condition.

In one embodiment, the OX40L-mediated disease or condition is GvHD or transplant rejection, in particular GvHD. GvHD grading may be determined as described herein (see concepts 101 to 105 and 119 hereinabove). In one embodiment, the subject is a human having Grade II clinical symptoms of GvHD.

Concept 144. A method, an antibody or fragment for the use, a composition for the use, or the use according to any preceding concept, wherein the OX40L-mediated disease or condition is selected from an autoimmune disease or condition, a systemic inflammatory disease or condition, or transplant rejection.

Concept 145. A method, an antibody or fragment for the use, a composition for the use, or the use according to concept 144, wherein the OX40L-mediated disease or condition is selected from inflammatory bowel disease (IBD), Crohn's disease, rheumatoid arthritis, transplant rejection, allogeneic transplant rejection, graft-versus-host disease (GvHD), ulcerative colitis, systemic lupus erythematosus (SLE), diabetes, uveitis, ankylosing spondylitis, contact hypersensitivity, multiple sclerosis and atherosclerosis.

Concept 146. A method, an antibody or fragment for the use, a composition for the use, or the use according to concept 145, wherein the OX40L-mediated disease or condition is GvHD or transplant rejection.

Concept 147. A method, an antibody or fragment for the use, a composition for the use, or the use according to concept 146, wherein the OX40L-mediated disease or condition is GvHD.

Concept 148. A method, an antibody or fragment for the use, a composition for the use, or the use according to concept 146, wherein the transplant is a cell, tissue or organ transplant (e.g. liver, lung, heart, kidney or bowel), or a blood transplant (e.g. autologous or allogeneic), for example where the blood is bone marrow-derived, is cord-blood derived (umbilical), or is peripheral-blood derived.

Concept 149. A method, an antibody or fragment for the use, a composition for the use, or the use according to any one of concepts 146 to 148, wherein the anti-OX40L antibody or fragment thereof is administered before transplant.

Concept 150. A method, an antibody or fragment for the use, a composition for the use, or the use according to any one of concepts 146 to 148, wherein the anti-OX40L antibody or fragment thereof is administered after transplant.

Concept 151. A method, an antibody or fragment for the use, a composition for the use, or the use according to concept 149 or concept 150, wherein the further therapeutic agent is administered after transplant.

In one embodiment, the further therapeutic agent is rapamycin (sirolimus). In one embodiment, the further therapeutic agent is tacrolimus. In one embodiment, the further therapeutic agent is a combination of tacrolimus and methotrexate. In one embodiment, the further therapeutic agent is cyclophosphamide. In one embodiment, the further therapeutic agent is ciclosporin. In one embodiment, the further therapeutic agent is a combination of ciclosporin and methotrexate. In one embodiment, the further therapeutic agent is mycophenolate mofetil. In one embodiment, the further therapeutic agent is methyl predinsolonel.

Concept 152. A method, an antibody or fragment for the use, a composition for the use, or the use according to concept 149 or concept 150, wherein the further therapeutic agent is administered before transplant.

In one embodiment, the further therapeutic agent is rapamycin (sirolimus). In one embodiment, the further therapeutic agent is tacrolimus. In one embodiment, the further therapeutic agent is a combination of tacrolimus and methotrexate. In one embodiment, the further therapeutic agent is cyclophosphamide. In one embodiment, the further therapeutic agent is ciclosporin. In one embodiment, the further therapeutic agent is a combination of ciclosporin and methotrexate. In one embodiment, the further therapeutic agent is mycophenolate mofetil.

Concept 153. A pharmaceutical composition comprising an anti-OX40L antibody or fragment thereof and a pharmaceutically acceptable excipient, diluent or carrier and further comprising a further therapeutic agent independently selected from the group consisting of rapamycin (sirolimus), tacrolimus, ciclosporin, corticosteroids (e.g. methylprednisolone), methotrexate, mycophenolate mofetil, anti-CD28 antibodies, anti-IL12/IL-23 antibodies (e.g. ustekinumab), anti-CD20 antibodies (e.g. rituximab), anti-CD30 antibodies (e.g. brentuximab), CTLA4-Fc molecules (e.g. abatacept), CCR5 receptor antagonists (e.g. maraviroc), anti-CD40L antibodies, anti-VLA4 antibodies (e.g. natalizumab), anti-LFA1 antibodies, fludarabine, anti-CD52 antibodies (e.g. alemtuzumab), anti-CD45 antibodies, cyclophosphamide, anti-thymocyte globulins, anti-complement C5 antibodies (e.g. eculizumab), anti-a4b7 integrin antibodies (e.g. vedolizumab), anti-IL6 antibodies (e.g. tocilizumab), anti-IL2R antibodies (e.g. basilixumab), anti-CD25 antibodies (e.g. daclizumab), anti-TNFa/TNFa-Fc molecules (e.g. etanercept, adalimumab, infliximab, golimumab or certolizumab pegol) and Vorinostat.

In one embodiment, there is provided a composition or kit for treating and/or preventing a OX40L-mediated condition or disease, the composition or kit comprising an antibody or fragment of the invention in combination with a further therapeutic agent optionally in combination with a label or instructions for use to treat and/or prevent said disease or condition in a human; optionally wherein the label or instructions comprise a marketing authorisation number (e.g., an FDA or EMA authorisation number); optionally wherein the kit comprises an IV or injection device that comprises the antibody or fragment.

The composition may be as described in aspect 105, 106 or 107 herein. Excipients for use in pharmaceutical formulations are well-known to the skilled person and may be as defined on page 97 herein, or in the section entitled "Pharmaceutical Compositions" beginning on page 118 herein, or in the section entitled "Methods of Administration and Dosing" beginning on page 130 herein.

Concept 154. A method, an antibody or fragment for the use, a composition for the use, the use or the composition according to any preceding concept, wherein the further therapeutic agent is independently selected from the group consisting of rapamycin (sirolimus), tacrolimus, ciclosporin, corticosteroids (e.g. methylprednisolone), methotrexate, mycophenolate mofetil, anti-CD28 antibodies, CTLA4-Fc molecules (e.g. abatacept), anti-CD40L antibodies, anti-LFA1 antibodies, anti-CD52 antibodies (e.g. alemtuzumab), cyclophosphamide and anti-thymocyte globulins.

Other combinations may be with the anti-inflammatory drugs described in aspect 46 herein, or as described in aspect 103. Other combinations are as described in concepts 81 to 83 hereinabove, or in any of concepts 101 to 153 hereinabove.

Concept 155. A method, an antibody or fragment for the use, a composition for the use, the use or the composition according to any preceding concept, further comprising administering to the human a therapeutically effective amount, or a prophylactically effective amount of a further therapeutic agent independently selected from the group consisting of rapamycin, tacrolimus, ciclosporin, cyclophosphamide, corticosteroids (e.g. methylprednisolone), methotrexate or mycophenolate mofetil, anti-CD28 antibodies, CTLA4-Fc molecules (e.g. abatacept) and anti-thymocyte globulins.

Concept 156. A method, an antibody or fragment for the use, a composition for the use, the use or the composition according to any preceding concept, further comprising administering to the human a therapeutically effective amount, or a prophylactically effective amount of a further therapeutic agent independently selected from the group consisting of rapamycin, tacrolimus, ciclosporin, cyclophosphamide, corticosteroids (e.g. methylprednisolone), methotrexate and mycophenolate mofetil.

Concept 157. A method, an antibody or fragment for the use, a composition for the use, the use or the composition according to any preceding concept, further comprising administering to the human a therapeutically effective amount, or a prophylactically effective amount of a further therapeutic agent independently selected from the group consisting of an immunosuppressant that modulate IL-2 signalling (e.g. tacrolimus, ciclosporin, rapamycin (sirolimus)), and anti-CD25 antibodies (e.g. basilixumab, daclizumab).

Concept 158. A method, an antibody or fragment for the use, a composition for the use, the use or the composition according to any preceding concept, further comprising administering to the human a therapeutically effective amount, or a prophylactically effective amount of a further therapeutic agent independently selected from the group consisting of calcineurin inhibitors (e.g. tacrolimus, ciclosporin), mTOR inhibitors (e.g. rapamycin (sirolimus)), and antiproliferative agents (e.g. mycophenolate mofetil, cyclophosphamide).

Concept 159. A method, an antibody or fragment for the use, a composition for the use, the use or the composition according to any preceding concept, further comprising administering to the human a therapeutically effective amount, or a prophylactically effective amount of rapamycin.

Concept 160. A method, an antibody or fragment for the use, a composition for the use, the use or the composition according to any preceding concept, further comprising administering to the human a therapeutically effective amount, or a prophylactically effective amount of tacrolimus.

Concept 161. A method, an antibody or fragment for the use, a composition for the use, the use or the composition according to any preceding concept, further comprising administering to the human a therapeutically effective amount, or a prophylactically effective amount of tacrolimus and methotrexate.

Concept 162. A method, an antibody or fragment for the use, a composition for the use, the use or the composition according to any preceding concept, further comprising administering to the human a therapeutically effective amount, or a prophylactically effective amount of ciclosporin.

Concept 163. A method, an antibody or fragment for the use, a composition for the use, the use or the composition according to any preceding concept, further comprising administering to the human a therapeutically effective amount, or a prophylactically effective amount of ciclosporin and methotrexate.

Concept 164. A method, an antibody or fragment for the use, a composition for the use, the use or the composition according to any preceding concept, further comprising administering to the human a therapeutically effective amount, or a prophylactically effective amount of cyclophosphamide.

Concept 165. A method, an antibody or fragment for the use, a composition for the use, the use or the composition according to any preceding concept, further comprising administering to the human a therapeutically effective amount, or a prophylactically effective amount of mycophenolate mofetil.

Concept 166. A method, an antibody or fragment for the use, a composition for the use, the use or the composition according to any preceding concept, further comprising administering to the human a therapeutically effective amount, or a prophylactically effective amount of a corticosteroid (e.g. methyl prednisolone).

Concept 167. A method, an antibody or fragment for the use, a composition for the use, the use or the composition according to any preceding concept, wherein the further therapeutic agent is administered sequentially or simultaneously with the anti-hOX40L antibody or fragment.

As explained in the examples, the inventors devised a set of criteria that is particularly useful for identifying antibodies and fragments of the invention, these criteria being:—

(a) The ability of the antibody or fragment to bind cell-surface hOX40L on CHO-S cells (optionally transfected with full length human OX40L) and/or bind recombinant hOX40L in a HTRF assay;
(b) The ability of the antibody or fragment to neutralise human OX40 (e.g. neutralise human OX40L binding to human OX40 Receptor) in a receptor neutralisation HTRF assay and/or a flow cytometry receptor neutralisation assay; and
(c) The ability of the antibody or fragment to specifically bind both human and rhesus monkey OX40L (useful so that the PK, PD, efficacy and other parameters of the antibody or fragment can be assessed in the rhesus model as a surrogate for humans).

Thus, in an example of the invention the antibody or fragment meets criteria (a), (b) and (c).

In an example, criterion (a) is set so that the antibody or fragment shows <70% receptor binding by FACS to hOX40L expressed by CHO-S cells.

In an example, criterion (a) is set so that the antibody or fragment shows <90% of receptor binding to OX40L in the HTRF assay.

In an example, criterion (a) is set so that the antibody or fragment shows at least a 20% effect in the HTRF assay.

In an example, OX40 is used in criterion (b).

In an embodiment, assaying or testing of an antibody or fragment of the invention is carried out at or substantially at pH7 (e.g., for in vitro tests and assays) and at or substantially at rtp.

Optionally, the antibody or fragment specifically binds hOX40L with an affinity (apparent affinity, Kd) of less than 1 microM, 1000 nM to 100 nM, 100 nM to 10 nM, 10 nM to 1 nM, 1000 pM to 500 pM, 500 pM to 200 pM, less than 200 pM, 200 pM to 150 pM, 200 pM to 100 pM, 100 pM to 10 pM, 10 pM to 1 pM, e.g., in the range of 1 mM to 1 pM (e.g., 1 mM to 100 pM; 10 nM to 100 pM; 1 nM to 10 pM; or 100 pM to 1 pM) as determined by SPR, e.g., under SPR conditions disclosed herein). Additionally or alternatively, the antibody or fragment specifically binds rhesus monkey OX40L with an affinity (apparent affinity, Kd) of less than 1 microM, 1000 nM to 100 nM, 100 nM to 10 nM, 10 nM to 1 nM, 1000 pM to 500 pM, 500 pM to 200 pM, less than 200 pM, 200 pM to 150 pM, 200 pM to 100 pM, 100 pM to 10 pM, 10 pM to 1 pM, e.g., in the range of 1 mM to 1 pM (e.g., 1 mM to 100 pM; 10 nM to 100 pM; 1 nM to 10 pM; or 100 pM to 1 pM) as determined by SPR, e.g., under SPR conditions disclosed herein). Such binding measurements can be made using a variety of binding assays known in the art, e.g., using surface plasmon resonance (SPR), such as by Biacore™ or using the ProteOn XPR36™ (Bio-Rad®), using KinExA® (Sapidyne Instruments, Inc), or using ForteBio Octet (Pall ForteBio Corp.).

OX40L binding ability, specificity and affinity (Kd, $K_{off}$ and/or $K_{on}$) can be determined by any routine method in the art, e.g., by surface plasmon resonance (SPR). The term "Kd", as used herein, is intended to refer to the equilibrium dissociation constant of a particular antibody-antigen interaction.

In one embodiment, the surface plasmon resonance (SPR) is carried out at 25° C. In another embodiment, the SPR is carried out at 37° C.

In one embodiment, the SPR is carried out at physiological pH, such as about pH7 or at pH7.6 (e.g., using Hepes buffered saline at pH7.6 (also referred to as HBS-EP)).

In one embodiment, the SPR is carried out at a physiological salt level, e.g., 150 mM NaCl.

In one embodiment, the SPR is carried out at a detergent level of no greater than 0.05% by volume, e.g., in the presence of P20 (polysorbate 20; e.g., Tween-20™) at 0.05% and EDTA at 3 mM.

In one example, the SPR is carried out at 25° C. or 37° C. in a buffer at pH7.6, 150 mM NaCl, 0.05% detergent (e.g., P20) and 3 mM EDTA. The buffer can contain 10 mM Hepes. In one example, the SPR is carried out at 25° C. or 37° C. in HBS-EP. HBS-EP is available from Teknova Inc (California; catalogue number H8022).

In an example, the affinity of the antibody or fragment is determined using SPR by
1. Coupling anti-mouse (or other relevant human, rat or non-human vertebrate antibody constant region species-matched) IgG (e.g., Biacore™ BR-1008-38) to a biosensor chip (e.g., GLM chip) such as by primary amine coupling;
2. Exposing the anti-mouse IgG (or other matched species antibody) to a test IgG antibody to capture test antibody on the chip;
3. Passing the test antigen over the chip's capture surface at 1024 nM, 256 nM, 64 nM, 16 nM, 4 nM with a 0 nM (i.e. buffer alone); and
4. And determining the affinity of binding of test antibody to test antigen using surface plasmon resonance, e.g., under an SPR condition discussed above (e.g., at 25° C. in physiological buffer). SPR can be carried out using any standard SPR apparatus, such as by Biacore™ or using the ProteOn XPR36™ (Bio-Rad®).

Regeneration of the capture surface can be carried out with 10 mM glycine at pH1.7. This removes the captured antibody and allows the surface to be used for another interaction. The binding data can be fitted to 1:1 model inherent using standard techniques, e.g., using a model inherent to the ProteOn XPR36™ analysis software.

In an example, the antibody or fragment of the invention is contained in a medical container, e.g., a vial, syringe, IV container or an injection device (e.g., an intraocular or intravitreal injection device). In an example, the antibody or fragment is in vitro, e.g., in a sterile container. In an example, the invention provides a kit comprising the antibody or fragment of the invention, packaging and instructions for use in treating or preventing or diagnosing in a human a disease or condition mediated by the OX40L. In an example, the instructions indicate that the human should be genotyped for an OX40L variant sequence of the invention before administering the antibody or fragment to the human. In an example, the instructions indicate that the human should be phenotyped for an OX40L variant of the invention before administering the antibody or fragment to the human. In an example, the human is of Chinese (e.g., Han or CHS) ethnicity and the instructions are in Chinese (e.g., Mandarin).

In an example the binding site(s) of the antibody or fragment are selected from a plurality (e.g., library) of binding sites. For example, the plurality of binding sites comprises or consists of a plurality of 4-chain antibodies or fragments thereof, e.g., dAbs, Fabs or scFvs. Suitable methods for producing pluralities of binding sites for screening include phage display (producing a phage display library of antibody binding sites), ribosome display (producing a ribosome display library of antibody binding sites), yeast display (producing a yeast display library of antibody binding sites), or immunisation of a non-human vertebrate (e.g., a rodent, e.g., a mouse or rat, e.g., a Velocimouse™, Kymouse™, Xenomouse™, Aliva Mouse™, HuMab Mouse™, Omnimouse™, Omnirat™ or MeMo Mouse™) with hOX40L or a hOX40L epitope and isolation of a repertoire of antibody-producing cells (e.g., a B-cell, plasma cell or plasmablast repertoire) and/or a repertoire of isolated antibodies, fragments or binding sites.

The term "epitope" is a region of an antigen that is bound by an antibody or fragment. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

The term "isolated" with reference to any aspect of the invention, e.g., an antibody or fragment, means that a subject antibody or fragment etc. (1) is free of at least some other proteins with which it would normally be found, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is operably associated (by covalent or noncovalent interaction) with a polypeptide with which it is not associated in nature, or (6) does not occur in nature. Typically, an "isolated" antibody, fragment, etc. constitutes at least about 5%, at least about 10%, at least about 25%, or at least about 50%, 60%, 70%, 80%, 85%, 90%, 92%, 95%, 97%, 98%, 99% or >99% of a given sample. Genomic DNA, cDNA, mRNA or other RNA, of synthetic origin, or any combination thereof can encode such an isolated antibody, fragment, etc. Preferably, the isolated antibody, fragment, etc. is substantially free from proteins or polypeptides or other contaminants that are found in its natural environment that would interfere with its therapeutic, diagnostic, prophylactic, research or other use.

For example, an "isolated" antibody is one that has been identified, separated and/or recovered from a component of its production environment (e.g., naturally or recombinantly). Preferably, the isolated polypeptide is free of association with all other components from its production environment, e.g., so that the antibody has been isolated to an FDA-approvable or approved standard. Contaminant components of its production environment, such as that resulting from recombinant transfected cells, are materials that would typically interfere with research, diagnostic or therapeutic uses for the antibody, and may include enzymes, hormones, and other proteinaceous or non-proteinaceous solutes. In preferred embodiments, the polypeptide will be purified: (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or, preferably, silver stain. Isolated antibody includes the antibody in situ within recombinant cells since at least one component of the antibody's natural environment will not be present. Ordinarily, however, an isolated polypeptide or antibody will be prepared by at least one purification step.

Immunoconjugates

The invention encompasses the antibody or fragment conjugated to a therapeutic moiety ("immunoconjugate"), such as a cytotoxin, a chemotherapeutic drug, an immunosuppressant or a radioisotope. Cytotoxin agents include any agent that is detrimental to cells. Examples of suitable cytotoxin agents and chemotherapeutic agents for forming immunoconjugates are known in the art, see for example, WO 05/103081, which is incorporated by reference herein in its entirety.

Bispecifics

The antibodies and fragments of the present invention may be monospecific, bispecific, or multispecific. Multispecific mAbs may be specific for different epitopes of one target polypeptide or may contain antigen-binding domains specific for more than one target polypeptide. See, e.g., Tutt et al., (1991) J. Immunol. 147:60-69. The human anti-hOX40L antibodies or fragments can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment, to produce a bispecific or a multispecific antibody with a second binding specificity.

An exemplary bi-specific antibody format that can be used in the context of the present invention involves the use of a first immunoglobulin (Ig) CH3 domain and a second Ig CH3 domain, wherein the first and second Ig CH3 domains differ from one another by at least one amino acid, and wherein at least one amino acid difference reduces binding of the bispecific antibody to Protein A as compared to a bi-specific antibody lacking the amino acid difference. In one embodiment, the first Ig CH3 domain binds Protein A and the second Ig CH3 domain contains a mutation that reduces or abolishes Protein A binding such as an H95R modification (by IMGT exon numbering; H435R by EU numbering). The second CH3 may further comprise a Y96F modification (by IMGT; Y436F by EU). Further modifications that may be found within the second CH3 include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bi-specific antibody format described above are contemplated within the scope of the present invention.

In certain embodiments, the antibody or OX40L binding fragment thereof comprises less than six CDRs. In some embodiments, the antibody or antigen binding fragment thereof comprises or consists of one, two, three, four, or five CDRs selected from the group consisting of HCDR1, HCDR2, HCDR3, LCDR1, LCDR2, and LCDR3. In specific embodiments, the antibody or antigen binding fragment thereof comprises or consists of one, two, three, four, or five CDRs selected from the group consisting of the HCDR1, HCDR2, HCDR3, LCDR1, LCDR2, and LCDR3 sequences in the sequence listing (i.e. Seq ID No:4, Seq ID No: 10, Seq ID No:36, Seq ID No:42, Seq ID No:68, Seq ID No:74, Seq ID No:96 or Seq ID No: 102, in particular, Seq ID No:36 or Seq ID No:42 for HCDR1; Seq ID No:6, Seq ID No: 12, Seq ID No:38, Seq ID No:44, Seq ID No:70, Seq ID No:76, Seq ID No:98 or Seq ID No: 104, in particular Seq ID No:38 or Seq ID No:44 for HCDR2; Seq ID No:8, Seq ID No:14, Seq ID No:40, Seq ID No:46, Seq ID No:72, Seq ID No:78, Seq ID No: 100 or Seq ID No: 106, in particular Seq ID No:40 or Seq ID No:46 for HCDR3; Seq ID No: 18, Seq ID No:24, Seq ID No:50, Seq ID No:56, Seq ID No:82, Seq ID No:88, Seq ID No: 110 or Seq ID No: 116, in particular Seq ID No:50 or Seq ID No:56 for LCDR1; Seq ID No:20, Seq ID No:26, Seq ID No:52, Seq ID No:58, Seq ID No:84, Seq ID No:90, Seq ID No: 112 or Seq ID No: 118, in particular Seq ID No:52 or Seq ID No:58 for LCDR2; and Seq ID No:22, Seq ID No:28, Seq ID No:54, Seq ID No:60, Seq ID No:86, Seq ID No:92, Seq ID No: 114 or Seq ID No: 120, in particular Seq ID No:54 or Seq ID No:60 for LCDR3).

In specific embodiments, an antibody of the invention is a fully human antibody, a monoclonal antibody, a recombinant antibody, an antagonist antibody, a hOX40L-neutralising antibody or any combination thereof or the invention provides a hOX40L binding fragment thereof. In an example, the antibody is a chimaeric antibody comprising human variable domains and non-human (e.g., mouse or rat or rabbit) constant domains. In particular embodiments, the antibody is a fully human antibody, such as a fully human monoclonal antibody, or antigen binding fragment thereof, that specifically binds to hOX40L. In preferred embodiments, the antibody is an antagonist antibody. In preferred embodiments, the antibody is a neutralising antibody.

In an example, the antibody or fragment is a lambda-type antibody or fragment (i.e., whose variable domains are lambda variable domains). Optionally, the antibody or fragment also comprises lambda constant domains.

In certain embodiments, the antibody competes (e.g., in a dose dependent manner) with OX40 or a fusion protein thereof (e.g., Fc:OX40), for binding to hOX40L, such as a cell surface-expressed hOX40L or soluble hOX40L. Exemplary competitive blocking tests are provided in the Examples herein.

In another aspect, provided herein are isolated nucleic acids encoding antibodies that specifically bind to a hOX40L polypeptide (e.g., a cell surface-expressed or soluble hOX40L), a hOX40L polypeptide fragment, or a hOX40L epitope. In certain embodiments, the nucleic acid encodes a VH chain, VL chain, VH domain, VL domain, HCDR1, HCDR2, HCDR3, LCDR1, LCDR2, and LCDR3 as disclosed in the sequence listing (i.e. Seq ID No:30 or Seq ID No:62 for VH chains; Seq ID No:32 or Seq ID No:64 for VL chains; Seq ID No: Seq ID No:2, Seq ID No:34, Seq ID No:66 or Seq ID No:94, in particular Seq ID No:34 for VH domains; Seq ID No: 16, Seq ID No:48, Seq ID No:80, or Seq ID No: 108, in particular Seq ID No:48 for VL domains; Seq ID No:4, Seq ID No: 10, Seq ID No:36, Seq ID No:42, Seq ID No:68, Seq ID No:74, Seq ID No:96 or Seq ID No: 102, in particular, Seq ID No:36 or Seq ID No:42 for HCDR1; Seq ID No:6, Seq ID No: 12, Seq ID No:38, Seq ID No:44, Seq ID No:70, Seq ID No:76, Seq ID No:98 or Seq ID No: 104, in particular Seq ID No:38 or Seq ID No:44 for HCDR2; Seq ID No:8, Seq ID No: 14, Seq ID No:40, Seq ID No:46, Seq ID No:72, Seq ID No:78, Seq ID No: 100 or Seq ID No: 106, in particular Seq ID No:40 or Seq ID No:46 for HCDR3; Seq ID No: 18, Seq ID No:24, Seq ID No:50, Seq ID No:56, Seq ID No:82, Seq ID No:88, Seq ID No: 110 or Seq ID No: 116, in particular Seq ID No:50 or Seq ID No:56 for LCDR1; Seq ID No:20, Seq ID No:26, Seq ID No:52, Seq ID No:58, Seq ID No:84, Seq ID No:90, Seq ID No: 112 or Seq ID No: 118, in particular Seq ID No:52 or Seq ID No:58 for LCDR2; and Seq ID No:22, Seq ID No:28, Seq ID No:54, Seq ID No:60, Seq ID No:86, Seq ID No:92, Seq ID No: 114 or Seq ID No: 120, in particular Seq ID No:54 or Seq ID No:60 for LCDR3).

In another aspect, provided herein are vectors and host-cells comprising nucleic acids encoding antibodies or fragments of the invention.

In certain embodiments, the antibody specifically binds to one or more single nucleotide polymorphism (SNP) variants of hOX40L. In an example of any aspect of the invention, the hOX40L is a trimer of monomers.

In an aspect, provided herein is a method for decreasing (e.g., by at least 20, 30, 40 50 or 60%, or 70%, 80%, 90%, 95% or >90%) or completely inhibiting binding of hOX40L to OX40 in a subject (e.g., a human subject), comprising administering to the subject an effective amount of an antibody or fragment thereof of the invention that specifically binds to hOX40L (e.g., a cell surface-expressed or soluble hOX40L).

In an aspect, provided herein is a method of treating or preventing a hOX40L-mediated disease or condition in a subject (e.g., a human subject), the method comprising administering to the subject an effective amount of an antibody or fragment thereof of the invention that specifically binds to hOX40L (e.g., a cell surface-expressed or soluble hOX40L), wherein the disease or condition is treated or prevented by the antibody or fragment. In an example, the method comprises decreasing or inhibiting a hOX40L biological activity, such as secretion of one, more or all of IL-2, IL-8, TNF alpha and interferon gamma, in the subject. In an example, the biological activity is selected from the secretion of one, more or all of IL-2, TNF alpha and interferon gamma. In an example, the biological activity is selected from the secretion of one, more or all of IL-8, CCL20 and RANTES.

In an aspect, provided herein is a method of decreasing or inhibiting a hOX40L biological activity, such as secretion of one, more or all of IL-2, IL-8, TNF alpha and interferon gamma, in a subject (e.g., a human subject), the method comprising administering to the subject an effective amount of an antibody or fragment thereof of the invention that specifically binds to hOX40L (e.g., a cell surface-expressed or soluble hOX40L), wherein hOX40L biological activity is decreased by the antibody or fragment. In an example, the biological activity is selected from the secretion of one, more or all of IL-2, TNF alpha and interferon gamma. In an example, the biological activity is selected from the secretion of one, more or all of IL-8, CCL20 and RANTES.

The term "about" or "approximately" means within 20%, preferably within 10%, and more preferably within 5% (or 4%, or 3% or 2%, or, in an example, 1% or less) of a given value or range.

As used herein, "administer" or "administration" refers to the act of injecting or otherwise physically delivering a substance as it exists outside the body (e.g., an anti-hOX40L antibody provided herein) into a patient, such as by mucosal, intradermal, intravenous, intramuscular delivery and/or any other method of physical delivery described herein or known in the art. When a disease, or a symptom thereof, is being treated, administration of the substance typically occurs after the onset of the disease or symptoms thereof. When a disease, or symptoms thereof, are being prevented, administration of the substance typically occurs before the onset of the disease or symptoms thereof.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/ total number of positions×100%). In one embodiment, the two sequences are the same length.

The determination of percent identity between two sequences (e.g., amino acid sequences or nucleic acid sequences) can also be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264 2268, modified as in Karlin and Altschul, 1993, Proc. Natl. Acad. Sci. U.S.A. 90:5873 5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecules of the present invention. BLAST protein searches can be performed with the XBLAST program parameters set, e.g., to score 50, wordlength=3 to obtain amino acid sequences homologous to a protein molecule of the present invention. To obtain gapped alignments for comparison purposes, Gapped BLAST can be utilized as described in Altschul et al., 1997, Nucleic Acids Res. 25:3389 3402. Alternatively, PSI BLAST can be used to perform an iterated search which detects distant relationships between molecules (Id.). When utilizing BLAST, Gapped BLAST, and PSI Blast programs, the default parameters of the respective programs (e.g., of XBLAST and NBLAST) can be used (see, e.g., National Center for Biotechnology Information (NCBI) on the worldwide web, ncbi.nlm.nih.gov). Another preferred, non-limiting example of a mathematical algorithm utilized for the comparison of sequences is the algorithm of Myers and Miller, 1988, CABIOS 4:11 17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

As used herein, an "antagonist" or "inhibitor" of hOX40L refers to a ligand (e.g., antibody or fragment) that is capable of inhibiting or otherwise decreasing one or more of the biological activities of hOX40L, such as in a cell expressing hOX40L or in a cell expressing a hOX40L ligand. For example, in certain embodiments, antibodies of the invention are antagonist antibodies that inhibit or otherwise decrease secretion of CCL20, IL-8 and/or RANTES from a cell having a cell surface-expressed OX40 when said antibody is contacted with said cell. In some embodiments, an antagonist of hOX40L (e.g., an antagonistic antibody of the invention) may, for example, act by inhibiting or otherwise decreasing the activation and/or cell signalling pathways of the cell expressing OX40L, thereby inhibiting a hOX40L-mediated biological activity of the cell the relative to the hOX40L-mediated biological activity in the absence of antagonist. In certain embodiments, the antibodies provided herein are fully human, antagonistic anti-hOX40L antibodies, preferably fully human, monoclonal, antagonistic anti-hOX40L antibodies.

The term "antibody" and "immunoglobulin" or "Ig" may be used interchangeably herein. An antibody or a fragment thereof that specifically binds to a hOX40L antigen may be cross-reactive with related antigens. Preferably, an antibody or a fragment thereof that specifically binds to a hOX40L antigen does not cross-react with other antigens (but may optionally cross-react with OX40L of a different species, e.g., rhesus, or murine). An antibody or a fragment thereof that specifically binds to a hOX40L antigen can be identified, for example, by immunoassays, BIAcore™, or other techniques known to those of skill in the art. An antibody or a fragment thereof binds specifically to a hOX40L antigen when it binds to a hOX40L antigen with higher affinity than to any cross-reactive antigen as determined using experimental techniques, such as radioimmunoassays (RIA) and enzyme-linked immunosorbent assays (ELISAs). Typically a specific or selective reaction will be at least twice background signal or noise and more typically more than 10 times background. See, e.g., Paul, ed., 1989, Fundamental Immunology Second Edition, Raven Press, New York at pages 332-336 for a discussion regarding antibody specificity.

Antibodies of the invention include, but are not limited to, synthetic antibodies, monoclonal antibodies, recombinantly produced antibodies, multispecific antibodies (including bi-specific antibodies), human antibodies, humanized antibodies, chimeric antibodies, intrabodies, single-chain Fvs (scFv) (e.g., including monospecific, bispecific, etc.), camelized antibodies, Fab fragments, F(ab') fragments, disulfide-linked Fvs (sdFv), anti-idiotypic (anti-Id) antibodies, and epitope-binding fragments of any of the above. In particular, antibodies of the present invention include immunoglobulin molecules and immunologically active portions of immunoglobulin molecules, i.e., antigen binding domains or molecules that contain an antigen-binding site that specifically binds to a hOX40L antigen (e.g., one or more complementarity determining regions (CDRs) of an anti-hOX40L antibody). The antibodies of the invention can be of any type (e.g., IgG, IgE, IgM, IgD, IgA and IgY), any class (e.g., IgG1, IgG2, IgG3, IgG4, IgA1 and IgA2, in particular IgG4), or any subclass (e.g., IgG2a and IgG2b) of immunoglobulin molecule. In preferred embodiments, the hOX40L antibodies are fully human, such as fully human monoclonal hOX40L antibodies. In certain embodiments, antibodies of the invention are IgG antibodies, or a class (e.g., human IgG1 or IgG4) or subclass thereof. In certain embodiments, the antibodies of the invention comprise a human gamma 4 constant region. In another embodiment, the heavy chain constant region does not bind Fc-γ receptors, and e.g. comprises a Leu235Glu mutation. In another embodiment, the heavy chain constant region comprises a Ser228Pro mutation to increase stability. In another embodiment, the heavy chain constant region is IgG4-PE.

The term "antigen binding domain," "antigen binding region," "antigen binding fragment," and similar terms refer to that portion of an antibody which comprises the amino acid residues that interact with an antigen and confer on the binding agent its specificity and affinity for the antigen (e.g., the complementarity determining regions (CDRs)). The antigen binding region can be derived from any animal species, such as rodents (e.g., rabbit, rat or hamster) and humans. Preferably, the antigen binding region will be of human origin.

As used herein, the term "composition" is intended to encompass a product containing the specified ingredients (e.g., an antibody of the invention) in, optionally, the specified amounts, as well as any product which results, directly or indirectly, from combination of the specified ingredients in, optionally, the specified amounts.

In the context of a polypeptide, the term "derivative" as used herein refers to a polypeptide that comprises an amino acid sequence of a hOX40L polypeptide, a fragment of a hOX40L polypeptide, or an antibody that specifically binds to a hOX40L polypeptide which has been altered by the introduction of amino acid residue substitutions, deletions or additions. The term "derivative" as used herein also refers to a hOX40L polypeptide, a fragment of a hOX40L polypeptide, or an antibody that specifically binds to a hOX40L polypeptide which has been chemically modified, e.g., by the covalent attachment of any type of molecule to the polypeptide. For example, but not by way of limitation, a hOX40L polypeptide, a fragment of a hOX40L polypeptide, or a hOX40L antibody may be chemically modified, e.g., by glycosylation, acetylation, pegylation, phosphorylation, amidation, derivatization by known protecting/blocking groups, proteolytic cleavage, linkage to a cellular ligand or other protein, etc. The derivatives are modified in a manner that is different from naturally occurring or starting peptide or polypeptides, either in the type or location of the molecules attached. Derivatives further include deletion of one or more chemical groups which are naturally present on the peptide or polypeptide. A derivative of a hOX40L polypeptide, a fragment of a hOX40L polypeptide, or a hOX40L antibody may be chemically modified by chemical modifications using techniques known to those of skill in the art, including, but not limited to specific chemical cleavage, acetylation, formulation, metabolic synthesis of tunicamycin, etc. Further, a derivative of a hOX40L polypeptide, a fragment of a hOX40L polypeptide, or a hOX40L antibody may contain one or more non-classical amino acids. A polypeptide derivative possesses a similar or identical function as a hOX40L polypeptide, a fragment of a hOX40L polypeptide, or a hOX40L antibody described herein.

The term "effective amount" as used herein refers to the amount of a therapy (e.g., an antibody or pharmaceutical composition provided herein) which is sufficient to reduce and/or ameliorate the severity and/or duration of a given disease and/or a symptom related thereto. This term also encompasses an amount necessary for the reduction or amelioration of the advancement or progression of a given disease, reduction or amelioration of the recurrence, development or onset of a given disease, and/or to improve or enhance the prophylactic or therapeutic effect(s) of another therapy (e.g., a therapy other than anti-hOX40L antibody provided herein). In some embodiments, the effective amount of an antibody of the invention is from about 0.1 mg/kg (mg of antibody per kg weight of the subject) to about 100 mg/kg. In certain embodiments, an effective amount of an antibody provided therein is about 0.1 mg/kg, about 0.5 mg/kg, about 1 mg/kg, 3 mg/kg, 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg about 90 mg/kg or about 100 mg/kg (or a range therein). In some embodiments, "effective amount" as used herein also refers to the amount of an antibody of the invention to achieve a specified result (e.g., inhibition of a hOX40L biological activity of a cell, such as inhibition of secretion of CCL20, IL-8 or RANTES, or INF-γ, TNF-α or IL-2, in particular INF-γ from the cell).

The term "epitope" as used herein refers to a localized region on the surface of an antigen, such as hOX40L polypeptide or hOX40L polypeptide fragment, that is capable of being bound to one or more antigen binding regions of an antibody, and that has antigenic or immunogenic activity in an animal, preferably a mammal, and most preferably in a human, that is capable of eliciting an immune response. An epitope having immunogenic activity is a portion of a polypeptide that elicits an antibody response in an animal. An epitope having antigenic activity is a portion of a polypeptide to which an antibody specifically binds as determined by any method well known in the art, for example, by the immunoassays described herein. Antigenic epitopes need not necessarily be immunogenic. Epitopes usually consist of chemically active surface groupings of molecules such as amino acids or sugar side chains and have specific three dimensional structural characteristics as well as specific charge characteristics. A region of a polypeptide contributing to an epitope may be contiguous amino acids of the polypeptide or the epitope may come together from two or more non-contiguous regions of the polypeptide. The epitope may or may not be a three-dimensional surface feature of the antigen. In certain embodiments, a hOX40L epitope is a three-dimensional surface feature of a hOX40L polypeptide (e.g., in a trimeric form of a hOX40L polypeptide). In other embodiments, a hOX40L epitope is linear feature of a hOX40L polypeptide (e.g., in a trimeric form or monomeric form of the hOX40L polypeptide). Antibodies provided herein may specifically bind to an epitope of the monomeric (denatured) form of hOX40L, an epitope of the trimeric (native) form of hOX40L, or both the monomeric (denatured) form and the trimeric (native) form of hOX40L. In specific embodiments, the antibodies provided herein specifically bind to an epitope of the trimeric form of hOX40L but do not specifically bind the monomeric form of hOX40L.

The term "excipients" as used herein refers to inert substances which are commonly used as a diluent, vehicle, preservatives, binders, or stabilizing agent for drugs and includes, but not limited to, proteins (e.g., serum albumin, etc.), amino acids (e.g., aspartic acid, glutamic acid, lysine, arginine, glycine, histidine, etc.), fatty acids and phospholipids (e.g., alkyl sulfonates, caprylate, etc.), surfactants (e.g., SDS, polysorbate, nonionic surfactant, etc.), saccharides (e.g., sucrose, maltose, trehalose, etc.) and polyols (e.g., mannitol, sorbitol, etc.). See, also, Remington's Pharmaceutical Sciences (1990) Mack Publishing Co., Easton, Pa., which is hereby incorporated by reference in its entirety.

In the context of a peptide or polypeptide, the term "fragment" as used herein refers to a peptide or polypeptide that comprises less than the full length amino acid sequence. Such a fragment may arise, for example, from a truncation at the amino terminus, a truncation at the carboxy terminus, and/or an internal deletion of a residue(s) from the amino acid sequence. Fragments may, for example, result from alternative RNA splicing or from in vivo protease activity. In certain embodiments, hOX40L fragments include polypeptides comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least contiguous 100 amino acid residues, at least 125 contiguous amino acid residues, at least 150 contiguous amino acid residues, at least 175 contiguous amino acid residues, at least 200 contiguous amino acid residues, or at least 250 contiguous amino acid residues of the amino acid sequence of a hOX40L polypeptide or an antibody that specifically binds to a hOX40L polypeptide. In a specific embodiment, a fragment of a hOX40L polypeptide or an antibody that specifically binds to a hOX40L antigen retains at least 1, at least 2, or at least 3 functions of the polypeptide or antibody.

The terms "fully human antibody" or "human antibody" are used interchangeably herein and refer to an antibody that comprises a human variable region and, most preferably a human constant region. In specific embodiments, the terms refer to an antibody that comprises a variable region and constant region of human origin. "Fully human" anti-hOX40L antibodies, in certain embodiments, can also encompass antibodies which bind hOX40L polypeptides and are encoded by nucleic acid sequences which are naturally occurring somatic variants of human germline immunoglobulin nucleic acid sequence. In a specific embodiment, the anti-hOX40L antibodies provided herein are fully human antibodies. The term "fully human antibody" includes antibodies having variable and constant regions corresponding to human germline immunoglobulin sequences as described by Kabat et al. (See Kabat et al. (1991) Sequences of Proteins of Immunological Interest, Fifth Edition, U.S. Department of Health and Human Services, NIH Publication No. 91-3242). Exemplary methods of producing fully human antibodies are provided, e.g., in the Examples herein, but any method known in the art may be used.

The phrase "recombinant human antibody" includes human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse or cow) that is transgenic and/or transchromosomal for human immunoglobulin genes (see e.g., Taylor, L. D. et al. (1992) Nucl. Acids Res. 20:6287-6295) or antibodies prepared, expressed, created or isolated by any other means that involves splicing of human immunoglobulin gene sequences to other DNA sequences. Such recombinant human antibodies can have variable and constant regions derived from human germline immunoglobulin sequences (See Kabat, E. A. et al. (1991) Sequences of Proteins of Immunological Interest, Fifth Edition, U.S. Department of Health and Human Services, NIH Publication No. 91-3242). In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "fusion protein" as used herein refers to a polypeptide that comprises an amino acid sequence of an antibody and an amino acid sequence of a heterologous polypeptide or protein (i.e., a polypeptide or protein not normally a part of the antibody (e.g., a non-anti-hOX40L antigen antibody)). The term "fusion" when used in relation to hOX40L or to an anti-hOX40L antibody refers to the joining of a peptide or polypeptide, or fragment, variant and/or derivative thereof, with a heterologous peptide or polypeptide. Preferably, the fusion protein retains the biological activity of the hOX40L or anti-hOX40L antibody. In certain embodiments, the fusion protein comprises a hOX40L antibody VH domain, VL domain, VH CDR (one, two or three VH CDRs), and/or VL CDR (one, two or three VL CDRs), wherein the fusion protein specifically binds to a hOX40L epitope.

The term "heavy chain" when used in reference to an antibody refers to five distinct types, called alpha (α), delta (δ), epsilon (ε), gamma (γ) and mu (μ), based on the amino acid sequence of the heavy chain constant domain. These distinct types of heavy chains are well known and give rise to five classes of antibodies, IgA, IgD, IgE, IgG and IgM, respectively, including four subclasses of IgG, namely IgG1, IgG1, IgG3 and IgG4. Preferably the heavy chain is a human heavy chain. In one example, the heavy chain is a disabled IgG isotype, e.g. a disabled IgG4. In certain embodiments, the antibodies of the invention comprise a human gamma 4 constant region. In another embodiment, the heavy chain constant region does not bind Fc-γ receptors, and e.g. comprises a Leu235Glu mutation. In another embodiment, the heavy chain constant region comprises a Ser228Pro mutation to increase stability. In another embodiment, the heavy chain constant region is IgG4-PE.

The term "host" as used herein refers to an animal, preferably a mammal, and most preferably a human.

The term "host cell" as used herein refers to the particular subject cell transfected with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

The term "immunomodulatory agent" and variations thereof including, but not limited to, immunomodulatory agents, as used herein refer to an agent that modulates a host's immune system. In certain embodiments, an immunomodulatory agent is an immunosuppressant agent. In certain other embodiments, an immunomodulatory agent is an immunostimulatory agent. In accordance with the invention, an immunomodulatory agent used in the combination therapies of the invention does not include an anti-hOX40L antibody or antigen-binding fragment. Immunomodulatory agents include, but are not limited to, small molecules, peptides, polypeptides, proteins, fusion proteins, antibodies, inorganic molecules, mimetic agents, and organic molecules.

As used herein, the term "in combination" in the context of the administration of other therapies refers to the use of more than one therapy. The use of the term "in combination" does not restrict the order in which therapies are administered to a subject with a disease. A first therapy can be administered before (e.g., 1 minute, 45 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks), concurrently, or after (e.g., 1 minute, 45 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks) the administration of a second therapy to a subject which had, has, or is susceptible to a hOX40L-mediated disease. Any additional therapy can be administered in any order with the other additional therapies. In certain embodiments, the antibodies of the invention can be administered in combination with one or more therapies (e.g., therapies that are not the antibodies of the invention that are currently administered to prevent, treat, manage, and/or ameliorate a hOX40L-mediated disease. Non-limiting examples of therapies that can be administered in combination with an antibody of the invention include analgesic agents, anesthetic agents, antibiotics, or immunomodulatory agents or any other agent listed in the U.S. Pharmacopoeia and/or Physician's Desk Reference.

An "isolated" or "purified" antibody is for example substantially free of cellular material or other contaminating proteins from the cell or tissue source from which the antibody is derived, or substantially free of chemical precursors or other chemicals when chemically synthesized. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, or 5% (by dry weight) of heterologous protein (also referred to herein as a "contaminating protein"). When the antibody is recombinantly produced, it is also preferably substantially free of culture medium, i.e., culture medium represents less than about 20%, 10%, or 5% of the volume of the protein preparation. When the antibody is produced by chemical synthesis, it is preferably substantially free of chemical precursors or other chemicals, i.e., it is separated from chemical precursors or other chemicals which are involved in the synthesis of the protein. Accordingly such preparations of the antibody have less than about 30%, 20%, 10%, 5% (by dry weight) of chemical precursors or compounds other than the antibody of interest. In a preferred embodiment, antibodies of the invention are isolated or purified.

An "isolated" nucleic acid molecule is one which is separated from other nucleic acid molecules which are present in the natural source of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. In a specific embodiment, a nucleic acid molecule(s) encoding an antibody of the invention is isolated or purified.

The term "human OX40L," "hOX40L" or "hOX40L polypeptide" and similar terms refers to the polypeptides ("polypeptides," "peptides" and "proteins" are used interchangeably herein) comprising the amino acid sequence in the sequence listing and related polypeptides, including SNP variants thereof. Related polypeptides include allelic variants (e.g., SNP variants); splice variants; fragments; derivatives; substitution, deletion, and insertion variants; fusion polypeptides; and interspecies homologs, preferably, which retain hOX40L activity and/or are sufficient to generate an anti-hOX40L immune response. Also encompassed are soluble forms of hOX40L which are sufficient to generate an anti-hOX40L immunological response. As those skilled in the art will appreciate, an anti-hOX40L antibody of the invention can bind to a hOX40L polypeptide, polypeptide fragment, antigen, and/or epitope, as an epitope is part of the larger antigen, which is part of the larger polypeptide fragment, which, in turn, is part of the larger polypeptide hOX40L can exist in a trimeric (native) or monomeric (denatured) form.

The terms "Kabat numbering," and like terms are recognized in the art and refer to a system of numbering amino acid residues which are more variable (i.e. hypervariable) than other amino acid residues in the heavy chain variable regions of an antibody, or an antigen binding portion thereof (Kabat et al. (1971) Ann. N.Y. Acad. Sci. 190:382-391 and, Kabat et al. (1991) Sequences of Proteins of Immunological Interest, Fifth Edition, U.S. Department of Health and Human Services, NIH Publication No. 91-3242). For the heavy chain variable region, the hypervariable region typically ranges from amino acid positions 31 to 35 for CDR1, amino acid positions 50 to 65 for CDR2, and amino acid positions 95 to 102 for CDR3.

The term "monoclonal antibody" refers to an antibody obtained from a population of homogenous or substantially homogeneous antibodies, and each monoclonal antibody will typically recognize a single epitope on the antigen. In preferred embodiments, a "monoclonal antibody," as used herein, is an antibody produced by a single hybridoma or other cell, wherein the antibody specifically binds to only a hOX40L epitope as determined, e.g., by ELISA or other antigen-binding or competitive binding assay known in the art or in the Examples provided herein. The term "monoclonal" is not limited to any particular method for making the antibody. For example, monoclonal antibodies of the invention may be made by the hybridoma method as described in Kohler et al.; Nature, 256:495 (1975) or may be isolated from phage libraries using the techniques as described herein, for example. Other methods for the preparation of clonal cell lines and of monoclonal antibodies expressed thereby are well known in the art (see, for example, Chapter 11 in: Short Protocols in Molecular Biology, (2002) 5th Ed., Ausubel et al., eds., John Wiley and Sons, New York). Other exemplary methods of producing other monoclonal antibodies are provided in the Examples herein.

The term "naturally occurring" or "native" when used in connection with biological materials such as nucleic acid molecules, polypeptides, host cells, and the like, refers to those which are found in nature and not manipulated by a human being.

The term "pharmaceutically acceptable" as used herein means being approved by a regulatory agency of the Federal or a state government, or listed in the U.S. Pharmacopeia, European pharmacopeia or other generally recognized pharmacopeia for use in animals, and more particularly in humans.

"Polyclonal antibodies" as used herein refers to an antibody population generated in an immunogenic response to a protein having many epitopes and thus includes a variety of different antibodies directed to the same and to different epitopes within the protein. Methods for producing polyclonal antibodies are known in the art (See, e.g., see, for example, Chapter 11 in: Short Protocols in Molecular Biology, (2002) 5th Ed., Ausubel et al., eds., John Wiley and Sons, New York).

As used herein, the term "polynucleotide," "nucleotide," nucleic acid" "nucleic acid molecule" and other similar terms are used interchangeable and include DNA, RNA, mRNA and the like.

As used herein, the terms "prevent," "preventing," and "prevention" refer to the total or partial inhibition of the development, recurrence, onset or spread of a hOX40L-mediated disease and/or symptom related thereto, resulting from the administration of a therapy or combination of therapies provided herein (e.g., a combination of prophylactic or therapeutic agents, such as an antibody of the invention).

As used herein, the term "prophylactic agent" refers to any agent that can totally or partially inhibit the development, recurrence, onset or spread of a hOX40L-mediated disease and/or symptom related thereto in a subject. In certain embodiments, the term "prophylactic agent" refers to an antibody of the invention. In certain other embodiments, the term "prophylactic agent" refers to an agent other than an antibody of the invention. Preferably, a prophylactic agent is an agent which is known to be useful to or has been or is currently being used to prevent a hOX40L-mediated disease and/or a symptom related thereto or impede the onset, development, progression and/or severity of a hOX40L-mediated disease and/or a symptom related thereto. In specific embodiments, the prophylactic agent is a frilly human anti-hOX40L antibody, such as a fully human anti-hOX40L monoclonal antibody.

In an embodiment, the prophylaxis prevents the onset of the disease or condition or of the symptoms of the disease or condition. In one embodiment, the prophylactic treatment prevents the worsening, or onset, of the disease or condition. In one embodiment, the prophylactic treatment prevents the worsening of the disease or condition.

In another embodiment, an anti-OX40L antibody of the invention is administered intravenously (e.g. before or concomitantly with a transplant, e.g. blood or organ transplant). In another embodiment, said antibody is administered at a dose of about 5-10 mg/kg (e.g. at about 8 mg/kg). In another embodiment, said antibody is administered at a dose selected from about 0.1 mg/kg, about 0.5 mg/kg, about 1 mg/kg, 3 mg/kg, 5 mg/kg, about 10 mg/kg, about 15 mg/kg, about 20 mg/kg, about 25 mg/kg, about 30 mg/kg, about 40 mg/kg, about 50 mg/kg, about 60 mg/kg, about 70 mg/kg, about 80 mg/kg about 90 mg/kg or about 100 mg/kg, in particular about 1 mg/kg, or about 3 mg/kg.

In another embodiment, said antibody is administered 1-4 days before transplant (e.g. of blood or organs), e.g. 1-3 days before transplant or 1-2 days before transplant. In another embodiment, said antibody is administered weekly, bi-weekly or monthly following transplant, e.g. bi-weekly. In a further embodiment, said antibody is administered intravenously prophylactically 1-3 days before transplant at a dose of about 5-10 mg/kg (e.g. about 8 mg/kg) and then intravenously, bi-weekly at a dose of about 5-10 mg/kg (e.g. about 8 mg/kg).

In another embodiment, the patient is monitored periodically post-transplant, for the presence of a biomarker predictive for the development of transplant rejection or of GvHD (e.g. acute GvHD), and the anti-OX40L antibody of the invention is administered once the biomarker levels are such that the patient is determined to be at risk of developing transplant rejection or of GvHD (e.g. acute GvHD). This strategy would avoid unnecessary dosing of drug and unnecessary suppression of the immune system. Examples of biomarkers which may be useful as predictive biomarkers of acute GvHD may be those identified in Levine et al., "A prognostic score for acute graft-versus-host disease based on biomarkers: a multicentre study", Lancet Haematol 2015; 2:e21-29. These biomarkers include, but are not limited to TNFR1, ST-2, elafin and IL2R$\alpha$ and Reg3$\alpha$.

A region of a hOX40L contributing to an epitope may be contiguous amino acids of the polypeptide or the epitope may come together from two or more non-contiguous regions of the polypeptide. The epitope may or may not be a three-dimensional surface feature of the antigen. A localized region on the surface of a hOX40L antigen that is capable of eliciting an immune response is a hOX40L epitope. The epitope may or may not be a three-dimensional surface feature of the antigen.

A "hOX40L-mediated disease" and "hOX40L-mediated condition" are used interchangeably and refer to any disease or condition that is completely or partially caused by or is the result of hOX40L. In certain embodiments, hOX40L is aberrantly (e.g., highly) expressed on the surface of a cell. In some embodiments, hOX40L may be aberrantly upregulated on a particular cell type. In other embodiments, normal, aberrant or excessive cell signaling is caused by binding of hOX40L to a hOX40L ligand. In certain embodiments, the hOX40L ligand is OX40, for example, that is expressed on the surface of a cell, such as a colonic epithelial cell. In certain embodiments, the hOX40L-mediated disease is an inflammatory bowel disease (IBD), such as Crohn's disease (CD) or ulcerative colitis (UC). In other embodiments, the hOX40L-mediated disease is graft-versus-host disease (GVHD). In other embodiments, the hOX40L-mediated disease is selected from pyoderma gangrenosum, giant cell arteritis, Schnitzler syndrome, non-infectious scleritis and uveitis (non-infectious/autoimmune and/or systemic). In other embodiments, a hOX40L mediated disease or condition selected from an autoimmune disease or condition, a systemic inflammatory disease or condition, or transplant rejection; for example inflammatory bowel disease (IBD), Crohn's disease, rheumatoid arthritis, transplant rejection, allogeneic transplant rejection, graft-versus-host disease (GvHD), ulcerative colitis, systemic lupus erythematosus (SLE), diabetes, uveitis, ankylosing spondylitis, contact hypersensitivity, multiple sclerosis and atherosclerosis, in particular GvHD.

The terms "hOX40L receptor" or "hOX40L binding receptor" are used interchangeably herein and refer to a receptor polypeptide that binds to hOX40L. In specific embodiments, the hOX40L receptor is Hox40. In some embodiments, the hOX40L receptor is expressed on the surface of a cell, such as a colonic epithelial cell; or on graft or transplant tissue or on host tissue.

As used herein, the terms "subject" and "patient" are used interchangeably. As used herein, a subject is preferably a mammal such as a non-primate (e.g., cows, pigs, horses, cats, dogs, rats, etc.) or a primate (e.g., monkey and human), most preferably a human. In one embodiment, the subject is a mammal, preferably a human, having a hOX40L-mediated disease. In another embodiment, the subject is a mammal, preferably a human, at risk of developing a hOX40L-mediated disease.

As used herein "substantially all" refers to refers to at least about 60%, at least about 70%, at least about 75%, at least about 80%, at least about 85%, at least about 90%, at least about 95%, at least about 98%, at least about 99%, or about 100%.

The term "substantially free of surfactant" as used herein refers to a formulation of an antibody that specifically binds to a hOX40L antigen, said formulation containing less than 0.0005%, less than 0.0003%, or less than 0.0001% of surfactants and/or less than 0.0005%, less than 0.0003%, or less than 0.0001% of surfactants.

The term "substantially free of salt" as used herein refers to a formulation of an antibody that specifically binds to a hOX40L antigen, said formulation containing less than 0.0005%, less than 0.0003%, or less than 0.0001% of inorganic salts.

The term "surfactant" as used herein refers to organic substances having amphipathic structures; namely, they are composed of groups of opposing solubility tendencies, typically an oil-soluble hydrocarbon chain and a water-soluble ionic group. Surfactants can be classified, depending on the charge of the surface-active moiety, into anionic, cationic, and nonionic surfactants. Surfactants are often used as wetting, emulsifying, solubilizing, and dispersing agents for various pharmaceutical compositions and preparations of biological materials.

As used herein, the term "tag" refers to any type of moiety that is attached to, e.g., a polypeptide and/or a polynucleotide that encodes a hOX40L or hOX40L antibody or antigen binding fragment thereof. For example, a polynucleotide that encodes a hOX40L, hOX40L antibody or antigen binding fragment thereof can contain one or more additional tag-encoding nucleotide sequences that encode a, e.g., a detectable moiety or a moiety that aids in affinity purification. When translated, the tag and the antibody can be in the form of a fusion protein. The term "detectable" or "detection" with reference to a tag refers to any tag that is capable of being visualized or wherein the presence of the tag is otherwise able to be determined and/or measured (e.g., by quantitation). A non-limiting example of a detectable tag is a fluorescent tag.

As used herein, the term "therapeutic agent" refers to any agent that can be used in the treatment, management or amelioration of a hOX40L-mediated disease and/or a symptom related thereto. In certain embodiments, the term "therapeutic agent" refers to an antibody of the invention. In certain other embodiments, the term "therapeutic agent" refers to an agent other than an antibody of the invention. Preferably, a therapeutic agent is an agent which is known to be useful for, or has been or is currently being used for the treatment, management or amelioration of a hOX40L-mediated disease or one or more symptoms related thereto. In specific embodiments, the therapeutic agent is a fully human anti-hOX40L antibody, such as a fully human anti-hOX40L monoclonal antibody.

The combination of therapies (e.g., use of prophylactic or therapeutic agents) which is more effective than the additive effects of any two or more single therapy. For example, a synergistic effect of a combination of prophylactic and/or therapeutic agents permits the use of lower dosages of one or more of the agents and/or less frequent administration of said agents to a subject with a hOX40L-mediated disease. The ability to utilize lower dosages of prophylactic or therapeutic therapies and/or to administer said therapies less frequently reduces the toxicity associated with the administration of said therapies to a subject without reducing the efficacy of said therapies in the prevention, management, treatment or amelioration of a hOX40L-mediated disease. In addition, a synergistic effect can result in improved efficacy of therapies in the prevention, or in the management, treatment or amelioration of a hOX40L-mediated disease. Finally, synergistic effect of a combination of therapies (e.g., prophylactic or therapeutic agents) may avoid or reduce adverse or unwanted side effects associated with the use of any single therapy.

In one embodiment, the combination comprises an anti-OX40L antibody of the invention and a further therapeutic agents independently selected from the group consisting of rapamycin (sirolimus), tacrolimus, ciclosporin, corticosteroids (e.g. methylprednisolone), methotrexate, mycophenolate mofetil, anti-CD28 antibodies, anti-IL12/IL-23 antibodies (e.g. ustekinumab), anti-CD20 antibodies (e.g. rituximab), anti-CD30 antibodies (e.g. brentuximab), CTLA4-Fc molecules (e.g. abatacept), CCR5 receptor antagonists (e.g. maraviroc), anti-CD40L antibodies, anti-VLA4 antibodies (e.g. natalizumab), anti-LFA1 antibodies, fludarabine, anti-CD52 antibodies (e.g. alemtuzumab), anti-CD45 antibodies, cyclophosphamide, anti-thymocyte globulins, anti-complement C5 antibodies (e.g. eculizumab), anti-a4b7 integrin antibodies (e.g. vedolizumab), anti-IL6 antibodies (e.g. tocilizumab), anti-IL2R antibodies (e.g. basilixumab), anti-CD25 antibodies (e.g. daclizumab), anti-TNFa/TNFa-Fc molecules (e.g. etanercept, adalimumab, infliximab, golimumab or certolizumab pegol) and Vorinostat. In another embodiment the combination comprises an anti-OX40L antibody of the invention and a further therapeutic agents independently selected from the group consisting of rapamycin (sirolimus), tacrolimus, ciclosporin, corticosteroids (e.g. methylprednisolone), methotrexate, mycophenolate mofetil, anti-CD28 antibodies, CTLA4-Fc molecules (e.g. abatacept), anti-CD40L antibodies, anti-LFA1 antibodies, anti-CD52 antibodies (e.g. alemtuzumab), cyclophosphamide and anti-thymocyte globulins.

In some embodiments the combination comprises an anti-OX40L antibody of the invention and further therapeutic agents independently selected from the group consisting of calcineurin inhibitors (e.g. tacrolimus, ciclosporin), mTOR inhibitors (e.g. rapamycin (sirolimus)), and antiproliferative agents (e.g. mycophenolate mofetil, cyclophosphamide).

In further embodiments the combination comprises an anti-OX40L antibody of the invention and further therapeutic agents independently selected from the group consisting of immunosuppressants that modulate IL-2 signalling (e.g. tacrolimus, ciclosporin, rapamycin (sirolimus), and anti-CD25 antibodies (e.g. basilixumab, daclizumab).

Figure 6A:
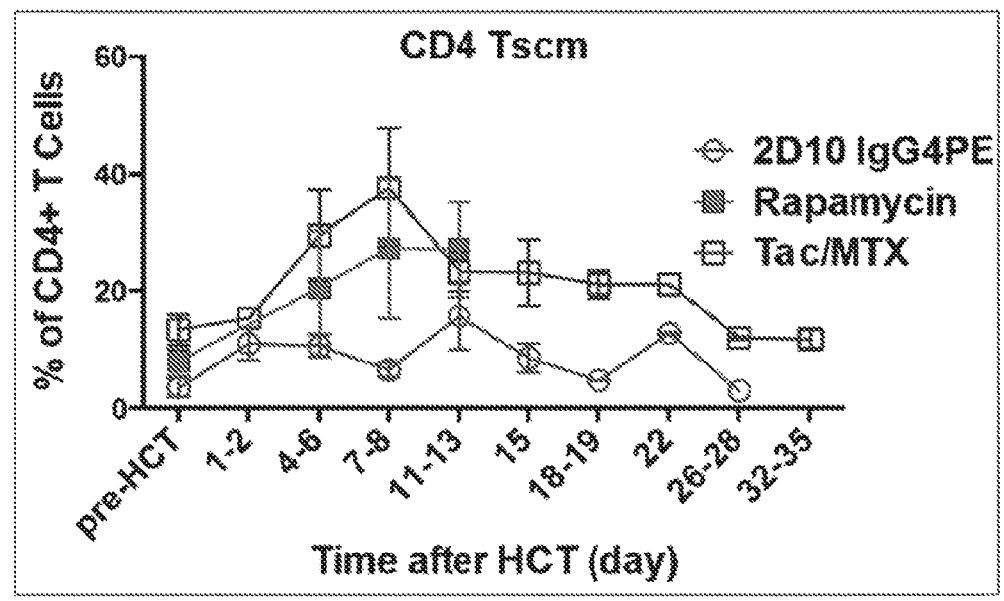
FIG. 6A shows effects of OX40L blockade on SCM CD4+ T-cells. Datapoints for 02D10 Ig4PE are shown by circles, rapamycin by filled squares and tacrolimus plus methotrexate (Tac/MTX) by open squares.
Figure 6B:
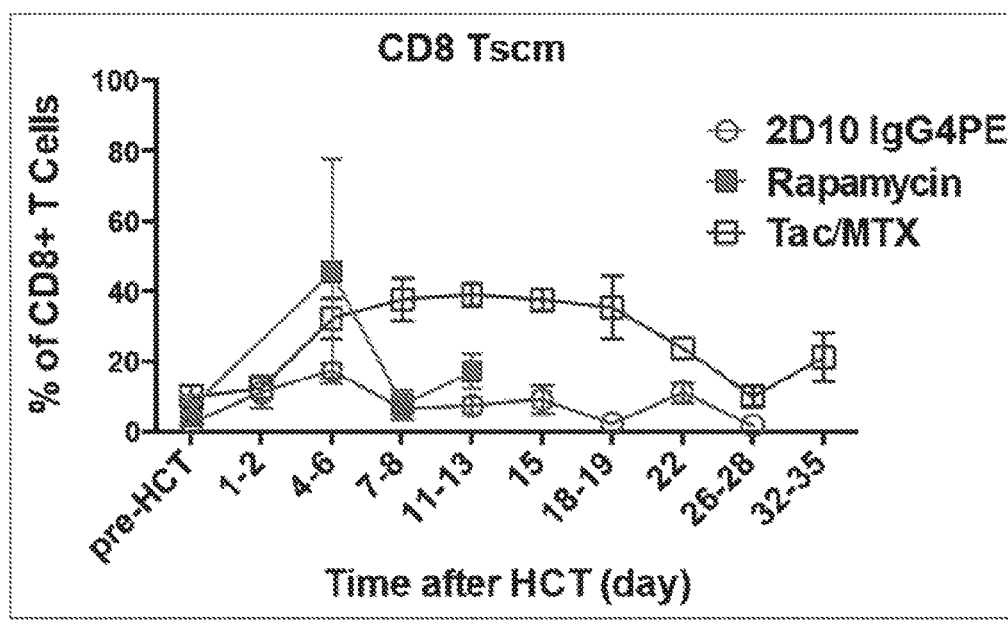
FIG. 6B shows effects of OX40L blockade on SCM CD8+ T-cells. Datapoints for 02D10 Ig4PE are shown by circles, rapamycin by filled squares and Tac/MTX by unfilled squares.
Figure 7:
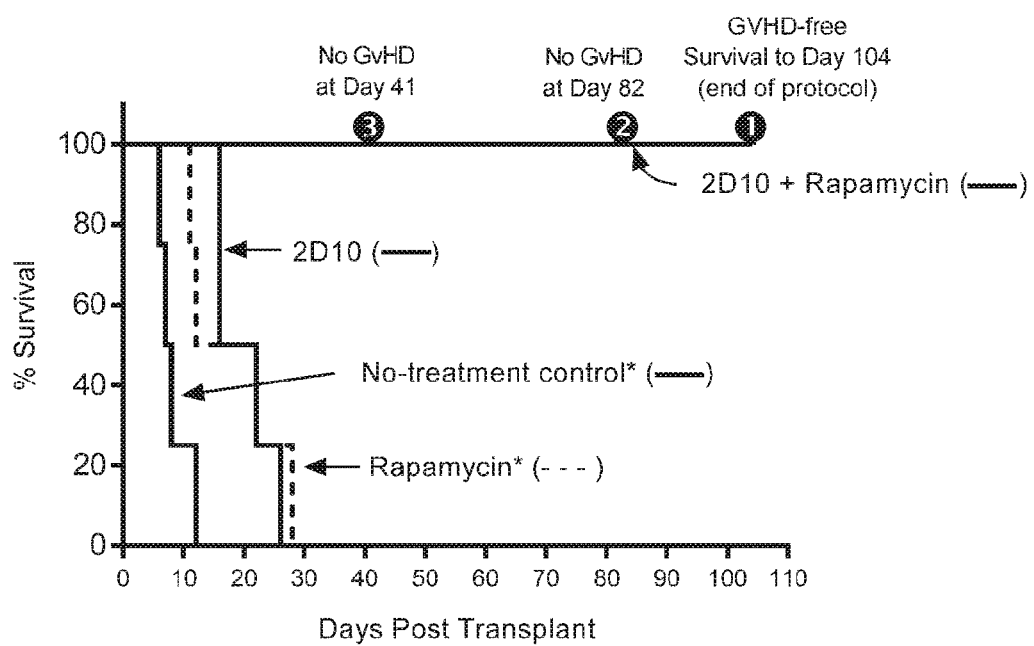
FIG. 7 shows Kaplan-Meier survival curve for rhesus monkey recipients of hematopoietic stem cell transplants derived from the peripheral blood of haploidentical half-sibling donors. Results are shown for animals that did not receive post-transplant prophylactic therapy (No-treatment control; median survival time, MST=8 days; n=4), and those receiving rapamycin monotherapy (MST=17 days; n=4), 2D10 monotherapy (MST=19 days; n=4), or rapamycin plus 2D10 (MST>82 days; n=3). Note that animals 2 and 3 indicated on the figure were on-study at the time of drafting; neither showed signs of GVHD at Day 82 or Day 41 post-transplant, respectively. Asterix * for the no treatment control and rapamycin monotherapy groups is data taken from Furlan et al., 2015, Science Translational Medicine, vol 7 (315), 315ra191.

Without being bound by theory, it is thought that the mechanism of action of an anti-OX40L antibody of the invention is complementary to further therapeutic agents which modulate immune function. In particular, agents that modulate IL-2 signalling or that inhibit IL-2/IL-2R-mediated T cell proliferation may synergistically combine with an anti-OX40L antibody resulting in greater immune modulation than would be observed with either agent alone. As shown in Examples 7 and 9 hereinbelow, both tacrolimus and rapamycin display immune modulating activity. Tacrolimus and rapamycin are both agents which are known to modulate IL-2 signalling. In particular, rapamycin is known to act as an mTOR inhibitor, which reduces IL-2 and IL2R transcription, and inhibits cell cycle progression evoked by IL2R activation, but there may be other mechanisms on proliferation of T cells by which mTOR inhibitors may function (Thomson et al, Nat. Rev. Immunol., 2009, 9(5), 324-337; Scheffert & Raza, J. Thorac. Dis., 2014, 6(8), 1039-1053). FIG. 6 herein shows that the mechanism of an anti-OX40L antibody is different with regards to Tscm population to both these agents, and FIG. 7 shows a synergistic effect on survival of an anti-OX40L antibody of the invention in combination with rapamycin. It is therefore thought that other agents having a similar mechanism of action to rapamycin and/or tacrolimus will also result in a synergistic effect when used in combination with the anti-OX40L antibodies of the invention.

In one embodiment, the combination comprises an anti-OX40L antibody of the invention and rapamycin (sirolimus).

In one embodiment, the combination comprises an anti-OX40L antibody of the invention and tacrolimus. In one embodiment, the combination comprises an anti-OX40L antibody of the invention and a combination of tacrolimus and methotrexate. In another embodiment, the combination comprises an anti-OX40L antibody of the invention and ciclosporin. In another embodiment, the combination comprises an anti-OX40L antibody of the invention and ciclosporin and methotrexate. In another embodiment, the combination comprises an anti-OX40L antibody of the invention and cyclophosphamide. In another embodiment, the combination comprises an anti-OX40L antibody of the invention and mycophenolate mofetil.

As used herein, the term "therapy" refers to any protocol, method and/or agent that can be used in the prevention, management, treatment and/or amelioration of a hOX40L-mediated disease (e.g., IBD or GVHD). In certain embodiments, the terms "therapies" and "therapy" refer to a biological therapy, supportive therapy, and/or other therapies useful in the prevention, management, treatment and/or amelioration of a hOX40L-mediated disease known to one of skill in the art such as medical personnel.

As used herein, the terms "treat," "treatment" and "treating" refer to the reduction or amelioration of the progression, severity, and/or duration of a hOX40L-mediated disease (e.g., IBD or GVHD) resulting from the administration of one or more therapies (including, but not limited to, the administration of one or more prophylactic or therapeutic agents, such as an antibody of the invention). In specific embodiments, such terms refer to the reduction or inhibition of the binding of hOX40L to OX40, the reduction or inhibition of the production or secretion of CCL20 from a cell expressing hOX40 or hOX40L, the reduction or inhibition of the production or secretion of IL-8 from a cell expressing hOX40 or hOX40L, the reduction or inhibition of the production or secretion of RANTES from a cell expressing hOX40 or hOX40L, and/or the inhibition or reduction of one or more symptoms associated with a hOX40L-mediated disease, such as an IBD or GVHD. In specific embodiments, such terms refer to the reduction or inhibition of the binding of hOX40L to OX40, the reduction or inhibition of the production or secretion of INF-γ from a cell expressing hOX40 or hOX40L, the reduction or inhibition of the production or secretion of TNF-α from a cell expressing hOX40 or hOX40L, the reduction or inhibition of the production or secretion of IL-2 from a cell expressing hOX40 or hOX40L, and/or the inhibition or reduction of one or more symptoms associated with a hOX40L-mediated disease, such as an IBD or GVHD (in particular GvHD). In an example, the cell is a human cell. In specific embodiments, a prophylactic agent is a fully human anti-hOX40L antibody, such as a fully human anti-hOX40L monoclonal antibody.

The term "variable region" or "variable domain" refers to a portion of the OX40L and heavy chains, typically about the amino-terminal 120 to 130 amino acids in the heavy chain and about 100 to 110 amino acids in the light chain, which differ extensively in sequence among antibodies and are used in the binding and specificity of each particular antibody for its particular antigen. The variability in sequence is concentrated in those regions called complimentarily determining regions (CDRs) while the more highly conserved regions in the variable domain are called framework regions (FR). The CDRs of the OX40L and heavy chains are primarily responsible for the interaction of the antibody with antigen. Numbering of amino acid positions used herein is according to the EU Index, as in Kabat et al. (1991) Sequences of proteins of immunological interest. (U.S. Department of Health and Human Services, Washington, D.C.) 5th ed. ("Kabat et al."). In preferred embodiments, the variable region is a human variable region.

Antibodies

Antibodies of the invention include, but are not limited to, synthetic antibodies, monoclonal antibodies, recombinantly produced antibodies, multispecific antibodies (including bi-specific antibodies), human antibodies, humanized antibodies, chimeric antibodies, intrabodies, single-chain Fvs (scFv) (e.g., including monospecific, bispecific, etc.), camelized antibodies, Fab fragments, F(ab') fragments, disulfide-linked Fvs (sdFv), anti-idiotypic (anti-Id) antibodies, and epitope-binding fragments of any of the above.

In particular, antibodies provided herein include immunoglobulin molecules and immunologically active portions of immunoglobulin molecules, i.e., molecules that contain an antigen binding site that specifically binds to a hOX40L antigen. The immunoglobulin molecules provided herein can be of any type (e.g., IgG, IgE, IgM, IgD, IgA and IgY), class (e.g., IgG1, IgG2, IgG3, IgG4, IgA1 and IgA2) or subclass of immunoglobulin molecule. In a specific embodiment, an antibody provided herein is an IgG antibody, preferably an IgG1 or IgG4. In certain embodiments, the antibodies of the invention comprise a human gamma 4 constant region. In another embodiment, the heavy chain constant region does not bind Fc-γ receptors, and e.g. comprises a Leu235Glu mutation. In another embodiment, the heavy chain constant region comprises a Ser228Pro mutation to increase stability. In another embodiment, the heavy chain constant region is IgG4-PE.

Variants and derivatives of antibodies include antibody fragments that retain the ability to specifically bind to an epitope. Preferred fragments include Fab fragments; Fab' (an antibody fragment containing a single anti-binding domain comprising an Fab and an additional portion of the heavy chain through the hinge region); F(ab')$_2$ (two Fab' molecules joined by interchain disulfide bonds in the hinge regions of the heavy chains; the Fab' molecules may be directed toward the same or different epitopes); a bispecific Fab (a Fab molecule having two antigen binding domains, each of which may be directed to a different epitope); a single chain Fab chain comprising a variable region, also known as, a sFv; a disulfide-linked Fv, or dsFv; a camelized VH (the variable, antigen-binding determinative region of a single heavy chain of an antibody in which some amino acids at the VH interface are those found in the heavy chain of naturally occurring camel antibodies); a bispecific sFv (a sFv or a dsFv molecule having two antigen-binding domains, each of which may be directed to a different epitope); a diabody (a dimerized sFv formed when the VH domain of a first sFv assembles with the VL domain of a second sFv and the VL domain of the first sFv assembles with the VH domain of the second sFv; the two antigen-binding regions of the diabody may be directed towards the same or different epitopes); and a triabody (a trimerized sFv, formed in a manner similar to a diabody, but in which three antigen-binding domains are created in a single complex; the three antigen binding domains may be directed towards the same or different epitopes). Derivatives of antibodies also include one or more CDR sequences of an antibody combining site. The CDR sequences may be linked together on a scaffold when two or more CDR sequences are present. In certain embodiments, the antibody to be used with the invention comprises a single-chain Fv ("scFv"). scFvs are antibody fragments comprising the VH and VL domains of an antibody, wherein these domains are present in a single polypeptide chain. Generally, the scFv polypeptide further comprises a polypeptide linker between the VH and VL domains which enables the scFv to form the desired structure for antigen binding. For a review of scFvs see Pluckthun in The Pharmacology of Monoclonal Antibodies, vol. 113, Rosenburg and Moore eds. Springer-Verlag, New York, pp. 269-315 (1994).

The antibodies of the invention may be from any animal origin including birds and mammals (e.g., human, murine, donkey, sheep, rabbit, goat, guinea pig, camel, horse, or chicken). In certain embodiments, the antibodies of the invention are human or humanized monoclonal antibodies.

As used herein, "human" antibodies include antibodies having the amino acid sequence of a human immunoglobulin and include antibodies isolated from human immunoglobulin libraries or from mice that express antibodies from human genes.

In preferred embodiments, the antibodies of the invention are fully human antibodies, such as fully human antibodies that specifically bind a hOX40L polypeptide, a hOX40L polypeptide fragment, or a hOX40L epitope. Such fully human antibodies would be advantageous over fully mouse (or other full or partial non-human species antibodies), humanized antibodies, or chimeric antibodies to minimize the development of unwanted or unneeded side effects, such as immune responses directed toward non-fully human antibodies (e.g., anti-hOX40L antibodies derived from other species) when administered to the subject.

The antibodies of the present invention may be monospecific, bispecific, trispecific or of greater multispecificity. Multispecific antibodies may be specific for different epitopes of a hOX40L polypeptide or may be specific for both a hOX40L polypeptide as well as for a heterologous epitope, such as a heterologous polypeptide or solid support material. In preferred embodiments, the antibodies provided herein are monospecific for a given epitope of a hOX40L polypeptide and do not specifically bind to other epitopes.

Also provided herein is a B-cell (e.g., an immortalised B-cell) or a hybridoma that produces an anti-hOX40L antibody or fragment described herein.

In certain embodiments, an isolated antibody is provided herein that specifically binds to a hOX40L epitope wherein the binding to the hOX40L epitope by the antibody is competitively blocked (e.g., in a dose-dependent manner) by an antibody or fragment of the invention. The antibody may or may not be a fully human antibody. In preferred embodiments, the antibody is a fully human monoclonal anti-hOX40L antibody, and even more preferably a fully human, monoclonal, antagonist anti-hOX40L antibody. Exemplary competitive blocking tests that can be used are provided in the Examples herein.

In some embodiments, the antibody or fragment of the invention competes (e.g., in a dose-dependent manner) with OX40 Receptor (or a fusion protein thereof) for binding to cell surface-expressed hOX40L. In other embodiments, the antibody or fragment of the invention competes (e.g., in a dose-dependent manner) with OX40 Receptor (or a fusion protein thereof) for binding to soluble hOX40L. Exemplary competitive binding assays that can be used are provided in the Examples herein. In one embodiment, the antibody or fragment partially or completely inhibits binding of hOX40 to cell surface-expressed OX40L, such as hOX40L. In another embodiment, the antibody partially or completely inhibits binding of hOX40 to soluble hOX40L. In some embodiments, the antibody or fragment partially or completely inhibits the secretion of CCL20, IL-8, and/or RANTES, or INF-γ, TNF-α or IL-2, in particular INF-γ from a cell having cell surface-expressed OX40. In certain embodiments, the cell expressing the OX40 is a colonic epithelial cell.

Preferably, the antibodies of the invention are fully human, monoclonal antibodies, such as fully human, monoclonal antagonist antibodies, that specifically bind to hOX40L.

In some embodiments, the antibody or fragment provided herein binds to a hOX40L epitope that is a three-dimensional surface feature of a hOX40L polypeptide (e.g., in a trimeric form of a hOX40L polypeptide). A region of a hOX40L polypeptide contributing to an epitope may be contiguous amino acids of the polypeptide or the epitope may come together from two or more non-contiguous regions of the polypeptide A hOX40L epitope may be present in (a) the trimeric form ("a trimeric hOX40L epitope") of hOX40L, (b) the monomeric form ("a monomeric hOX40L epitope") of hOX40L, (c) both the trimeric and monomeric form of hOX40L, (d) the trimeric form, but not the monomeric form of hOX40L, or (e) the monomeric form, but not the trimeric form of hOX40L.

For example, in some embodiments, the epitope is only present or available for binding in the trimeric (native) form, but is not present or available for binding in the monomeric (denatured) form by an anti-hOX40L antibody. In other embodiments, the hOX40L epitope is linear feature of the hOX40L polypeptide (e.g., in a trimeric form or monomeric form of the hOX40L polypeptide). Antibodies provided herein may specifically bind to (a) an epitope of the monomeric form of hOX40L, (b) an epitope of the trimeric form of hOX40L, (c) an epitope of the monomeric but not the trimeric form of hOX40L, (d) an epitope of the trimeric but not the monomeric form of hOX40L, or (e) both the monomeric form and the trimeric form of hOX40L. In preferred embodiments, the antibodies provided herein specifically bind to an epitope of the trimeric form of hOX40L but do not specifically bind to an epitope the monomeric form of hOX40L.

The present invention also provides antibodies that specifically bind to a hOX40L epitope, the antibodies comprising derivatives of the VH domains, VH CDRs, VL domains, and VL CDRs described herein that specifically bind to a hOX40L antigen. The present invention also provides antibodies comprising derivatives of antibodies disclosed in the Examples, wherein said antibodies specifically bind to a hOX40L epitope. Standard techniques known to those of skill in the art can be used to introduce mutations in the nucleotide sequence encoding a molecule of the invention, including, for example, site-directed mutagenesis and PCR-mediated mutagenesis which results in amino acid substitutions. Preferably, the derivatives include less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the original molecule. In another embodiment, the derivatives have conservative amino acid substitutions. In a preferred embodiment, the derivatives have conservative amino acid substitutions are made at one or more predicted non-essential amino acid residues. Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed and the activity of the protein can be determined.

In another embodiment, an antibody that specifically binds to a hOX40L epitope comprises a variable domain amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to a variable domain amino acid sequence of the sequence listing.

In specific embodiments, the antibody is a fully human anti-human antibody, such as a fully human monoclonal antibody. Fully human antibodies may be produced by any method known in the art. Exemplary methods include immunization with a hOX40L antigen (any hOX40L polypeptide capable of eliciting an immune response, and optionally conjugated to a carrier) of transgenic animals (e.g., mice) that are capable of producing a repertoire of human antibodies in the absence of endogenous immunoglobulin production; see, e.g., Jakobovits et al., (1993) Proc. Natl. Acad. Sci., 90:2551; Jakobovits et al., (1993) Nature, 362:255 258 (1993); Bruggermann et al., (1993) Year in Immunol., 7:33. Other methods of producing fully human anti-hOX40L antibodies can be found in the Examples provided herein.

Alternatively, fully human antibodies may be generated through the in vitro screening of phage display antibody libraries; see e.g., Hoogenboom et al., J. Mol. Biol., 227:381 (1991); Marks et al., J. Mol. Biol., 222:581 (1991), incorporated herein by reference. Various antibody-containing phage display libraries have been described and may be readily prepared by one skilled in the art. Libraries may contain a diversity of human antibody sequences, such as human Fab, Fv, and scFv fragments, that may be screened against an appropriate target.

The antibodies and fragments of the invention include antibodies and fragments that are chemically modified, i.e., by the covalent attachment of any type of molecule to the antibody. For example, but not by way of limitation, the antibody derivatives include antibodies that have been chemically modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formulation, metabolic synthesis of tunicamycin, etc. Additionally, the antibody may contain one or more non-classical amino acids.

The present invention also provides antibodies that specifically bind to a hOX40L antigen which comprise a framework region known to those of skill in the art (e.g., a human or non-human fragment). The framework region may, for example, be naturally occurring or consensus framework regions. Most preferably, the framework region of an antibody of the invention is human (see, e.g., Chothia et al., 1998, J. Mol. Biol. 278:457-479 for a listing of human framework regions, which is incorporated by reference herein in its entirety). See also Kabat et al. (1991) Sequences of Proteins of Immunological Interest (U.S. Department of Health and Human Services, Washington, D.C.) 5th ed.

In a specific embodiment, the present invention provides for antibodies that specifically bind to a hOX40L antigen, said antibodies comprising the amino acid sequence of one or more of the CDRs in the sequence listing (i.e. Seq ID No:4, Seq ID No: 10, Seq ID No:36, Seq ID No:42, Seq ID No:68, Seq ID No:74, Seq ID No:96 or Seq ID No: 102, in particular, Seq ID No:36 or Seq ID No:42 for HCDR1; Seq ID No:6, Seq ID No: 12, Seq ID No:38, Seq ID No:44, Seq ID No:70, Seq ID No:76, Seq ID No:98 or Seq ID No: 104, in particular Seq ID No:38 or Seq ID No:44 for HCDR2; Seq ID No:8, Seq ID No: 14, Seq ID No:40, Seq ID No:46, Seq ID No:72, Seq ID No:78, Seq ID No: 100 or Seq ID No: 106, in particular Seq ID No:40 or Seq ID No:46 for HCDR3; Seq ID No: 18, Seq ID No:24, Seq ID No:50, Seq ID No:56, Seq ID No:82, Seq ID No:88, Seq ID No: 110 or Seq ID No: 116, in particular Seq ID No:50 or Seq ID No:56 for LCDR1; Seq ID No:20, Seq ID No:26, Seq ID No:52, Seq ID No:58, Seq ID No:84, Seq ID No:90, Seq ID No: 112 or Seq ID No: 118, in particular Seq ID No:52 or Seq ID No:58 for LCDR2; and Seq ID No:22, Seq ID No:28, Seq ID No:54, Seq ID No:60, Seq ID No:86, Seq ID No:92, Seq ID No: 114 or Seq ID No: 120, in particular Seq ID No:54 or Seq ID No: 60 for LCDR3) and human framework regions with one or more amino acid substitutions at one, two, three or more of the following residues: (a) rare framework residues that differ between the murine antibody framework (i.e., donor antibody framework) and the human antibody framework (i.e., acceptor antibody framework); (b) Vernier zone residues when differing between donor antibody framework and acceptor antibody framework; (c) interchain packing residues at the VH/VL interface that differ between the donor antibody framework and the acceptor antibody framework; (d) canonical residues which differ between the donor antibody framework and the acceptor antibody framework sequences, particularly the framework regions crucial for the definition of the canonical class of the murine antibody CDR loops; (e) residues that are adjacent to a CDR; (g) residues capable of interacting with the antigen; (h) residues capable of interacting with the CDR; and (i) contact residues between the VH domain and the VL domain. In certain embodiments, antibodies that specifically bind to a hOX40L antigen comprising the human framework regions with one or more amino acid substitutions at one, two, three or more of the above-identified residues are antagonistic hOX40L antibodies.

The present invention encompasses antibodies that specifically bind to a hOX40L antigen, said antibodies comprising the amino acid sequence of the VH domain and/or VL domain in the sequence listing (i.e. Seq ID No:2, Seq ID No:34, Seq ID No:66 or Seq ID No:94, in particular Seq ID No:34 for VH domains; Seq ID No: 16, Seq ID No:48, Seq ID No:80, or Seq ID No: 108, in particular Seq ID No:48 for VL domains) but having mutations (e.g., one or more amino acid substitutions) in the framework regions. In certain embodiments, antibodies that specifically bind to a hOX40L antigen comprise the amino acid sequence of the VH domain and/or VL domain or an antigen-binding fragment thereof of an antibody disclosed in the Examples with one or more amino acid residue substitutions in the framework regions of the VH and/or VL domains.

In some embodiments, antibodies provided herein decrease or inhibit binding of hOX40L hOX40, and/or decrease or inhibit a hOX40L biological activity, such as secretion of CCL20, IL8 and/or RANTES, or INF-γ, TNF-α or IL-2, in particular INF-γ, in subject (e.g., a human subject). In certain embodiments, antibodies provided herein, such as a human monoclonal anti-hOX40L antibody, decreases or inhibits binding of a soluble or cell-surface expressed hOX40L to hOX40, and/or decreases or inhibits secretion of CCL20 and/or RANTES, or INF-γ, TNF-α or IL-2, in particular INF-γ after contact with a soluble or cell-surface expressed hOX40L, in a subject. Blocking activity of an antibody provided herein of hOX40L binding to hOX40 can be detected using an assay as described in the Examples. Inhibition of biological activity of cells expressing OX40 by a hOX40L antibody provided herein can be detected using an assay as described in the Examples.

The present invention also provides for fusion proteins comprising an antibody provided herein that specifically binds to a hOX40L antigen and a heterologous polypeptide. In some embodiments, the heterologous polypeptide to which the antibody is fused is useful for targeting the antibody to cells having cell surface-expressed hOX40L.

Antibody Conjugates and Fusion Proteins

The following discussion on conjugates and fusion proteins also applies to fragments so that disclosure mentioning antibodies can also apply mutatis mutandis to fragments of the invention.

In some embodiments, antibodies of the invention are conjugated or recombinantly fused to a diagnostic, detectable or therapeutic agent or any other molecule. The conjugated or recombinantly fused antibodies can be useful, e.g., for monitoring or prognosing the onset, development, progression and/or severity of a hOX40L-mediated disease as part of a clinical testing procedure, such as determining the efficacy of a particular therapy.

Such diagnosis and detection can be accomplished, for example, by coupling the antibody to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidin/biotin and avidin/biotin; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as, but not limited to, iodine ($^{131}$I, $^{125}$I, $^{123}$I, and $^{121}$I), carbon ($^{14}$C), sulfur ($^{35}$S), tritium ($^{3}$H), indium ($^{115}$In, $^{113}$In, $^{112}$In, and $^{111}$In), technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{153}$Gd, $^{169}$Yb, $^{51}$Cr, $^{54}$Mn, $^{75}$Se, $^{113}$Sn, and $^{117}$Sn; and positron emitting metals using various positron emission tomographies, and non-radioactive paramagnetic metal ions.

The present invention further encompasses uses of the antibodies of the invention conjugated or recombinantly fused to a therapeutic moiety (or one or more therapeutic moieties). The antibody may be conjugated or recombinantly fused to a therapeutic moiety, such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells. Therapeutic moieties include, but are not limited to, antimetabolites (e.g., methotrexate, 6-mercaptopurine, 6-thioguanine, cytarabine, 5-fluorouracil decarbazine); alkylating agents (e.g., mechlorethamine, thioepa chlorambucil, melphalan, carmustine (BCNU) and lomustine (CCNU), cyclothosphamide, busulfan, dibromomannitol, streptozotocin, mitomycin C, and cisdichlorodiamine platinum (II) (DDP), and cisplatin); anthracyclines (e.g., daunorubicin (formerly daunomycin) and doxorubicin); antibiotics (e.g., d actinomycin (formerly actinomycin), bleomycin, mithramycin, and anthramycin (AMC)); Auristatin molecules (e.g., auristatin PHE, bryostatin 1, and solastatin 10; see Woyke et al., Antimicrob. Agents Chemother. 46:3802-8 (2002), Woyke et al., Antimicrob. Agents Chemother. 45:3580-4 (2001), Mohammad et al., Anticancer Drugs 12:735-40 (2001), Wall et al., Biochem. Biophys. Res. Commun 266: 76-80 (1999), Mohammad et al., Int. J. Oncol. 15:367-72 (1999), all of which are incorporated herein by reference); hormones (e.g., glucocorticoids, progestins, androgens, and estrogens), DNA-repair enzyme inhibitors (e.g., etoposide or topotecan), kinase inhibitors (e.g., compound ST1571, imatinib mesylate (Kantarjian et al., Clin Cancer Res. 8(7): 2167-76 (2002)); cytotoxic agents (e.g., paclitaxel, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucorticoids, procaine, tetracaine, lidocaine, propranolol, and puromycin and analogues or homologs thereof and those compounds disclosed in U.S. Pat. Nos. 6,245,759, 6,399,633, 6,383,790, 6,335,156, 6,271,242, 6,242,196, 6,218,410, 6,218,372, 6,057,300, 6,034,053, 5,985,877, 5,958,769, 5,925,376, 5,922,844, 5,911,995, 5,872,223, 5,863,904, 5,840,745, 5,728,868, 5,648,239, 5,587,459); farnesyl transferase inhibitors (e.g., R115777, BMS-214662, and those disclosed by, for example, U.S. Pat. Nos. 6,458,935, 6,451,812, 6,440,974, 6,436,960, 6,432,959, 6,420,387, 6,414,145, 6,410,541, 6,410,539, 6,403,581, 6,399,615, 6,387,905, 6,372,747, 6,369,034, 6,362,188, 6,342,765, 6,342,487, 6,300,501, 6,268,363, 6,265,422, 6,248,756, 6,239,140, 6,232,338, 6,228,865, 6,228,856, 6,225,322, 6,218,406, 6,211,193, 6,187,786, 6,169,096, 6,159,984, 6,143,766, 6,133,303, 6,127,366, 6,124,465, 6,124,295, 6,103,723, 6,093,737, 6,090,948, 6,080,870, 6,077,853, 6,071,935, 6,066,738, 6,063,930, 6,054,466, 6,051,582, 6,051,574, and 6,040,305); topoisomerase inhibitors (e.g., camptothecin; irinotecan; SN-38; topotecan; 9-aminocamptothecin; GG-211 (GI 147211); DX-8951f; IST-622; rubitecan; pyrazoloacridine; XR-5000; saintopin; UCE6; UCE1022; TAN-1518A; TAN 1518B; KT6006; KT6528; ED-110; NB-506; ED-110; NB-506; and rebeccamycin); bulgarein; DNA minor groove binders such as Hoescht dye 33342 and Hoechst dye 33258; nitidine; fagaronine; epiberberine; coralyne; beta-lapachone; BC-4-1; bisphosphonates (e.g., alendronate, cimadronte, clodronate, tiludronate, etidronate, ibandronate, neridronate, olpandronate, risedronate, piridronate, pamidronate, zolendronate) HMG-CoA reductase inhibitors, (e.g., lovastatin, simvastatin, atorvastatin, pravastatin, fluvastatin, statin, cerivastatin, lescol, lupitor, rosuvastatin and atorvastatin); antisense oligonucleotides (e.g., those disclosed in the U.S. Pat. Nos. 6,277,832, 5,998,596, 5,885, 834, 5,734,033, and 5,618,709); adenosine deaminase inhibitors (e.g., Fludarabine phosphate and 2-Chlorodeoxyadenosine); ibritumomab tiuxetan (Zevalin®); tositumomab (Bexxar®)) and pharmaceutically acceptable salts, solvates, clathrates, and prodrugs thereof.

Further, an antibody of the invention may be conjugated or recombinantly fused to a therapeutic moiety or drug moiety that modifies a given biological response. Therapeutic moieties or drug moieties are not to be construed as limited to classical chemical therapeutic agents. For example, the drug moiety may be a protein, peptide, or polypeptide possessing a desired biological activity. Such proteins may include, for example, a toxin such as abrin, ricin A, *pseudomonas* exotoxin, cholera toxin, or diphtheria toxin; a protein such as tumor necrosis factor, γ-interferon, α-interferon, nerve growth factor, platelet derived growth factor, tissue plasminogen activator, an apoptotic agent, e.g., TNF-γ, AIM I (see, International Publication No. WO 97/33899), AIM II (see, International Publication No. WO 97/34911), Fas Ligand (Takahashi et al., 1994, J. Immunol., 6:1567-1574), and VEGF (see, International Publication No. WO 99/23105), an anti-angiogenic agent, e.g., angiostatin, endostatin or a component of the coagulation pathway (e.g., tissue factor); or, a biological response modifier such as, for example, a lymphokine (e.g., interferon gamma, interleukin-1 ("IL-1"), interleukin-2 ("IL-2"), interleukin-5 ("IL-5"), interleukin-6 ("IL-6"), interleukin-7 ("IL-7"), interleukin 9 ("IL-9"), interleukin-10 ("IL-10"), interleukin-12 ("IL-12"), interleukin-15 ("IL-15"), interleukin-23 ("IL-23"), granulocyte macrophage colony stimulating factor ("GM-CSF"), and granulocyte colony stimulating factor ("G-CSF")), or a growth factor (e.g., growth hormone ("GH")), or a coagulation agent (e.g., calcium, vitamin K, tissue factors, such as but not limited to, Hageman factor (factor XII), high-molecular-weight kininogen (HMWK), prekallikrein (PK), coagulation proteins-factors II (pro-thrombin), factor V, XIIa, VIII, XIIIa, XI, XIa, IX, IXa, X, phospholipid, and fibrin monomer).

The present invention encompasses antibodies of the invention recombinantly fused or chemically conjugated (covalent or non-covalent conjugations) to a heterologous protein or polypeptide (or fragment thereof, preferably to a polypeptide of about 10, about 20, about 30, about 40, about 50, about 60, about 70, about 80, about 90 or about 100 amino acids) to generate fusion proteins. In particular, the invention provides fusion proteins comprising an antigen-binding fragment of an antibody of the invention (e.g., a Fab fragment, Fd fragment, Fv fragment, F(ab)2 fragment, a VH domain, a VH CDR, a VL domain or a VL CDR) and a heterologous protein, polypeptide, or peptide. In one embodiment, the heterologous protein, polypeptide, or peptide that the antibody is fused to is useful for targeting the antibody to a particular cell type, such as a cell that expresses hOX40L or an hOX40L receptor. For example, an antibody that specifically binds to a cell surface receptor expressed by a particular cell type (e.g., an immune cell) may be fused or conjugated to a modified antibody of the invention.

A conjugated or fusion protein of the invention comprises any antibody of the invention described herein and a heterologous polypeptide. In one embodiment, a conjugated or fusion protein of the invention comprises the variable domains of an antibody disclosed in the Examples and a heterologous polypeptide.

In addition, an antibody of the invention can be conjugated to therapeutic moieties such as a radioactive metal ion, such as alpha-emitters such as $^{213}$Bi or macrocyclic chelators useful for conjugating radiometal ions, including but not limited to, $^{131}$In, $^{131}$Lu, $^{131}$Y, $^{131}$Ho, $^{131}$Sm, to polypeptides. In certain embodiments, the macrocyclic chelator is 1,4,7, 10-tetraazacyclododecane-N,N',N'',N'''-tetraacetic acid (DOTA) which can be attached to the antibody via a linker molecule. Such linker molecules are commonly known in the art and described in Denardo et al., 1998, Clin Cancer Res. 4(10):2483-90; Peterson et al., 1999, Bioconjug. Chem. 10(4):553-7; and Zimmerman et al., 1999, Nucl. Med. Biol., 26(8):943-50, each incorporated by reference in their entireties.

Moreover, antibodies of the invention can be fused to marker sequences, such as a peptide to facilitate purification. In preferred embodiments, the marker amino acid sequence is a hexa-histidine peptide, such as the tag provided in a pQE vector (QIAGEN, Inc.), among others, many of which are commercially available. As described in Gentz et al., 1989, Proc. Natl. Acad. Sci. USA 86:821-824, for instance, hexa-histidine provides for convenient purification of the fusion protein. Other peptide tags useful for purification include, but are not limited to, the hemagglutinin ("HA") tag, which corresponds to an epitope derived from the influenza hemagglutinin protein (Wilson et al., 1984, Cell 37:767), and the "FLAG" tag.

Methods for fusing or conjugating therapeutic moieties (including polypeptides) to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), Thorpe et al., 1982, Immunol. Rev. 62:119-58; U.S. Pat. Nos. 5,336,603, 5,622,929, 5,359,046, 5,349,053, 5,447,851, 5,723,125, 5,783,181, 5,908,626, 5,844,095, and 5,112,946; EP 307,434; EP 367, 166; EP 394,827; PCT publications WO 91/06570, WO 96/04388, WO 96/22024, WO 97/34631, and WO 99/04813; Ashkenazi et al., Proc. Natl. Acad. Sci. USA, 88: 10535-10539, 1991; Traunecker et al., Nature, 331:84-86, 1988; Zheng et al., J. Immunol., 154:5590-5600, 1995; Vil et al., Proc. Natl. Acad. Sci. USA, 89:11337-11341, 1992, which are incorporated herein by reference in their entireties.

Fusion proteins may be generated, for example, through the techniques of gene-shuffling, motif-shuffling, exon-shuffling, and/or codon-shuffling (collectively referred to as "DNA shuffling"). DNA shuffling may be employed to alter the activities of antibodies of the invention (e.g., antibodies with higher affinities and lower dissociation rates). See, generally, U.S. Pat. Nos. 5,605,793, 5,811,238, 5,830,721, 5,834,252, and 5,837,458; Patten et al., 1997, Curr. Opinion Biotechnol. 8:724-33; Harayama, 1998, Trends Biotechnol. 16(2):76-82; Hansson et al., 1999, J. Mol. Biol. 287:265-76; and Lorenzo and Blasco, 1998, Biotechniques 24(2):308-313 (each of these patents and publications are hereby incorporated by reference in its entirety). Antibodies, or the encoded antibodies, may be altered by being subjected to random mutagenesis by error-prone PCR, random nucleotide insertion or other methods prior to recombination. A polynucleotide encoding an antibody of the invention may be recombined with one or more components, motifs, sections, parts, domains, fragments, etc. of one or more heterologous molecules.

An antibody of the invention can also be conjugated to a second antibody to form an antibody heteroconjugate as described in U.S. Pat. No. 4,676,980, which is incorporated herein by reference in its entirety.

The therapeutic moiety or drug conjugated or recombinantly fused to an antibody of the invention that specifically binds to a hOX40L antigen should be chosen to achieve the desired prophylactic or therapeutic effect(s). In certain embodiments, the antibody is a modified antibody. A clinician or other medical personnel should consider the following when deciding on which therapeutic moiety or drug to conjugate or recombinantly fuse to an antibody of the invention: the nature of the disease, the severity of the disease, and the condition of the subject.

Antibodies of the invention may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Pharmaceutical Compositions

The following discussion on compositions also applies to fragments so that disclosure mentioning antibodies can also apply mutatis mutandis to fragments of the invention.

Therapeutic formulations containing one or more antibodies of the invention provided herein can be prepared for storage by mixing the antibody having the desired degree of purity with optional physiologically acceptable carriers, excipients or stabilizers (Remington's Pharmaceutical Sciences (1990) Mack Publishing Co., Easton, Pa.), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The antibodies of the invention provided herein can also, for example, be formulated in liposomes. Liposomes containing the molecule of interest are prepared by methods known in the art, such as described in Epstein et al. (1985) Proc. Natl. Acad. Sci. USA 82:3688; Hwang et al. (1980) Proc. Natl. Acad. Sci. USA 77:4030; and U.S. Pat. Nos. 4,485,045 and 4,544,545. Liposomes with enhanced circulation time are disclosed in U.S. Pat. No. 5,013,556.

Particularly useful immunoliposomes can be generated by the reverse phase evaporation method with a lipid composition containing phosphatidylcholine, cholesterol and PEG-derivatized phosphatidylethanolamine (PEG-PE). Liposomes are extruded through filters of defined pore size to yield liposomes with the desired diameter. Fab' fragments of an antibody provided herein can be conjugated to the liposomes as described in Martin et al. (1982) J. Biol. Chem. 257:286-288 via a disulfide interchange reaction. A chemotherapeutic agent (such as Doxorubicin) is optionally contained within the liposome; See Gabizon et al., (1989) J. National Cancer Inst. 81(19):1484.

Formulations, such as those described herein, can also contain more than one active compound as necessary for the particular indication being treated. In certain embodiments, formulations comprise an antibody of the invention and one or more active compounds with complementary activities that do not adversely affect each other. Such molecules are suitably present in combination in amounts that are effective for the purpose intended. For example, an antibody of the invention can be combined with one or more other therapeutic agents. Such combined therapy can be administered to the patient serially or simultaneously or in sequence.

In one embodiment, the combination comprises an anti-OX40L antibody of the invention and a further therapeutic agents independently selected from the group consisting of rapamycin (sirolimus), tacrolimus, ciclosporin, corticosteroids (e.g. methylprednisolone), methotrexate, mycophenolate mofetil, anti-CD28 antibodies, anti-IL12/IL-23 antibodies (e.g. ustekinumab), anti-CD20 antibodies (e.g. rituximab), anti-CD30 antibodies (e.g. brentuximab), CTLA4-Fc molecules (e.g. abatacept), CCR5 receptor antagonists (e.g. maraviroc), anti-CD40L antibodies, anti-VLA4 antibodies (e.g. natalizumab), anti-LFA1 antibodies, fludarabine, anti-CD52 antibodies (e.g. alemtuzumab), anti-CD45 antibodies, cyclophosphamide, anti-thymocyte globulins, anti-complement C5 antibodies (e.g. eculizumab), anti-a4b7 integrin antibodies (e.g. vedolizumab), anti-IL6 antibodies (e.g. tocilizumab), anti-IL2R antibodies (e.g. basilixumab), anti-CD25 antibodies (e.g. daclizumab), anti-TNFa/TNFa-Fc molecules (e.g. etanercept, adalimumab, infliximab, golimumab or certolizumab pegol) and Vorinostat. In another embodiment the combination comprises an anti-OX40L antibody of the invention and a further therapeutic agents independently selected from the group consisting of rapamycin (sirolimus), tacrolimus, ciclosporin, corticosteroids (e.g. methylprednisolone), methotrexate, mycophenolate mofetil, anti-CD28 antibodies, CTLA4-Fc molecules (e.g. abatacept), anti-CD40L antibodies, anti-LFA1 antibodies, anti-CD52 antibodies (e.g. alemtuzumab), cyclophosphamide and anti-thymocyte globulins.

In some embodiments the combination comprises an anti-OX40L antibody of the invention and further therapeutic agents independently selected from the group consisting of calcineurin inhibitors (e.g. tacrolimus, ciclosporin), mTOR inhibitors (e.g. rapamycin (sirolimus)), and antiproliferative agents (e.g. mycophenolate mofetil, cyclophosphamide).

In further embodiments the combination comprises an anti-OX40L antibody of the invention and further therapeutic agents independently selected from the group consisting of immunosuppressants that modulate IL-2 signalling (e.g. tacrolimus, ciclosporin, rapamycin (sirolimus), and anti-CD25 antibodies (e.g. basilixumab, daclizumab)

In one embodiment, the combination comprises an anti-OX40L antibody of the invention and rapamycin (sirolimus). In one embodiment, the combination comprises an anti-OX40L antibody of the invention and tacrolimus. In one embodiment, the combination comprises an anti-OX40L antibody of the invention and a combination of tacrolimus and methotrexate. In another embodiment, the combination comprises an anti-OX40L antibody of the invention and ciclosporin. In another embodiment, the combination comprises an anti-OX40L antibody of the invention and ciclosporin and methotrexate. In another embodiment, the combination comprises an anti-OX40L antibody of the invention and cyclophosphamide. In another embodiment, the combination comprises an anti-OX40L antibody of the invention and mycophenolate mofetil.

An antibody of the invention can also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (1990) Mack Publishing Co., Easton, Pa.

The formulations to be used for in vivo administration can be sterile. This is readily accomplished by filtration through, e.g., sterile filtration membranes.

Sustained-release preparations can also be prepared. Suitable examples of sustained-release preparations include semipermeable matrices of solid hydrophobic polymers containing the antagonist, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The pharmaceutical compositions provided herein contain therapeutically effective amounts of one or more of the antibodies of the invention provided herein, and optionally one or more additional prophylactic of therapeutic agents, in a pharmaceutically acceptable carrier. Such pharmaceutical compositions are useful in the prevention, treatment, management or amelioration of a hOX40L-mediated disease, such as an inflammatory bowel disease, transplant rejection, GvHD or one or more of the symptoms thereof.

Pharmaceutical carriers suitable for administration of the compounds provided herein include any such carriers known to those skilled in the art to be suitable for the particular mode of administration.

In addition, the antibodies of the invention may be formulated as the sole pharmaceutically active ingredient in the composition or may be combined with other active ingredients (such as one or more other prophylactic or therapeutic agents).

The compositions can contain one or more antibodies of the invention. In one embodiment, the antibodies are formulated into suitable pharmaceutical preparations, such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. In one embodiment, the antibodies described above are formulated into pharmaceutical compositions using techniques and procedures well known in the art (see, e.g., Ansel (1985) Introduction to Pharmaceutical Dosage Forms, 4th Ed., p. 126).

In the compositions, effective concentrations of one or more antibodies or derivatives thereof is (are) mixed with a suitable pharmaceutical carrier. The concentrations of the compounds in the compositions are effective for delivery of an amount, upon administration, that treats, prevents, or ameliorates a hOX40L-mediated disease or symptom thereof.

In one embodiment, the compositions are formulated for single dosage administration. To formulate a composition, the weight fraction of compound is dissolved, suspended, dispersed or otherwise mixed in a selected carrier at an effective concentration such that the treated condition is relieved, prevented, or one or more symptoms are ameliorated.

An antibody of the invention is included in the pharmaceutically acceptable carrier in an effective amount sufficient to exert a therapeutically useful effect in the absence of undesirable side effects on the patient treated. The therapeutically effective concentration can be determined empirically by testing the compounds in in vitro and in vivo systems using routine methods and then extrapolated therefrom for dosages for humans.

The concentration of antibody in the pharmaceutical composition will depend on, e.g., the physicochemical characteristics of the antibody, the dosage schedule, and amount administered as well as other factors known to those of skill in the art.

In one embodiment, a therapeutically effective dosage produces a serum concentration of antibody of from about 0.1 ng/ml to about 50-100 µg/ml. The pharmaceutical compositions, in another embodiment, provide a dosage of from about 0.001 mg to about 2000 mg of antibody per kilogram of body weight per day. Pharmaceutical dosage unit forms can be prepared to provide from about 0.01 mg, 0.1 mg or 1 mg to about 500 mg, 1000 mg or 2000 mg, and in one embodiment from about 10 mg to about 500 mg of the antibody and/or a combination of other optional essential ingredients per dosage unit form.

The antibody can be administered at once, or may be divided into a number of smaller doses to be administered at intervals of time. It is understood that the precise dosage and duration of treatment is a function of the disease being treated and can be determined empirically using known testing protocols or by extrapolation from in vivo or in vitro test data. It is to be noted that concentrations and dosage values can also vary with the severity of the condition to be alleviated. It is to be further understood that for any particular subject, specific dosage regimens can be adjusted over time according to the individual need and the professional judgment of the person administering or supervising the administration of the compositions, and that the concentration ranges set forth herein are exemplary only and are not intended to limit the scope or practice of the claimed compositions.

Upon mixing or addition of the antibody, the resulting mixture can be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The antibody is, in one embodiment, formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the antibody sufficient to produce the desired therapeutic effect, in association with the required pharmaceutical carrier, vehicle or diluent. Examples of unit-dose forms include ampoules and syringes and individually packaged tablets or capsules. Unit-dose forms can be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

In preferred embodiments, one or more anti-hOX40L antibodies of the invention are in a liquid pharmaceutical formulation. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered can also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents.

Actual methods of preparing such dosage forms are known, or will be apparent, to those skilled in this art; for example, see Remington's Pharmaceutical Sciences (1990) Mack Publishing Co., Easton, Pa.

Dosage forms or compositions containing antibody in the range of 0.005% to 100% with the balance made up from non-toxic carrier can be prepared. Methods for preparation of these compositions are known to those skilled in the art.

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules can be hard or soft gelatin capsules, while granules and powders can be provided in non-effervescent or effervescent form with the combination of other ingredients known to those skilled in the art.

In certain embodiments, the formulations are solid dosage forms. In certain embodiments, the formulations are capsules or tablets. The tablets, pills, capsules, troches and the like can contain one or more of the following ingredients, or compounds of a similar nature: a binder; a lubricant; a diluent; a glidant; a disintegrating agent; a colouring agent; a sweetening agent; a flavouring agent; a wetting agent; an emetic coating; and a film coating. Examples of binders include microcrystalline cellulose, gum tragacanth, glucose solution, acacia mucilage, gelatin solution, molasses, polyinylpyrrolidine, povidone, crospovidones, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include croscarmellose sodium, sodium starch glycolate, alginic acid, corn starch, potato starch, bentonite, methylcellulose, agar and carboxymethylcellulose. Colouring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavours. Flavouring agents include natural flavours extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

The antibodies of the invention can be provided in a composition that protects it/them from the acidic environment of the stomach. For example, the composition can be formulated in an enteric coating that maintains its integrity in the stomach and releases the active compound in the intestine. The composition can also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colourings and flavours.

The antibody can also be mixed with other active materials which do not impair the desired action, or with materials that supplement the desired action, such as antacids, H2 blockers, and diuretics. The active ingredient is an antibody or pharmaceutically acceptable derivative thereof as described herein. Higher concentrations, up to about 98% by weight of the active ingredient may be included.

In all embodiments, tablets and capsules formulations can be coated as known by those of skill in the art in order to modify or sustain dissolution of the active ingredient. Thus, for example, they may be coated with a conventional enterically digestible coating, such as phenylsalicylate, waxes and cellulose acetate phthalate.

In preferred embodiments, the formulations are liquid dosage forms. Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives.

Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Colouring and flavouring agents are used in all of the above dosage forms.

Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Colouring agents include any of the approved certified water soluble FD and C dyes, and mixtures thereof. Flavouring agents include natural flavours extracted from plants such fruits, and synthetic blends of compounds which produce a pleasant taste sensation.

For a solid dosage form, the solution or suspension, in for example propylene carbonate, vegetable oils or triglycerides, is, in one embodiment, encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, can be diluted with a sufficient quantity of a pharmaceutically acceptable liquid carrier, e.g., water, to be easily measured for administration.

Alternatively, liquid or semi-solid oral formulations can be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. RE28,819 and 4,358,603. Briefly, such formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

Parenteral administration, in one embodiment, is characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered can also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The antibody diffuses through the outer polymeric membrane in a release rate controlling step. The amount of antibody contained in such parenteral compositions is highly dependent on the specific nature thereof, as well as the activity of the compound and the needs of the subject.

Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations can be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcellulose, hydroxypropyl methylcellulose and polyvinylpyrrolidone. Emulsifying agents include Polysorbate 80 (TWEEN® 80). A sequestering or chelating agent of metal ions includes EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations can be packaged in an ampoule, a vial or a syringe with a needle. All preparations for parenteral administration can be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In one embodiment, a therapeutically effective dosage is formulated to contain a concentration of at least about 0.1% w/w up to about 90% w/w or more, in certain embodiments more than 1% w/w of the active compound to the treated tissue(s).

The antibody can be suspended in micronized or other suitable form. The form of the resulting mixture depends upon a number of factors, including the intended mode of administration and the solubility of the compound in the selected carrier or vehicle. The effective concentration is sufficient for ameliorating the symptoms of the condition and may be empirically determined.

In other embodiments, the pharmaceutical formulations are lyophilized powders, which can be reconstituted for administration as solutions, emulsions and other mixtures. They may also be reconstituted and formulated as solids or gels.

The lyophilized powder is prepared by dissolving an antibody provided herein, or a pharmaceutically acceptable derivative thereof, in a suitable solvent. In some embodiments, the lyophilized powder is sterile. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

Topical mixtures are prepared as described for the local and systemic administration. The resulting mixture can be a solution, suspension, emulsions or the like and can be formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The antibodies of the invention can be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflations, alone or in combination with an inert carrier such as lactose. In such a case, the particles of the formulation will, in one embodiment, have diameters of less than 50 microns, in one embodiment less than 10 microns.

The compounds can be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%-10% isotonic solutions, pH about 5-7, with appropriate salts.

Other routes of administration, such as transdermal patches, including iontophoretic and electrophoretic devices, and rectal administration, are also contemplated herein.

Transdermal patches, including iontophoretic and electrophoretic devices, are well known to those of skill in the art. For example, such patches are disclosed in U.S. Pat. Nos. 6,267,983, 6,261,595, 6,256,533, 6,167,301, 6,024,975, 6,010715, 5,985,317, 5,983,134, 5,948,433, and 5,860,957.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by moulding. The weight of a rectal suppository, in one embodiment, is about 2 to 3 gm.

Tablets and capsules for rectal administration can be manufactured using the same pharmaceutically acceptable substance and by the same methods as for formulations for oral administration.

The antibodies and other compositions provided herein may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874. In some embodiments, the anti-hOX40L antibodies of the invention are targeted (or otherwise administered) to the colon, such as in a patient having or at risk of having an IBD. In some embodiments, the anti-hOX40L antibodies of the invention are targeted (or otherwise administered) to the eye, such as in a patient having or at risk of having uveitis.

In one embodiment, liposomal suspensions, including tissue-targeted liposomes, such as tumour-targeted liposomes, may also be suitable as pharmaceutically acceptable carriers. These can be prepared according to methods known to those skilled in the art. For example, liposome formulations can be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

Methods of Administration and Dosing

The present invention further provides for compositions comprising one or more antibodies or fragments of the invention for use in the prevention, management, treatment and/or amelioration of a hOX40L-mediated disease (or symptom thereof). Discussion in respect of antibodies also applies mutatis mutandis to fragments of the invention. In an alternative, the present invention further provides for compositions comprising one or more antibodies or fragments of the invention for use in the prevention, management, treatment and/or amelioration of an OX40L-mediated disease (or symptom thereof) in a subject, wherein the OX40L is non-human (e.g., canine, feline, equine, bovine, ovine or porcine) and the subject is respectively a dog, cat, horse, cow, sheep or pig.

In certain embodiments, provided herein are compositions comprising one or more antibodies of the invention for use in the prevention, management, treatment and/or amelioration of a hOX40L-mediated disease, such as IBD (e.g., ulcerative colitis or Crohn's disease), or a symptom thereof. IBD symptoms may range from mild to severe and generally depend upon the part of the intestinal tract involved. Exemplary symptoms of IBD include abdominal cramps and pain, bloody diarrhoea, severe urgency to have a bowel movement, fever, loss of appetite, weight loss, anaemia, fatigue, and/or sores on lower legs, ankles, calves, thighs, and arms. Exemplary intestinal complications of IBD include profuse bleeding from the ulcers, perforation or rupture of the bowel, strictures and obstruction, fistulae (abnormal passage) and perianal disease, toxic megacolon (e.g., acute nonobstructive dilation of the colon), and/or malignancy (e.g., cancer of the colon or small intestine). Exemplary extraintestinal complications of IBD include arthritis, skin conditions, inflammation of the eye, liver and kidney disorders, and/or bone loss. Any combination of these symptoms may be prevented, managed, treated, and/or ameliorated using the compositions and methods provided herein.

In certain embodiments, provided herein are compositions comprising one or more antibodies of the invention for use in the prevention, management, treatment and/or amelioration of an hOX40L-mediated disease, such as GVHD, or a symptom thereof. GVHD generally occurs following allogeneic or matched unrelated bone marrow transplants (BMT).

In some embodiments, the GVHD is acute GVHD. The symptoms of acute GVHD can happen quickly and can be mild or severe. In certain instances, acute GVHD develops within about three months after transplant, such as when blood counts recover after transplant. It certain instances, the acute GVHD affects the skin, gastrointestinal (GI) tract and/or liver. For example, in some patients, acute skin GVHD begins with a rash, for example, on the palms of the patient's hands, soles of the feet, or shoulders. However, the rash can become widespread, and may be itchy and painful and/or might blister and peel. Acute liver GVHD may affect normal functions of the liver, such as liver enzymes, and may in turn, cause jaundice. Acute liver GVHD may also cause the patient's abdomen to become swollen and painful if the liver becomes enlarged. Finally, symptoms of acute gut GVHD (or GVHD of the digestive system) can include diarrhoea, mucus or blood in the stool, cramping or abdominal pain, indigestion, nausea and/or loss of appetite. Other general symptoms of acute GVHD can include anaemia, low grade fever, and/or being more prone to infections. Any combination of these symptoms of acute GVHD may be prevented, managed, treated, and/or ameliorated using the compositions and methods provided herein.

In other embodiments, the GVHD is chronic GVHD. Chronic GVHD can occur from about three months to about a year or longer after transplant. Chronic GVHD can be mild or severe, and generally includes symptoms similar to those of acute GVHD. Chronic GVHD can affect the skin and digestive system, including the liver but can also involve other organs and the immune system (e.g., making the patient more prone to infections) and/or connective tissues. Symptoms of chronic skin GVHD include a rash, dry skin, tight skin, itchy skin, darkening of the colour of the skin, thickening of the skin, and/or may affect hair (e.g., hair loss, turning grey) or nails (e.g., hard or brittle nails). Chronic gut GVHD can affect the digestive system, mouth, oesophagus, lining of the stomach, and/or lining of the bowel, and symptoms can include diarrhoea, dry or sore mouth, painful swallowing, low nutrient absorption by the stomach, bloating, stomach cramps. Chronic liver GVHD can cause damage and scarring of the liver (cirrhosis). Chronic GVHD of the eyes can affect the glands that make tears, causing eyes to become dry, burning and painful or difficult to tolerate bright light. Chronic lung GVHD can cause shortness of breath, wheezing, persistent cough, and/or being more prone to chest infections. Chronic GVHD affects tendons (e.g., inflammation) that connect muscle to bone causing difficulty straightening or bending your arms and legs. Any combination of these symptoms of chronic GVHD may be prevented, managed, treated, and/or ameliorated using the compositions and methods provided herein.

In certain embodiments provided herein are compositions comprising one or more antibodies of the invention for use in the prevention, management, treatment and/or amelioration of a hOX40L-mediated disease, such as uveitis, or a symptom thereof.

In certain embodiments provided herein are compositions comprising one or more antibodies of the invention for use in the prevention, management, treatment and/or amelioration of a hOX40L-mediated disease, such as pyoderma gangrenosum, giant cell arteritis, Schnitzler syndrome or non-infectious scleritis.

In certain embodiments provided herein are compositions comprising one or more antibodies of the invention for use in the prevention, management, treatment and/or amelioration of a hOX40L mediated disease or condition selected from an autoimmune disease or condition, a systemic inflammatory disease or condition, or transplant rejection; for example inflammatory bowel disease (IBD), Crohn's disease, rheumatoid arthritis, transplant rejection, allogeneic transplant rejection, graft-versus-host disease (GvHD), ulcerative colitis, systemic lupus erythematosus (SLE), diabetes, uveitis, ankylosing spondylitis, contact hypersensitivity, multiple sclerosis and atherosclerosis, in particular GvHD.

In a specific embodiment, a composition for use in the prevention, management, treatment and/or amelioration of a hOX40L-mediated disease comprises the OX40L binding sites of an antibody of the invention, e.g., an antibody disclosed in the Examples.

In another embodiment, a composition for use in the prevention, management, treatment and/or amelioration of a hOX40L-mediated disease comprises one or more antibodies comprising one or more VH domains having an amino acid sequence of any one of the VH domains in the sequence listing (i.e. Seq ID No:2, Seq ID No:34, Seq ID No:66 or Seq ID No:94, in particular Seq ID No:34). In another embodiment, a composition for use in the prevention, management, treatment and/or amelioration of a hOX40L-mediated disease comprises one or more antibodies comprising one or more VH CDR1s having an amino acid sequence of any one of the VH CDR1s in the sequence listing (i.e. Seq ID No:4, Seq ID No: 10, Seq ID No:36, Seq ID No:42, Seq ID No:68, Seq ID No:74, Seq ID No:96 or Seq ID No: 102, in particular, Seq ID No:36 or Seq ID No:42). In another embodiment, a composition for use in the prevention, management, treatment and/or amelioration of a hOX40L-mediated disease comprises one or more antibodies comprising one or more VH CDR2s having an amino acid sequence of any one of the VH CDR2s in the sequence listing (i.e. Seq ID No:6, Seq ID No: 12, Seq ID No:38, Seq ID No:44, Seq ID No:70, Seq ID No:76, Seq ID No:98 or Seq ID No: 104, in particular Seq ID No:38 or Seq ID No:44). In a preferred embodiment, a composition for use in the prevention, management, treatment and/or amelioration of a hOX40L-mediated disease comprises one or more antibodies comprising one or more VH CDR3s having an amino acid sequence of any one of the VH CDR3s in the sequence listing (i.e. Seq ID No:8, Seq ID No: 14, Seq ID No:40, Seq ID No:46, Seq ID No:72, Seq ID No:78, Seq ID No: 100 or Seq ID No: 106, in particular Seq ID No:40 or Seq ID No:46).

In another embodiment, a composition for use in the prevention, management, treatment and/or amelioration of a hOX40L-mediated disease comprises one or more antibodies comprising one or more VL domains having an amino acid sequence of any one of the VL domains in the sequence listing (i.e. Seq ID No:16, Seq ID No:48, Seq ID No:80, or Seq ID No: 108, in particular Seq ID No:48) (optionally comprising also the cognate VH domain as set out in the sequence listing (i.e. Seq ID No:2/16, Seq ID No:34/48, Seq ID No:66/80 or Seq ID No:94/108, in particular Seq ID No:34/48). In another embodiment, a composition for use in the prevention, management, treatment and/or amelioration of a hOX40L-mediated disease comprises one or more antibodies comprising one or more VL CDR1 s having an amino acid sequence of any one of the VL CDR1s in the sequence listing (i.e. Seq ID No: 18, Seq ID No:24, Seq ID No:50, Seq ID No:56, Seq ID No:82, Seq ID No:88, Seq ID No: 110 or Seq ID No: 116, in particular Seq ID No:50 or Seq ID No:56). In another embodiment, a composition for use in the prevention, management, treatment and/or amelioration of a hOX40L-mediated disease comprises one or more antibodies comprising one or more VL CDR2s having an amino acid sequence of any one of the VL CDR2s in the sequence listing (i.e. Seq ID No:20, Seq ID No:26, Seq ID No:52, Seq ID No:58, Seq ID No:84, Seq ID No:90, Seq ID No: 112 or Seq ID No: 118, in particular Seq ID No:52 or Seq ID No:58). In a preferred embodiment, a composition for use in the prevention, management, treatment and/or amelioration of a hOX40L-mediated disease comprises one or more antibodies comprising one or more VL CDR3s having an amino acid sequence of any one of the VL CDR3s in the sequence listing (i.e. Seq ID No:22, Seq ID No:28, Seq ID No:54, Seq ID No:60, Seq ID No:86, Seq ID No:92, Seq ID No: 114 or Seq ID No: 120, in particular Seq ID No:54 or Seq ID No:60).

In another embodiment, a composition for use in the prevention, management, treatment and/or amelioration of a hOX40L-mediated disease comprises one or more antibodies comprising one or more VH domains having an amino acid sequence of any one of the VH domains in the sequence listing (i.e. Seq ID No:2, Seq ID No:34, Seq ID No:66 or Seq ID No:94, in particular Seq ID No:34), and one or more VL domains having an amino acid sequence of any one of the VL domains in the sequence listing (i.e. Seq ID No:16, Seq ID No:48, Seq ID No:80, or Seq ID No: 108, in particular Seq ID No:48).

In another embodiment, a composition for use in the prevention, management, treatment and/or amelioration of a hOX40L-mediated disease comprises one or more antibodies comprising one or more VH CDR1s having an amino acid sequence of any one of the VH CDR1s in the sequence listing (i.e. Seq ID No:4, Seq ID No: 10, Seq ID No:36, Seq ID No:42, Seq ID No:68, Seq ID No:74, Seq ID No:96 or Seq ID No: 102, in particular, Seq ID No:36 or Seq ID No:42), and one or more VL CDR1s having an amino acid sequence of any one of the VL CDR1s in the sequence listing (i.e. Seq ID No: 18, Seq ID No:24, Seq ID No:50, Seq ID No:56, Seq ID No:82, Seq ID No:88, Seq ID No: 110 or Seq ID No: 116, in particular Seq ID No:50 or Seq ID No:56). In another embodiment, a composition for use in the prevention, management, treatment and/or amelioration of a hOX40L-mediated disease comprises one or more antibodies comprising one or more VH CDR1s having an amino acid sequence of any one of the VH CDR1s in the sequence listing (i.e. Seq ID No:4, Seq ID No: 10, Seq ID No:36, Seq ID No:42, Seq ID No:68, Seq ID No:74, Seq ID No:96 or Seq ID No: 102, in particular, Seq ID No:36 or Seq ID No:42), and one or more VL CDR2s having an amino acid sequence of any one of the VL CDR2s in the sequence listing (i.e. Seq ID No:20, Seq ID No:26, Seq ID No:52, Seq ID No:58, Seq ID No:84, Seq ID No:90, Seq ID No: 112 or Seq ID No: 118, in particular Seq ID No:52 or Seq ID No:58). In another embodiment, a composition for use in the prevention, management, treatment and/or amelioration of a hOX40L-mediated disease comprises one or more antibodies comprising one or more VH CDR1s having an amino acid sequence of any one of the VH CDR1s in the sequence listing (i.e. Seq ID No:4, Seq ID No: 10, Seq ID No:36, Seq ID No:42, Seq ID No:68, Seq ID No:74, Seq ID No:96 or Seq ID No: 102, in particular, Seq ID No:36 or Seq ID No:42), and one or more VL CDR3s having an amino acid sequence of any one of the VL CDR3s having an amino acid sequence of any one of the VL CDR3s in the sequence listing (i.e. Seq ID No:22, Seq ID No:28, Seq ID No:54, Seq ID No:60, Seq ID No:86, Seq ID No:92, Seq ID No: 114 or Seq ID No: 120, in particular Seq ID No:54 or Seq ID No:60).

As discussed in more detail elsewhere herein, a composition of the invention may be used either alone or in combination with other compounds or compositions. Moreover, the antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, radionucleotides, or toxins. See, e.g., PCT publications WO 92/08495; WO 91/14438; WO 89/12624; U.S. Pat. No. 5,314,995; and EP 396,387.

In some embodiments, provided herein are methods for decreasing or inhibiting binding of hOX40L to an OX40L receptor or cognate ligand (e.g., OX40) in a subject (e.g., a human subject), comprising administering to the subject an effective amount of an antibody that specifically binds to a hOX40L polypeptide (e.g., a cell surface-expressed or soluble hOX40L). In some embodiments, a hOX40L biological activity, such as secretion of CCL20, IL8 and/or RANTES, or INF-γ, TNF-α or IL-2, in particular INF-γ or another cytokine disclosed herein, is also decreased in the subject, for example decreased by at least 10, 20, 30, 40, 50 or 60%, or 70%, or 80%, or 90% or 95% or >95%.

In certain embodiments, provided herein are methods for decreasing or inhibiting a hOX40L biological activity, such as secretion of interferon gamma, IL-2, CCL20, IL8 and/or RANTES or other cytokine, or INF-γ, TNF-α or IL-2, in particular INF-γ in a subject (e.g., a human subject), comprising administering to the subject an effective amount of an antibody that specifically binds to a hOX40L polypeptide (e.g., a cell surface-expressed hOX40L), wherein hOX40L biological activity is decreased by the antibody.

In other embodiments, provided herein are methods for decreasing or inhibiting binding of hOX40L to an OX40L receptor or cognate ligand (e.g., OX40) in a cell having cell surface-expressed hOX40L, contacting the cell with an effective amount of an antibody that specifically binds to a hOX40L polypeptide (e.g., a cell surface-expressed or soluble hOX40L), such as a hOX40L polypeptide, a hOX40L polypeptide fragment, or a hOX40L epitope. In some embodiments, a hOX40L biological activity, such as secretion of interferon gamma, IL-2, CCL20, IL8 and/or RANTES, or INF-γ, TNF-α or IL-2, in particular INF-γ or other cytokine disclosed herein, is also decreased in the cell.

In certain embodiments, provided herein are methods for decreasing or inhibiting a hOX40L biological activity, such as secretion of interferon gamma, IL-2, CCL20, IL8 and/or RANTES or other cytokine disclosed herein, in a cell having a cell surface-expressed hOX40L receptor (such as OX40), contacting the cell with an effective amount of an antibody that specifically binds to a hOX40L polypeptide (e.g., a cell surface-expressed or soluble hOX40L) wherein hOX40L biological activity is decreased by the antibody.

Antibodies of the present invention may be used, for example, to purify, detect, and target hOX40L antigens, in both in vitro and in vivo diagnostic and therapeutic methods. For example, the modified antibodies have use in immunoassays for qualitatively and quantitatively measuring levels of hOX40L in biological samples. See, e.g., Harlow et al., Antibodies: A Laboratory Manual, (Cold Spring Harbor Laboratory Press, 2nd ed. 1988) (incorporated by reference herein in its entirety).

The invention also provides methods of preventing, managing, treating and/or ameliorating a hOX40L-mediated disease by administrating to a subject of an effective amount of an antibody, or pharmaceutical composition comprising an antibody of the invention. In one aspect, an antibody is substantially purified (i.e., substantially free from substances that limit its effect or produce undesired side-effects). In preferred embodiments, the antibody is a fully human monoclonal antibody, such as a fully human monoclonal antagonist antibody. The subject administered a therapy is preferably a mammal such as non-primate (e.g., cows, pigs, horses, cats, dogs, rodents, mice or rats) or a primate (e.g., a monkey, such as a rhesus or cynomolgous monkey, or a human). In a preferred embodiment, the subject is a human. In another preferred embodiment, the subject is a human infant or a human infant born prematurely. In another embodiment, the subject is a human with a hOX40L-mediated disease.

Various delivery systems are known and can be used to administer a prophylactic or therapeutic agent (e.g., an antibody of the invention), including, but not limited to, encapsulation in liposomes, microparticles, microcapsules, recombinant cells capable of expressing the antibody, receptor-mediated endocytosis (see, e.g., Wu and Wu, J. Biol. Chem. 262:4429-4432 (1987)), construction of a nucleic acid as part of a retroviral or other vector, etc. Methods of administering a prophylactic or therapeutic agent (e.g., an antibody of the invention), or pharmaceutical composition include, but are not limited to, parenteral administration (e.g., intradermal, intramuscular, intraperitoneal, intravenous and subcutaneous), epidural, and mucosal (e.g., intranasal and oral routes). In a specific embodiment, a prophylactic or therapeutic agent (e.g., an antibody of the present invention), or a pharmaceutical composition is administered intranasally, intramuscularly, intravenously, or subcutaneously. The prophylactic or therapeutic agents or compositions may be administered by any convenient route, for example by infusion or bolus injection, by absorption through epithelial or mucocutaneous linings (e.g., oral mucosa, intranasal mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entirety.

In a specific embodiment, it may be desirable to administer a prophylactic or therapeutic agent, or a pharmaceutical composition of the invention locally to the area in need of treatment. This may be achieved by, for example, and not by way of limitation, local infusion, by topical administration (e.g., by intranasal spray), by injection, or by means of an implant, said implant being of a porous, non-porous, or gelatinous material, including membranes, such as sialastic membranes, or fibers. Preferably, when administering an antibody of the invention, care must be taken to use materials to which the antibody does not absorb.

In another embodiment, a prophylactic or therapeutic agent, or a composition of the invention can be delivered in a vesicle, in particular a liposome (see Langer, 1990, Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In another embodiment, a prophylactic or therapeutic agent, or a composition of the invention can be delivered in a controlled release or sustained release system. In one embodiment, a pump may be used to achieve controlled or sustained release (see Langer, supra; Sefton, 1987, CRC Crit. Ref. Biomed. Eng. 14:20; Buchwald et al., 1980, Surgery 88:507; Saudek et al., 1989, N. Engl. J. Med. 321:574). In another embodiment, polymeric materials can be used to achieve controlled or sustained release of a prophylactic or therapeutic agent (e.g., an antibodies of the invention) or a composition of the invention (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J., Macromol. Sci. Rev. Macromol. Chem. 23:61; see also Levy et al., 1985, Science 228:190; During et al., 1989, Ann. Neurol. 25:351; Howard et al., 1989, J. Neurosurg. 7 1:105); U.S. Pat. No. 5,679,377; U.S. Pat. No. 5,916,597; U.S. Pat. No. 5,912,015; U.S. Pat. No. 5,989,463; U.S. Pat. No. 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In a preferred embodiment, the polymer used in a sustained release formulation is inert, free of leachable impurities, stable on storage, sterile, and biodegradable. In yet another embodiment, a controlled or sustained release system can be placed in proximity of the therapeutic target, i.e., the nasal passages or lungs, thus requiring only a fraction of the systemic dose (see, e.g., Goodson, in Medical Applications of Controlled Release, supra, vol. 2, pp. 115-138 (1984)). Controlled release systems are discussed in the review by Langer (1990, Science 249:1527-1533). Any technique known to one of skill in the art can be used to produce sustained release formulations comprising one or more antibodies of the invention. See, e.g., U.S. Pat. No. 4,526,938, PCT publication WO 91/05548, PCT publication WO 96/20698, Ning et al., 1996, "Intratumoral Radioimmunotherapy of a Human Colon Cancer Xenograft Using a Sustained-Release Gel," Radiotherapy & Oncology 39:179-189, Song et al., 1995, "Antibody Mediated Lung Targeting of Long-Circulating Emulsions," PDA Journal of Pharmaceutical Science & Technology 50:372-397, Cleek et al., 1997, "Biodegradable Polymeric Carriers for a bFGF Antibody for Cardiovascular Application," Pro. Int'l. Symp. Control. Rel. Bioact. Mater. 24:853-854, and Lam et al., 1997, "Microencapsulation of Recombinant Humanized Monoclonal Antibody for Local Delivery," Proc. Int'l. Symp. Control Rel. Bioact. Mater. 24:759-760, each of which is incorporated herein by reference in their entirety.

In a specific embodiment, where the composition of the invention is a nucleic acid encoding a prophylactic or therapeutic agent (e.g., an antibody of the invention), the nucleic acid can be administered in vivo to promote expression of its encoded prophylactic or therapeutic agent, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell surface receptors or transfecting agents, or by administering it in linkage to a homeobox-like peptide which is known to enter the nucleus (see, e.g., Joliot et al., 1991, Proc. Natl. Acad. Sci. USA 88:1864-1868), etc. Alternatively, a nucleic acid can be introduced intracellularly and incorporated within host cell DNA for expression by homologous recombination.

In a specific embodiment, a composition of the invention comprises one, two or more antibodies or fragments of the invention. In another embodiment, a composition of the invention comprises one, two or more antibodies or fragments of the invention and a prophylactic or therapeutic agent other than an antibody of the invention. Preferably, the agents are known to be useful for or have been or are currently used for the prevention, management, treatment and/or amelioration of a hOX40L-mediated disease. In addition to prophylactic or therapeutic agents, the compositions of the invention may also comprise a carrier.

The compositions of the invention include bulk drug compositions useful in the manufacture of pharmaceutical compositions (e.g., compositions that are suitable for administration to a subject or patient) that can be used in the preparation of unit dosage forms. In a preferred embodiment, a composition of the invention is a pharmaceutical composition. Such compositions comprise a prophylactically or therapeutically effective amount of one or more prophylactic or therapeutic agents (e.g., an antibody of the invention or other prophylactic or therapeutic agent), and a pharmaceutically acceptable carrier. Preferably, the pharmaceutical compositions are formulated to be suitable for the route of administration to a subject.

In a specific embodiment, the term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences (1990) Mack Publishing Co., Easton, Pa. Such compositions will contain a prophylactically or therapeutically effective amount of the antibody, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anaesthetic such as lignocamne to ease pain at the site of the injection. Such compositions, however, may be administered by a route other than intravenous.

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The invention also provides that an antibody of the invention is packaged in a hermetically sealed container such as an ampoule or sachette indicating the quantity of antibody. In one embodiment, the antibody is supplied as a dry sterilized lyophilized powder or water free concentrate in a hermetically sealed container and can be reconstituted, e.g., with water or saline to the appropriate concentration for administration to a subject. Preferably, the antibody is supplied as a dry sterile lyophilized powder in a hermetically sealed container at a unit dosage of at least 0.1 mg, at least 0.5 mg, at least 1 mg, at least 2 mg, or at least 3 mg, and more preferably at least 5 mg, at least 10 mg, at least 15 mg, at least 25 mg, at least 30 mg, at least 35 mg, at least 45 mg, at least 50 mg, at least 60 mg, at least 75 mg, at least 80 mg, at least 85 mg, at least 90 mg, at least 95 mg, or at least 100 mg. The lyophilized antibody can be stored at between 2 and 8° C. in its original container and the antibody can be administered within 12 hours, preferably within 6 hours, within 5 hours, within 3 hours, or within 1 hour after being reconstituted. In an alternative embodiment, an antibody is supplied in liquid form in a hermetically sealed container indicating the quantity and concentration of the antibody. Preferably, the liquid form of the antibody is supplied in a hermetically sealed container at least 0.1 mg/ml, at least 0.5 mg/ml, or at least 1 mg/ml, and more preferably at least 5 mg/ml, at least 10 mg/ml, at least 15 mg/ml, at least 25 mg/ml, at least 30 mg/ml, at least 40 mg/ml, at least 50 mg/ml, at least 60 mg/ml, at least 70 mg/ml, at least 80 mg/ml, at least 90 mg/ml, or at least 100 mg/ml.

The compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of a prophylactic or therapeutic agent (e.g., an antibody of the invention), or a composition of the invention that will be effective in the prevention, management, treatment and/or amelioration of a hOX40L-mediated disease can be determined by standard clinical techniques.

Accordingly, a dosage of an antibody or a composition that results in a serum titer of from about 0.1 µg/ml to about 450 µg/ml, and in some embodiments at least 0.1 µg/ml, at least 0.2 µg/ml, at least 0.4 µg/ml, at least 0.5 µg/ml, at least 0.6 µg/ml, at least 0.8 µg/ml, at least 1 µg/ml, at least 1.5 µg/ml, and preferably at least 2 µg/ml, at least 5 µg/ml, at least 10 µg/ml, at least 15 µg/ml, at least 20 µg/ml, at least 25 µg/ml, at least 30 µg/ml, at least 35 µg/ml, at least 40 µg/ml, at least 50 µg/ml, at least 75 µg/ml, at least 100 µg/ml, at least 125 µg/ml, at least 150 µg/ml, at least 200 µg/ml, at least 250 µg/ml, at least 300 µg/ml, at least 350 µg/ml, at least 400 µg/ml, or at least 450 µg/ml can be administered to a human for the prevention, management, treatment and/or amelioration of a hOX40L-mediated disease. In addition, in vitro assays may optionally be employed to help identify optimal dosage ranges. The precise dose to be employed in the formulation will also depend on the route of administration, and the seriousness of a hOX40L-mediated disease, and should be decided according to the judgment of the practitioner and each patient's circumstances.

Effective doses may be extrapolated from dose-response curves derived from in vitro or animal model test systems.

For the antibodies of the invention, the dosage administered to a patient is typically 0.1 mg/kg to 100 mg/kg of the patient's body weight. In some embodiments, the dosage administered to the patient is about 1 mg/kg to about 75 mg/kg of the patient's body weight. Preferably, the dosage administered to a patient is between 1 mg/kg and 20 mg/kg of the patient's body weight, more preferably 1 mg/kg to 5 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of the antibodies of the invention may be reduced by enhancing uptake and tissue penetration of the antibodies by modifications such as, for example, lipidation.

In one embodiment, approximately 100 mg/kg or less, approximately 75 mg/kg or less, approximately 50 mg/kg or less, approximately 25 mg/kg or less, approximately 10 mg/kg or less, approximately 5 mg/kg or less, approximately 1 mg/kg or less, approximately 0.5 mg/kg or less, or approximately 0.1 mg/kg or less of an antibody or fragment the invention is administered 5 times, 4 times, 3 times, 2 times or, preferably, 1 time to manage a hOX40L-mediated disease. In some embodiments, an antibody of the invention is administered about 1-12 times, wherein the doses may be administered as necessary, e.g., weekly, biweekly, monthly, bimonthly, trimonthly, etc., as determined by a physician. In some embodiments, a lower dose (e.g., 1-15 mg/kg) can be administered more frequently (e.g., 3-6 times). In other embodiments, a higher dose (e.g., 25-100 mg/kg) can be administered less frequently (e.g., 1-3 times). However, as will be apparent to those in the art, other dosing amounts and schedules are easily determinable and within the scope of the invention.

In a specific embodiment, approximately 100 mg/kg, approximately 75 mg/kg or less, approximately 50 mg/kg or less, approximately 25 mg/kg or less, approximately 10 mg/kg or less, approximately 5 mg/kg or less, approximately 1 mg/kg or less, approximately 0.5 mg/kg or less, approximately 0.1 mg/kg or less of an antibody or fragment the invention in a sustained release formulation is administered to a subject, preferably a human, to prevent, manage, treat and/or ameliorate a hOX40L-mediated disease. In another specific embodiment, an approximately 100 mg/kg, approximately 75 mg/kg or less, approximately 50 mg/kg or less, approximately 25 mg/kg or less, approximately 10 mg/kg or less, approximately 5 mg/kg or less, approximately 1 mg/kg or less, approximately 0.5 mg/kg or less, or approximately 0.1 mg/kg or less bolus of an antibody the invention not in a sustained release formulation is administered to a subject, preferably a human, to prevent, manage, treat and/or ameliorate a hOX40L-mediated disease, and after a certain period of time, approximately 100 mg/kg, approximately 75 mg/kg or less, approximately 50 mg/kg or less, approximately 25 mg/kg or less, approximately 10 mg/kg or less, approximately 5 mg/kg or less, approximately 1 mg/kg or less, approximately 0.5 mg/kg or less, or approximately 5 mg/kg or less of an antibody of the invention in a sustained release is administered to said subject (e.g., intranasally or intramuscularly) two, three or four times (preferably one time). In accordance with this embodiment, a certain period of time can be 1 to 5 days, a week, two weeks, or a month.

In some embodiments, a single dose of an antibody or fragment of the invention is administered to a patient to prevent, manage, treat and/or ameliorate a hOX40L-mediated disease two, three, four, five, six, seven, eight, nine, ten, eleven, twelve times, thirteen, fourteen, fifteen, sixteen, seventeen, eighteen, nineteen, twenty, twenty-one, twenty-two, twenty-three, twenty-four, twenty five, or twenty six at bi-weekly (e.g., about 14 day) intervals over the course of a year, wherein the dose is selected from the group consisting of about 0.1 mg/kg, about 0.5 mg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, about 100 mg/kg, or a combination thereof (i.e., each dose monthly dose may or may not be identical).

In another embodiment, a single dose of an antibody of the invention is administered to patient to prevent, manage, treat and/or ameliorate a hOX40L-mediated disease two, three, four, five, six, seven, eight, nine, ten, eleven, or twelve times at about monthly (e.g., about 30 day) intervals over the course of a year, wherein the dose is selected from the group consisting of about 0.1 mg/kg, about 0.5 mg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, about 100 mg/kg, or a combination thereof (i.e., each dose monthly dose may or may not be identical).

In one embodiment, a single dose of an antibody or fragment of the invention is administered to a patient to prevent, manage, treat and/or ameliorate a hOX40L-mediated disease two, three, four, five, or six times at about bi-monthly (e.g., about 60 day) intervals over the course of a year, wherein the dose is selected from the group consisting of about 0.1 mg/kg, about 0.5 mg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, about 100 mg/kg, or a combination thereof (i.e., each bi-monthly dose may or may not be identical).

In some embodiments, a single dose of an antibody or fragment of the invention is administered to a patient to prevent, manage, treat and/or ameliorate a hOX40L-mediated disease two, three, or four times at about tri-monthly (e.g., about 120 day) intervals over the course of a year, wherein the dose is selected from the group consisting of about 0.1 mg/kg, about 0.5 mg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, about 100 mg/kg, or a combination thereof (i.e., each tri-monthly dose may or may not be identical).

In certain embodiments, the route of administration for a dose of an antibody or fragment of the invention to a patient is intranasal, intramuscular, intravenous, or a combination thereof, but other routes described herein are also acceptable. In certain embodiments, the route of administration is intraocular. Each dose may or may not be administered by an identical route of administration. In some embodiments, an antibody or fragment of the invention may be administered via multiple routes of administration simultaneously or subsequently to other doses of the same or a different antibody or fragment of the invention.

In certain embodiments, antibodies or fragments of the invention are administered prophylactically or therapeutically to a subject. Antibodies or fragments of the invention can be prophylactically or therapeutically administered to a subject so as to prevent, lessen or ameliorate a hOX40L-mediated disease or symptom thereof.

Gene Therapy

In a specific embodiment, nucleic acids or nucleotide sequences of the invention are administered to prevent, manage, treat and/or ameliorate a hOX40L-mediated disease by way of gene therapy. Gene therapy refers to therapy performed by the administration to a subject of an expressed or expressible nucleic acid. In an embodiment of the invention, the nucleic acids produce their encoded antibody, and the antibody mediates a prophylactic or therapeutic effect.

Any of the methods for gene therapy available in the art can be used according to the present invention.

Diagnostic Use of Antibodies

Although antibodies are mentioned in respect of diagnostic uses, this disclosure is to be read as also applying mutatis mutandis to the fragments of the invention.

Labelled antibodies or of the invention and derivatives and analogues thereof, which specifically bind to a hOX40L antigen can be used for diagnostic purposes to detect, diagnose, or monitor a hOX40L-mediated disease. The invention provides methods for the detection of a hOX40L-mediated disease comprising: (a) assaying the expression of a hOX40L antigen in cells or a tissue sample of a subject using one or more antibodies of the invention that specifically bind to the hOX40L antigen; and (b) comparing the level of the hOX40L antigen with a control level, e.g., levels in normal tissue samples (e.g., from a patient not having a hOX40L-mediated disease, or from the same patient before disease onset), whereby an increase in the assayed level of hOX40L antigen compared to the control level of the hOX40L antigen is indicative of a hOX40L-mediated disease.

The invention provides a diagnostic assay for diagnosing a hOX40L-mediated disease comprising: (a) assaying for the level of a hOX40L antigen in cells or a tissue sample of an individual using one or more antibodies of the invention that specifically bind to a hOX40L antigen; and (b) comparing the level of the hOX40L antigen with a control level, e.g., levels in normal tissue samples, whereby an increase in the assayed hOX40L antigen level compared to the control level of the hOX40L antigen is indicative of a hOX40L-mediated disease. A more definitive diagnosis of a hOX40L-mediated disease may allow health professionals to employ preventative measures or aggressive treatment earlier thereby preventing the development or further progression of the hOX40L-mediated disease.

Antibodies of the invention can be used to assay hOX40L antigen levels in a biological sample using classical immunohistological methods as described herein or as known to those of skill in the art (e.g., see Jalkanen et al., 1985, J. Cell. Biol. 101:976-985; and Jalkanen et al., 1987, J. Cell. Biol. 105:3087-3096). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{125}$I, $^{121}$I) carbon ($^{14}$C), sulfur ($^{35}$S), tritium ($^{3}$H), indium ($^{121}$In), and technetium ($^{99}$Tc); luminescent labels, such as luminol; and fluorescent labels, such as fluorescein and rhodamine, and biotin.

One aspect of the invention is the detection and diagnosis of a hOX40L-mediated disease in a human. In one embodiment, diagnosis comprises: a) administering (for example, parenterally, subcutaneously, or intraperitoneally) to a subject an effective amount of a labelled antibody that specifically binds to a hOX40L antigen; b) waiting for a time interval following the administering for permitting the labelled antibody to preferentially concentrate at sites in the subject where the hOX40L antigen is expressed (and for unbound labelled molecule to be cleared to background level); c) determining background level; and d) detecting the labelled antibody in the subject, such that detection of labelled antibody above the background level indicates that the subject has a hOX40L-mediated disease. Background level can be determined by various methods including, comparing the amount of labelled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99}$Tc. The labelled antibody will then preferentially accumulate at the location of cells which contain the specific protein. In vivo tumour imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labelled antibody to preferentially concentrate at sites in the subject and for unbound labelled antibody to be cleared to background level is 6 to 48 hours or 6 to 24 hours or 6 to 12 hours. In another embodiment the time interval following administration is 5 to 20 days or 5 to 10 days.

In one embodiment, monitoring of a hOX40L-mediated disease is carried out by repeating the method for diagnosing the a hOX40L-mediated disease, for example, one month after initial diagnosis, six months after initial diagnosis, one year after initial diagnosis, etc.

Presence of the labelled molecule can be detected in the subject using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labelled with a radioisotope and is detected in the patient using a radiation responsive surgical instrument (Thurston et al., U.S. Pat. No. 5,441,050). In another embodiment, the molecule is labelled with a fluorescent compound and is detected in the patient using a fluorescence responsive scanning instrument. In another embodiment, the molecule is labelled with a positron emitting metal and is detected in the patient using positron emission-tomography. In yet another embodiment, the molecule is labelled with a paramagnetic label and is detected in a patient using magnetic resonance imaging (MRI).

Methods of Producing Antibodies

Antibodies and fragments of the invention that specifically bind to an antigen (OX40L) can be produced by any method known in the art for the synthesis of antibodies, in particular, by chemical synthesis or preferably, by recombinant expression techniques. The practice of the invention employs, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described in the references cited herein and are fully explained in the literature. See, e.g., Maniatis et al. (1982) Molecular Cloning: A Laboratory Manual, Cold Spring Harbor Laboratory Press; Sambrook et al. (1989), Molecular Cloning: A Laboratory Manual, Second Edition, Cold Spring Harbor Laboratory Press; Sambrook et al. (2001) Molecular Cloning: A Laboratory Manual, Cold Spring Harbor Laboratory Press, Cold Spring Harbor, N.Y.; Ausubel et al., Current Protocols in Molecular Biology, John Wiley & Sons (1987 and annual updates); Current Protocols in Immunology, John Wiley & Sons (1987 and annual updates) Gait (ed.) (1984) Oligonucleotide Synthesis: A Practical Approach, IRL Press; Eckstein (ed.) (1991) Oligonucleotides and Analogues: A Practical Approach, IRL Press; Birren et al. (eds.) (1999) Genome Analysis: A Laboratory Manual, Cold Spring Harbor Laboratory Press.

Polyclonal antibodies that specifically bind to an antigen can be produced by various procedures well-known in the art. For example, a human antigen can be administered to various host animals including, but not limited to, rabbits, mice, rats, etc. to induce the production of sera containing polyclonal antibodies specific for the human antigen. Various adjuvants may be used to increase the immunological response, depending on the host species, and include but are not limited to, Freund's (complete and incomplete), mineral gels such as aluminium hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling et al., in: Monoclonal Antibodies and T-Cell Hybridomas 563 681 (Elsevier, N.Y., 1981) (said references incorporated by reference in their entireties). The term "monoclonal antibody" as used herein is not limited to antibodies produced through hybridoma technology. Other exemplary methods of producing monoclonal antibodies are discussed elsewhere herein, such as e.g., use of the KM Mouse™. Additional exemplary methods of producing monoclonal antibodies are provided in the Examples herein.

Methods for producing and screening for specific antibodies using hybridoma technology are routine and well known in the art. Briefly, mice can be immunized with a hOX40L antigen and once an immune response is detected, e.g., antibodies specific for hOX40L antigen are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution.

Additionally, a RIMMS (repetitive immunization multiple sites) technique can be used to immunize an animal (Kilptrack et al., 1997 Hybridoma 16:381-9, incorporated by reference in its entirety). The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating antibodies by culturing a hybridoma cell secreting a modified antibody of the invention wherein, preferably, the hybridoma is generated by fusing splenocytes isolated from a mouse immunized with a hOX40L antigen with myeloma cells and then screening the hybridomas resulting from the fusion for hybridoma clones that secrete an antibody able to bind to a hOX40L antigen.

Antibody fragments which recognize specific hOX40L antigens may be generated by any technique known to those of skill in the art. For example, Fab and $F(ab')_2$ fragments of the invention may be produced by proteolytic cleavage of immunoglobulin molecules, using enzymes such as papain (to produce Fab fragments) or pepsin (to produce $F(ab')_2$ fragments). $F(ab')_2$ fragments contain the variable region, the Light chain constant region and the CH1 domain of the heavy chain. Further, the antibodies of the present invention can also be generated using various phage display methods known in the art.

For example, antibodies can also be generated using various phage display methods. In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of affected tissues). The DNA encoding the VH and VL domains are recombined together with an scFv linker by PCR and cloned into a phagemid vector. The vector is electroporated in E. coli and the E. coli is infected with helper phage. Phage used in these methods are typically filamentous phage including fd and M13 and the VH and VL domains are usually recombinantly fused to either the phage gene III or gene VIII. Phage expressing an antigen binding domain that binds to a particular antigen can be selected or identified with antigen, e.g., using labelled antigen or antigen bound or captured to a solid surface or bead. Examples of phage display methods that can be used to make the antibodies of the present invention include those disclosed in Brinkman et al., 1995, J. Immunol. Methods 182:41-50; Ames et al., 1995, J. Immunol. Methods 184:177-186; Kettleborough et al., 1994, Eur. J. Immunol. 24:952-958; Persic et al., 1997, Gene 187:9-18; Burton et al., 1994, Advances in Immunology 57:191-280; PCT Application No. PCT/GB91/01134; International Publication Nos. WO 90/02809, WO 91/10737, WO 92/01047, WO 92/18619, WO 93/1 1236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce Fab, Fab' and $F(ab')_2$ fragments can also be employed using methods known in the art such as those disclosed in PCT publication No. WO 92/22324; Mullinax et al., 1992, BioTechniques 12(6):864-869; Sawai et al., 1995, AJRI 34:26-34; and Better et al., 1988, Science 240:1041-1043 (said references incorporated by reference in their entireties).

To generate whole antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a VH constant region, e.g., the human gamma 4 constant region, and the PCR amplified VL domains can be cloned into vectors expressing a VL constant region, e.g., human kappa or lambda constant regions. The VH and VL domains may also cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

For some uses, including in vivo use of antibodies in humans and in vitro detection assays, it may be preferable to use human or chimeric antibodies. Completely human antibodies are particularly desirable for therapeutic treatment of human subjects. Human antibodies can be made by a variety of methods known in the art including phage display methods described above using antibody libraries derived from human immunoglobulin sequences. See also U.S. Pat. Nos. 4,444,887 and 4,716,111; and International Publication Nos. WO 98/46645, WO 98/50433, WO 98/24893, WO 98/16654, WO 96/34096, WO 96/33735, and WO 91/10741; each of which is incorporated herein by reference in its entirety.

In preferred embodiments, human antibodies are produced. Human antibodies and/or fully human antibodies can be produced using any method known in the art, including the Examples provided herein. For example, transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered nonfunctional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B-cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93). For a detailed discussion of this technology for producing human antibodies and human monoclonal antibodies and protocols for producing such antibodies, see, e.g., PCT publication Nos. WO 98/24893, WO 96/34096, and WO 96/33735; and U.S. Pat. Nos. 5,413,923, 5,625,126, 5,633,425, 5,569,825, 5,661,016, 5,545,806, 5,814,318, and 5,939,598, which are incorporated by reference herein in their entirety. Other methods are detailed in the Examples herein. In addition, companies such as Abgenix, Inc/Amgen. (Thousand Oaks, Calif.) OMT (Paolo Alto, Calif.), Argen-x (Breda, Netherlands), Ablexis (San Francisco, Calif.) or Harbour Antibodies (Cambridge, Mass.) can be engaged to provide human antibodies directed against a selected antigen using technology similar to that described above.

A chimeric antibody is a molecule in which different portions of the antibody are derived from different immunoglobulin molecules. Methods for producing chimeric antibodies are known in the art. See, e.g., Morrison, 1985, Science 229:1202; Oi et al., 1986, BioTechniques 4:214; Gillies et al., 1989, J. Immunol. Methods 125:191-202; and U.S. Pat. Nos. 5,807,715, 4,816,567, 4,816,397, and 6,331,415, which are incorporated herein by reference in their entirety.

A humanized antibody is an antibody or its variant or fragment thereof which is capable of binding to a predetermined antigen and which comprises a framework region having substantially the amino acid sequence of a human immunoglobulin and a CDR having substantially the amino acid sequence of a non-human immunoglobulin. A humanized antibody comprises substantially all of at least one, and typically two, variable domains (Fab, Fab', F(ab')$_2$, Fabc, Fv) in which all or substantially all of the CDR regions correspond to those of a non-human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. Ordinarily, the antibody will contain both the light chain as well as at least the variable domain of a heavy chain. The antibody also may include the CH1, hinge, CH2, CH3, and CH4 regions of the heavy chain. The humanized antibody can be selected from any class of immunoglobulins, including IgM, IgG, IgD, IgA and IgE, and any isotype, including IgG1, IgG2, IgG3 and IgG4. Usually the constant domain is a complement fixing constant domain where it is desired that the humanized antibody exhibit cytotoxic activity, and the class is typically IgG1. Where such cytotoxic activity is not desirable, the constant domain may be of the IgG2 class. In certain embodiments, the antibodies of the invention comprise a human gamma 4 constant region. In another embodiment, the heavy chain constant region does not bind Fc-γ receptors, and e.g. comprises a Leu235Glu mutation. In another embodiment, the heavy chain constant region comprises a Ser228Pro mutation to increase stability. In another embodiment, the heavy chain constant region is IgG4-PE. Examples of VL and VH constant domains that can be used in certain embodiments of the invention include, but are not limited to, C-kappa and C-gamma-1 (nG1m) described in Johnson et al. (1997) J. Infect. Dis. 176, 1215-1224 and those described in U.S. Pat. No. 5,824,307. The humanized antibody may comprise sequences from more than one class or isotype, and selecting particular constant domains to optimize desired effector functions is within the ordinary skill in the art. The framework and CDR regions of a humanized antibody need not correspond precisely to the parental sequences, e.g., the donor CDR or the consensus framework may be mutagenized by substitution, insertion or deletion of at least one residue so that the CDR or framework residue at that site does not correspond to either the consensus or the import antibody. Such mutations, however, will not be extensive. Usually, at least 75% of the humanized antibody residues will correspond to those of the parental FR and CDR sequences, more often 90%, and most preferably greater than 95%. Humanized antibodies can be produced using variety of techniques known in the art, including but not limited to, CDR-grafting (European Patent No. EP 239,400; International publication No. WO 91/09967; and U.S. Pat. Nos. 5,225,539, 5,530,101, and 5,585,089), veneering or resurfacing (European Patent Nos. EP 592,106 and EP 519,596; Padlan, 1991, Molecular Immunology 28(4/5):489-498; Studnicka et al., 1994, Protein Engineering 7(6):805-814; and Roguska et al., 1994, PNAS 91:969-973), chain shuffling (U.S. Pat. No. 5,565,332), and techniques disclosed in, e.g., U.S. Pat. No. 6,407,213, U.S. Pat. No. 5,766,886, WO 9317105, Tan et al., J. Immunol. 169:1119 25 (2002), Caldas et al., Protein Eng. 13(5):353-60 (2000), Morea et al., Methods 20(3):267 79 (2000), Baca et al., J. Biol. Chem. 272(16):10678-84 (1997), Roguska et al., Protein Eng. 9(10):895 904 (1996), Couto et al., Cancer Res. 55 (23 Supp):5973s-5977s (1995), Couto et al., Cancer Res. 55(8):1717-22 (1995), Sandhu J S, Gene 150(2):409-10 (1994), and Pedersen et al., J. Mol. Biol. 235(3):959-73 (1994). See also U.S. Patent Pub. No. US 2005/0042664 A1 (Feb. 24, 2005), which is incorporated by reference herein in its entirety. Often, framework residues in the framework regions will be substituted with the corresponding residue from the CDR donor antibody to alter, preferably improve, antigen binding. These framework substitutions are identified by methods well known in the art, e.g., by modelling of the interactions of the CDR and framework residues to identify framework residues important for antigen binding and sequence comparison to identify unusual framework residues at particular positions. (See, e.g., Queen et al., U.S. Pat. No. 5,585,089; and Reichmann et al., 1988, Nature 332:323, which are incorporated herein by reference in their entireties.)

Single domain antibodies, for example, antibodies lacking the light chains, can be produced by methods well-known in the art. See Riechmann et al., 1999, J. Immunol. 231:25-38; Nuttall et al., 2000, Curr. Pharm. Biotechnol. 1(3):253-263; Muylderman, 2001, J. Biotechnol. 74(4):277302; U.S. Pat. No. 6,005,079; and International Publication Nos. WO 94/04678, WO 94/25591, and WO 01/44301, each of which is incorporated herein by reference in its entirety.

Further, the antibodies that specifically bind to a hOX40L antigen can, in turn, be utilized to generate anti-idiotype antibodies that "mimic" an antigen using techniques well known to those skilled in the art. (See, e.g., Greenspan &

Bona, 1989, FASEB J. 7(5):437-444; and Nissinoff, 1991, J. Immunol., 147(8):2429-2438).

Kits

The invention also provides a pharmaceutical or diagnostic pack or kit comprising one or more containers filled with one or more of the ingredients of the pharmaceutical compositions of the invention, such as one or more antibodies or fragments provided herein. Optionally associated with such container(s) can be a notice in the form prescribed by a governmental agency regulating the manufacture, use or sale of pharmaceuticals or biological products, which notice reflects approval by the agency of manufacture, use or sale for human administration, e.g., an authorisation number.

The present invention provides kits that can be used in the above methods. In one embodiment, a kit comprises an antibody of the invention, preferably a purified antibody, in one or more containers. In a specific embodiment, the kits of the present invention contain a substantially isolated hOX40L antigen as a control. Preferably, the kits of the present invention further comprise a control antibody which does not react with the hOX40L antigen. In another specific embodiment, the kits of the present invention contain a means for detecting the binding of a modified antibody to a hOX40L antigen (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate). In specific embodiments, the kit may include a recombinantly produced or chemically synthesized hOX40L antigen. The hOX40L antigen provided in the kit may also be attached to a solid support. In a more specific embodiment the detecting means of the above described kit includes a solid support to which hOX40L antigen is attached. Such a kit may also include a non-attached reporter-labelled anti-human antibody. In this embodiment, binding of the antibody to the hOX40L antigen can be detected by binding of the said reporter-labelled antibody.

"Conservative amino acid substitutions" result from replacing one amino acid with another having similar structural and/or chemical properties, such as the replacement of a leucine with an isoleucine or valine, an aspartate with a glutamate, or a threonine with a serine. Thus, a "conservative substitution" of a particular amino acid sequence refers to substitution of those amino acids that are not critical for polypeptide activity or substitution of amino acids with other amino acids having similar properties (e.g., acidic, basic, positively or negatively charged, polar or non-polar, etc.) such that the substitution of even critical amino acids does not reduce the activity of the peptide, (i.e. the ability of the peptide to penetrate the blood brain barrier (BBB)). Conservative substitution tables providing functionally similar amino acids are well known in the art. For example, the following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). (See also Creighton, Proteins, W. H. Freeman and Company (1984), incorporated by reference in its entirety.) In some embodiments, individual substitutions, deletions or additions that alter, add or delete a single amino acid or a small percentage of amino acids can also be considered "conservative substitutions" if the change does not reduce the activity of the peptide. Insertions or deletions are typically in the range of about 1 to 5 amino acids. The choice of conservative amino acids may be selected based on the location of the amino acid to be substituted in the peptide, for example if the amino acid is on the exterior of the peptide and expose to solvents, or on the interior and not exposed to solvents.

In alternative embodiments, one can select the amino acid which will substitute an existing amino acid based on the location of the existing amino acid, i.e. its exposure to solvents (i.e. if the amino acid is exposed to solvents or is present on the outer surface of the peptide or polypeptide as compared to internally localized amino acids not exposed to solvents). Selection of such conservative amino acid substitutions are well known in the art, for example as disclosed in Dordo et al, J. Mol Biol, 1999, 217, 721-739 and Taylor et al., J. Theor. Biol. 119(1986); 205-218 and S. French and B. Robson, J. Mol. Evol., 19(1983)171. Accordingly, one can select conservative amino acid substitutions suitable for amino acids on the exterior of a protein or peptide (i.e. amino acids exposed to a solvent), for example, but not limited to, the following substitutions can be used: substitution of Y with F, T with S or K, P with A, E with D or Q, N with D or G, R with K, G with N or A, T with S or K, D with N or E, I with L or V, F with Y, S with T or A, R with K, G with N or A, K with R, A with S, K or P.

In alternative embodiments, one can also select conservative amino acid substitutions encompassed suitable for amino acids on the interior of a protein or peptide, for example one can use suitable conservative substitutions for amino acids is on the interior of a protein or peptide (i.e. the amino acids are not exposed to a solvent), for example but not limited to, one can use the following conservative substitutions: where Y is substituted with F, T with A or S, I with L or V, W with Y, M with L, N with D, G with A, T with A or S, D with N, I with L or V, F with Y or L, S with A or T and A with S, G, T or V. In some embodiments, non-conservative amino acid substitutions are also encompassed within the term of variants.

As used herein an "antibody" refers to IgG, IgM, IgA, IgD or IgE molecules or antigen-specific antibody fragments thereof (including, but not limited to, a Fab, F(ab')$_2$, Fv, disulphide linked Fv, scFv, single domain antibody, closed conformation multispecific antibody, disulphide-linked scfv, diabody), whether derived from any species that naturally produces an antibody, or created by recombinant DNA technology; whether isolated from serum, B-cells, hybridomas, transfectomas, yeast or bacteria. Antibodies can be humanized using routine technology.

As described herein, an "antigen" is a molecule that is bound by a binding site on an antibody agent. Typically, antigens are bound by antibody ligands and are capable of raising an antibody response in vivo. An antigen can be a polypeptide, protein, nucleic acid or other molecule or portion thereof. The term "antigenic determinant" refers to an epitope on the antigen recognized by an antigen-binding molecule, and more particularly, by the antigen-binding site of said molecule.

As used herein, the term "antibody fragment" refers to a polypeptide that includes at least one immunoglobulin variable domain or immunoglobulin variable domain sequence and which specifically binds a given antigen. An antibody fragment can comprise an antibody or a polypeptide comprising an antigen-binding domain of an antibody. In some embodiments, an antibody fragment can comprise a monoclonal antibody or a polypeptide comprising an antigen-binding domain of a monoclonal antibody. For example, an antibody can include a heavy (H) chain variable region (abbreviated herein as VH), and an OX40L (L) chain variable region (abbreviated herein as VL). In another example, an antibody includes two heavy (H) chain variable regions and two OX40L (L) chain variable regions. The term "antibody fragment" encompasses antigen-binding fragments of antibodies (e.g., single chain antibodies, Fab and sFab fragments, F(ab')2, Fd fragments, Fv fragments, scFv, and domain antibodies (dAb) fragments (see, e.g. dc Wildt et al., Eur J. Immunol., 1996; 26(3):629-39; which is incorporated by reference herein in its entirety)) as well as complete antibodies. An antibody can have the structural features of IgA, IgG, IgE, IgD, IgM (as well as subtypes and combinations thereof). Antibodies can be from any source, including mouse, rabbit, pig, rat, and primate (human and non-human primate) and primatized antibodies. Antibodies also include midibodies, humanized antibodies, chimeric antibodies, and the like.

As used herein, "antibody variable domain" refers to the portions of the OX40L and heavy chains of antibody molecules that include amino acid sequences of Complementarity Determining Regions (CDRs; i.e., CDR1, CDR2, and CDR3), and Framework Regions (FRs). VH refers to the variable domain of the heavy chain. VL refers to the variable domain of the Light chain. According to the methods used in this invention, the amino acid positions assigned to CDRs and FRs may be defined according to Kabat (Sequences of Proteins of Immunological Interest (National Institutes of Health, Bethesda, Md., 1987 and 1991)) or according to IMGT nomenclature.

As used herein, the term "antibody binding site" refers to a polypeptide or domain that comprises one or more CDRs of an antibody and is capable of binding an antigen. For example, the polypeptide comprises a CDR3 (e.g., HCDR3). For example the polypeptide comprises CDRs 1 and 2 (e.g., HCDR1 and 2) or CDRs 1-3 of a variable domain of an antibody (e.g., HCDRs1-3). In an example, the antibody binding site is provided by a single variable domain (e.g., a VH or VL domain). In another example, the binding site comprises a VH/VL pair or two or more of such pairs.

As used herein, "genotyping" refers to a process of determining the specific allelic composition of a cell and/or subject at one or more position within the genome, e.g. by determining the nucleic acid sequence at that position. Genotyping refers to a nucleic acid analysis and/or analysis at the nucleic acid level. As used herein, "phenotyping" refers a process of determining the identity and/or composition of an expression product of a cell and/or subject, e.g. by determining the polypeptide sequence of an expression product. Phenotyping refers to a protein analysis and/or analysis at the protein level.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder. The term "treating" includes reducing or alleviating at least one adverse effect or symptom of a condition, disease or disorder. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment). For treatment to be effective a complete cure is not contemplated. The method can in certain aspects include cure as well.

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

Multiple compositions can be administered separately or simultaneously. Separate administration refers to the two compositions being administered at different times, e.g. at least 10, 20, 30, or 10-60 minutes apart, or 1, 2, 3, 4, 5, 6, 7, 8, 9, 10, 12 hours apart. One can also administer compositions at 24 hours apart, or even longer apart. Alternatively, two or more compositions can be administered simultaneously, e.g. less than 10 or less than 5 minutes apart. Compositions administered simultaneously can, in some aspects, be administered as a mixture, with or without similar or different time release mechanism for each of the components.

As used herein, "authorization number" or "marketing authorization number" refers to a number issued by a regulatory agency upon that agency determining that a particular medical product and/or composition may be marketed and/or offered for sale in the area under the agency's jurisdiction. As used herein "regulatory agency" refers to one of the agencies responsible for evaluating, e.g., the safety and efficacy of a medical product and/or composition and controlling the sales/marketing of such products and/or compositions in a given area. The Food and Drug Administration (FDA) in the US and the European Medicines Agency (EPA) in Europe are but two examples of such regulatory agencies. Other non-limiting examples can include SDA, MPA, MHPRA, IMA, ANMAT, Hong Kong Department of Health-Drug Office, CDSCO, Medsafe, and KFDA.

As used herein, "injection device" refers to a device that is designed for carrying out injections, an injection including the steps of temporarily fluidically coupling the injection device to a person's tissue, typically the subcutaneous tissue. An injection further includes administering an amount of liquid drug into the tissue and decoupling or removing the injection device from the tissue. In some embodiments, an injection device can be an intravenous device or IV device, which is a type of injection device used when the target tissue is the blood within the circulatory system, e.g., the blood in a vein. A common, but non-limiting example of an injection device is a needle and syringe.

As used herein, a "buffer" refers to a chemical agent that is able to absorb a certain quantity of acid or base without undergoing a strong variation in pH.

As used herein, "packaging" refers to how the components are organized and/or restrained into a unit fit for distribution and/or use. Packaging can include, e.g., boxes, bags, syringes, ampoules, vials, tubes, clamshell packaging, barriers and/or containers to maintain sterility, labeling, etc.

As used herein, "instructions" refers to a display of written, printed or graphic matter on the immediate container of an article, for example the written material displayed on a vial containing a pharmaceutically active agent, or details on the composition and use of a product of interest included in a kit containing a composition of interest. Instructions set forth the method of the treatment as contemplated to be administered or performed.

As used herein the term "comprising" or "comprises" is used in reference to antibodies, fragments, uses, compositions, methods, and respective component(s) thereof, that are essential to the method or composition, yet open to the inclusion of unspecified elements, whether essential or not.

The term "consisting of" refers to antibodies, fragments, uses, compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (4 ed.), Cold Spring Harbor Laboratory Press, Cold Spring Harbor, N.Y., USA (2012); Davis et al., Basic Methods in Molecular Biology, Elsevier Science Publishing, Inc., New York, USA (1995); or Methods in Enzymology: Guide to Molecular Cloning Techniques Vol. 152, S. L. Berger and A. R. Kimmel Eds., Academic Press Inc., San Diego, USA (1987); Current Protocols in Protein Science (CPPS) (John E. Coligan, et al., ed., John Wiley and Sons, Inc.), Current Protocols in Cell Biology (CPCB) (Juan S. Bonifacino et al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in OX40L of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

It will be understood that particular configurations, concepts, aspects, examples, clauses and embodiments described herein are shown by way of illustration and not as limitations of the invention. The principal features of this invention can be employed in various embodiments without departing from the scope of the invention. Those skilled in the art will recognize, or be able to ascertain using no more than routine study, numerous equivalents to the specific procedures described herein. Such equivalents are considered to be within the scope of this invention and are covered by the claims. All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference. The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Any part of this disclosure may be read in combination with any other part of the disclosure, unless otherwise apparent from the context.

All of the compositions and/or methods disclosed and claimed herein can be made and executed without undue experimentation in OX40L of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

EXAMPLES

Example 1

Antigen Preparation, Immunization Procedures, and Hybridoma Generation

The following example provides a detailed description of the generation and identification of a panel of anti-human OX40L monoclonal antibodies using the KyMouse™ system (see, e.g., WO2011/004192). To this end, genetically engineered mice containing a large number of human immunoglobulin genes were immunized with soluble recombinant human OX40L (commercial or in-house produced) or surface expressed human OX40L displayed on mouse embryonic fibroblast (MEF) cells. Various immunization regimes, including conventional intraperitoneal injections as well as a rapid immunisation at multiple sites regime were set up, boosting animals over several weeks. At the end of each regime, secondary lymphoid tissue such as the spleen, and in some cases, the lymph nodes were removed. Tissues were prepared into a single cell suspension and fused with SP2/0 cells to generate a stable hybridoma cell line.

Materials and Methods

Cloning Expression and Purification of Recombinant Rhesus and Human OX40L cDNA encoding the extracellular domain of human OX40L was cloned into a pREP4 expression plasmid (Invitrogen) using standard molecular biology techniques. The constructs also contained a FLAG peptide motif to aid purification and an isoleucine zipper motif to aid trimerisation. Constructs were sequenced to ensure their correct sequence composition.

Rhesus (*Macaca mulatta*) OX40L was created using the human OX40L plasmid created above as a template and using site directed mutagenesis to introduce the amino acid changes.

Human OX40L well as Rhesus monkey OX40L were expressed transiently to produce recombinant protein using Invitrogen's FreeStyle™ CHO-S suspension adapted cell line. Plasmids were transfected into the cells using PEI (polyethylenimine MW 40000) and left to overgrow for a period of 13 days before harvesting the supernatant for purification. Cells were fed during the overgrow process with ActiCHO™ Feeds A and B from GE Healthcare to help boost productivity and promote longevity of the cells. During the overgrow process samples were taken regularly to monitor cell growth and viability.

FLAG-tagged OX40L proteins were purified in a two-step process; firstly the clarified tissue culture supernatants from the CHO-S expression were purified using M2 anti-FLAG affinity chromatography. The eluted fractions containing the OX40L protein were then subjected to size exclusion chromatography and assessed for purity by SDS-PAGE analysis and quantified by spectrophotometer reading at OD280 nm.

Cloning Expression and Purification of Recombinant Human OX40 Receptor cDNA encoding the extracellular domain of human OX40 Receptor was cloned into a pREP4 expression plasmid (Invitrogen) using standard restriction enzyme digestion and ligation. The construct contained a human Fc portion to aid purification. Constructs were sequenced to ensure their correct sequence composition.

Human OX40 Receptor was expressed transiently to produce recombinant protein using Invitrogen's FreeStyle™ CHO-S suspension adapted cell line. Plasmids were transfected into the cells using PEI (polyethylenimine MW 40000) and left to overgrow for a period of 13 days before harvesting the supernatant for purification. Cells were fed during the overgrow process with ActiCHO™ Feeds A and B from GE Healthcare to help boost productivity and promote longevity of the cells. During the overgrow process, samples were taken regularly to monitor cell growth and viability.

The Fc tagged OX40 Receptor protein was purified in a two-step process; firstly the clarified tissue culture supernatants from the CHO-S expression were purified using Protein G affinity chromatography. The eluted fractions containing the OX40 Receptor protein were then subjected to size exclusion chromatography and assessed for purity by SDS-PAGE analysis and quantified by spectrophotometer reading at OD280 nm.

Generation of Stably Transfected MEF and CHO-S Cells Expressing Human OX40L

The full human OX40L sequences were codon optimized (Seq ID No: 173) for mammalian expression and cloned into an expression vector under the CMV promoter flanked by 3' and 5' piggyBac specific terminal repeat sequences facilitating stable integration into the cell genome (see: "A hyperactive piggyBac transposase for mammalian applications"; Yusa K, Zhou L, Li M A, Bradley A, Craig N L. Proc Natl Acad Sci USA. 2011 Jan. 25). Furthermore, the expression vector contained either a puromycin or neomycin selection cassette to facilitate stable cell line generation. The hOX40L expression plasmid was co-transfected with a plasmid encoding piggyBac transposase into an in-house derived mouse embryonic fibroblast (MEF) cell line (embryos used to generate this line were obtained from a 129S5 crossed to C57BL6 female mouse) and CHO-S cells using the FreeStyle Max transfection reagent (Invitrogen) according to manufacturer instructions. 24 hours after transfection, the media was supplemented with G418 or neomycin and grown for at least 2 weeks to select a stable cell line, with media being exchanged every 3-4 days. The expression of hOX40L was assessed by flow cytometry using an anti-human OX40L-PE conjugated antibody (eBioscience). Complete MEF media was made up of Dulbecco's Modified Eagle's Medium (Gibco) supplemented with 10% v/v fetal bovine scrum (Gibco). Complete CHO-S media was made up of CD-CHO media supplemented with 8 mM glutamax (Gibco).

Generation of HT1080 Expressing OX40R and NF-Kappa Reporter Gene

The full human OX40 receptor sequence was codon optimized (Seq ID No: 175) for mammalian expression and cloned into an expression vector under the CMV promoter flanked by 3' and 5' piggyBac specific terminal repeat sequences facilitating stable integration into the cell genome (see: "A hyperactive piggyBac transposase for mammalian applications"; Yusa K, Zhou L, Li M A, Bradley A, Craig N L. Proc Natl Acad Sci USA. 2011 Jan. 25). Furthermore, the expression vector contained either a puromycin selection cassette to facilitate stable cell line generation. The hOX40 receptor expression plasmid was co-transfected with a plasmid encoding piggyBac transposase into HT1080 cells (ATCC® CCL-121) using the FreeStyle Max transfection reagent (Invitrogen) according to manufacturer instructions. 24 hours after transfection, the media was supplemented with puromycin and grown for at least 2 weeks to select a stable cell line with media being exchanged every 3-4 days. The expression of OX40 receptor was assessed by flow cytometry using an anti-human OX40 receptor-PE conjugated antibody (R&D, clone 443318). Following the generation of a stable cell line expressing the OX40 receptor, cells were transfected with the pNiFty-2-SEAP plasmid (invivogen) containing 5 repeated NFkB transcription factor binding sites followed by secreted alkaline phosphatase. Stable cells were selected with the addition to zeocin to the media with fresh media being added every 3-4 days. Complete HT1080 media was made up of MEM supplemented with 10% fetal calf serum.

Preparation of MEF Cells for Mouse Immunizations:

Cell culture medium was removed and cells washed once with 1×PBS. Cells were treated for 5 minutes with trypsin to loosen cells from tissue culture surface. Cells were collected and trypsin neutralized by the addition of complete media containing 10% v/v fetal bovine serum (FCS). Cells were then centrifuged at 300×g for 10 minutes and washed with 25 mL of 1×PBS. Cells were counted and resuspended at the appropriate concentration in 1×PBS.

Immunization Procedure:

Transgenic Kymice were immunized with hOX40L in either soluble recombinant form, expressed by CHO-S cells, or membrane bound form, expressed by stably transfected MEF cells.

When immunizing with cells, the adjuvant was mixed with cells at a 1:1 v/v ratio and gently mixed by pipetting before injecting intraperitoneally. When immunizing with protein, the adjuvant was mixed with protein at a 1:1 v/v ratio and vortexed repeatedly. All mice were bled before being primed and then boosted every three weeks. At least 3 serial bleeds spaced apart at least 2 weeks were collected and analysed for hOX40L specific IgG titre using an ELISA or flow cytometry based assay Determination of Serum Titers by FACS Using CHO-S Expressed hOX40L CHO-S cells expressing hOX40L or untransfected CHO-S cells, diluted in FACS buffer (PBS+1% w/v BSA+ 0.1% w/v NaN$_3$) were distributed to a 96 well V-bottom plate (Greiner) at a density of 1×10$^5$ cells per well. Cells were washed with 150 µL of PBS and centrifuged at 300×g for 3 min. Supernatant was aspirated and 150 µL of PBS added. This wash step was repeated. A titration of mouse serum was prepared, diluting samples in FACS buffer. 50 µL/well of this titration was then added to the cell plate. To determine the change in activity level due to immunization, serum from each animal prior to immunization was diluted to 1 in 100 in FACS buffer and 50 µL/well added to the cells. A suitable reference antibody (anti-OX40L antibody MAB10541, R&D systems) or mouse IgG1 control antibody (Sigma) were diluted in FACS buffer (between 1-9 µg/mL) and 50 µL added to cells. Cells were incubated at 4° C. for 30 minutes. Cells were washed twice with 150 µL of PBS, centrifuging after each wash step and aspirating supernatant (centrifuged at 300×g for 3 minutes). To detect antibody binding, APC goat-anti-mouse IgG (Jackson ImmunoResearch) was diluted 1 in 500 in FACS buffer and 50 µL was added to the cells. Cells were incubated 30 minutes at 4° C. in dark. Cells were washed twice with 150 µL of PBS centrifuging after each wash step and aspirating supernatant (centrifuged at 300×g for 3 minutes). To fix cells 100 µL 2% v/v paraformaldehyde was added and cells incubated for 30 minutes at 4° C., cells were pelleted by centrifugation at 300×g and the plates resuspended in 50 µL of FACS buffer. APC signal intensity (geomean) was measured by flow cytometry using a BD FACS Array instrument.

Determination of Serum Titers by DELFIA Immunoassay Using Recombinant hOX40L

Titers in mouse serum samples were determined using a reverse OX40L ELISA protocol. Anti-mouse IgG capture antibody (Southern Biotech) (4 µg/mL diluted in PBS, 50 µL/well) was adsorbed to 96 well low auto-fluorescent, high protein binding plates (Costar) overnight at 4° C. Excess IgG was removed by washing with PBS-Tween (0.1% v/v) and the wells were blocked with 1% w/v bovine serum albumin (BSA, Sigma) in PBS for 1 hr at RT, after which plates were washed as described previously. A titration of mouse serum was prepared, diluting samples in reagent diluent (0.1% w/v BSA/PBS). 50 µL/well of this titration was then added to ELISA plates. To determine the change in activity level due to immunization, serum from each animal prior to immunization was diluted to 1 in 100 in reagent diluent and 50 µL/well added to the ELISA plate. As a positive control for biotinylated OX40L binding an anti-OX40L antibody (MAB10541, R&D systems) diluted to 1 µg/mL was added to plates at 50 µL. Mouse IgG1 isotype control (Sigma) was included as a negative control and was diluted to 1 µg/mL in reagent diluent and 50 µL/well added to ELISA plate. In some instances serum sample from a mouse immunized with a non-relevant antigen was diluted 1 in 1000 and 50 µL/well was added to the ELISA plate. The plates were incubated at room temperature for at least 1 hour. Following incubation, plates were washed as before to remove unbound proteins. Biotinylated OX40L (100 ng/mL in reagent diluent; 50 µL/well) was then added to the plates and incubated at RT for 1 hour. Unbound biotinylated OX40L was removed by washing with PBS-Tween (0.1% v/v), while the remaining biotinylated OX40L was detected by streptavidin-Europium3+conjugate (DELFIA® detection, PerkinElmer) diluted in DELFIA® assay buffer (Perkin Elmer) or streptavidin-HRP diluted in reagent diluent.

In the case of streptavidin-HRP, the plates were washed as described before and 50 μL of TMB (Sigma) was added to the plate. Then the reaction was stopped by adding 50 μL of 1M sulfuric acid (Fluka analytical). The OD at 450 nm was measured on an Envision plate reader (PerkinElmer).

In case of streptavidin-Europium3, the plates were washed with TBS (Tris buffered saline)-Tween (0.1% v/v) and 200 μL/well of DELFIA Enhancement solution (Perkin Elmer) was added to the plate. The time-resolved fluorescence was measured at 615 nm on an Envision plate reader (PerkinElmer). Fluorescence data was plotted as Europium counts.

Murine Tissue Isolation and Preparation:

Spleens were excised from immunised mice and washed in 1×PBS and kept on ice until further processing. Tissues were prepared in buffer containing 1×PBS (Invitrogen) and 3% heat-inactivated FBS (Invitrogen). Splenocytes were dispersed by mashing the tissue through a 45 μm strainer (BD Falcon) and rinsing with 30 mL 3% FBS/PBS buffer before centrifugation at 700 g for 10 minutes at 4° C. To remove red blood cells, the pelleted splenocytes were resuspended in 4 mL of Red Blood Cell Lysis Buffer (Sigma). After 4 minutes of incubation, the lysis reaction was stopped by addition of 3% FBS/1×PBS buffer. Cell clumps were filtered out with a 45 μm strainer. The remaining splenocytes were pelleted for further procedures Hybridoma Fusion For the KM055 experiment, pelleted splenocytes were progressed directly to fusion without any selection or overnight CpG stimulation. For the KM040 experiment, B-cells were subjected to a positive selection method using the MACS® Separation system. Cells were resuspended in 80 μL 3% FBS/PBS buffer per 1×10$^7$ cells, before adding the anti-mouse IgG1 plus anti-mouse IgG2a+b MicroBeads (Miltenyi Biotec) and incubated for 15 minutes at 4° C. The cells/MicroBeads mixture was then applied to a pre-wetted LS column placed in a magnetic MACS Separator and washed with 3% FBS/PBS buffer. IgG positive cells were collected in the labelled, column-bound fraction in 3% FBS/PBS buffer.

For the KM040 experiment, enriched B-cells were treated with CpG overnight (final concentration 25 μM) and the following day washed once in BSA fusion buffer (0.3M D-Sorbitol, 0.11 mM calcium acetate hydrate, 0.5 mM magnesium acetate tetrahydrate and 0.1% BSA (v/w), adjusted to pH7.2). For the KM055 experiment, pelleted splenocytes from red blood cell lysis were washed once in BSA fusion buffer on the same day as tissue preparation. Fusion proceeded in the same way for both experiments after this point. Washed cells were resuspended in 200 μL of BSA fusion buffer and cell count determined. SP2/0 cells were treated in the same way, but washed twice with BSA fusion buffer. B-cells were fused at a ratio of 3:1 with SP2/0 myeloma cells by electrofusion using a BTX ECM 2001 Electro Cell Manipulator (Harvard Apparatus). Each fusion was left overnight in recovery medium (Dulbecco's Modified Eagle's Medium-high glucose (no phenol red, no L-G) containing OPI (Sigma), L-Glutamax (Gibco), 20% FBS (Gibco, batch-tested for hybridoma) and 2-mercaptoethanol). On the final day, cells were pelleted and resuspended in 1 part recovery medium to 9 parts semi-solid medium (ClonaCell-HY Hybridoma Selection Medium D, Stemcell Technologies) and then seeded onto 10 cm petri dishes. Colonies were picked 12 days later into 96-well plates and cultured for another 2-3 days prior to screening.

Example 2

Hybridoma Supernatant Screening

After generation of hybridoma clones, the hybridoma supernatant was assessed in a sequential primary and secondary screen and appropriate hybridoma clones selected based on criteria of antibody binding to CHO expressed hOX40L and receptor neutralization activity (see details in materials and methods) (Table 1).

For the primary screen, the inventors devised the following selection criteria: wells containing hybridoma clones were selected if antibodies present in the supernatant could bind to natively displayed hOX40L expressed on the cell surface. This assay was set up by plating CHO-S cells expressing hOX40L on the cell surface, followed by incubation with hybridoma supernatant, followed by a fluorescent detection antibody. The presence of an anti-OX40L antibody in the supernatant was read-out using a plate reader capable of reading the appropriate fluorescence. Furthermore, the inventors assessed hybridoma supernatant for binding to recombinantly expressed human OX40L using an HTRF (Homogeneous Time Resolved Fluorescence) assay. The inventors also determined whether the hybridoma supernatant had the ability to reduce the binding of human recombinant OX40L to human OX40R Fc. Clones meeting certain selection criteria (see further detailed description below), using data from the above mentioned three primary screen assays, were then cherry-picked and moved on to a secondary screen where the ability of each antibody to neutralize hOX40L binding to its receptors, OX40 Receptor (aka CD134), was determined. The inventors decided to assess this using a receptor neutralization HTRF assay and a flow cytometry-based receptor neutralization assay. Lastly, the inventors decided to analyse hybridoma supernatant by SPR to evaluate apparent affinity of the antibodies to recombinant trimeric human OX40L as well as cross-reactivity to Rhesus *monkey OX*40L.

Antibodies were defined as a secondary hit when antibodies in hybridoma supernatant bound to hOX40L, with high apparent affinity as well as cross-reacted with recombinant Rhesus *monkey OX*40L. Additionally, antibodies in the supernatant had to show the ability to neutralize OX40L binding to its receptor, i.e. OX40 Receptor (aka CD134) in either HTRF or flow cytometry based assay.

Materials and Methods

Primary Screen—Binding to Cell Expressed Human OX40L

Supernatants collected from hybridoma cells were tested to assess the ability of secreted antibodies to bind to hOX40L expressed on the surface of CHO-S cells. To determine CHO-S hOX40L binding, cells were plated in clear bottom tissue culture treated 384-well plates (Costar or BRAND) at 2×10$^4$ cells/well in F12 media (GIBCO) supplemented with 10% v/v FBS (GIBCO) and cultured overnight. Culture media was removed from 384-well assay plates. At least 40 μL of hybridoma supernatant or positive control anti-human OX40L reference antibody (at a final concentration of 1 μg/mL) or isotype IgG1 control antibody (referred to in some instances as Cm7, Sigma M9269, at a final concentration of 1 μg/mL) diluted in hybridoma maintaining media (HMM) were added to each well. Hybridoma maintaining media was made up of, Advanced DMEM (Gibco) supplemented with 1×Glutamax (Gibco), 20% v/v FBS (Gibco), 0.05 mM β-Mercaptoethanol, 1×HT supplement (Gibco), and 1× penicillin/streptomycin (Gibco). Plates were incubated for 1 hour at 4° C. Culture media was aspirated and 50 μL of goat anti-mouse Alexa Fluor 790 (Jackson ImmunoResearch, 115-655-071) at 1000 ng/mL supplemented with 0.2 μM DRAQ5 (Biostatus) diluted in FACS Buffer (PBS+1% w/v BSA+0.1% v/v NaN$_3$) were added. Plates were again incubated for 1 hour at 4° C. Supernatant was aspirated and 25 μL of 4% v/v paraformaldehyde added and plates were incubated 15 minutes at room temperature. Plates were washed twice with 100 μL PBS and then the wash buffer was completely removed. Fluorescence intensity was read by scanning plates using an Odyssey Infrared Imaging System (LI-COR®). Anti-mouse binding (800 nm channel) was normalised to cell number (700 nm channel) according to LI-COR® recommended algorithm. Percent effect was calculated as detailed below (Equation 1). Total binding was defined using reference antibody at a final assay concentration of 1 μg/ml. Non specific binding was defined using mouse IgG1 isotype control (Sigma) at a final assay concentration of 1 μg/mL. Wells were defined as hits where percent effect was greater than or equal to 5%.

Equation 1: Calculation of Percentage Effect from Primary Screen (LI-COR) and HTRF (Using 800% Resp Values (LI-COR) or 665/620 nm Ratio (See Equation 2) (HTRF)

$$\text{Percent effect} = \frac{\text{sample well} - \text{non specific binding}}{\text{total binding} - \text{non specific binding}}$$

Non-specific binding=values from wells containing isotype control mouse IgG1 or HMM or buffer Total Binding (Binding HTRF and LICOR)=values from wells containing reference antibody Total binding (OX40L/OX40RFc assay)=OX40L and OX40RFc Primary Screen: Binding to Recombinant Human OX40L:

In parallel to screening for binding to CHO-S expressed OX40L, supernatants collected from hybridoma wells were also tested to assess the ability of secreted antibodies to bind to hOX40L expressed as a recombinant protein (produced in-house, see details in Example 1). Binding of secreted antibodies to recombinant hOX40L were identified by HTRF® (Homogeneous Time-Resolved Fluorescence, Cisbio) assay format using biotinylated hOX40L. 5 μL of hybridoma supernatant was transferred to a white 384 well low volume non binding surface polystyrene plate (Greiner). Then 5 μL of biotinylated hOX40L (working concentration 20 nM) diluted in HTRF buffer (PBS (Sigma)+0.53 M KF (Sigma)+0.1% w/v BSA (Sigma) was added. 5 μL of combined detection reagents Streptavidin D2 (Cisbio) diluted 1:100 in HTRF assay buffer for final dilution 1:400 and goat anti-mouse IgG (Southern Biotech) labelled with europium cryptate (Cisbio) diluted 1:100 in HTRF assay buffer for final dilution 1:400 were added. The concentration of goat anti-mouse IgG (Southern Biotech) labelled with europium cryptate was batch dependent and in some cases a dilution of 1:1000 was performed to achieve a final assay concentration of 1:4000. To adjust the total assay volume to 20 μL, 5 μL of HTRF assay buffer was added to all wells. To define non-specific binding, addition of positive control antibody or hybridoma media was replaced with HTRF assay buffer or HMM. The plate was left to incubate in dark for 3 hours prior to reading time resolved fluorescence at 620 nm and 665 nm emission wavelengths using an EnVision plate reader (Perkin Elmer). More details of the HTRF® assay technology can be found in Mathis (1995) Clinical Chemistry 41(9), 1391-1397. Data were analysed by calculating 665/620 ratio and percent effect for each sample according to Equation 2 and Equation 1 respectively.

Equation 2: Calculation of 665/620 Ratio

665/620 ratio=(sample 665/620 nm value)×10000

For clones derived from KM040-1 and KM055-1 a selection criteria of greater than or equal to 20 percent effect was applied by the inventors to define a well as a hit from recombinant hOX40L binding as described in Table 1.

Primary Screen: Human OX40L/Human OX40R Fc Binding Assay:

In order to determine whether supernatants collected from hybridoma wells inhibited the binding of OX40L to OX40RFc, secreted antibodies were tested in an OX40L/OX40RFc binding HTRF assay. 5 μL of hybridoma supernatant was transferred to a white 384 well low volume non-binding surface polystyrene plate (Greiner). Biotinylated OX40L was diluted in HTRF assay buffer to a working concentration of 2.4 nM and 5 μL added. OX40RFc was then diluted to working concentration of 4.8 nM and 5 μL added. Non-specific binding was defined by replacing OX40RFc with assay buffer or HMM. Streptavidin cryptate (CISBIO) and anti-human Fc D2 (CISBIO) were diluted in HTRF assay buffer to working concentration of 1:100 and 5 nM respectively. Plates were covered, protected from light and incubated at room temperature for 3 hrs prior to reading time resolved fluorescence at 620 nm and 665 nm emission wavelengths using an EnVision plate reader (Perkin Elmer). Data were analysed by calculating 665/620 ratio and percent effect for each sample according to Equation 2 and Equation 5 respectively.

For clones derived from KM040-1 and KM055-1, a selection criteria of less than or equal to 90 percent of the assay signal of OX40 receptor Fc binding to OX40L was applied by the inventors to define a well as a hit as described in Table 1.

Secondary Screen: Binding to Cell Expressed and Recombinant Human OX40L

To determine whether wells selected using the primary screen selection criteria had the required characteristics set by the inventors, a number of assays were performed. Hybridoma clones selected as hits from primary screening were cultured for 3 days and the supernatants collected from hybridoma cells were tested to assess whether the secreted antibodies that bind to CHO-S expressed hOX40L, in some case bind to untransfected CHO-S cells and whether they neutralise recombinant OX40R Fc binding to CHO-S hOX40L and ability to neutralise OX40R binding to recombinant biotinylated hOX40L.

Binding to CHO-S Expressed hOX40L and Receptor Neutralisation:

CHO-S cells expressing hOX40L or untransfected CHO-S cells, diluted in FACS buffer (PBS+1% w/v BSA+0.1% w/v NaN$_3$) were distributed to a 96 well V-bottom plate (Greiner) at a density of 1×10$^5$ cells per well. Cells were washed with 150 μL of PBS and centrifuged at 300×g for 3 min. Supernatant was aspirated and 150 μL of PBS added. This wash step was repeated.

25 μL of hybridoma supernatant or purified antibody from hybridoma supernatant diluted in FACS buffer was added to the washed cells and incubated for 10-15 minutes. Reference Antibody or mouse IgG1 control antibody (Sigma) were diluted in FACS buffer to 20 μg/mL and 25 μL added to cells. 25 μL of human OX40R Fc (in-house) diluted to 1000 ng/mL in FACS buffer were then added to wells. Cells were incubated at 4° C. for 30 minutes.

Cells were washed twice with 150 μL of PBS centrifuging after each wash step and aspirating supernatant (centrifuged at 300×g for 3 minutes).

To detect antibody and receptor binding, 50 μL of Goat anti-human IgG-PE (Jackson ImmunoResearch) and APC anti-mouse IgG (Jackson ImmunoResearch) diluted 1 in 500 in FACS buffer was added to the cells. Cells were incubated 30 minutes at 4° C. in the dark.

Cells were washed twice with 150 μL of PBS centrifuging after each wash step and aspirating supernatant (centrifuged at 300×g for 3 minutes).

To fix cells 100 μL 2% v/v paraformaldehyde was added and cells incubated for 30 minutes at 4° C., cells were pelleted by centrifugation 300×g and the plates and resuspended in 50 μL of FACS buffer. PE and APC signal intensity (geomean) was measured by flow cytometry using a BD FACS Array instrument.

% of control binding was calculated using geomean fluorescence as described in equation 1 where total binding was defined as reference antibody at 10 μg/mL and non-specific binding as mouse IgG1 antibody at 10 μg/mL. % receptor binding was calculated using Equation 3.

Equation 3: Percentage of Receptor Binding (FACS) Based on Geomean Fluorescence $$\% \text{ of Receptor binding} = \frac{\text{sample value} - \text{non specific binding}}{\text{total binding} - \text{non specific binding}} \times 100$$

Non-specific binding=No antibody, no receptor
Total binding=receptor (OX40R) only binding (no inhibitor)+isotype control at 10 μg/mL Secondary Screen—HTRF Ligand/Receptor Neutralisation To determine whether antibodies identified from primary screen neutralise OX40L binding to OX40RFc an human OX40L/human OX40R Fc binding assay was performed as described for primary screen.

Plates were left to incubate in dark for 3 hours prior to reading time resolved fluorescence at 620 nm and 665 nm emission wavelengths using an EnVision plate reader (Perkin Elmer). More details of the HTRF® assay technology can be found in Mathis (1995) Clinical Chemistry 41(9), 1391-1397. Data were analysed by calculating delta F as described in Equation 4 and percentage of receptor for each sample according to Equation 5.

Equation 4: Calculation of % DeltaF $$\% \text{ delta } F = \frac{\text{(sample 665/620 nm ratio value)} - \text{(non-specific control 665/620 nm ratio value)}}{\text{(non-specific control 665/620 nm ratio)}} \times 100$$

Equation 5: Percentage of Receptor Binding (HTRF)
Based on calculation of % deltaF (Equation 4) or 665/620 ratio (Equation 2)

$$\% \text{ of Receptor binding} = \frac{\text{sample value} - \text{non specific binding}}{\text{total binding} - \text{non specific binding}} \times 100$$

Non specific binding=HMM or buffer+OX40L (no receptor)
Total binding=receptor (OX40R) and OX40L (no inhibitor)

Hit Criteria Selection from Secondary Screening:

A panel of hits were selected based on binding and neutralisation assays. Hits in CHO-S OX40L binding assay were defined by the inventors as significant binding to CHO-S OX40L cells and no binding to CHO-S cells by FACS. Hits were further defined as having the ability to significantly reduce OX40RFc binding to recombinant OX40L (HTRF) and significantly reduce OX40RFc binding to hOX40L expressed on CHO cells. Data is summarised in Table 1. Apparent affinity measurements by SPR were also considered.

Example 3

Antibody Lead Characterization

Based on the screening selected wells were expanded and murine/human chimeric antibodies purified using a standard Protein G based affinity chromatography purification (see method below). The antibodies were subjected to various assays to assess their ability to block hOX40L binding to it receptor OX40R, as well as the ability of each antibody to bind to human as well as Rhesus *monkey OX*40L with high apparent affinity. To decipher which antibodies were the best, selected clones were tested using OX40L/OX40RFc HTRF assay and OX40L induced IL2 release from primary human T-cells.

TABLE 1

| | | | | | |
|---|---|---|---|---|---|
| mAb Lead Summary | | | | | |
| Antibody | FACS Binding | HTRF Receptor Neutralisation IC$_{50}$ nM (+/− SEM) | Primary T-cell Assay IC$_{50}$ nM (+/− SEM) | Apparent Affinity hOX40L (nM) | Apparent Affinity RhsOX40L (nM) |
| 10A07 (hybridoma) | YES | +++ | +++ | CNROR | CNROR |
| 10A07 (human) | ND | +++ 1.2 nM (+/−0.17) | +++ 0.83 nM (+/−1.2) | CNROR | CNROR |
| 2D10 (hybridoma) | YES | +++ | ND | CNROR | CNROR |
| 2D10 (human) | ND | +++ 0.75 nM (+/−0.04) | +++ 0.81 nM (+/−0.06) | CNROR | CNROR |
| 9H04 (hybridoma) | YES | + | ND | 5.3 | ND |

TABLE 1-continued mAb Lead Summary

| Antibody | FACS Binding | HTRF Receptor Neutralisation IC$_{50}$ nM (+/− SEM) | Primary T-cell Assay IC$_{50}$ nM (+/− SEM) | Apparent Affinity hOX40L (nM) | Apparent Affinity RhsOX40L (nM) |
|---|---|---|---|---|---|
| 19H01 (hybridoma) | YES | ++ | ND | 2.2 | ND |

CNROR = Cannot resolve off-rate
IC$_{50}$ data represents arithmetic mean +/− standard error of mean (SEM) for three independent experiments or donors.

Materials and Methods:
Purification of Antibodies from Hybridoma Supernatant:

Antibodies were purified using Protein G affinity chromatography. Antibodies were eluted from the Protein G media using IgG Elute reagent (Pierce) and the eluted antibodies were buffer swapped into PBS prior to use. Antibody purity was assessed by SDS-PAGE analysis and quantified by spectrophotometer reading at OD280 nm.

Binding of antibodies purified from hybridoma supernatant was carried out as described herein.
HTRF Ligand/Receptor Neutralisation:

The following methods were carried out with a titration of inhibitor in order to establish the clone potency as measured by IC$_{50}$ values in the assay. Antibody purified from hybridoma was titrated by diluting in HTRF assay buffer and 5 µL of this titration transferred to a white 384 well low volume non-binding surface polystyrene plate (Greiner). Biotinylated OX40L was diluted in HTRF assay buffer to a working concentration of 2.4 nM and 5 µL added. OX40RFc was then diluted to working concentration of 4.8 nM and 5 µL added. Non-specific binding was defined by replacing OX40RFc with assay buffer or HMM. Streptavidin cryptate (CISBIO) and anti-human Fc D2 (CISBIO) were diluted in HTRF assay buffer to working concentration of 1:100 and 5 nM respectively. Plates were covered, protected from light and incubated at room temperature for 3 hrs prior to reading time resolved fluorescence at 620 nm and 665 nm emission wavelengths using an EnVision plate reader (Perkin Elmer). Data were analysed by calculating delta F as described in Equation 4 and percentage of receptor for each sample according to Equation 5 or in some cases Equation 6. IC$_{50}$ values were determined using GraphPad Prism software by curve fitting using a four-parameter logistic equation (Equation 7).

Equation 6: Percentage of Receptor Binding (HTRF) Based on Calculation of % DeltaF (Equation 8)

$$\% \text{ of Receptor binding} = \frac{\text{sample value}}{\text{total binding}} \times 100$$

Total binding=receptor (OX40R) and OX40L (no inhibitor)
Equation 7: Four Parameter Logistic Calculation $$Y = \text{Bottom} + (\text{Top} - \text{Bottom})/(1 + 10^{((\text{Log } IC50 - X) * \text{HillSlope})})$$

X=logarithm of concentration.
Y=specific binding (equation 6)
Top and Bottom=Plateaus in same units as Y (specific binding)

Log IC$_{50}$ in same units as X. Y starts at Bottom and goes to Top with a sigmoid shape. Specific binding decreases as X increases.
Profiling of Fully Human Recombinant Anti-OX40L Antibodies in HTRF Ligand/Receptor Neutralisation Assay In order to determine whether recombinantly expressed fully human purified IgG inhibit human OX40L binding to OX40RFc the following method was carried out. Fully human purified IgG or other inhibitor were tested in order to establish the clone potency as measured by IC$_{50}$ values in the assay. Antibodies recombinantly expressed and purified were titrated by diluting in HTRF assay buffer and 5 µL of this titration transferred to a white 384 well low volume non-binding surface polystyrene plate (Greiner). Biotinylated OX40L was diluted in HTRF assay buffer to a working concentration of 2.4 nM and 5 µL added. OX40RFc directly labelled with AF647 was then diluted to working concentration of 10 nM and 5 µL added. Non-specific binding was defined by replacing OX40RFc-AF647 with assay buffer or HMM. Streptavidin cryptate (CISBIO) was diluted in HTRF assay buffer to working concentration of 1:100 and 5 µL added to all wells of the plate. Plates were covered, protected from light and incubated at room temperature for 3 hrs prior to reading time resolved fluorescence at 620 nm and 665 nm emission wavelengths using an EnVision plate reader (Perkin Elmer). Data were analysed by calculating delta F as described in Equation 4 and percentage of receptor for each sample according to Equation 5 or in some cases Equation 6. IC$_{50}$ values were determined using GraphPad Prism software by curve fitting using a four-parameter logistic equation (Equation 7) (FIG. 1).
Determining Effect of Anti-OX40L Antibodies on Recombinant OX40L Induced IL2 Release from Primary Isolated T-Cells Recombinant human OX40L (in house) was diluted in culture media to a concentration of 400 ng/mL and 50 µL added to a tissue culture treated 96 well plate (Costar). Anti-OX40L antibodies or appropriate species isotype control (Sigma or in house) were titrated in culture media in a 96 well plate (greiner) and then 50 µL of titration transferred to the 96 well plate containing 50 µL OX40L. The antibody titration was incubated for 30 minutes at room temperature with the recombinant OX40L before CD3 positive T-cells were added.

PBMCs were isolated from leukoreduction system chambers (NHSBT) using Ficoll-Paque plus (GE Healthcare) by density gradient centrifugation. CD3 positive cells (T-cells) were isolated from human PBMC by negative selection using magnetic microbeads (Miltenyi Biotech) according to manufacturer's recommendations. The isolated cells were centrifuged at 300×g/5 min, resuspended in culture media (culture media was defined as either RPMI (Gibco)+10% v/v FBS or RPMI+5% v/v human AB serum) and 50 µL of the cell suspension added to the 96 well plate containing the recombinant OX40L and antibody titration to a achieve final concentration of $2 \times 10^5$ cells/well.

Then 50 µL of PHA at 8 µg/mL was added to all wells to achieve a final assay concentration of 2 µg/mL. The cells were incubated at 37° C. for 3 days before supernatant were harvested and analysed for IL-2 concentration. Maximal IL-2 release was defined by OX40L stimulation in the absence of inhibitor. Minimal IL-2 release was defined by culture media only (no OX40L).

IL-2 levels in supernatants were determined using human IL-2 Duoset ELISA kit (R & D) Systems) according to manufacturer's recommendations. IL-2 capture antibody (4 µg/mL diluted in PBS, 50 µL/well) was adsorbed to 96 well low auto-fluorescent, high protein binding plates (Costar) overnight at 4° C. Excess IgG was removed by washing with PBS-Tween and the wells were blocked with 1% bovine serum albumin (BSA) in PBS for 1 hour at room temperature, after which plates were washed as described previously. 50 µL/well of conditioned culture media was then added IL-2 standards (from 2000 µg/mL, 1:2 dilution) were also added to ELISA plates as an ELISA control and the plates were incubated at room temperature for at least 1 hour.

Following incubation, plates were washed as before to remove unbound proteins. Biotinylated IL-2 detection Ab (200 ng/mL in reagent diluent (0.1% BSA/PBS); 50 µL/well) was then added to the plates and incubated at RT for 1 h. Unbound detection antibody was removed by washing with PBS-Tween (0.1% v/v), while the remaining biotinylated antibody was detected by streptavidin-Europium3+conjugate (DELFIA® detection, PerkinElmer). Time-resolved fluorescence was measured at 615 nm on an Envision plate reader (PerkinElmer). Fluorescence data was plotted as Europium counts or concentration of IL-2 release calculated from standard curve by linear regression according to manufacturer's recommendations. $IC_{50}$ values were determined using GraphPad Prism software by curve fitting using a four-parameter logistic equation (Equation 7).

Surface Plasmon Resonance Analysis:

SPR analysis was carried out using the ProteOn™ XPR36 Array System (BioRad). Anti-mouse IgG (GE Healthcare BR-1008-38) was immobilised on a GLM biosensor surface using amine coupling, the surface was then blocked using 1 M ethanolamine. Test antibodies were captured on this surface and recombinant hOX40L (human and rhesus) were used at a single concentration of 256 nM, binding sensorgrams were double referenced using a buffer injection (i.e. 0 nM) to remove baseline drift and injection artefacts. Apparent affinities for the OX40L-antibody interaction were determined using the 1:1 model inherent to the ProteOn XPR36 analysis software. The assay was run using HBS-EP (Teknova) as running buffer and carried out at 25° C.

Example 4

Sequence Recovery of Lead Antibody Candidates

After the selection and characterization of lead candidates, their fully human variable domains were recovered using RT-PCR using a mixture of forward and reverse primers. Antibodies were reformatted into a human IgG4 backbone (IgG4-PE) and expressed using a transient expression system in CHO-S cells. A summary of all sequences is displayed in the Sequence Listing.

RNA Isolation from Hybridoma Cells:

Total RNA was extracted from hybridoma cells using TRIzol™ Reagent (Invitrogen). The quantity and quality of the isolated RNA was analysed spectrophotometrically.

Antibody Variable Domain Recovery by RT-PCR:

Selected clones were used for preparing total RNA, which was used in an RT-PCR reaction to recover the heavy chain V-regions. IgG specific reverse primers and Ig leader sequence specific forward primer sets or alternatively IgG specific reverse primers and Ig 5' untranslated region (UTR) sequence specific forward primer sets were used for the heavy chains. Kappa constant region specific reverse primers and kappa leader sequence specific forward primer sets or alternatively Kappa constant region specific reverse primers and kappa 5'UTR sequence specific forward primer sets were used for the kappa OX40L chains. The RT-PCR products were separated by agarose gel electrophoresis with the DNA of the predicted size being sequenced in the forward and reverse directions. Alternatively, the RT-PCR products were subcloned into a cloning vector and DNA of individual colonies submitted for sequencing.

Cloning of Recombinant Antibodies

DNA encoding the heavy chain variable region of mAb 10A7 was cloned into a pREP4 expression plasmid (Invitrogen) in frame with the Human IgG1 constant region and DNA encoding the light chain variable region of mAb 10A7 was cloned into a pREP4 expression plasmid in frame with the Human Kappa constant region using standard restriction enzyme digestion and ligation.

The heavy chain variable region coding sequences of mAbs 10A7 and 2D10 in frame with the Human IgG4-PE constant region were codon optimized for mammalian expression and cloned into a pXC-18.4 expression plasmid (Lonza) and the light chain coding sequences of mAbs 10A7 and 2D10 in frame with the Human Kappa constant region were codon optimized for mammalian expression and cloned into a pXC-17.4 expression plasmid (Lonza) using standard restriction enzyme digestion and ligation. For the simultaneous expression of the heavy and light chains the vectors a pXC-17.4 and a pXC-18.4 were fused into one single vector using standard restriction enzyme digestion and ligation.

All constructs were sequenced to ensure their correct sequence composition.

Transient Expression of OX40L Antibodies

Antibodies were expressed transiently to produce recombinant protein using Invitrogen's FreeStyle™ CHO-S suspension adapted cell line. Plasmids were transfected into the cells using PEI (polyethylenimine MW 40000) and left to overgrow for a period of 13 days before harvesting the supernatant for purification. Cells were fed during the overgrow process with ActiCHO™ Feeds A and B from GE Healthcare to help boost productivity and promote longevity of the cells. During the overgrow process samples were taken regularly to monitor cell growth and viability.

Generation of Stable Lonza Pools

In order to produce the gram amounts required for toxicology studies, 10A7 and 2D10 OX40L antibodies were transferred to the Lonza GS Xceed system for stable expression. The HC and LC for each antibody was first codon optimised for expression in CHO cells by Genewiz. The HC cassette (containing the optimised IgG4PE constant region) was then cloned into Lonza's pXC18.4 vector and LC cassette (containing the optimised kappa constant region) cloned into Lonza's pXC17.4 vector using standard restriction enzyme digestion and ligation. A double gene vector (DGV) encoding both the HC and LC sequences was then created by restriction enzyme digestion and ligation and sequence confirmed before expression.

Prior to stable pool creation; the single gene vectors encoding the HC and LC's separately as well as the DGV containing both, were expressed in the Lonza CHOK1SVKO cell line transiently using PEI (polyethylenimine MW 40000). Cells were left to overgrow for a period of 13 days before harvesting the supernatant for purification. During this period cells were fed with ActiCHO™ Feeds A and B from GE Healthcare to help boost productivity and promote longevity of the cells. During the overgrow process samples were taken regularly to monitor cell growth and viability. Once transient expression was confirmed and purified material analysed the antibodies were expressed as stable pools.

Stable pools were generated using Lonza's proprietary methods and media. 4 pools were created per antibody and left to recover over a period of 10-15 days. After the cells had recovered, pre-seed stocks (PSS) of cells were frozen down for later recovery and creation of MCB. Small scale (50 mL) shake flask fed batch overgrows were then set up using Lonza's proprietary media. Cells were left to overgrow for a period of 14 days. During this period cells were monitored for growth, viability and glucose levels. Cells were supplemented accordingly with Lonza's proprietary feed and 400 g/L glucose. Samples were also taken throughout the process for crude sample quantification. At the end of the overgrow process the supernatant was harvested for purification.

Stable pools were generated using Lonza's proprietary methods and media. 4 pools were created per antibody and left to recover over a period of 10-15 days. After the cells had recovered, pre-seed stocks (PSS) of cells were frozen down for later recovery and creation of MCB. Small scale (50 mL) shake flask fed batch overgrows were then set up using Lonza's proprietary media. Cells were left to overgrow for a period of 14 days. During this period cells were monitored for growth, viability and glucose levels. Cells were supplemented accordingly with Lonza's proprietary feed and 400 g/L glucose. Samples were also taken throughout the process for crude sample quantification. At the end of the overgrow process the supernatant was harvested for purification.

Whilst the 2D10 and 10A07 were similar in sequence, there expression profiles in the stable Lonza pools were different, 10A07 expressed to very low titres, whereas 2D10 expressed at much greater titres (see Table 2) under optimal conditions when using shake flasks in 4 separate generated stable pools.

TABLE 2

(Concentration in mg/L)

| Stable pool | Day 7 | Day 8 | Day 9 | Day 10 | Day 11 | Day 12 | Day 13 | Day 14 |
|---|---|---|---|---|---|---|---|---|
| 2D10-1 | 261 | 492 | 681 | 993 | 1157 | 1590 | 1530 | 1575 |
| 2D10-2 | 245 | 461 | 665 | 983 | 1127 | 1485 | 2025 | 1995 |
| 2D10-3 | 317 | 528 | 731 | 1163 | 1367 | 1785 | 1905 | 1860 |
| 2D10-4 | 372 | 677 | 785 | 1286 | 1350 | 1935 | 1965 | 1800 |
| Control Antibody 1 | 92 | 129 | 167 | 229 | 297 | 357 | 416 | N/A |
| Control Antibody 1 | 66 | 95 | 127 | 161 | 208 | 238 | 266 | N/A |
| Control Antibody 1 | 68 | 102 | 132 | 192 | 266 | 324 | 314 | N/A |
| Control Antibody 1 | 88 | 129 | 165 | 245 | 328 | 410 | 385 | N/A |

After expression, the antibody to be used in the Rhesus Macaque GvHD model was purified using a two-step purification process. The antibodies were first purified using MabSelect SuRe (GE Healthcare) affinity chromatography. Antibodies were eluted from the MabSelect SuRe media using IgG Elute reagent (Pierce) and the eluted antibodies were dialysed in sodium acetate (pH 5.5) buffer prior to the second purification step. Antibodies were then purified by cation exchange and eluted with sodium chloride in sodium acetate buffer. Eluted antibodies were dialysed in PBS. Antibodies were quantified by spectrophotometer reading at OD280 nm and adjusted to the desired concentration (10 mg/ml). Antibody purity was assessed by SDS-PAGE analysis and size exclusion chromatography. Endotoxin concentration was measured with Endosafe PTS and LAL Test Cartridges (Charles River Laboratories).

Example 5

Determining Effect of Anti-OX40L Antibodies in Allogeneic PBMC Mixed Lymphocyte Reaction PBMCs are isolated from leukoreduction system chambers (NHSBT) using Ficoll-Paque plus (GE Healthcare) density gradient centrifugation. PBMC are pre-incubated with mitomycin C (Sigma) at 10 µg/mL in PBS for one hour at 37° C. Cells are then washed 3 times in PBS centrifuging at 300×g for 3 minutes, aspirating the supernatant after each wash. Allogeneic PBMC (not treated with mitomycin C) are added to a 96-well plate in RPMI supplemented with 10% v/v FBS at a concentration of $2 \times 10^6$/ml, 50 µL/well. Anti-OX40L antibodies are diluted in culture media and added to 96 well plate containing PBMC (not mitomycin C treated) at 50 µL/well. Mitomycin C treated PBMC are then added to allogeneic PBMC (not treated with mitomycin C) in 96-well plate at a final cell ratio in range of 1:1 to 4:1 mitomycin C treated to non mitomycin C based on number of cells/well. The cells are incubated for five days at 37° C./5% $CO_2$. After five days TNF-α, IFN-γ, and IL-2 are measured by duoset ELISA (R&D Systems) according to manufacturer's recommendations. Proliferation is measured by CFSE dilution according to manufacturer's recommendations.

PBMCs were isolated from leukoreduction system chambers (NHSBT) using Ficoll-Paque plus (GE Healthcare) density gradient centrifugation. PBMC were pre-incubated with mitomycin C (Sigma) at 10 µg/mL in PBS for one hour at 37° C. Cells were then washed 3 times in PBS centrifuging at 300×g for 3 minutes, aspirating the supernatant after each wash. T-lymphocytes (T-cells) in some cases CD3 positive and in other cases CD4 and CD8 positive were isolated from allogeneic PBMC by negative selection using magnetic microbeads (Miltenyi Biotech) according to manufacturer's recommendations. In some cases, non-mytomycin C treated PBMC were used instead of T-cells. The isolated cells were centrifuged at 300×g/5 min, resuspended in culture media (culture media was defined as either RPMI (Gibco)+10% v/v FBS or RPMI+5% v/v human AB serum) and 50 µL of the cell suspension added to the 96 well plate containing the recombinant OX40L and antibody titration to a achieve final concentration of $2 \times 10^5$ cells/well. Anti-OX40L antibodies were diluted in culture media to a final assay concentration 100 nM or in some cases a titration of antibody was used. The antibodies were added to 96 well plate containing T-cells or non-mytomycin C treated PBMC at 50 µL/well. Mitomycin C treated PBMC were then added to Tcells or non mytomycin C treated PBMC in 96-well plate at a final cell ratio in range of 1:1 to 4:1 mitomycin C treated PBMC to T-cells (or PBMC) based on number of cells/well.

The cells were incubated for five days at 37° C./5% $CO_2$. After five days, IFN-γ was measured by duoset ELISA (R&D Systems) according to manufacturer's recommendations.

Anti-OX40L antibodies were defined as inhibitors in allogeneic PBMC/T cell MLR or PBMC/PBMC1 MLR when >20% inhibition (see Equation 8) of factor release (IFN-γ,) or were observed relative to control wells in the absence of antibody. From four experiments performed, one experiment was a technical failure, defined as no MLR response (IFN-γ release) detected between allogeneic donors. Of the three remaining experiments, all three showed inhibition (>20% inhibition of factor release (IFN-γ,) observed relative to control wells in the absence of antibody) with 2D10, 10A07 and positive control 1, however in one of three experiments, significant inhibition was also observed with the isotype control antibody (FIG. 2). For PBMC/PBMC MLR, three experiments were performed. Of three experiments, two were regarded as technical failure as there was no or low IFN-γ release. However, in another experiment 10A07 inhibited IFN-γ release when compared to the isotype control.

Equation 8: Percentage Inhibition (MLR)

Based on values from IFN-γ or IL2 release (pg/mL) determined as described $$\% \text{ inhibition} = 100 - \frac{\text{sample value} - \text{no stimulus}}{\text{No } IgG - \text{no stimulus}} \times 100$$

No Stimulus=wells where only T-cells or non-mytomycin C treated PBMC are added (no mitomycin C treated PBMC)

No IgG=wells where T-cells or in some cases non-mytomycin C treated PBMC along with mytomycin C treated PBMC are added but no IgG Example 6

Determining Effect of Anti-OX40L Antibodies on CD3 Primed Primary Human T Lymphocytes In order to determine whether anti-OX40L had the ability to induce T-cell responses in the absence of OX40L, the assay below was performed using method adapted from Wang et al., Hybridoma (Larchmt)., 2009 August; 28(4):269-76, in which an agonist anti-OX40L antibody was described.

A mouse anti-human CD3 antibody (Becton Dickinson) was diluted to 0.5 µg/mL in sterile PBS and 50 µL/well added to a 96 well high binding sterile plate and incubated overnight at 4° C.

Following overnight incubation, the plate was washed three times with 100 µL of sterile PBS.

T-cells (CD3 positive) were isolated from PBMC derived from leukoreduction system chambers (NHSBT) as described in Example 3. Following isolation, the cells were added to wells in 100 µL to achieve a final concentration of $1 \times 10^5$ cells/well.

Test antibodies were diluted in RPMI+10% FBS and 50 µL or 100 µL/well added to cell plate to achieve a final assay concentration of 10 µg/mL. In some cases, a mouse anti-human CD28 antibody (Becton Dickinson) was also added to wells at a final concentration of 1 µg/ml The assay was incubated for 5 days. After 5 days, harvest supernatants and IFN-γ levels in supernatant were determined as described in Example 5.

The assay was performed in four independent donors and no effect of adding 10A07 or 2D10 in IgG4PE format was observed (IFN-γ release) over that observed with human IgG4PE isotype control.

Example 7

Rhesus Macaque Graft Versus Host Disease (GvHD) Model

The effectiveness of antibody 2D10 IgG4PE as a monotherapy prophylactic for the prevention of GvHD was examined in a Rhesus Macaque model of haploidentical hematopoietic stem cell transplantation (HSCT). It had been previously described that monkeys undergoing HSCT in this model had a survival time of 6-8 days (Miller, Weston P., et al. "*GVHD after haploidentical transplantation: a novel, MHC-defined rhesus macaque model identifies CD28⁻ CD8⁺ Tcells as a reservoir of breakthrough T cell proliferation during costimulation blockade and sirolimus-based immunosuppression.*" Blood, 116, 24(2010):5403-5418.)

All transplants were between half-sibling pairs that are mismatched at one MHC haplotype ("haploidentical-HCTs"). Recipient animals had irradiation based pre-myeloablative pre-transplant conditioning using a linear accelerator. Dose rate: 7 cGy/min. Dose 1020 cGy given in 4 fractions. The leukapheresis donor animal underwent GCSF mobilisation and underwent leukapheresis using a Spectra Optia apheresis machine. The table below gives the dose per kg of total nucleated cells (TNC) dose of $CD3^+$ cells, and $CD34^+$ cells for the four successful experiments.

TABLE 3

| Recipient ID# | Animal No. | Recipient Bodyweight (kg) | TNC $(10^9$/kg) | $CD3^+$ T-cells $10^6$/kg | $CD34^+$ cells $10^6$/kg |
|---|---|---|---|---|---|
| A14079 | #2 | 9.75 | 1.13 | 149.76 | 0.51 |
| A14081 | #4 | 7.02 | 2.99 | 389.08 | 4.79 |
| A14082 | #5 | 7.6 | 2.24 | 312.95 | 2.69 |
| A14087 | #6 | 5.75 | 3.44 | 385.66 | 9.99 |

2D10 IgG4PE was dosed at 10 mg/kg i.v. according to a planned dosing schedule to take place on Day−2, Day+5, Day+12, Day+19, Day+26, Day+33, Day+40, Day+47 post-transplant. No serious adverse dosing side effects were seen with any of the animals as a result of administering 2D10 IgG4PE.

Samples were taken during the course of the study to monitor donor chimerism (Table 4) and white blood cell counts. The primary end point was based on survival, with a survival to 15 days deemed to be a sign of successful prophylactic therapy (and compared to the documented survival of 6-8 days with no prophylaxis; Miller et al 2010, supra). Though full pathology and histology with GvHD grading scores, markers of T-cell proliferation and activation (such as Ki-67 and granzyme B) and gene array analysis are planned, they were not available for inclusion at the time of drafting.

Methods for these studies are essentially as described in Miller W P et al., (2010) "*GVHD after haploidentical transplantation: a novel, MHC-defined rhesus macaque model identifies CD28–CD8+ T cells as a reservoir of breakthrough T-cell proliferation during costimulation blockade and sirolimus-based immunosuppression*", Blood 116:5403-5418.

Clinical Staging of GvHD

Scoring of clinical symptoms was based on observational assessments and clinical chemistry, classified according to the criteria set out in Table 5.

Histopathology

Tissues, including lung, liver, skin and gastrointestinal tract were collected at necropsy and fixed in formalin and paraffin-embedded. Sections were cut, slide-mounted and stained with haematoxylin/eosin or with T cell markers for visualisation of tissue infiltration by lymphocytes. Prepared slides are read by a histopathologist with specific expertise in GvHD using a semiquantitative scoring system.

Flow Cytometry

Longitudinal peripheral blood samples were collected before and after haematopoietic stem cell transplant and at necropsy for flow cytometric analysis of lymphocyte subsets. Lung, liver, colon spleen and lymph node (axillary and inguinal) tissues were collected at necropsy and dissociated or enzymatically digested as appropriate for subsequent analysis of lymphocyte infiltrates by flow cytometry. Samples were analysed by multicolour flow cytometry using a LSRFortessa cell analyser (BD Biosciences) using the following T lymphocyte marker probes: CD3 (APC-Cy7 label; clone SP34-2, BD Biosciences), CD4 (BV786 label; clone L200, BD Biosciences), CD8 (BUV395 label; clone RPA-T8, BD Biosciences), CD28 (PE-Cy7 label; clone CD28.2, eBioscience), CD95 (BV605 label; clone DX2, Biolegend). Proliferating cell populations were identified using Ki-67 (FITC label, Dako). CD4+ or CD8+ T cell subcompartments were labelled as follows: naïve T-cells (CD28+/CD95−), central memory T-cells (CD28+/CD95+), effector memory T-cells (CD28−/CD95+).

Blood was collected into tubes with Sodium EDTA, and then red blood cells were lysed with lysis buffer containing ammonium chloride. Remaining leukocytes were washed with FACS buffer (PBS with 2% FBS) and stained with antibody cocktail (Table 7) for 30 minutes at 4° C. After staining, cells were washed and fixed in 1×BD Stabilizing Fixative. Acquisition of flow data was performed on BD LSR Fortessa cytometer. Data were analyzed using FloJo. T-cells were defined as CD3+ CD14/CD20− lymphocytes.

TABLE 7

List of used antibodies for T cell immunophenotyping by flow cytometry

| Antibody | Fluorochrome | Clone | Company |
|---|---|---|---|
| CD3 | APC-Cy7 | SP34-2 | BD Biosciences |
| CD4 | BV786 | L200 | BD Biosciences |
| CD8 | BUV395 | RPA-T8 | BD Biosciences |
| CD14 | PerCP-Cy5.5 | M5E2 | BD Biosciences |
| CD20 | PerCP-Cy5.5 | 2H7 | eBioscience |
| CD28 | PE-Cy7 | CD28.2 | eBioscience |
| CD45RA | APC | 2H4LDH11LDB9 | Beckman Coulter |
| CD95 | BV605 | DX2 | Biolegend |
| CCR7 (CD197) | BV421 | G043H7 | Biolegend |
| OX40 (CD134) | PE | L106 | BD Biosciences |

Results:

1: Expansion of Memory Stem T-Cells after Transplantation

Figure 3A:
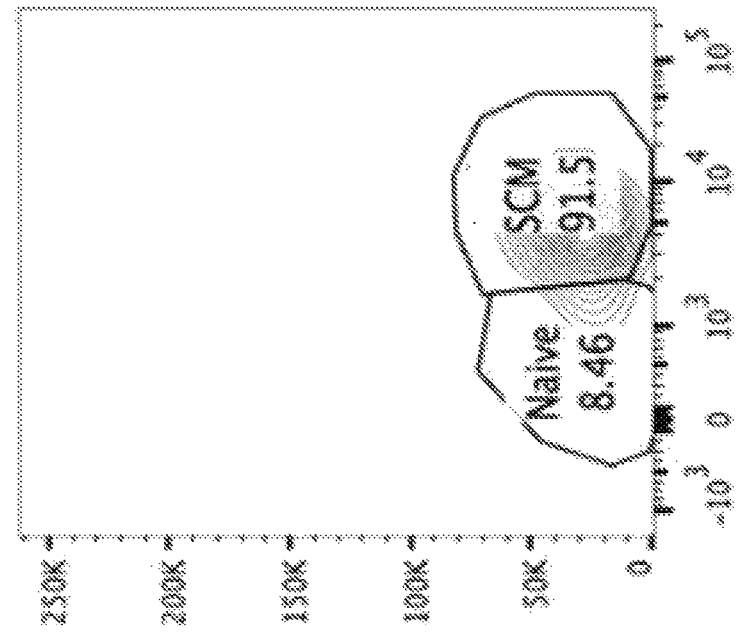
FIGS. 3A-3B show expansion of Tscm cells following allogeneic HCT. Plots are gated on CD4+CD45RA+CCR7+ T-cells.
Figure 3B:
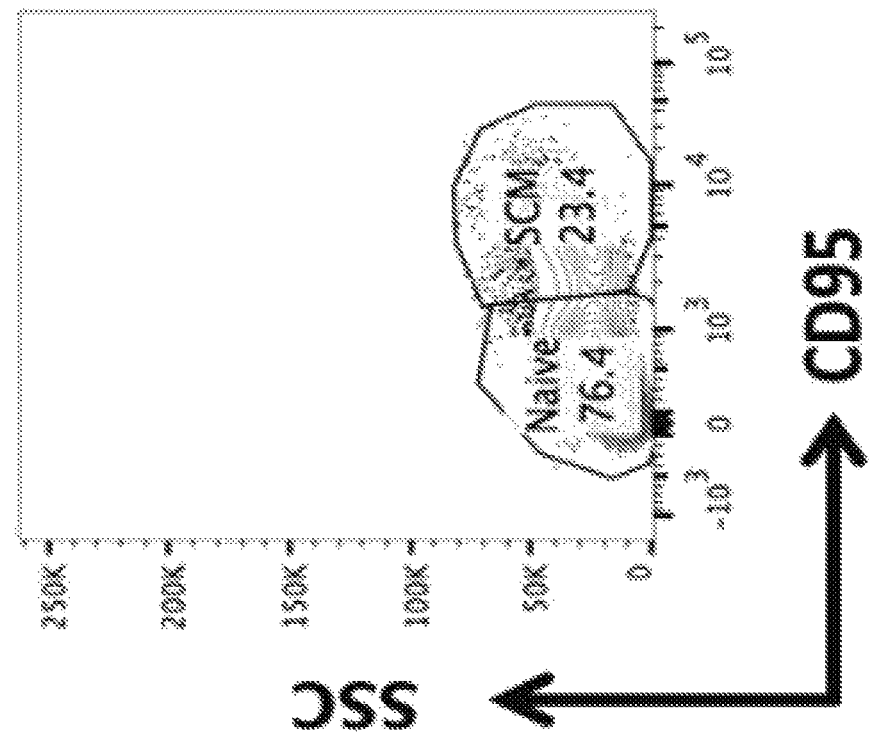

In a non-human primate model of acute Graft-versus-Host disease (GVHD), allogeneic hematopoietic cell transplantation (HCT) results in early expansion of both CD4 and CD8 memory stem T-cells (Tscm: CD45RA+CCR7+CD95+) at the expense of reconstitution of bona fide naïve T-cells (Tn: CD45RA+CCR7+CD95−) (FIG. 3). These Tscm cells circulate in the blood, and also reside in both lymphoid (lymph nodes, spleen) and non-lymphoid organs (lung, liver and colon).

2: 2D10 IgG4PE Limits Expansion of Tscm

Treatment with the blocking anti-OX40L antibody, 2D10 IgG4PE, results in prolonged survival of animals after allogeneic HCT and reduces clinical symptoms of acute GVHD. This delay in GVHD progression was associated with limited CD4+ Tscm expansion and preservation of CD4+ Tn cells (FIG. 4).

3: CD4 Tscm Cells Express OX40 on their Surface

As shown in FIG. 5, CD4+ Tscm express OX40 on their surface, but naïve T-cells do not. Moreover, the level of OX40 expression was comparable between CD4+ Tscm and central memory cells (Tcm). Importantly, OX40 expression was detected on CD4+ Tscm cells broadly. They are detected in naïve monkeys before transplantation (both in the blood and lymphoid organs), as well as in leukopheresis products. This expression is also seen in allogeneic HCT recipients longitudinally after transplantation.

4: Comparative Analysis of Tscm in 02D10 Ig4PE Treated Animals Compared to Standard GvHD Therapies The proportion of post-HCT Tscm cells evident in the peripheral blood of rhesus monkeys that received 02D10 IgG4PE were compared with Tscm from separate groups of animals administered either sirolimus (rapamycin) or a combination of tacrolimus plus methotrexate (Tac/MTX). The results for CD4+ Tscm cells are shown in FIG. 6a, and the results for CD8+ Tscm cells are shown in FIG. 6b. Data indicate that treatment with anti-OX40L antibody 02D10 IgG4PE results in a sustained inhibition of the proportion of Tscm cells compared with the sirolimus and Tac/MTX treatment.

Conclusions:

An OX40-expressing subset of Tscm might be sensitive to 2D10 IgG4PE-mediated OX40L-blockade. This blockade may control Tscm expansion and therefore limit the progression of acute GVHD. The OX40 pathway is a potentially novel mechanism of Tscm regulation, which can be used in clinical practice to treat immune-mediated diseases or improve the outcome of adoptive immunotherapy.

Chimerism

Peripheral blood or T cell (CD3+/CD20−) chimerism was determined using divergent donor- and recipient-specific MHC-linked microsatellite markers, by comparing peak heights of the donor- and recipient-specific amplicons (Penedo M C et al., (2005) "*Microsatellite typing of the rhesus macaque MHC region*", Imunogenetics 57:198-209).

TABLE 5

| Stage | Skin | Liver (Billirubin) | GI |
|---|---|---|---|
| 0 | No GVHD rash | <4-fold increase over baseline | No diarrhea |
| 1 | Rash <25% of surface area | 4- to 8-fold increase | "Mild" diarrhea |
| 2 | Rash 25-50% of surface area | 8- to 20-fold increase | "Moderate" diarrhea |
| 3 | Rash >50% of surface area | 20- to 50-fold increase | "Severe" diarrhea |

TABLE 5-continued

| Stage | Skin | Liver (Billirubin) | GI |
|---|---|---|---|
| 4 | Generalized erythroderma with bullous formation | >50-fold increase | "Very severe" diarrhea |

A total of six animals were selected to receive HSCT. Of these 6 animals, two of the experiments were deemed a technical failure, one animal experienced viral reactivation which may have hampered engraftment and it was seen that donor chimerism initially climbed but then dropped, indicating that second reconstitution was autologous repopulation. A single high cytomegalovirus (CMV) and Rhesus macaque Lymphocryptovirus (rhLCV) reading was seen at the same time as the drop in chimerism and autologous repopulation. The second technical failure was the result of failure of the apheresis machine to produce a suitable product for transplantation. Since the recipient animal had already been irradiated, it had to be sacrificed. The four other animals all survived to the primary endpoint of 15 days, exhibiting extended survival compared to both historical and contemporaneous no-prophylaxis controls. Table 6 below outlines the summary of each animal in this study.

Example 8

Pharmacokinetics

Rhesus macaques were dosed with 10 mg/kg of 2D10 or appropriate non-functional isotype control antibody on Day 0. Samples were taken, after +15 minutes, +1 hour, +8 hours, +24-36 hours, +72 hours, +96 hours, +Day 8, +Day 11, +Day 15, +Day 18, +Day 22, +Day 25. On Day 29, animals were dosed with 3 mg/kg of 2D10 or appropriate non-functional isotype control antibody. Samples were taken on Day 29 after +15 minutes, +1 hour, +8 hours and then 24-36 hours after Day 29. Samples continued to be taken on +Day 32, +Day 33, +Day 36, +Day 39, +Day 43, +Day 46, +Day 50, +Day 53, +Day 57, +Day 60, +Day 64, +Day 67 and +Day 71.

To determine the PK, anti-human IgG is diluted to 8 µg/mL in PBS and is adsorbed to 96 well low auto-fluorescent, high protein binding plates (Costar) overnight at 4° C. Excess IgG is removed by washing with PBS-Tween and wells are blocked with 5% w/v non-fat dried milk (blocking buffer) for 1 hour at room temperature. Following incubation period, plates are washed. Plasma samples are diluted in blocking buffer (multiple dilutions). A standard curve is also generated using a titration of positive control anti-OX40L antibody diluted in blocking buffer from 10 µg/mL (1 in 3 dilution). Either titration or diluted plasma sample are added to plate and incubated for 1 hr at room temperature. Plates are then washed and biotinylated human OX40L is diluted to 500 ng/mL in blocking buffer added for 1 hour at room temperature. Plates are then washed and streptavidin-Europium3+conjugate (DELFIA® detection, PerkinElmer) diluted in DELFIA® assay buffer (Perkin Elmer) is added. Plates are then washed 3 times in Tris Buffered Saline +0.1% tween. Then, DELFIA Enhancement solution (Perkin Elmer) is added to the plate and time-resolved fluorescence is measured at 615 nm on an Envision plate reader (PerkinElmer). The concentration of anti-OX40L antibody in the plasma is calculated by extrapolating fluorescence values from sample wells to those obtained from the standard curve generated from the titration of the positive control anti-OX40L antibody using a four parameter logistics curve fitting algorithm.

Example 9

Rhesus Macaque (GvHD) Model: Effect of Combined Prophylaxis with 2D10 IgG4PE Plus Rapamycin A further rhesus macaque GvHD study was conducted to determine the effect of combined post-HSCT prophylaxis with 2D10 IgG4PE and rapamycin. The study was performed as described in Example 7, with dosing as follows: 2D10 IgG4PE was administered i.v. at 10 mg/kg on Day−2, Day+5, Day+12, Day+19, Day+26, Day+33, Day+40, Day+47 and Day+56 post-transplant. Rapamycin was administered at a loading dose of 0.1 mg/kg i.m. on Day−14, followed by daily i.m. maintenance doses of 0.025 mg/kg until the scheduled termination of the study at Day+100. Rapamycin dosing was adjusted to maintain serum trough levels within the range 5-15 ng/mL.

Results:

Post-HSCT administration of 2D10 IgG4PE together with rapamycin resulted in extended GvHD-free and absolute survival (median survival time, MST>82 days; n=3) compared to historical control animals that did not receive post-HSCT experimental treatment (MST=8 days; n=4; Furlan et al, Science Translational Medicine, Vol 7 (315); 315ra1910). The effect of combined 2D10 IgG4PE plus rapamycin dosing appeared also to be greater than the additive effect of each molecule when administered alone (FIG. 7: MST for post-HSCT 2D10 IgG4PE and rapamycin were 19 and 17 days, respectively; both n=4). It is also noted that Furlan et al discloses a MST for combined prophylaxis with tacrolimus plus methotrexate of 49 days. It is expected that a combination of tacrolimus plus methotrexate and an anti-OX40L antibody (such as 2D10), or indeed a combination of tacrolimus and an anti-OX40L antibody (such as 2D10), would also provide the synergistic results as seen in this Example.

TABLE 4

| Animal No. | Animal ID | Survival Duration (days) | Whole Blood Chimerism (%) | | | | | | | | | | | | | | | |
|---|---|---|---|---|---|---|---|---|---|---|---|---|---|---|---|---|---|---|
| | | | Day 0 | Day 1 | Day 4 | Day 5 | Day 6 | Day 7 | Day 8 | Day 11 | Day 12 | Day 14 | Day 15 | Day 16 | Day 18 | Day 20 | Day 21 | Day 23 | Day 26 |
| (#1) | (13189) | (24) | 0 | | 6.6 | | | 27.5 | | 90.4 | | 81.8 | | | 19.7 | | 0 | | |
| #2 | 14079 | 16 | 0 | 5.7 | | 31.7 | | | 66.3 | | 82.3 | | 88.2 | 79.8 | | | | | |
| (#3) | (14075) | (0) | | | | | | | | | | | | | | | | | |
| #4 | 14081 | 26 | | 22.9 | | 68.2 | | | 82.9 | | 92.1 | | 97.5 | | | 98.4 | | 98.8 | 98.7 |

TABLE 4-continued

|  |  | Survival Dura- | Whole Blood Chimerism (%) | | | | | | | | | | | | | | | | |
|---|---|---|---|---|---|---|---|---|---|---|---|---|---|---|---|---|---|---|---|
| Animal No. | Animal ID | tion (days) | Day 0 | Day 1 | Day 4 | Day 5 | Day 6 | Day 7 | Day 8 | Day 11 | Day 12 | Day 14 | Day 15 | Day 16 | Day 18 | Day 20 | Day 21 | Day 23 | Day 26 |
| #5 | 14082 | 22 | | | | 91.4 | | | 98.4 | | 98.6 | | 99.1 | | | 99.2 | | 98.6 | |
| #6 | 14087 | 16 | | 16.6 | | 66.3 | | | 97.4 | | 99.5 | | 99.4 | | | | | | |

Data in brackets indicates experimental failure due to infection (animal 1) or technical failure (animal 3).

TABLE 6

2D10 IgG4PE Rhesus GvHD Study

Animal Details

| | |
|---|---|
| #1 | Survival to day 24. Received 4 doses of 2D10 IgG4PE. Biphasic hematopoietic reconstitution; peripheral blood chimerism data indicated initial donor engraftment followed by autologous repopulation concurrent with evidence of CMV and rhLCV infection. Viral infection considered possible cause of graft failure. Recorded as Technical Failure. |
| #2 | Survival to Day 16. Received 3 doses of 2D10 IgG4PE. Peak peripheral blood donor chimerism of 88% at Day 15. No evidence of CMV or rhLCV infection. Study terminated on veterinary advice due to wound at catheter site (not deemed to be treatment or GvHD related). GvHD staging at necropsy: skin 1 (rash <25%); liver 0 (no bilirubin elevation); GI 0 (no diarrhoea). |
| #3 | Recorded as Technical Failure. Apheresis equipment failure resulted in drastically suboptimal donor blood product. |
| #4 | Survival to Day 26. Received 4 doses of 2D10 IgG4PE. Clear hematopoietic reconstitution with peak peripheral blood donor chimerism of 99% by Day 23. No evidence of CMV or rhLCV infection. Study terminated on veterinary advice due to scrotal oedema. GvHD staging at necropsy: skin 2 (rash 25-50%); liver 0 (no bilirubin elevation); GI 0 (no diarrhoea). Gross necropsy confirmed no overt visceral GvHD. |
| #5 | Survival to Day 22. Received 4 doses of 2D10 IgG4PE. Clear hematopoietic reconstitution with peak peripheral blood donor chimerism of 99% by Day 12. No evidence of CMV or rhLCV infection. Study terminated due to persistent low platelet count with high bleeding risk and developing signs of acute systemic GVHD. GvHD staging at necropsy: skin 3 (rash >50%); liver 1 (4-8 × bilirubin elevation); GI 3 (severe diarrhoea). |
| #6 | Survival to Day 16. Received 3 doses of 2D10 IgG4PE. Clear hematopoietic reconstitution with peak peripheral blood donor chimerism of 100% on Day 12. No evidence of CMV or rhLCV infection. GvHD staging at necropsy: skin 2 (rash 25-50%); liver 1 (4-8 × bilirubin elevation); GI 2 (moderate diarrhoea). |

| SEQ ID NO: | SEQUENCE LISTING | |
|---|---|---|
| 1 | 10A07 | VH Nucleotide Sequence | GAGGTGCAACTGGTGGAGTCTGGGGGAGGCTTGGTACAGCCGGGGG GGTCCCTGAGACTCTCCTGTGCAGCCTCTGGATTCACCTTTAGCAGT TATATTATGACTTGGGTCCGCCAGGCTCCAGGGAAGGGGCTGGAGT GGGTCTCAGGTATTAGTGGTAGTGGTGGTACATACTACGCAGA CTCCATGAAGGGCCGGTTCACCATCTCCAGAGACAATTCCAAGAAC ACGCTGTATCTGCAGATGAACAGCCTGAGAGTCGAGGACACGGCCG TATATTACTGTGCGAAAGATCGGTTAGGTCCGATTACTTTGGTTCGG GGGGCTATTACTACGGTATGGACGTCTGGGGCCAAGGGACCACGG TCACCGTCTCCTCA |
| 2 | | VH Amino Acid Sequence | EVQLVESGGVLVQPGGSLRLSCAASGFTFSSYIMTWVRQAPGKGLEW VSGISGSGGGTYYADSMKGRFTISRDNSKNTLYLQMNSLRVEDTAVYY CAKDRLGPITLVRGYYYGMDVWGQGTTVTVSS |
| 3 | | HCDR1 Nucleotide Sequence (IMGT) | GGATTCACCTTTAGCAGTTATATT |
| 4 | | HCDR1 Amino Acid Sequence (IMGT) | GFTFSSYI |
| 5 | | HCDR2 Nucleotide Sequence (IMGT) | ATTAGTGGTAGTGGTGGTACA |
| 6 | | HCDR2 Amino Acid Sequence (IMGT) | ISGSGGGT |
| 7 | | HCDR3 Nucleotide Sequence (IMGT) | GCGAAAGATCGGTTAGGTCCGATTACTTTGGTTCGGGGGGCTATT ACTACGGTATGGACGTC |
| 8 | | HCDR3 Amino Acid Sequence (IMGT) | AKDRLGPITLVRGGYYYGMDV |
| 9 | | HCDR1 Nucleotide Sequence (KABAT) | AGTTATATTATGACT |
| 10 | | HCDR1 Amino Acid Sequence (KABAT) | SYIMT |
| 11 | | HCDR2 Nucleotide Sequence (KABAT) | GGTATTAGTGGTAGTGGTGGTGGTACATACTACGCAGACTCCATGA AGGGC |
| 12 | | HCDR2 Amino Acid Sequence (KABAT) | GISGSGGGTYYADSMKG |
| 13 | | HCDR3 Nucleotide Sequence (KABAT) | GATCGGTTAGGTCCGATTACTTTGGTTCGGGGGGCTATTACTACGG TATGGACGTC |
| 14 | | HCDR3 Amino Acid Sequence (KABAT) | DRLGPITLVRGGYYYGMDV |
| 15 | | VL Nucleotide Sequence | GACATCCAGATGACCCAGTCTCCATCCCCTGTCTGCATCTGTAGG AGACAGAGTCACCATCACTTGCCGGGCAAGTCAGAGCATTAGCGAC TATTTAAATTGGTATCAGCAGAAACCAGGGAAAGCCCCTAAGTTCC TGATCTATGCTGCATCCAGTTTGCAAAGTGGAGTCCCATCAAGGTTC AGTGGCAGTGGATCTGGGACAGATTTCACTCTCACCGTCAGCAGTC |

-continued

| SEQ ID NO: | | SEQUENCE LISTING |
|---|---|---|
| 16 | VL Amino Acid Sequence | TGCAACCTGAAGATTTGCAACTTACTACTGTCAACAGAGTTACAGT ACCCCTCGGACGTTCGGCCAAGGGACCAGGGTGGAAATCAAA |
| | | DIQMTQSPSSLSASVGDRVTITCRASQSISDYLNWYQQKPGKAPKFLIY AASSLQSGVPSRFSGSGSGTDFTLTVSSLQPEDFATYYCQQSYSTPRTFG QGTRVEIK |
| 17 | LCDR1 Nucleotide Sequence (IMGT) | CAGAGCATTAGCGACTAT |
| 18 | LCDR1 Amino Acid Sequence (IMGT) | QSISDY |
| 19 | LCDR2 Nucleotide Sequence (IMGT) | GCTGCATCC |
| 20 | LCDR2 Amino Acid Sequence (IMGT) | AAS |
| 21 | LCDR3 Nucleotide Sequence (IMGT) | CAACAGAGTTACAGTACCCCTCGGACG |
| 22 | LCDR3 Amino Acid Sequence (IMGT) | QQSYSTPRT |
| 23 | LCDR1 Nucleotide Sequence (KABAT) | CGGGCAAGTCAGAGCATTAGCGACTATTTAAAT |
| 24 | LCDR1 Amino Acid Sequence (KABAT) | RASQSISDYLN |
| 25 | LCDR2 Nucleotide Sequence (KABAT) | GCTGCATCCAGTTTGCAAAGT |
| 26 | LCDR2 Amino Acid Sequence (KABAT) | AASSLQS |
| 27 | LCDR3 Nucleotide Sequence (KABAT) | CAACAGAGTTACAGTACCCCTCGGACG |
| 28 | LCDR3 Amino Acid Sequence (KABAT) | QQSYSTPRT |
| 29 | Heavy Chain Nucleotide Sequence | GAGGTCCAGCTCGTGGAAAGCGGAGGAGTGCTCGTGCAGCCTGGA GGCAGCCTCAGGCTGTCCTGTGCCGCCTCCGGCTTCACCTTCAGCAG CTACATCATGAACTGGGTCCGACAGGCTCCCGGAAAAGGCCTGGAG TGGGTGTCCGGCATCTCCGGAGGAGGCACATATACGCCG ACAGCATGAAGGGCCGGTTCACCATCAGCCGGGACAATAGCAAGA ATACCCTCTACCTGCAAATGAACAGCCTGCGGGTGGAGGATACCGC CGTGTACTACTGCGCCAAAGATAGGCTGGGCCCCATTACCCTCGTG AGGGAGGCTATTACTACGGCATGGATGTGTGGGGCCAGGGCACCA CCGTGACAGTGTCCAGCGCCAGCACCAAGGGCCCTTCCGTGTTCCC CCTGGCCCCTTGCAGCAGGAGCACTTTCCCGAGCCCGTGCCCTG GGCTGTCTGGTGAAGGACTACTTTCCCGAGCCCGTGACCGTGAGCT GGAACAGCGGCGTCGACATCCGGCGTCCACACCTTTCCTGCGT CCTGCAGTCCTCCGGACTCTACTCCCTGTCCTCCGTGGTGACCGTGC CTAGCTCCTCCTGCCACCAAGGTGGACAAGACGGTCGAGAGCAAGTA CAAACCCTCCAACACCAAGGTGGACAAGAGAGTTGAGAGCAAGTA CGGCCCCTCCTGCCCGAGTTCGAAGGCGAC |

| SEQ ID NO: | | SEQUENCE LISTING |
|---|---|---|
| | | CCAGCGTGTTCCTGTTCCCTCCTAAGCCCAAGGACACCCTCATGATC
AGCCGGACACCCGAGGTGACCTGCGTGGTGGTGGATGTGAGCCAGG
AGGACCCTGAGGTCCAGTTCAACTGGTATGTGGATGGCGTGGAGGT
GCACAACGCCAAGACAAAGCCCCGGGAGGAGCAGTTCAACTCCAC
CTACCGGGTGGTCAGCGTGCTGACCGTGCATCAGGACTGGCTG
AACGGCAAGGAGTACAAGTGCAAGGTCTCCAAGGGCCTCCCC
AGCAGCATCGAGAAGACCATCTCCAAGGCTAAAGGCCAGCCCCGG
GAACCCAGGTGTACACCCTGCCTCCCAGCCAGGAGGAGATGACCA
AGAACCAGGTGAGCCTGACCTGCCTGGTCAAGGGATTCTACCCTTC
CGACATCGCCGTGGAGTGGGAGTCAAACGGCCAGCCCGAGAACA
TTATAAGACCACCCCTCCCGTGCTGGATAAGTCAGGTGCAGGAAGGCAA
TGTACTCCAGGCTGACCGTGGACAAGAGCAGGTGGCAGGAAGGCAA
CGTGTTCAGCTGCTCCGTGATGCACGAGGCCCTGCACAATCACTAC
ACCCAGAAGTCCCTGAGCCTGTCCCTGGGAAAG |
| 30 | Heavy Chain Amino Acid Sequence | EVQLVESGGGVLVQPGGSLRLSCAASGMTSSYIMTWVRQAPGKGLEW
VSGISGSGGGTYYADSMKGRFTISRDNSKNTLYLQMNSLRVEDTAVYY
CAKDRLGPITLVRGGYYYGMDVWGQGTTVTVSSASTKGPSVFPLAPC
SRSTSESTAALGCLVKDYFPEPVTVSWNSGALTSGVHTFPAVLQSSGLY
SLSSVVTVPSSSLGTKTYTCNVDHKPSNTKVDKRVESKYGPPCPPCPAP
EFEGGPSVFLFPPKPKDTLMISRTPEVTCVVVDVSQEDPEVQFNWYVD
GVEVHNAKTKPREEQFNSTYRVVSVLTVLHQDWLNGKEYKCKVSNK
GLPSSIEKTISKAKGQPREPQVYTLPPSQEEMTKNQVSLTCLVKGFYPS
DIAVEWESNGQPENNYKTTPPVLDSDGSFFLYSRLTVDKSRWQEGNVF
SCSVMHEALHNHYTQKSLSLSLGK |
| 31 | Light Chain Nucleotide Sequence | GACATCCAGATGACCCAGTCCCCTTCCTCCCTGTCCGCCTCCGTGGG
AGACAGGGTGACCATCACCTGCCGGGCCAGCCAGTCCATCAGCGAC
TACCTGAACTGGTATCAGCAGAAGCCCGGCAAGGCCCCTAAGTTCC
TGATCTACGCCGCTTCCTCCCTGCAGAGTGGCGTGCCCAGCAGGTTT
TCCGGCTCCGGATCCGGCACCGACTTCACCCTGACCATCAGCAGCCT
GCAGCCCGAGGACTTCGCCACCTACTACTGCCAGCAGAGCTACAGC
ACCCCCAGAGACATTTGGCAGGGCACCCGGGTGGAGATCAAGAGG
ACCGTCGCTCGCCCCTCCGTGTTTATCTTCCCCCAGCGACGAGCA
GCTGAAATCCGGCACCGCCTCCGTGGTCTGCCTGCTGAATAACTTCT
ACCCTCGGAGGCCAAGGTCCAGTGCAAGGTGGACAACGCCCTGC
AGAGCGGAAACTCCCAGGAGAGCGTGACCGAGCAGGACTCCAAGG
ACTCCACATACTCCCTGTCCTCCACCCTGACACTGTCCAAGGCCGAT
TACGAAGACCAAGGTGTACGCCTGCGAGGTGACCACCACCAGGA
CTGTCCTCCCCCGTGACCAAGTCCTTCAACCGGGGCGAGTGC |
| 32 | Light Chain Amino Acid Sequence | DIQMTQSPSSLSASVGDRVTITCRASQSISDYLNWYQQKPGKAPKFLIY
AASSLQSGVPSRFSGSGSGTDFTLTVSSLQPEDFATYYCQQSYSTPRTFG
QGTRVEIKRTVAAPSVFIFPPSDEQLKSGTASVVCLLNNFYPREAKVQW
KVDNALQSGNSQESVTEQDSKDSTYSLSSTLTLSKADYEKHKVYACEV
THQGLSSPVTKSFNRGEC |

-continued

| SEQ ID NO: | | SEQUENCE LISTING |
|---|---|---|
| 33 | 02D10 VH Nucleotide Sequence | GAGGTGCAGTTGGTGGAGTCTGGGGGAGGCTTGGTACAGCCTGGGG GGTCCCTGAGACTCTCCTGTGCAGCCTCTGGATTCACTTTTAGCAAC TATGCCATGAACTGGGTCCGCCAGGCTCCAGGGAAGGGGCTGGAGT GGGTCTCAACTATTAGCGGAAGTGGTGTGCCACAAGGTATGCAGA CTCCGTGAAGGGCCGATTCACCATATCCAGAGACAATTCCAGGAAC ACGGTGTATCTGCAAATGAACAGCCTGAGAGTCGAGGACACGGCCG TTTTTTACTGTGCGAAAGATCGGCTCATTATGGCTACGGTTCGGGGA CCCTATTACTACGGTATGGACGTCTGGGGCCAAGGGACCACGGTCA CCGTCTCCTCA |
| 34 | VH Amino Acid Sequence | EVQLVESGGGLVQPGGSLRLSCAASGFTFSNYAMNWVRQAPGKGLE WVSTISGSGATRYADSVKGRFTISRDNSRNTVYLQMNSLRVEDTAVF YCTKDRLIMATVRGPYYYGMDVWGQGTTVTVSS |
| 35 | HCDR1 Nucleotide Sequence (IMGT) | GGATTCACTTTTAGCAACTATGCC |
| 36 | HCDR1 Amino Acid Sequence (IMGT) | GFTFSNYA |
| 37 | HCDR2 Nucleotide Sequence (IMGT) | ATTAGCGGAAGTGGTGTGCCACA |
| 38 | HCDR2 Amino Acid Sequence (IMGT) | ISGSGGAT |
| 39 | HCDR3 Nucleotide Sequence (IMGT) | ACGAAAGATCGGCTCATTATGGCTACGGTTCGGGGACCCTATTACT ACGGTATGGACGTC |
| 40 | HCDR3 Amino Acid Sequence (IMGT) | TKDRLIMATVRGPYYYGMDV |
| 41 | HCDR1 Nucleotide Sequence (KABAT) | AACTATGCCATGAAC |
| 42 | HCDR1 Amino Acid Sequence (KABAT) | NYAMN |
| 43 | HCDR2 Nucleotide Sequence (KABAT) | ACTATTAGCGGAAGTGGTGCCACAAGGTATGCAGACTCCGTGA AGGGC |
| 44 | HCDR2 Amino Acid Sequence (KABAT) | TISGSGGATRYADSVKG |
| 45 | HCDR3 Nucleotide Sequence (KABAT) | GATCGGCTCATTATGGCTACGGTTCGGGGACCCTATTACTACGGTAT GGACGTC |
| 46 | HCDR3 Amino Acid Sequence (KABAT) | DRLIMATVRGPYYYGMDV |
| 47 | VL Nucleotide Sequence | GACATCCAGATGACCCAGTCTCCATCCTCCCTGTCTGCATCTGTAGG AGACAGAGTCACCATCACTTGCCGGGCAAGTCAGAGCATTAGCAGC TATTTAAATTGGTATCAGCAGAAACCAGGGAAAGCCCCTAACCTCC TGATCTATGCTGCATCCAGTTTGCAAAGTGGGTCCCATCCAAGTTC AGTGGCAGTGGATCTGAGACAGATTTCACTCTCACCATCAGCAGTC |

| SEQ ID NO: | SEQUENCE LISTING | |
|---|---|---|
| 48 | VL Amino Acid Sequence | TGCAACCTGAAGATTTGCAACTTACTACTGTCAACAGAGTCACAG<br>TGTCTCATTCACTTTCGGCCCTGGGACCAAAGTGGATATCAAA<br><br>DIQMTQSPSSLSASVGDRVTITCRASQSISSYLNWYQQKPGKAPNLLIY<br>AASSLQSGVPSRFSGSGSETDFTLTISSLQPEDFATYYCQQSHSVSFTFG<br>PGTKVDIK |
| 49 | LCDR1 Nucleotide Sequence (IMGT) | CAGAGCATTAGCAGCTAT |
| 50 | LCDR1 Amino Acid Sequence (IMGT) | QSISSY |
| 51 | LCDR2 Nucleotide Sequence (IMGT) | GCTGCATCC |
| 52 | LCDR2 Amino Acid Sequence (IMGT) | AAS |
| 53 | LCDR3 Nucleotide Sequence (IMGT) | CAACAGAGTCACAGTGTCTCATTCACT |
| 54 | LCDR3 Amino Acid Sequence (IMGT) | QQSHSVSFT |
| 55 | LCDR1 Nucleotide Sequence (KABAT) | CGGGCAAGTCAGAGCATTAGCAGCTATTTAAAT |
| 56 | LCDR1 Amino Acid Sequence (KABAT) | RASQSISSYLN |
| 57 | LCDR2 Nucleotide Sequence (KABAT) | GCTGCATCCAGTTTGCAAAGT |
| 58 | LCDR2 Amino Acid Sequence (KABAT) | AASSLQS |
| 59 | LCDR3 Nucleotide Sequence (KABAT) | CAACAGAGTCACAGTGTCTCATTCACT |
| 60 | LCDR3 Amino Acid Sequence (KABAT) | QQSHSVSFT |
| 61 | Heavy Chain Nucleotide Sequence | GAAGTGCAACTGGTGGAGTCCGGAGGAGGCCTGGTGCAGCCTGGA<br>GGAAGCCTGAGGCTGAGCTGCGCCGCCAGCGGCTTCACCTTCAGCA<br>ACTACGCCATGAACTGGGTGCGACAGGCCCCTGGCAAGGGACTGG<br>AGTGGGTCTCCACCATCAGCGGCTCCGAGGCGTACACGGTACGC<br>CGATAGCGTGAAGGGCCGGTTTACCATTTCCCGGGACAACTCCGG<br>AACACCGTGTACCTCCAGATGAACAGCCTGAGGGTGGAGGATACCG<br>CCGTGTTCTACTGCACCAAGGACACAGGTGTTGGGCCAGGGCACCGTGAG<br>GGGACCTTACTACTATGGCATGGATGTGTGGGGCCAGGGCACAACC<br>GTCACCGTGTCCTCCGCCTCCAGGTCCACAAGGCAGTCCACCGTGTTCCCTCT<br>CGCCCCTGCTGTTCCAGGTCCACAAGGCAGTCCACCGTGCCCCTCGGCT<br>GTCTGGTGAAAGACTACTTTCCCGAGCCTGTGACAGTGCGCTGCT<br>AGCGGAGCCCTGACCTCCGGCGTGCACACCATTTCCGCCGTGCTGC<br>AGAGCAGCGGACTGTATAGCCTGAGCAGCGTGGTGACCGTGCCCAG<br>CTCCAGCCTGCGACCCAAAACTACACCTGCAACGTGGACCACAAG<br>CCCCTTGCCCCTCCTTGTCCTGCCCTGAGTTCGAGGAGGAGACCCTC |

| SEQ ID NO: | | SEQUENCE LISTING |
|---|---|---|
| | | CGTGTTCCTGTTTCCCCCAAACCCAAGGACACCCTGATGATCTCCC
GGACACCCGAGGTGACCTGTGTGGTCGTGGACGTCAGCCAGGAGGA
CCCCGAGGTGCAGTTCAACTGGTATGTGGACGGCGTGGAGGTGCAC
AATGCCAAAACCAAGCCCAGGGAGGAGCAGTTCAATTCCACCTACA
GGGTTGTGAGCGTGCTGACCGTCCTGCATCAGGATTGGCTGAACGG
CAAGGAGTACAAGTGCAAGGTGTCCAACAAGGGACTGCCCAGCTCC
ATCGAGAAGACCATCAGCAAGGCTAAGGGCCAGCCCAGGGAGCCC
CAGGTGTATACCCTGCCTCCTAGCCAGGAAGAGATGACCAAGAACC
AAGTGTCCCTGACCTGCCTGGTGAAGGATTCTACCCCTCCGACATC
GCCGTGGAGTGGGAGAGCAATGGCCAGCCCGAGAACAACTACAAA
ACAACCCCTCCGTGCTGGATAGCGACGGCAGCTTCTTTCTCTACAG
CCGGCTGACAGTGGACAAGAGCAGGTGGCAGGAGGGCAACGTGTT
CTCCTGTTCCGTGATGCACGAGGCCCTGCACAATCACTACACCCAG
AAGAGCCTCTCCCTGTCCCTGGGCAAG |
| 62 | Heavy Chain Amino Acid Sequence | EVQLVESGGGLVQPGGSLRLSCAASGFTFSNYAMNWVRQAPGKGLE
WVSTISGSGGATRYADSVKGRFTISRDNSRNTVYLQMNSLRVEDTAVF
YCTKDRLIMATVRGPYYYGMDVWGQGTTVTVSSASTKGPSVFPLAPC
SRSTSESTAALGCLVKDYFPEPVTVSWNSGALTSGVHTFPAVLQSSGLY
SLSSVVTVPSSSLGTKTYTCNVDHKPSNTKVDKRVESKYGPPCPPCPAP
EFEGGPSVFLFPPKPKDTLMISRTPEVTCVVVDVSQEDPEVQFNWYVD
GVEVHNAKTKPREEQFNSTYRVVSVLTVLHQDWLNGKEYKCKVSNK
GLPSSIEKTISKAKGQPREPQVYTLPPSQEEMTKNQVSLTCLVKGFYPS
DIAVEWESNGQPENNYKTTPPVLDSDGSFFLYSRLTVDKSRWQEGNVF
SCSVMHEALHNHYTQKSLSLSLGK |
| 63 | Light Chain Nucleotide Sequence | GACATCCAGATGACCCAGTCCCCTTCCTCCCTGAGCGCTAGCGTGG
GAGATAGGGTGACCATCACCTGCAGGGCCTCCCAAAGCATTCTCTC
CTACCTGAACTGGTACCAGCAGAAACCCGGCAAGGCCCCCAAACTG
CTGATCTACGCTGCCTCCTCCAGTCCGGCGTGCCCTAGCAGGTT
TAGCGGCTCCGGAAGCGGAGCCGACTTCACCCTGACCATCTCCTC
CTGCAGCCCGAGGACTTCGCCACCTACTACTGCCAGCAATCCACA
GCGTGTCCTTCACCTTCGGCCCGGCACCAAGGTGGACATCAAGAG
GACCGTGGCCGCCCCCTCCGTGTTCATCTTTCCCCCTCCGATGAAC
AGCTGAAGAGCGGCACCGCTAGCGTGGTGTGCCTGCTGAACAACTT
CTACCCCCAGGGAGGCCAAGGTGCAGTGGAAGGTGGACAATGCCT
GCAGTCCGGCAACAGCCAGGAGAGCGTGACCGAGCAGGACTCCAA
GGACAGCACCTACAGCCTCTCCACCCTGACCCTGTCCAAGGCC
GACTACGAGAAGCACAAAGTGTACGCCTGCGAAGTGACCCATCAG
GGCCTGAGCTCCCCGTGACCAAGTCCTTTAACAGGGGCGAGTGC |
| 64 | Light Chain Amino Acid Sequence | DIQMTQSPSSLSASVGDRVTITCRASQSISSYLNWYQQKPGKAPNLLIY
AASSLQSGVPSRFSGSGSETDFTLTISSLQPEDFATYYCQQSHSVSFTFG
PGTKVDIKRTVAAPSVFIFPPSDEQLKSGTASVVCLLNNFYPREAKVQW
KVDNALQSGNSQESVTEQDSKDSTYSLSSTLTLSKADYEKHKVYACEV
THQGLSSPVTKSFNRGEC |

| SEQ ID NO: | | SEQUENCE LISTING |
|---|---|---|
| 65 | 09H04 VH Nucleotide Sequence | CAGGTGCAGCTGGTGGAGTCTGGGGGAGGCTTGGTCAAGCCTGGAG GGTCCCTGAGACTCTCCTGTGCAGCCTCTGGATTCACCCTCAGTGAC TACTACATGACCTGGATCCGCCAGGCTCCAGGGAAGGGGCTGGAGT GGGTTTCATACATTAGTAGTAGTGGTAATACCATATACGCAGA CTCTGTGAAGGGCCGATTCACCATCTCCAGGGACAACGCCAAGAAC TCACTGTATCTGCAAATGAACAGCCTGAGAGCCGAGGACACGGCCG TGTATTACTGTGCGAGAGATCTGAGTGGGAGCTACTGGGACTACTA CTACGGTATGGACGTCTGGGGCCAAGGGACCACGGTCACCGTCTCC TCA |
| 66 | VH Amino Acid Sequence | QVQLVESGGGLVKPGGSLRLSCAASGFTLSDYYMTWIRQAPGKGLEW VSYISSSGNTIYADSVKGRFTISRDNAKNSLYLQMNSLRAEDTAVYY CARDLSGSYWDYYYGMDVWGQGTTVTVSS |
| 67 | HCDR1 Nucleotide Sequence (IMGT) | CGATTCACCCTCAGTGACTACTAC |
| 68 | HCDR1 Amino Acid Sequence (IMGT) | RFTLSDYY |
| 69 | HCDR2 Nucleotide Sequence (IMGT) | ATTAGTAGTAGTGGTAATACCATA |
| 70 | HCDR2 Amino Acid Sequence (IMGT) | ISSSGNTI |
| 71 | HCDR3 Nucleotide Sequence (IMGT) | GCGAGAGATCTGAGTGGGAGCTACTGGGACTACTACTACGGTATGG ACGTC |
| 72 | HCDR3 Amino Acid Sequence (IMGT) | ARDLSGSYWDYYYGMDV |
| 73 | HCDR1 Nucleotide Sequence (KABAT) | GACTACTACATGACC |
| 74 | HCDR1 Amino Acid Sequence (KABAT) | DYYMT |
| 75 | HCDR2 Nucleotide Sequence (KABAT) | TACATTAGTAGTAGTGGTAATACCATATACTACGCAGACTCTGTGA AGGGC |
| 76 | HCDR2 Amino Acid Sequence (KABAT) | YISSSGNTIYYADSVKG |
| 77 | HCDR3 Nucleotide Sequence (KABAT) | GATCTGAGTGGGAGCTACTGGGACTACTACTACGGTATGGACGTC |
| 78 | HCDR3 Amino Acid Sequence (KABAT) | DLSGSYWDYYYGMDV |
| 79 | VL Nucleotide Sequence | GCCATCCAGTTGACCCAGTCTCCATCTCCCCTGTCTACATCTGTAGG AGACAGAGTCACCATCACTTGCCGGGCAAGTCAGGGCATTAACAAT GCTTTAGCCTGGTATCAGCAGAAACCAGGGAAAGCTCCTAAGCTCC TGATCTATGATGCCTCCAGTTTGGAAAGTGGGGTCCCATCAAGGTTC AGCGGCAGTGGATCTGGGACAGATTTCACTCTCACCATCAGCAGCC TGCAGCCTGAAGATTTTGCAACTTATTACTGTCAACAGTTTAATAGT TACCCTCGGACGTTCGGCCAAGGGACCAAGGTGGAAATCAAA |

| SEQ ID NO: | | SEQUENCE LISTING |
|---|---|---|
| 80 | VL Amino Acid Sequence | AIQLTQSPSSLSTSVGDRVTIACRASQGINNALAWYQQKPGKAPKLLIYDASSLESGVPSRFSGSGSGTDFTLTISSLQPEDFATYYCQQFNSYPRTFGQGTKVEIK |
| 81 | LCDR1 Nucleotide Sequence (IMGT) | CAGGGCATTAACAATGCT |
| 82 | LCDR1 Amino Acid Sequence (IMGT) | QGINNA |
| 83 | LCDR2 Nucleotide Sequence (IMGT) | GATGCCTCC |
| 84 | LCDR2 Amino Acid Sequence (IMGT) | DAS |
| 85 | LCDR3 Nucleotide Sequence (IMGT) | CAACAGTTTAATAGTTACCCTCGGACG |
| 86 | LCDR3 Amino Acid Sequence (IMGT) | QQFNSYPRT |
| 87 | LCDR1 Nucleotide Sequence (KABAT) | CGGGCAAGTCAGGGCATTAACAATGCTTTAGCC |
| 88 | LCDR1 Amino Acid Sequence (KABAT) | RASQGINNALA |
| 89 | LCDR2 Nucleotide Sequence (KABAT) | GATGCCTCCAGTTTGGAAAGT |
| 90 | LCDR2 Amino Acid Sequence (KABAT) | DASSLES |
| 91 | LCDR3 Nucleotide Sequence (KABAT) | CAACAGTTTAATAGTTACCCTCGGACG |
| 92 | LCDR3 Amino Acid Sequence (KABAT) | QQFNSYPRT |
| 93 19H01 | VH Nucleotide Sequence | GAGGTGCAGCTGGTGGAGTCTGGGGGAGGCTTGGTAAAGCCTGGGGGGTCCCTTAGACTCTCCTGTGCAGCCTCTGGATTCACTTTCAGTAACGCCTGGATGAGCTGGGTCCGCCAGGCTCCAGGGAAGGGGCTGGAGTGGGTTGGCCGTATTAAAAGCAAAACTGAAGGTGGACAACAGACTACGCTGCACCCGTGAAAGGCAGATTCACCATCTCAAGAGATGATTCAAAAACACGCTGTATCTGCAAATGAACAGCCTGAAAACCGAGGACACAGCCGTGTATTACTGTGGGGCCAGGGAACCCTGGTCACCGTCTCCTCA |
| 94 | VH Amino Acid Sequence | EVQLVESGGGLVKPGGSLRLSCAASGFTFSNAWMSWVRQAPGKGLEWVGRIKSKTEGGTTDYAAPVKGRFTISRDDSKNTLYLQMNSLKTEDTAVYYCTTDFLMFGEPFDYWGQGTLVTVSS |
| 95 | HCDR1 Nucleotide Sequence (IMGT) | GGATTCACTTTCAGTAACGCCTGG |
| 96 | HCDR1 Amino Acid Sequence (IMGT) | GFTFSNAW |

| SEQ ID NO: | SEQUENCE LISTING | |
|---|---|---|
| 97 | HCDR2 Nucleotide Sequence (IMGT) | ATTAAAAGCAAAACTGAAGGTGGGACAACA |
| 98 | HCDR2 Amino Acid Sequence (IMGT) | IKSKTEGGTT |
| 99 | HCDR3 Nucleotide Sequence (IMGT) | ACCACAGATTTCTATGGTTCGGGGAGTTCCCTTTTGACTAC |
| 100 | HCDR3 Amino Acid Sequence (IMGT) | TTDFLWFGEFPFDY |
| 101 | HCDR1 Nucleotide Sequence (KABAT) | AACGCCTGGATGAGC |
| 102 | HCDR1 Amino Acid Sequence (KABAT) | NAWMS |
| 103 | HCDR2 Nucleotide Sequence (KABAT) | CGTATTAAAAGCAAAACTGAAGGTGGGACAACAGACTACGCTGCACCCGTGAAAGGC |
| 104 | HCDR2 Amino Acid Sequence (KABAT) | RIKSKTEGGTTDYAAPVKG |
| 105 | HCDR3 Nucleotide Sequence (KABAT) | GATTTCTATGGTTCGGGGAGTTCCCTTTTGACTAC |
| 106 | HCDR3 Amino Acid Sequence (KABAT) | DFLWFGEFPFDY |
| 107 | VL Nucleotide Sequence | GACATCCAGATGACCCAGTCTCCATCTCCCCTGTCTGCATCTGTAGGAGACAGAGTCACCATCACTTGCCGGGCGAGTCAGGGCATTAGCAATTATTTAGCCTGGTATCAGCAGAAACCAGGGAAAGCCCCTAAGCTCCTGATCTATGCTGCATCCACTTTGCAATCAGGGGTCCCATCTCGGTTCAGTGGCAGTGGATCTGGGACAGATTTCACTCTCACCATCAGCAGCCTGCAGCCTGAAGATGTTGCAACTTATTACTGTCAAAAGTATAACAGTGCCCCTCGGACGTTCGGCCAAGGGACCAAGGTGGAAATCAAA |
| 108 | VL Amino Acid Sequence | DIQMTQSPSSLSASVGDRVTITCRASQGISNYLAWYQQKPGKIPKLLIYAASTLQSGVPSRFSGSGSGTDFTLTISSLQPEDVATYYCQKYNSAPRTFGQGTKVEIK |
| 109 | LCDR1 Nucleotide Sequence (IMGT) | CAGGGCATTAGCAATTAT |
| 110 | LCDR1 Amino Acid Sequence (IMGT) | QGISNY |
| 111 | LCDR2 Nucleotide Sequence (IMGT) | GCTGCATCC |
| 112 | LCDR2 Amino Acid Sequence (IMGT) | AAS |
| 113 | LCDR3 Nucleotide Sequence (IMGT) | CAAAAGTATAACAGTGCCCCTCGGACG |
| 114 | LCDR3 Amino Acid Sequence (IMGT) | QKYNSAPRT |
| 115 | LCDR1 Nucleotide Sequence (KABAT) | CGGGCGAGTCAGGGCATTAGCAATTATTTAGCC |

| SEQ ID NO: | | SEQUENCE LISTING |
|---|---|---|
| 116 | LCDR1 Amino Acid Sequence (KABAT) | RASQGISNYLA |
| 117 | LCDR2 Nucleotide Sequence | GCTGCATCCACTTTGCAATCA |
| 118 | LCDR2 Amino Acid Sequence (KABAT) | AASTLQS |
| 119 | LCDR3 Nucleotide Sequence | CAAAAGTATAACAGTGCCCCTCGACG |
| 120 | LCDR3 Amino Acid Sequence (KABAT) | QKYNSAPRT |
| 121 | Human IgG4 heavy chain constant region #1 | IGHG Heavy Chain Constant Region Nucleotide *01 Sequence | gcttccaccaagggcccatccgtcttccccctggcgccctgctccaggagcacctccgagagcacagcggcc tggctgcctggtcaaggactacttcccccgaaccggtgacggtgtcgtggaactcaggcgccctgaccagcgg cgtgcacaccttcccggctgtcctacagtcctcaggactctactccctcagcagcgtggtgaccgtgcctcag cagcttgggcacgaagaccctcaacagcaacaccaagtggacaagagagt tgagtccaaatatgtctccccatgcccaccatgcccagcacctgagttcctggggggaccatcagtcttcctgttc cccccaaaacccaaggacactctcatgatctcccggacccctgaggtcacgtgcgtggtggtggacgtgagcc aggaagaccccgaggtccagttcaactggtacgtggacggcgtggaggtgcataatgccaagacaaagccgc gggaggagcagttcaacagcacgtaccgtgtggtcagcgtcctcaccgtcctgcaccaggactggctgaacgg caaggagtacaagtgcaaggtctccaacaaaggcctcccgtcctccatcgagaaaaccatctccaaagccaaa gggcagccccgagagccacaggtgtacaccctgccccccatctccgggagatgaccaagaaccaggtcag cctgacctgcctggtcaaaggcttctacccccgcgacatcgccgtggagtgggagagcaatgggcagccggga gaacaactacaagaccacgcctcccgtgctggactccgacggctccttcttcctctacagcaagctcaccgtgga caagagcaggtggcaggaggggaatgtcttctcatgctccgtgatgcatgaggctctgcacaaccactacacac agaagagcctctccctgtctctgggtaaa |
| 122 | | Heavy Chain Constant Region Amino Acid Sequence | ASTKGPSVFPLAPCSRSTSESTAALGCLVKDYFPEPVTVSWNSGALTSG VHTFPAVLQSSGLYSLSSVVTVPSSSLGTKTYTCNVDHKPSNTKVDKR VESKYGPPCPSCPAPEFLGGPSVFLFPPKPKDTLMISRTPEVTCVVVDVS QEDPEVQFNWYVDGVEVHNAKTKPREEQFNSTYRVVSVLTVLHQDW LNGKEYKCKVSNKGLPSSIEKTISKAKGQPREPQVYTLPPSQEEMTKNQ VSLTCLVKGFYPSDIAVEWESNGQPENNYKTTPPVLDSDGSFFLYSRLT VDKSRWQEGNVFSCSVMHEALHNHYTQKSLSLSLGK |
| 123 | Human IgG4 heavy chain constant region #2 | IGHG Heavy Chain Constant Region Nucleotide *02 Sequence | gcttccaccaagggcccatccgtcttccccctggcgccctgctccaggagcacctccgagagcacagcgcc tggctgcctggtcaaggactacttccccgaaccggtgacggtgtcgtggaactcaggcgccctgaccagcgg cgtgcacaccttcccggctgtcctacagtcctcaggactctactccctcagcagcgtggtgaccgtgcctccag cagcttgggcacgaagaccctcaacgatcgccagccccaacacccaagtggacaagagt tgagtccaaatatgtctccccatgcccaccatgcccagcacctgagttcctggggggaccatcagtcttcctgttc cccccaaaacccaaggacactctcatgatctcccgacccctgaggtcacgtgcgtggtggtggacgtgagcc aggaagaccccgaggtccagttcaactggtacgtggatggcgtggaggtgcataatgccaagacaaagccgc gggaggagcagttcaacagcacgtaccgtgtggtcagcgtcctcaccgtcctgcaccaggactggctgaacgg caaggagtacaagtgcaaggtctccaacaaaggcctcccgtcctccatcgagaaaaccatctccaaagccaaa gggcagccccgagagccacaggtgtacaccctgcccccatccgggaggagatgaccaagaaccaggtcag cctgacctgcctggtcaaaggcttctacccccagcgacatcgccgtggagtgggagagcaatggcagccgga gaacaactacaagaccacgcctccctgtgctggactccgacggctccttcttcctctacagcaagctcaccgtgga caagagcaggtggcaggaggggaatgtcttctcatgctccgtgatgcatgaggctctgcacaaccactacacgc agaagagcctctccctgtctctgggtaaa |

-continued

| SEQ ID NO: | | SEQUENCE LISTING |
|---|---|---|
| 124 | Heavy Chain Constant Region Amino Acid Sequence | ASTKGPSVFPLAPCSRSTSESTAALGCLVKDYFPEPVTVSWNSGALTSG VHTFPAVLQSSGLYSLSSVVTVPSSSLGTKTYTCNVDHKPSNTKVDKR VESKYGPPCPSCPAPEFLGGPSVFLFPPKPKDTLMISRTPEVTCVVVDVS QEDPEVQFNWYVDGVEVHNAKTKPREEQFNSTYRVVSVLTVVHQDW LNGKEYKCKVSNKGLPSSIEKTISKAKGQPREPQVYTLPPSQEEMTKNQ VSLTCLVKGFYPSDIAVEWESNGQPENNYKTTPPVLDSDGSFFLYSRLT VDKSRWQEGNVFSCSVMHEALHNHYTQKSLSLSLGK |
| 125 | Human IgG4 heavy chain constant region #3 | IGHG *03 Heavy Chain Constant Region Nucleotide Sequence | gcttccaccaaggcccatccgtctttccccctgcgccctgctccaggagcacctccgagagcacgccgcc tggggctgcctggtcaagactacttccccgaaccggtgacggtgtcgtggaactcaggcgccctgaccagcgg cgtcacaccttccggctgtccctacagtcctcaggactctactcctccagcagcggtgtgaccgtgccctccag cagcttgggcacgaagacctacacctgcaacgtagatcacaagcccagcaacaccaaggtggacaagagagt tgagtccaaatatgtccccccatcccgagtcccattctcaggggggaccatcagtcttcctgttc ccccccaaaaccccaaggacacccaggaggagatgaccaagaaccaggtcagcctgacctgcctggtcaaag gcttctaccccagcgacatcgccgtggagtgggagagcaatgggcagccggagaacaactacaagaccacg cctcccgtgctggactccgacggctccttcttcctctacagcaggctaaccgtggacaagagcaggtggcag gagggcaatgtcttcatgcatgtatgaggctgcacaaccactaacg cagaagagctctccctgtctctgggtaaa |
| 126 | Heavy Chain Constant Region Amino Acid Sequence | ASTKGPSVFPLAPCSRSTSESTAALGCLVKDYFPEPVTVSWNSGALTSG VHTFPAVLQSSGLYSLSSVVTVPSSSLGTKTYTCNVDHKPSNTKVDKR VESKYGPPCPSCPAPEFLGGPSVFLFPPKPKDTLMISRTPEVTCVVVDVS QEDPEVQFNWYVDGVEVHNAKTKPREEQFNSTYRVVSVLTVLHQDW LNGKEYKCKVSNKGLPSSIEKTISKAKGQPREPQVYTLPPSQEEMTKNQ VSLTCLVKGFYPSDIAVEWESNGQPENNYKTTPPVLDSDGSFFLYSKLT VDKSRWQEGNVFSCSVMHEALHNHYTQKSLSLSLGK |
| 127 | IgG4 heavy chain constant region | Heavy Chain Constant Region Nucleotide Sequence - Synthetic Version A | gcttccaccaaggcccatccgtcttccccctgctccaggagcacctccgagagcacggccgcc ctggggctgcctggtcaagactacttcccccgaaccagtgacggtgtcgtggaactcaggcgccctgaccagc ggtgtcacacccttccggctgtccctacagtcctcaggactctactctccagcagcggtgtgaccgtgccacca gcagcttgggcacgaagacctacacctgcaacgtagatcacaagcccagcaacaccaaggtggacaagagag ttgagtccaaatatgtccccccatcccgagtcccgaatttgaggtggaccatcagtcttcctgtt cccccccaaaaccccaaggacacctcatgatctcccggaccctgaggtcacgtgcgtggtggactgtgagc caggaagaccccgaggtccagttcaactggtacgtggatggcgtggaggtgcataatgccaagacaaagccg cgggaggagcagtacaacagcacgtaccgtgtggtcagcgtcctcaccgtcctgcaccaggactggctgaacg gcaaggagtacaagtgcaaggtctccaacaaaggcctcccagccccatcgagaaaaccatctccaaagccaa gggcagcccccgagaaccacaggtgtacacccctgcccccatcgcgggaggagatgaccaagaaccaggtca gcctgacctgcctggtcaaaggcttctaccccagcgacatcgccgtggagtgggagagcaatgggcagccgg agaacaactacaagaccacgcctcccgtgctggactccgacggctccttcttcctctacagcaggctaaccgtgg acaagagcaggtggcaggaggggaatgtcttctcatgctccgtgatgcatgaggctctgcacaaccactacaca cagaagagcctctccctgtctccgggtaaa |

| SEQ ID NO: | | SEQUENCE LISTING |
|---|---|---|
| 128 | IgG4 heavy chain constant region -IgG4-PE Heavy Chain Constant Region Amino Acid Sequence - Encoded by Synthetic Version A, B & C | ASTKGPSVFPLAPCSRSTSESTAALGCLVKDYFPEPVTVSWNSGALTSG VHTFPAVLQSSGLYSLSSVVTVPSSSLGTKTYTCNVDHKPSNTKVDKR VESKYGPPCPPCPAPEFEGGPSVFLFPPKPKDTLMISRTPEVTCVVVDVS QEDPEVQFNWYVDGVEVHNAKTKPREEQFNSTYRVVSVLTVLHQDW LNGKEYKCKVSNKGLPSSIEKTISKAKGQPREPQVYTLPPSQEEMTKNQ VSLTCLVKGFYPSDIAVEWESNGQPENNYKTTPPVLDSDGSFFLYSRLT VDKSRWQEGNVFSCSVMHEALHNHYTQKSLSLSLGK |
| 129 | IgG4 heavy chain constant region | Heavy Chain Constant Region Nucleotide Sequence - Synthetic Version B<br>Gcctccaccaaggacctagcgtgttcctcctgcccctgttccagtccaaagcagtcaccgtgcct cggctgcttgtgaagactacttccgagccccgtgaccgtctcctggaatagcggagccctgacctccggcgt gcacactttccgcgtgtcagagcagcggactgtatagcctgagcagcgtggtgaccgtgcccagctcc agcctcggcaccaaaactacacctgcaacgtggaccatagccccaagcctgagcagtgacaagtggtg gagcaagtacggccccccccttgtcctcgcctcagttcgaggaggaccctcgtgttcctgttc ccccaaaccaaccgacccccgtgatcctgtcgagatcaccggactgtgtgtgtgtcaggcaacgggccca ggaagaccccgaggtgcagttcaactggtatgtggacggcgtggaggtgcacaatgccaagaccaag ggaagagcagttcaattccactacagggtggtgagcgtgctgaccgtcctgcatcaggaacgccagcgtc aggtgtacagcgcaagtgtccccaaccaagggactgccaagctgcctctctagccagacccggagaccttcgaagccccagagatgaccaagaaccagtgtcctc gaccgcctgtgaagggattcctaccctccggtgtcggacaaaggaagagatgaccaagaacgccgaaa caactacaaaacaaccctccggtgctggaccgtgaccaagatgtcaccgacccgcgagcgatggtgcagacagtggacaa gagcaggtggcaggaggcaaccgtcgtcgtgccgtcgacggcgacatcctgcacaataactacacccag aagagcctctccctgtccctgggcaag |
| 130 | IgG4 heavy chain constant region | Heavy Chain Constant Region Nucleotide Sequence - Synthetic Version C<br>gcctccaccaagggccctcgtccctctctccgtcccctgcctgcagcagcacctccgaatccacagtgccct gggctgtctgtgaagactacttccgacacccgtggaccctggaaacagccgctgaccatgccgg gtccaccacttcctgcggtcttcgctgctccggcacaactgagccctgtacctctcctgcggtgcctgcagttctccta gcttcggcaccaagacctacacctgcaacgtggaccacaaaccctcaaccagtaggctgacaagaggcga gagcaagtacggcctccctgccctctgtctgcgcacacccgagttcgaaggcggaccagcgttcctgttccc tcctaagccccaaggacaccctgatgcaacggactgcggatgcggtgatggcggtgtggatgtgagcaag gaggcagtcaacctacagggtgcagttcaactggtacgtggacggcgtggaggtgcacacgcgcaagacgaag ccgccccggaaccaggcgcgaaggattctccctactccccggaacgccaggtgcacagcgtcgtcaaggtcgtcacggtctcggtctcccagccagccagccgtccagagcgccagccgctccacagcgtctgtgcagccacggtcagaccacgaccagcgctg ctggctggttggaagaaccagtgctcctttctactggctcccggtgatgccggtgatggcgaccagcctggg acaattataagaaccacaacccgtctccggacgtgaacagtggatgccgcctccaggcgaccctggataa gtccagtggcaggaaggcaacgttcagctgactgtgcagcgttcatgcagcgagacccctggtcgccacgcatacactcccagca agtccctgagcctgtccctgggaaag |
| 131 | IgG4 heavy chain constant region | Heavy Chain Constant Region Nucleotide Sequence - Synthetic Version D<br>gcctccaccaaggccccatccgtcttccccctgccctgcagagacacctccgagagcacggccgcc ctgggctgcctggtcaaggactacttccccgaaccagtgaccgtgtcgtggaactcgggcgccctgaccagcg gcgtgcacaccttcccggctgtcctacagtcctcaggactctactccctcagcagcgtggtgaccgtgccctcca gcagcttgggcaacgaagaccatcgtacaacctgcaacgacacccaccgagcctcagtccaacaccaagtggacaaagagag ttgagtccaaatatggtccccatgccagccccgagttcctgggaggaccatcagtcttcctgtt ccccaaaacccaaggacaccctcatgatctcccggacccctgaggtcacgtggtggtgtgggtgagc caggaagagcccgaggtccagttcaactggtacgtggacggcgtggaggtggcataatgccaagacaaagccg cggaggagcagttcaacagcacgtaccgtgtggtcagcgtcctcaccgtcctgcaccaggactggctgaacg gcaaggagtacaagtgcaaggtctccaacaaagggctcccgtcctccatcgagaaaaccatctccaaagccaa |

| SEQ ID NO: | | SEQUENCE LISTING |
|---|---|---|
| | | agggcagcccgagagccacaaggtgtacaccctgccccagcagcgtgctgaccagtca gcctgacctgcctgtcaaggcttctaccccagcgacatcgccgtggagtgggagcagccgg agaacaactacaagacacgcccgtgctggactcgacgatccttcttcctctacagcaggctaaccgtgg acaagaccaggtggcaggaggggaatgtcttctcatgctccgtgatgcatgaggctctgcacaaccactacacac cagaagaccctctccctgtctccgggtaaa |
| 132 | Heavy Chain Constant Region Amino Acid Sequence - encoded by Synthetic Version D | ASTKGPSVFPLAPCSRSTSESTAALGCLVKDYFPEPVTVSWNSGALTSG VHTFPAVLQSSGLYSLSSVVTVPSSSLGTKTYTCNVDHKPSNTKVDKR VESKYGPPCPPCPAPPVAGGPSVFLFPPKPKDTLMISRTPEVTCVVVD VSQEDPEVQFNWYVDGVEVHNAKTKPREEQFNSTYRVVSVLTVLHQD WLNGKEYKCKVSNKGLPSSIEKTISKAKGQPREPQVYTLPPSQEEMTK NQVSLTCLVKGFYPSDIAVEWESNGQPENNYKTTPPVLDSGSFFLYSR LTVDKSRWQEGNVFSCSVMHEALHNHYTQKSLSLSLGK |
| 133 | Heavy chain constant region Human IgG1 | Heavy Chain Constant Region Nucleotide Sequence gcctccaccaaggcgccatcggtcttcccctggcaccctcctgggggcacagcggcc tggctgcctggtcaaggactactccgaaccgtgacggtgtcgtggaactcaggcgctgaccagcgg cgtcacacctcccggctcgctctactccctcaggatctcctacagcagcgtggtgaccgtgccctccag cagctgggcacccagagccagctgaatcacaagccacgtggaccaccaaggtgacaagaaagtg gagcccaaatctgacaaaactcacacatgcccaccgtgcccagcacctgaactcggagggggcaccgctgcag tcttcctcttcccccaaaaacccaaggacaccctcatgatctccggacccctgaggtcacagtgtggtggtgg acgtgagccacggagcacgtgaagtgaaggggcggcggtggaggtgcataatgccaaagac aaagccgggaggagcagtacaagtgcaaggtctccaacaaaggcctcccagtcctccatcgaa gctgaatgcaaagggcagccccgagaaccacaggtgtacaccctgccccatcccgggatgagctgaccaagaa ccaggtcagcctgacctgcctggtcaaggcttcatccagcgacatcgccgtggactccgagtgggagcaatggg cagccggagaacaactacaagacacgcctcccgtgctggactcagacgccttcttctctctacagcaagct cacctgacaagaagccagggggaacgtcttctcatgtccgtgatgcatgaggctctgcacaac cactcacgcagaagagcctctccctgctctccgggtaaa |
| 134 | Heavy Chain Constant Region Amino Acid Sequence | ASTKGPSVFPLAPSSKSTSGGTAALGCLVKDYFPEPVTVSWNSGALTSG VHTFPAVLQSSGLYSLSSVVTVPSSSLGTQTYICNVNHKPSNTKVDKKV EPKSCDKTHTCPPCPAPELAGAPSVFLFPPKPKDTLMISRTPEVTCVVV DVSHEDPEVKFNWYVDGVEVHNAKTKPREEQYNSTYRVVSVLTVLH QDWLNGKEYKCKVSNKALPAPIEKTISKAKGQPREPQVYTLPPSRDEL TKNQVSLTCLVKGFYPSDIAVEWESNGQPENNYKTTPPVLDSDGSFFL YSKLTVDKSRWQQGNVFSCSVMHEALHNHYTQKSLSLSPGK |
| 135 | Human Cκ constant region | IGKC Cκ Light Chain Constant Region *01 Nucleotide Sequence cgtacggtggctgccgctcccctcgtgtctcatcttcccaccttccgacgagcagctgaagtccggaactgcctgtcttg tgcctgctgaacaactctaccccgcagagtgccaaggtgcaagtggacaacgccctgcagtccgg caactcccagaatccgtgaccgagcaggacactccaaggacactccaaggacatctgtacctacactccaggaactgtccccaccctgacctgct ccaaggcgactacgagaagcacaaggtgtacgcctgcgaagtgacccaccacagggcctgtcagccgtga ccagtctttcaaccggcgcgagtgt |
| 136 | Cκ Light Chain Constant Region Amino Acid Sequence | RTVAAPSVFIFPPSDEQLKSGTASVVCLLNNFYPREAKVQWKVDNALQ SGNSQESVTEQDSKDSTYSLSSTLTLSKADYEKHKVYACEVTHQGLSS PVTKSFNRGEC |

| SEQ ID NO: | | SEQUENCE LISTING |
|---|---|---|
| 137 | Human Cκ constant region | IGKC Cκ Light Chain Constant Region *02 Nucleotide Sequence | cgaactggctgcaccatctgtcttcatcttcccgccatctgatgagcagttgaaatctggaactgctctgttg tgtgcctgctgaataacttctatcccagagaggccaaagtacagtggaaggtggataacgcctccaatcgggtaa ctcccaggagagtgtcacagaagcaggaggagcaagcactacagcctcagcagcacccctgacgctgag caagcagactacgagaaacacaaagttctacgccgcgaagtcacccatcagggcctgagctcgcccgtcac aaagagcttcaacaggggagagtgt |
| 138 | | Cκ Light Chain Constant Region Amino Acid Sequence | RTVAAPSVFIFPPSDEQLKSGTASVVCLLNNFYPREAKVQWKVDNALQ SGNSQESVTEQESKDSTYSLSSTLTLSKADYEKHKVYAGEVTHQGLSSP VTKSFNRGEC |
| 139 | Human Cκ constant region | IGKC Cκ Light Chain Constant Region *03 Nucleotide Sequence | cgaactggctgcaccatctgtcttcatcttcccgccatctgatgagcagttgaaatctggaactgctctgttg tgtgcctgctgaataacttctatcccagagaggccaaagtacagcggaaggtggataacgccctccaatcgggta gctcccaggagagtgtcacagaagcaggaggagcaagcactacagcctcagcagcacccctgacgctga gcaaagcagactacgagaaacacaaagtctacgccgcgaagtctacgccctgagctcgcccgtcac aaagagcttcaacaggggagagtgt |
| 140 | | Cκ Light Chain Constant Region Amino Acid Sequence | RTVAAPSVFIFPPSDEQLKSGTASVVCLLNNFYPREAKVQRKVDNALQ SGNSQESVTEQDSKDSTYSLSSTLTLSKADYEKHKVYACEVTHQGLSSP VTKSFNRGEC |
| 141 | Human Cκ constant region | IGKC Cκ Light Chain Constant Region *04 Nucleotide Sequence | cgaactggctgcaccatctgtcttcatcttcccgccatctgatgagcagttgaaatctggaactgctctgttg tgtgcctgctgaataacttctatcccagagaggccaaagtacagtggaaggtggataacgccctccaatcgggtaa ctcccaggagagtgtcacagaagcaggaggagcaagcactacagcctcagcagcacccctgacgctgag caaagcagactacgagaaacacaaactctacgccgtgcgaagtcacccatcagggcctgagacgcccgtcaca aaagagcttcaacaggggagagtgt |
| 142 | | Cκ Light Chain Constant Region Amino Acid Sequence | RTVAAPSVFIFPPSDEQLKSGTASVVCLLNNFYPREAKVQWKVDNALQ SGNSQESVTEQDSKDSTYSLSSTLTLSKADYEKHKLYACEVTHQGLSSP VTKSFNRGEC |
| 143 | Human Cκ constant region | IGKC Cκ Light Chain Constant Region *05 Nucleotide Sequence | cgaactggctgcaccatctgtcttcatcttcccgccatctgatgagcagttgaaatctggaactgctctgttg tgtgcctgctgaataacttctatcccagagaggccaaagtacagtggaaggtggataacgccctccaatcgggtaa ctcccaggagagtgtcacagaagcaggaggagcaagcactacagcctcagcagcacccctgacgctgagc aagcagactacgagaaacacaaagtctacgccgtgagtcacccatcagggcctgagcgcccgtcacaa agagcttcaacaggggagagtgc |
| 144 | | Cκ Light Chain Constant Region Amino Acid Sequence | RTVAAPSVFIFPPSDEQLKSGTASVVCLLNNFYPREAKVQWKVDNALQ SGNSQESVTEQDSKDSTYSLSNTLTLSKADYEKHKVYACEVTHQGLSS PVTKSFNRGEC |
| 145 | Human Cλ constant region | IGCλ Cλ Light Chain Constant Region 1*01 Nucleotide Sequence | cccaaggccaaccccacgtcactctgtcccgccctcctctgaggagctccaagccaacaaggccacactagt gtgtctgatcagtgacttcacccgggagctgtgacagtggcctggaaggcagatggcagcccgtcaaggcg gagtggacgacgaatccaaacctcaaaacagaacacaaagtaccagctcagcagcctacctgagctgacg ccgagcagtggaagtcccacagaagctacagctgccaggtcacgcatcagcgagcaccgtgagaagac agtggcccctacagaatgttca |

-continued

SEQUENCE LISTING

| SEQ ID NO: | | SEQUENCE LISTING | |
|---|---|---|---|
| 146 | Cλ Light Chain Constant Region Amino Acid Sequence | | PKANPTVTLFPPSSEELQANKATLVCLISDFYPGAVTVAWKADGSPVK AGVETTKPSKQSNNKYAASSYLSLTPEQWKSHRSYSCQVTHEGSTVEK TVAPTECS |
| 147 | Human Cλ constant region | IGCλ Cλ Light Chain Constant Region 1*02 Nucleotide Sequence | ggtcagcccaaggcccaacccactgtcactctgttcccgccctcctctgaggagctcactctgtca actagtgtctgatcagtgaccctctaccgggagctgtgacagtggcctgaaggcagatgcagccccgtca aggcggagtggagaccacaaccctccaaacagagcaacaaagtacgcggccagctacctgagc ctgacgcccgagcagtggaagtcccacagaagctacagctgcccaggtcacgcatgaaggagcaccgtggca gaagacagtggcccctacagaatgttca |
| 148 | | Cλ Light Chain Constant Region Amino Acid Sequence | GQPKANPTVTLFPPSSEELQANKATLVCLISDFYPGAVTVAWKADGSP VKAGVETTKPSKQSNNKYAASSYLSLTPEQWKSHRSYSCQVTHEGSTV EKTVAPTECS |
| 149 | Human Cλ constant region | IGCλ Cλ Light Chain Constant Region 2*01 Nucleotide Sequence - Version A | ggtcagcccaaggccaacccactgtcactctgttcccgccctcctctgaggagctcactctgtca actagtgtctgatcagtgaccctctaccgggagctgtgacagtggcctgaaggcagatgcagccccgtca aggcggagtggagaccacaaccctccaaacagagcaacaaagtacgcggccagctacctgagc ctgacgcccgagcagtggaagtcccacagaagctacagctgcccaggtcacgcatgaaggagcaccgtgga gaagacagtggcccctacagaatgttca |
| 150 | | Cλ Light Chain Constant Region Nucleotide Sequence - Version B | ggccagcctaaggccgctcttctgtgaccctgtcccccatcctcgaggagctgttgacctcgaggaactgaggctgaggctgataggcctctctgtgaa cctctgtgctgcctgatcagcgactctaccctggccgtcgatcagcgactctaccctggccgtcgatagctctctgtaa ggccggcgtggaaaccaccacccctccaagcagtccaacagtcctacagtcctacagtgcccaagcagtccaacaaatacgccgctcctcctacttgtccctga cccctgaacgtggaagtcccacgtctactctgtcaggtgaccccacgaggtcccaccgaggtcaccgtgaaaga cgtcgccccccaccgagtgctcc |
| 151 | | Cλ Light Chain Constant Region Nucleotide Sequence - Version C | ggccagcctaaagctgccccagtgccctaacctaaacctcaccctctgaccctcccccccagcgaggagctcaggcagctcaagtccccaaggccagccga ccctcgtgtgcctgatctccgaattctatccggcgtgaccgtgccctggaaagccgactcagcctgctcaatacgccgcctcagctatctcctg acccctgagcagtggaagtcccactctactctgtcagtggtgaccccacgaggtcccaccgaggtccaccgaggtcaccgtgaaaga cgtcgccccccaccgagtgctcc |
| 152 | | Cλ Light Chain Constant Region Amino Acid Sequence - Encoded by Version A, B & C | GQPKANPTVTLFPPSSEELQANKATLVCLISDFYPGAVTVAWKADGSP VKAGVETTKPSKQSNNKYAASSYLSLTPEQWKSHRSYSCQVTHEGSTV EKTVAPTECS |
| 153 | Human Cλ constant region | IGCλ Cλ Light Chain Constant Region 2*02 Nucleotide Sequence | ggtcagcccaaggctgccccctgtcactctgttcccgccctcctctgaggagcttcaagccaacaaggccac actgtgtctcataagtgacttctaccgggagctgcttgaaggcagatagcagccccgtca aggcggagtggagaccaccacctccaaacaagctaacaacaaaagtacgcggccagctatctgagc ctgacgcccgagcagtggaagtcccaagaagctacagctgcccaggtcacgcatgaaggagcaccgtgagc aagacagtggcccctacagaatgttca |
| 154 | | Cλ Light Chain Constant Region Amino Acid Sequence | GQPKAAPSVTLFPPSSEELQANKATLVCLISDFYPGAVTVAWKADSSPV KAGVETTPSKQSNNKYAASSYLSLTPEQWKSHIRSYSCQVTHEGSTVE KTVAPTECS |

| SEQ ID NO: | | SEQUENCE LISTING |
|---|---|---|
| 155 | Human Cλ constant region | IGCλ Cλ Light Chain Constant Region 3*01 Nucleotide Sequence | cccaaggtgccccctcgtcactctgttcccaccctcctctgaggagcttcaagccaacaaggccacactgtg tgtccataagtgacttctacccggagcgtgacagtgcctgaagcagcagatagcagccccgtcaaggcggg ggtggagaccaacaaggcacccccaaaagtacagcctgccaggtccacgcatgaaggggagtcagtcacagtgacgcc tgacagtggaagtccacagctacagctgccaggtcacgcatgaaggggagcaccgtggagaagacagt tgccctacggaatgttca |
| 156 | | Cλ Light Chain Constant Region Amino Acid Sequence | PKAAPSVTLFPPSSEELQANKATLVCLISDFYPGAVTVAWKADSSPVKA GVETTTPSKQSNNKYAASSYLSLTPEQWKSHKSYSCQVTHEGSTVEKT VAPTECS |
| 157 | Human Cλ constant region | IGCλ Cλ Light Chain Constant Region 3*02 Nucleotide Sequence | ggtcagcccaaggctgcccctcggtcactctgttcccaccctcctctgaggagcttcaagccaacaaggccac actgtgtctcataagtgacttctacccggcgcagtgacagtgcctgaaggcagtagcagccccgtcaa gcggggtggagaccaacaaggcacccccaaacaagtacaacaaagtacagcctgccaggtcacgcgccagagctacctgagcc tgacgcctgagcagtggaagtccacaagtacgcctgccaggtcacgcatgaaggggagcaccgtggaga agacagtgcccctacggaatgttca |
| 158 | | Cλ Light Chain Constant Region Amino Acid Sequence | GQPKAAPSVTLFPPSSEELQANKATLVCLISDFYPGAVTVAWKADSSPV KAGVETTTPSKQSNNKYAASSYLSLTPEQWKSHKSYSCQVTHEGSTVE KTVAPTECS |
| 159 | Human Cλ constant region | IGCλ Cλ Light Chain Constant Region 3*03 Nucleotide Sequence | ggtcagcccaaggctgcccctcggtcactctgttcccaccctcctctgaggagcttcaagccaacaaggccacgtca actgtgtctcataagtgacttctacccggagcagtgacagtgcctgaaggcctgaaggcagtagcagccccgtca agcgggagtggagaccaacaagcaacaccccaaacaagcaacaaagtacgcgccagcagagctactgagc ctgacgcctgagcagtggaagtccacaagctacagctgccaggtcacgctgccaggtcacgtgaaggggagcaccgtggag aagacagtggcccctacagaatgttca |
| 160 | | Cλ Light Chain Constant Region Amino Acid Sequence | GQPKAAPSVTLFPPSSEELQANKATLVCLISDFYPGAVTVAWKADSSPV KAGVETTTPSKQSNNKYAASSYLSLTPEQWKSHKSYSCQVTHEGSTVE KTVAPTECS |
| 161 | Human Cλ constant region | IGCλ Cλ Light Chain Constant Region 3*04 Nucleotide Sequence | ggtcagcccaaggctgcccctcggtcactctgttcccgccctcctctgaggagcttcaagccaacaaggccac actgtgtctcataagtgacttctacccggagcagtgacagtgcctgaaggcctgaaggcagtagcagccccgtca agcgggagtggagaccaacaagcaacaccccaaacaagcaacaaagtacgcgccagcagagctactgagc ctgacgcctgagcagtggaagtccacaagctacagctgccaggtcacgctgccaggtcacgtgaaggggagcaccgtggag aagacagtgcccctacagaatgttca |
| 162 | | Cλ Light Chain Constant Region Amino Acid Sequence | GQPKAAPSVTLFPPSSEELQANKATLVCLISDFYPGAVTVAWKADSSPV KAGVETTTPSKQSNNKYAASSYLSLTPEQWKSHKSYSCQVTHEGSTVE KTVAPTECS |
| 163 | Human Cλ constant region | IGCλ Cλ Light Chain Constant Region 6*01 Nucleotide Sequence | ggtcagcccaaggctgcccatggtcactctgttcccgccctcctctgaggagcttcaagccaacaaggccac actgtgtgcctgatcagtgacttctacccggagctgggaagtggtgaaggcctgaaggcagtagcagccccgtca acacggagtggagaccaacaaccacccaaacagaagcaaaaccagaagtacgcgccagcagagctacctgagc ctgacgcccgagcagtggaagtccacagagctacagctgccaggtcacgctgccaggtcacgtgaaggggagcaccgtggag aagacagtgcccctgcagaatgttca |

| SEQ ID NO: | | SEQUENCE LISTING |
|---|---|---|
| 164 | Cλ Light Chain Constant Region Amino Acid Sequence | GQPKAAPSVTLFPPSSEELQANKATLVCLISDFYPGAVKVAWKADGSP VNTGVETTTPSKQSNNKYAASSYLSLTPEQWKSHRSYSCQVTHEGSTV EKTVAPAECS |
| 165 | Human Cλ constant region IGCλ Cλ Light Chain Constant Region 7*02 Nucleotide Sequence | ggtcagcccaaggctgccccatcgtcactctgttcccaccctctgaggagcttcaagccaacaaggccac actgtgtgtctgtaagtgacttctacccgggagccgtgacagtggcctgaaggcagatggcagccccgtca aggtggagtggagaccaccaaacctccaaacaaagctacacagtgcaagctgcggcctgaaggaagccac tgacgcccgagcagtggaagtccacagaagctacagctgccggtcaccgtgacccgagccgtgaggagcaccgtggag aagacagtggcccctgcagaatgctct |
| 166 | Cλ Light Chain Constant Region Amino Acid Sequence | GQPKAAPSVTLFPPSSEELQANKATLVCLVSDFYPGAVTVAWKADGSP VKVGVETTKPSKQSNNKYAASSYLSLTPEQWKSHRSYSCRVTHEGSTV EKTVAPAECS |
| 167 | Recombinant Human OX40L (Leader sequence, Isoleucine Zipper and FLAG Sequence Included) Nucleotide Sequence | ATGGGCTGGTCCTGCATCATCCTGTTTCTGGTGGCCACCGCCACCGG CGTGCACAGCGATTACAAGGATGACGACGATAAGCGTATGAAACA GATCGAAGATAAAATTGAAGAGATCTTGAGCAAAATCTATCATATC GAAAACGAAATTGCCCGTATCAAAAAGCTGATTGCGCAGGTGCAGGAT GGTGGCAGCGGTGGCGGTGGCTAGCGCGGTGGCAGCGGTGTCCACC GATACCCCAGGATCCAGTCCATCAAGGTCCAGTTCACCGAGTACAA AAAGGAGGAGGGATTCATCCTGACCTCCCAAAAGGAGGAGCAGAT CATGAAGGTGCAAAACAACTCCGTGATCATCAACTGCGACGGCTTC TACCTGATCTCCCTGAAGGGCTACTTCTCCCAGAGGTGAACATCTC CCTGCACTACCAGAAGGACGAGGAGCCCCTGTTCCAGCTGACAAGG GTGAGGTCCGTGAATTCCCTGATGGTGGCCAGCCTGACCTACAAGG ACAAGGTCTACCTGAACGGCGCGGAGCTGATCCTGATCCATCAGAACCCC CTTCCATGTCAACGGCGGCGAGCTGATCCTGATCCATCAGAACCCC GGCGAGTTTTGCGTCCTG |
| 168 | Amino Acid Sequence | MGWSCIILFLVATATGVHSDYKDDDDKRMKQIEDKIEEILSKIYHIENEI ARIKKLIGERGGSGGGSGGSGGSQVSHRYPRIQSIKVQFTEYKKEKGFILT SQKEDEIMKVQNNSVIINCDGFYLISLKGYFSQEVNISLHYQKDEEPLFQ LKKVRSVNSLMVASLTYKDKVYLNVTTDNTSLDDFHVNGGELILIHQN PGEFCVL |
| 169 | Recombinant Rhesus OX40L (Leader sequence, FLAG and Isoleucine zipper included) Nucleotide Sequence | ATGGGCTGGTCCTGCATCATCCTGTTTCTGGTGGCCACCGCCACCGG CGTGCACAGCGATTACAAGGATGACGACGATAAGCGTATGAAACA GATCGAAGATAAAATTGAAGAGATCTTGAGCAAAATCTATCATATC GAAAACGAAATTGCCCGTATCAAAAAGCTGATTGCGCAGGTGCAGGAT GGTGGCAGCGGTGGCGGTGGCTAGCGCGGTGGCAGCGGTGTCCACC AATACCCCAGGATCCAGTCCATCAAGGTCCAGTTCACCGAGTACAA AAAGGAGGAGGGATTCATCCTGACCTCCCAAAAGGAGGAGCAGAT CATGAAGGTGCAAAACAACTCCGTGATCATCAACTGCGACGGCTTC TACCTGATCTCCCTGAAGGGCTACTTCTCCCAGAGGTGAACATCTC CCTGCACTACCAGAAGGACGAGGAGCCCCTGTTCCAGCTGACAAGG GTGAGGTCCGTGAATTCCCTGATGGTGGCCAGCCTGACCTACAAGG |

| SEQ ID NO: | | SEQUENCE LISTING |
|---|---|---|
| | | ACAAGGTCTACCTGAACGTGACCACCGACCAACACCAGCCTGACGA CTTCCATGTCAACGGCGGCGAGCTGATCCTGATCCATCAGAACCC GGCGAGTTTTGCGTCCTG |
| 170 | Amino Acid Sequence | MGWSCIILFLVATATGVHSDYKDDDDKRMKQIEDKIEEILSKIYHIENEI ARIKKLIGERGGSGGSGGSGGSGGSQVSHQYPRIQSIKVQFTEYKKEEGFILT SQKEDEIMKVQNNSVIINCDGFYLISLKGYFSQEVNISLHYQKDEEPLFQ LKKVRSVNSLMVASLTYKDKVYLNVTTDNTSLDDFHVNGGELILIHQN PGEPFCVL |
| 171 | Recombinant Human OX40R (Leader Sequence and Human Fc sequence included) Nucleotide Sequence | ATGGGCTGGTCCTGCATCATCCTGTTTCTGGTGGCCACCGCCACCGG CGTGCACAGCCTGCATTGCGTGGGCGACACCTATCCTCCAACGAC AGTTGCTGCCACGAGTGCAGGCCTGGAAACGCATGGTGAGCAGG TGCACCGGTCCAGAATACGTGTAGCCGTCTGCGGCCCGGCT TTTACAACGACGTGGTGTCCTCCAAGCCCTGCAAGCCCTGCACATG GTGCAACCTGCGTCCAGCAGGAGAGAAGCAGCTGCACAGCC ACCCAGGACACCGTCTGTAGGTGTAGGGCTGGCACCCAGCCTCTGG ACTCCTACAAGCCCGGCGTGGATTGCTCCTTGCCTGCACCAACTGTA TTCTCCCCTGGCCGGCAACCAGGCTTGCAAGCCCTGACCAACTGTA CCCTGGCCGGCAAGCATACCTGCAGCCTGCTTCCAACTCCTCGA CGCTATCTGCGAGGATAGGGACCCCCTGCCACACAACCCAGGAG ACACAGCCCCCTCCTGCTAGGCCCATCACAGTCCAACCACCGAAG CCTGGCCCAGGACATCCCAAGGCCCTTCCACCAGCCTGTGGAAGT GCCTGGAGGAAGGGCTGTGGCCATCCACACCTGTCCCCCTTGTCTCCTGA ACTGCTGGGCGGACCTTCCGTGTTCCCCCCAAAGCCCAAGG ACACCCTGATGATCTCCCGGACCCTGAAGTGACCTGCGGTGGTGT GGATGTGTCCACGAGGACCCTGAAGTGAAGTTCAATTGGTACGTG GACGGCGTGGAAGTGCAACGCCAAGACCAAGCCTAGAGAGGAA CAGTACAACTCCACCTACCGGGTGGTCCTGCTGACCGTCCTGCTGC ACCAGGATTGGCTGAACGGCAAGGAGTACAAGTGCAAGGTGTCCA ACAAGGCCCTGCCTGCCCCATCGAAAAGACCATCTCCAAGGCCAA GGGCAGCCCCGGAACCCAGGGTGTACACACTGCCCCCTAGCAGG GACGAGCTGACCAAGAACCAGGTGTCCCTGACCTGTCTGAAAG GCTTCTACCCCTCCGATATCGCCGTGGAATGGGAGTCCAACGGCCA GCCTGAGAACAACTACAAGACCACCCCCCCTGTGCTGGACTCCGAC GGCTCATTCTTCCTGTACAGCAAGCTGACAGTGACAAGTCCCGT GGCAGGGCAACCCTGTTCTCCCTGATGCACGAGGCCCT GCACAACCACTACACCCAGAAGTCCCTGTCCCTGAGCCCCTGA |
| 172 | Amino Acid Sequence | MGWSCIILFLVATATGVHSLHCVGDTYPSNDRCCHECRPGNGMVSRCS RSQNTVCRPCGPGFYNDVVSSKPCKPCTWCNLRSGSERKQLCTATQDT VCRCRAGTQPLDSYKPGVDCAPCPPGHFSPGDNQACKPWTNCTLAGK HTLQPASNSSDAICEDRDPPATQPQETQGPPARPITVQPTEAWPRTSQG PSTRPVEVPGGRAVAIEGRMDEPKSCDKHTCPPCPAPELLGGPSVFLF PPKPKDTLMISRTPEVTCVVVDVSHEDPEVKFNWYVDGVEVHNAKTK PREEQYNSTYRVVSVLTVLHQDWLNGKEYKCKVSNKALPAPIEKTISK |

SEQUENCE LISTING

| SEQ ID NO: | | SEQUENCE LISTING |
|---|---|---|
| | | AKGQPREPQVYTLPPSRDELTKNQVSLTCLVKGFYPSDIAVEWESNGQ PENNYKTTPPVLDSDGSFFLYSKLTVDKSRWQQGNVFSCSVMHEALH NHYTQKSLSLSP |
| 173 Cell Expressed OX4OL (CHO/MEF) (Leader sequence included) | Nucleotide Sequence | ATGGAGAGGTGCAGCCCCTCGAGGAGAACGTGGAAACGCCGCC AGGCCTAGGTTCGAGAGGAACAAGTGCTGCTGGTGGCTTCCGTGA TCCAAGGACTCGGCCTGCTCTGCTTCACCTACATCTGCCTCCAC TTCAGCGCCCTGCAGGTGTCCACCGATACCCCAGGATCCAGTCCA TCAAGGTCCAGTTCACCGAGTACAAAAAGGAGAAGGGATTCATCCT GACCTCCCAAAAGGAGACGAGATCATGAAGGTGCAAAACAACTC CGTGATCATCAACTGCGACGGCTTCTACCTGATCTCCCTGAAGGGCT ACTTCTCCAGGAGGTGAACATTCCCTGCACTACCAGAAGGACGA GGAGCCCCTGTTCCAGCTGAAGAAGGTGAGGTCCGTGAATTCCTG ATGGTGGCCAGCCTGACCTACAAGGACAAGGTCTACCTGAACGTGA CCACCGACAACACCAGCCTGGACGACTTCCATGTCAACGGCGCGA GCTGATCCTGATCCATCAGAACCCCGGCAGTTTGCGTCCTGTAA |
| 174 | Amino Acid Sequence | MERVQPLEENVGNAARPRFERNKLLLVASVIQLGLGLLLCFTYICLHFSA LQVSHRYPRIQSIKVQFTEYKKEKGFILTSQKEDEIMKVQNNSVIINCDG FYLISLKGYFSQEVNISLHYQKDEEPLFQLKKVRSVNSLMVASLTYKDK VYLNVTTDNTSLDDFHVNGGELILIHQNPGEFC |
| 175 Cell Expressed OX40 receptor (HT1080) | Nucleotide Sequence | ATGTGCGTGGGGCTCGGCGGCTCGGGCCCGGGGCCTGTGCGGCTC TGCTCCTCCTGGGCCTGGGCTGAGCACCCTGACGCGGGGCTCCACTG TGTCGGGGACACCTACCCCAGCAACGACCGGTGCTGCCACGAGTGC AGGCCAGGCAACGGGATGTGAGCCGCTGCAGCCGCTCCCAGAAC ACGGTGTGCGTCCGTCGGCGGCCGGGCTTCTACAACGACGTGGTCA GCTCCAAGCCGTGCAAGCCCTGCACGTGGTGTAACCTCAGAAGTGG GAGTGAGCCGGAAGCAGCTGTGCACGGCCACACAGGACACAGTCTG CCGCTGCCGGGCGGGCCCAGCCCTGCACCTCCAGGCACTTCTCCCAGGCGACAA GTTGCACTGTGCCCCTGCCCCAGCCAACTGCACCTTGCTGGGAAGCAC ACCCTGCAGCCGGCCAGCAATAGCTCGACGCAATCTGTGAGGACA GGGACCCCCAGCCACGCAGCCCCAGGAGACCCAGGGCCCCGG CCAGCCCATCACTGTCCAGCCCACTGAAGCTGCCCAGAACCTC ACAGGGACCCCTCCACCGGCCTGGAGGTCCCCGGGGCCGTGCG GTTGCCGCCATCCTGGCCTGGCCCTGTACCTGCTCCGGAGGACCAGAG CCTGCCCATCCTGCGATGCCCACAGCCCCTGGGGAGGCAGTTTCCGG ACCCCATCCAAGAGGAGCAGGCCCACGCCCACTCCACCCTGGCCA AGATCTGA |
| 176 | Amino Acid Sequence | MCVGARRLGRGPCAALLLGLGLSTVTGLHCVGDTYPSNDRCCHECR PGNGMVSRCSRSQNTVCRPCGPGFYNDVVSSKPCKPCTWCNLRSGSER KQLCTATQDTVCRCRAGTQPLDSYKPGVDCAPCPPGHFSPGDNQACK |

| SEQ ID NO: | | SEQUENCE LISTING |
|---|---|---|
| | | PWTNCTLAGKHTLQPASNSSDAICEDRDPPATQPQETQGPPARPITVQP TEAWPRTSQGPSTRPVEVPGGRAVAAILGLGLVIGLLGPLAILLALYLL RRDQRLPPDAHKPPGGGSFRTPIQEEQADAHSTLAKI |
| 177 | OX40L15B07 Amino Acid Sequence of OX40L15B07 (Seq ID No 179 in WO2011/073180, Table A-1) | EVQLVESGGGLVQAGGSLRLSCAASRSIGRLDRMGWYRHRTGEPREL VATITGGSSINYGDFVKGRFTISIDNAKNTVYLQMNNLKPEDTAVYYC NFNKYVTSRDTWGQGTQVTVSS |
| 178 | OX40L01B11 Amino Acid Sequence of OX40L01B11 (Seq ID No 180 in WO2011/073180, Table A-1) | EVQLVESGGGLVQAGGSLRLSCVASGRSFSTYIMGWFRQAPGKEREFV ATISRSGIITRSADSVKGRFTISRDNAKNTVYLQMNSLKPEDTAVYYCA AGPYVEQTLGLYQTLGPWDYWGQGTQVTVSS |
| 179 | OX40L01E07 Amino Acid Sequence of OX40L01E07 (Seq ID No 181 in WO2011/073180, Table A-1) | EVQLVESGGGLVQAGGSLRLSCAASGRTFSSIYAKGWFRQAPGKEREF VAAISRGRSTSYADSVKGRFTISRDNAKNTVYLQMNSLKPEDTAVYY CAAVCGATTVTASEWDYWGLGTQVTVSS |
| 180 | OX40L01E10 Amino Acid Sequence of OX40L01E10 (Seq ID No 182 in WO2011/073180, Table A-1) | EVQLVESGGGLVQAGDSLRLSCAASGLTFSSFAMGWFRQAPGKEREF VAAISRGYGTSEADSVRDRFIISRDNAKNTVTLHLSRLKPEDTAVYYC AAEHTLGRPSRSQINYLYWGQGTQVTVSS |
| 181 | OX40L18E09 Amino Acid Sequence of OX40L18E09 (Seq ID No 183 in WO2011/073180, Table A-1) | EVQLVESGGGLVQAGGSLRLSCAASRNILSLNTMGWYRHAPGKPREL VARISSNSKTDYADSVKGRFTISRDNAKNTVLLQMNSLKPEDTGVYYC NLNVWRTSSDYWGQGTQVTVSS |
| 182 | OX40L19A07 Amino Acid Sequence of OX40L19A07 (Seq ID No 184 in WO2011/073180, Table A-1) | EVQLVESGGGLVQAGGSLRLSCAASGFTLDDYAIAWFRQAPGKEREG VSRIKISNGRTTYAGSVKGRFTISSDNAKNTVYLQMNSLNAEDTAVYY CAADRSSLLFGSNWDRKARYDYWGQGTQVTVSS |
| 183 | OX40L19D08 Amino Acid Sequence of OX40L19D08 (Seq ID No 185 in WO2011/073180, Table A-1) | EVQLVESGGGLVQAGASLRLSCAASGRRFISNYAMGWFRQAPGQERA FVAAISRSGSITYYTDSVKGRFSIRDYAKSTVVLQMDNLKPEDTAVYY CAADGGAVRDLTTNLPDYWGRGTQVTVSS |
| 184 | OX40L075 Amino Acid Sequence of OX40L075 (Seq ID No 199 in WO2011/073180, Table A-2) | EVQLVESGGGLVQPGGSLRLSCAASGRSFSTYIMGWFRQAPGKEREFV ATISRSGIITRSADSVKGRFTISRDNSKNTVYLQMNSLRPEDTAVYYCA AGPYVEQTLGLYQTLGPWDYWGQGTLVTVSS |
| 185 | OX40L024 Amino Acid Sequence of OX40L024 (Seq ID No 200 in WO2011/073180, Table A-2) | EVQLVESGGG LVQPGGSLRLSCAASG RTFSSIYAKGWFRQAPG KERE FV AAISRSG RSTSYADSVKG RFTISRD NAKNTVYLQM NSLRPEDTAVYYCAA VGGATTVTASEWDYWGLGTLVTVSS |
| 186 | OX40L025 Amino Acid Sequence of OX40L025 (Seq ID No 201 in WO2011/073180, Table A-2) | EVQLVESGGG LVQPGGSLRLSCAASG RTFSSIYAKGWFRQAPG KERE FV AAISRSG RSTSYADSVKG RFTISRD NSKNTVYLQM NSLRPEDTAVYYCAA VGGATTVTASEWDYWGLGTLVTVSS |

-continued

| SEQ ID NO: | | SEQUENCE LISTING |
|---|---|---|
| 187 | OX40L026 Amino Acid Sequence of OX40L026 (Seq ID No 202 in WO2011/073180, Table A-2) | EVQLVESGGG LVQPGGSLRLSCAASG RTFSSIYAKGWFRQAPG KERE FV AAISRSG RSTSYADSVKG RFTISRD NAKNTVYLQM NSLRPEDTAVYYCAA VGGATTVTASEWDYWGQGTLVTVSS |
| 188 | OX40L027 Amino Acid Sequence of OX40L027 (Seq ID No 203 in WO2011/073180, Table A-2) | EVQLVESGGG LVQPGGSLRLSCAASG RTFSSIYAKGWFRQAPG KERE FV AAISRSG RSTSYADSVKG RFTISRDNSKNTVYLQM NSLRPEDTAVYYCAA VGGATTVTASEWDYWGQGTLVTVSS |
| 189 | OX40L028 Amino Acid Sequence of OX40L028 (Seq ID No 204 in WO2011/073180, Table A-2) | DVQLVESGGG LVQPGGSLRLSCAASG RTFSSIYAKGWFRQAPG KEREFV AAISRSG RSTSYADSVKG RFTISRD NAKNTVYLQM NSLRPEDTAVYYCAA VGGATTVTASEWDYWGLGTLVTVSS |
| 190 | OX40L039 Amino Acid Sequence of OX40L039 (Seq ID No 205 in WO2011/073180, Table A-2) | LVQLVESGG LVQPGGSLRLSCAASG RTFSSIYAKGWFRQAPG KERE FV AAISRSG RSTSYADSVKG RFTISRD NSKNTVYLQM NSLRPEDTAVYYCAA VGGATTVTASEWDYWGQGTLVTVSS |
| 191 | OX40L030 Amino Acid Sequence of OX40L030 (Seq ID No 206 in WO2011/073180, Table A-2) | DVQLVESGGGLVQAGGSLRLSCAASRSIGRLDRMGWYRHRTGEPREL V ATITGGSSINYG D FVKG RFTISID NAKNTVYLQM N N LKPEDTAVYYCN FN KYVTSRDTWGQGTQVTVSS |
| 192 | OX40L040 Amino Acid Sequence of OX40L040 (Seq ID No 207 in WO2011/073180, Table A-2) | DVQLVESGGGLVQPGGSLRLSCAASRSIGRLDRMGWYRHRTGEPREL V ATITGGSSINYG D FVKG RFTISRDNSKNTVYLQM NSLRPEDTAVYYCN FN KYVTSRDTWGQGTLVTVSS |
| 193 | OX40L041 Amino Acid Sequence of OX40L041 (Seq ID No 208 in WO2011/073180, Table A-2) | DVQLVESGGGLVQPGGSLRLSCAASRSIGRLDRMGWYRHATGEPREL V ATITGGSSINYG D FVKG RFTISRDNSKNTVYLQM NSLRPEDTAVYYCN FN KYVTSRDTWGQGTLVTVSS |
| 194 | OX40L042 Amino Acid Sequence of OX40L042 (Seq ID No 209 in WO2011/073180, Table A-2) | DVQLVESGGGLVQPGGSLRLSCAASRSIGRLDRMGWYRHPGEPREL V |

| SEQ ID NO: | | SEQUENCE LISTING |
|---|---|---|
| | 2) | ATITGGSSINYG D FVKG RFTISRDNSKNTVLQM NSLRPEDTAVYYCN FN KYVTSRDTWGQGTLVTVSS |
| 195 OX40L043 | Amino Acid Sequence of OX40L043 (Seq ID No 210 in WO2011/073180, Table A-2) | DVQLVESGGGLVQPGGSLRLSCAASRSIGRLDRMGWYRHRTGKPREL V ATITGGSSINYG D FVKG RFTISRDNSKNTVLQM NSLRPEDTAVYYCN FN KYVTSRDTWGQGTLVTVSS |
| 196 OX40L044 | Amino Acid Sequence of OX40L044 (Seq ID No 211 in WO2011/073180, Table A-2) | DVQLVESGGGLVQPGGSLRLSCAASRSIGRLDRMGWYRHAPGEPREL V ATITGGSSINYG D FVKG RFTISRDNSKNTVLQM NSLRPEDTAVYYCN FN KYVTSRDTWGQGTLVTVSS |
| 197 OX40L045 | Amino Acid Sequence of OX40L045 (Seq ID No 212 in WO2011/073180, Table A-2) | DVQLVESGGG LVQPGGSLRLSCAASRSIG RLD RMGWYRHATG KPRE LV ATITGGSSINYG D FVKG RFTISRDNSKNTVLQM NSLRPEDTAVYYCN FN KYVTSRDTWGQGTLVTVSS |
| 198 OX40L046 | Amino Acid Sequence of OX40L046 (Seq ID No 213 in WO2011/073180, Table A-2) | DVQLVESGGGLVQPGGSLRLSCAASRSIGRLDRMGWYRHRPGKPREL V ATITGGSSINYG D FVKG RFTISRDNSKNTVLQM NSLRPEDTAVYYCN FN KYVTSRDTWGQGTLVTVSS |
| 199 OX40L047 | Amino Acid Sequence of OX40L047 (Seq ID No 214 in WO2011/073180, Table A-2) | DVQLVESGGGLVQPGGSLRLSCAASRSIGRLDRMGWYRHAPGKPREL V ATITGGSSINYG D FVKG RFTISRDNSKNTVLQM NSLRPEDTAVYYCN FN KYVTSRDTWGQGTLVTVSS |
| 200 OX40L048 | Amino Acid Sequence of OX40L048 (Seq ID No 215 in WO2011/073180, Table A-2) | DVQLVESGGGLVQPGGSLRLSCAASRSIGRLDRMGWYRHRTGEPREL V ATITGGSSINYADFVKG RFTISRD NSKNTVLQM NSLRPEDTAVYYCN FN KYVTSRDTWGQGTLVTVSS |
| 201 OX40L049 | Amino Acid Sequence of OX40L049 (Seq ID No 216 in WO2011/073180, Table A-2) | DVQLVESGGGLVQPGGSLRLSCAASRSIGRLDRMGWYRHRTGEPREL V ATITGGSSINYG DSVKG RFTISRDNSKNTVLQM NSLRPEDTAVYYCN FN KYVTSRDTWGQGTLVTVSS |

| SEQ ID NO: | | SEQUENCE LISTING |
|---|---|---|
| 202 OX40L050 | Amino Acid Sequence of OX40L050 (Seq ID No 217 in WO2011/073180, Table A-2) | DVQLVESGGGLVQPGGSLRLSCAASRSIGRLDRMGWYRHRTGEPREL V ATITGGSSINYADSVKG RFTISRD NSKNTVLQM NSLRPEDTAVYYCN FN KYVTSRDTWGQGTLVTVSS |
| 203 OX40L053 | Amino Acid Sequence of OX40L053 (Seq ID No 218 in WO2011/073180, Table A-2) | DVQLVESGGGLVQPGGSLRLSCAASRSIGRLDRMGWYRHRTGEPREL V ATITGGSSINYGDFVKGRFTISIDNSKNTVYLQM NSLRPEDTAVYYCN FNK YVTSRDTWGQGTLVTVSS |
| 204 OX40L054 | Amino Acid Sequence of OX40L054 (Seq ID No 219 in WO2011/073180, Table A-2) | DVQLVESGGGLVQPGGSLRLSCAASRSIGRLDRMGWYRHRTGEPREL V ATITGGSSINYG D FVKG RFTISRDNAKNTVYLQM NSLRPEDTAVYYCN FN KYVTSRDTWGQGTLVTVSS |
| 205 OX40L055 | Amino Acid Sequence of OX40L055 (Seq ID No 220 in WO2011/073180, Table A-2) | DVQLVESGGGLVQPGGSLRLSCAASRSIGRLDRMGWYRHRTGEPREL V ATITGGSSINYGDFVKGRFTISRDNSKNTVYLQM NN LRPEDTAVYYCN FN KYVTSRDTWGQGTLVTVSS |
| 206 OX40L056 | Amino Acid Sequence of OX40L056 (Seq ID No 221 in WO2011/073180, Table A-2) | DVQLVESGGGLVQPGGSLRLSCAASRSIGRLDRMGWYRHRPGKPREL V ATITGGSSINYADSVKG RFTISRD NSKNTVYLQM NSLRPEDTAVYYCN FN KYVTSRDTWGQGTLVTVSS |
| 207 OX40L069 | Amino Acid Sequence of OX40L069 (Seq ID No 222 in WO2011/073180, Table A-2) | DVQLVESGGGLVQPGGSLRLSCAASRSIGRLDRMGWYRHRPGKPREL V ATITGGSSINYADSVKG RFTISI DNSKNTVYLQM NSLRPE DTAVYYCN FN K YVTSRDTWGQGTLVTVSS |
| 208 OX40L070 | Amino Acid Sequence of OX40L070 (Seq ID No 223 in WO2011/073180, Table A-2) | DVQLVESGGGLVQPGGSLRLSCAASRSIGRLDRMGWYRHRPGKPREL V ATITGGSSINYADSVKG RFTISRD NSKNTVYLQM N N LRPEDTAVYYCN FN KYVTSRDTWGQGTLVTVSS |
| 209 OX40L071 | Amino Acid Sequence of OX40L071 (Seq ID No 224 in WO2011/073180, Table A-2) | DVQLVESGGGLVQPGGSLRLSCAASRSIGRLDRMGWYRHRPGKPREL V |

-continued

| SEQ ID NO: | | SEQUENCE LISTING |
|---|---|---|
| | 2) | ATITGGSSINYADSVKG RFTISI DNSKNTVYLQM N N LRPEDTAVYYCN FN KYVTSRDTWGQGTLVTVSS |
| 210 OX40L082 | Amino Acid Sequence of OX40L082 (Seq ID No 225 in WO2011/073180, Table A-2) | EVQLVESGGGLVQPGGSLRLSCAASRSIGRLDRMGWYRHRPGEPRELV A TITGGSSINYGDSVKGRFTISIDNSKNTVYLQM NSLRPEDTAVYYCNFNKY VTS RDTWGQGTLVTVSS |
| 211 OX40L083 | Amino Acid Sequence of OX40L083 (Seq ID No 226 in WO2011/073180, Table A-2) | EVQLVESGGGLVQPGGSLRLSCAASRSIGRLDRMGWYRHRPGKPREL V ATITGGSSINYGDSVKGRFTISIDNSKNTVYLQMNSLRPEDTAVYYCN FNK YVTSRDTWGQGTLVTVSS |
| 212 OX40L benchmark antibody heavy chain | Amino acid sequence of OX40L benchmark antibody heavy chain (Seq ID No: 177 in WO2011/073180, Table A-5) | EVQLLESGGGLVQPGGSLRLSCAASGFTFNSYAMSWVRQAPGKGLEW VSIISGSGG FTYYADSVKG RFTISRDNSRTTLYLQM NSLRAEDTAVYYCA KDRLVAPGTFDYWGQGALVTVSSASTKG PSVFPLAPSSKSTSGGTAALG CLVKDYFPEPVTVSWNSGALTSGVHTFPAVLQSSG LYSLSSVVTVPSSSL GTQTYICNVNH KPSNTKVDKKVEPKSCDKTHTCPPCPAPELLGGPSVFLF P PKPKDTLM ISRTPEVTCVVVDVSH E D P EVKFNWYVDGVEVH NAKTKP REEQYNSTYRVVSVLTVLHQDWLNG KEYKCKVSN KALPAPI EKTISKAKG QPREPQVYTLPPSRDELTKNQVSLTCLVKG FYPSDIAVEWESNGQPE N N YKTTPPVLDSDGSFFLYSKLTVD KSRWQQG NVFSCSVM H EALH N HYTQ KSLSLSPGK |
| 213 OX40L benchmark antibody light chain | Amino acid sequence of OX40L benchmark antibody light chain (Seq ID No: 178 in WO2011/073180, Table A-5) | DIQMTQSPSSLSASVGDRVTITCRASQGISSWLAWYQQKPEKAPKSLIY AASSLQSGVPSRFSGSGSGTDFTLTISSLQPED FATYYCQQYNSYPTFG QGTKLEIKRTVAAPSVFIFPPSD EQLKSGTASVVCLLN N FYPREAKVQWK VDNALQSG NSQESVTEQDSKDSTYSLSSTLTLSKADYEKH KVYACEVTH QGLSSPVTKSFNRGEC |
| 214 κ light chain variable region of LC.001 | Amino acid sequence of kappa light chain variable region of LC.001 (Seq ID No: 1 WO2006/029879) | DIQMTQSPSSLSASVGDRVTITCRASQGISSWLAWYQQKPEKAPKSLIY AASSLQSGVPSRFSGSGSGTDFTLTISSLQPEDFATYYCQQYNSYPTFG QGTKLEIK |

SEQUENCE LISTING

| SEQ ID NO: | | |
|---|---|---|
| 215 | γ heavy chain variable region of LC.001 | in Amino acid sequence of γ heavy chain variable region of LC.001 (Seq ID No: 2 in WO2006/029879) | EVQLLESGGGLVQPGGSLRLSCAASGFTFNSYAMSWVRQAPGKGLEW VSIISGSGGFTYYADSVKGRFTISRDNSRTTLYLQMNSLRAEDTAVYYC AKDRIVAPGTFDYWGQGALVTVSS |
| 216 | κ light chain variable region of LC.005 | Amino acid sequence of kappa light chain variable region of LC.005 (Seq ID No: 3 in WO2006/029879) | EIVLTQSPGTLSLSPGERATLSCRASQSVSSNYLAWYQQKPGQAPRLLI YGASSRATGIPDRFSGSGSGTDFTLTISRLEPEDFAVYYCQQYGSSFTFG PGTKVDIK |
| 217 | γ heavy chain variable region of LC.005 | Amino acid sequence of γ heavy chain variable region of LC.005 (Seq ID No: 4 in WO2006/029879) | QVQLVESGGGVVQPGRSLRLSCAASGFTFSNFGMHWVRQAPGKGLE WVAAIWYDGHDKYYSYYVKGRFTISRDNSKNTLFLQMNSLRAEDTAV YYCARDSSSWYRYFDYWGQGTLVTVSS |
| 218 | κ light chain variable region of LC.010 | Amino acid sequence of kappa light chain variable region of LC.010 (Seq ID No: 5 in WO2006/029879) | EIVLTQSPGTLSLSPGERATLSCRASQSVSSSYLAWYQQKPGQAPRLLIY GASSRATGIPDRFSGSGSGTDFTLTISRLEPEDFAVYYCQQYGSSFTFGP GTKVDIK |
| 219 | γ heavy chain variable region of LC.010 | Amino acid sequence of γ heavy chain variable region of LC.010 (Seq ID No: 6 in WO2006/029879) | QVQLVESGGGVVQPGRSLRLSCAASGFTFSNFGMHWVRQAPGKGLE WVAAIWYDGHDKYYAYYVKGRFTISRDNSKNTLFLQMNSLRAEDTA VYYCARDSSSWYRYFDYWGQGTLVTVSS |
| 220 | κ light chain variable region of LC.029 | Amino acid sequence of kappa light chain variable region of LC.029 (Seq ID No: 7 in WO2006/029879) | QVQLVESGGGVVQPGRSLRLSCAASGFTFSNFGMHWVRQAPGKGLE WVAAIWYDGHDKYYSYYVKGRFTISRDNSKNTLFLQMNSLRAEDTAV YYCARDSSSWYRYFDYWGQGTLVTVSS |
| 221 | γ heavy chain variable region of LC.029 | Amino acid sequence of γ heavy chain variable region of LC.029 (Seq ID No: 8 in WO2006/029879) | QVQLVESGGGVVQPGRSLRLSCAASGFTFSSYTMHWVRQAPGKGLEW VAVIWYDGSNKYYVDSVKGRFTISRDNSKNTLYLQMNSLRAEDTAVY YCARKNWSFDFWGQGTLVTVSS |
| 222 | κ light chain variable region of LC.019 | Amino acid sequence of kappa light chain variable region of LC.019 (Seq ID No: 9 in WO2006/029879) | EIVLTQSPATLSLSPGERATLSCRASQVSRYLAWYQQKPGQAPRLLIY DASNRATGIPARVSSGSGPGTDFTLTISSLEPEDFAVDYCQQRSNWQYTF GQGTKLEI |
| 223 | γ heavy chain variable region of LC.019 | Amino acid sequence of γ heavy chain variable region of LC.019 (Seq ID No: 10 in WO2006/029879) | QKQLVEFGGGVVQPGRSLRLSCAASGFTFSNYGMIHWVRQAPGKGLE WVAVIWNDGSNKYYVDSVKGRFIISRDNSKNTLYLQMNSLRAEDTAV YYCARDRMGIYYYGMDVWGQGTTVTVSS |
| 224 | κ light chain variable region of LC.033 | Amino acid sequence of kappa light chain variable region of LC.033 (Seq ID No: 11 in WO2006/029879) | EIVLTQSPATLSLSPGERATLSCRASQSVSSYLAWYQQKPGQAPRLLIY DASNRATGIPARFSGSGSGTDFTLTISSLEPEDFAVYYCQQRSNWTFGQ GTKVEI |
| 225 | γ heavy chain variable region of LC.033 | Amino acid sequence of γ heavy chain variable region of LC.033 (Seq ID No: 12 in WO2006/029879) | EVQLLESGGGLVQPGGSLRLSCAASGFTFNSYAMSWVRQAPGKGLEW VSIISGSGGFTYYADSVKGRFTISRDNSRTTLYLQMNSLRAEDTAVYYC AKDRIVAPGTFDYWGQGALVTVSS |
| 226 | mutant κ light chain variable | Amino acid sequence of mutant kappa light chain variable region of LC.033 | EIVLTQSPGTLSLSPGERATLSCRASQSVSSNYLAWYQQKPGQAPRLLI YGASSRATGIPDRFSGSGSGTDFTLTISRLEPEDFAVYYCQQYGSSFTFG |

-continued

SEQUENCE LISTING

| SEQ ID NO: | | |
|---|---|---|
| region of LC.033 | (Seq ID No: 16 in WO2006/029879) | PGTKVDIK |
| 227 γ heavy chain variable region of LC.059 | Amino acid sequence of γ heavy chain variable region of LC.059 (Seq ID No: 17 in WO2006/029879) | EVQLLESGGGLVQPGGSLRLSCAASGFTFSSYAMNWVRQAPGKGLEW VSIISGSGGFTYYADSVKGRFTISRDNSKNTLYLQMNRLRAEDTAIYFC AKDDIPAAGTFDPWGQGTLVTVSS |
| 228 κ light chain variable region of LC.060 | Amino acid sequence of kappa light chain variable region of LC.060 (Seq ID No: 18 in WO2006/029879) | AIQLTQSPSSLSASVGDRVTITCRASQGISSALAWYQQKPGKAPKLLIY DVSSLESGVPSRFSGSGSGTDFTLTISSLQPEDFATYYCQQFNSYWTFG QGTKVEIK |
| 229 γ heavy chain variable region of LC.060 | Amino acid sequence of γ heavy chain variable region of LC.060 (Seq ID No: 19 in WO2006/029879) | EVQLLESGGGLVQPGGSLRLSCAASGFTFSSYAMSWVRQAPGKGLEW VSLISGSGGLTKYADSVKGRFTISRDNSKRTLYLQMNSLRAEDTAVYY CAKDILVTGALDYWGQGTLVTVSS |
| 230 γ heavy chain variable region of LC.063 | Amino acid sequence of γ heavy chain variable region of LC.063 (Seq ID No: 20 in WO2006/029879) | EVQLLESGGGLVQPGGSLRLSCAASGFTFSSYAMNWVRQAPGKGLEW VSIISGSGGFTYYADSVKGRFTISRDNSKKTLYLQMSRLRAEDTAIYFC AKDDIPAAGTFDPWGQGTLVTVSS |
| 231 8E12 light chain variable region | Amino acid sequence of 8E12 light chain variable region (Seq ID No: 13 in U.S. Pat. No. 7,812,133) | DILMTQTPLSLPVSLGDQASISCRSSQSIVHGNGNTYLEWHLQKPGQSP KLLIYRVSNRFSGVPDRFSGSGSGTDFTLKINRVEAEDLGVYYCFQGSH VPYTFGGGTKVEIKR |
| 232 8E12 heavy chain variable region | Amino acid sequence of 8E12 heavy chain variable region (Seq ID No: 14 in U.S. Pat. No. 7,812,133) | DIVMTQTPLSLPVSLGDQASMYCRSSQSPVHSNGNTYLHWYLQKPGQS PKWYKVSNRFSGVPDRFSGSGSGTDFTLKISRVEAEDLGVYFCSQSTH IPWTFGGGTKVEIKR |
| 233 13G5 light chain variable region | Amino acid sequence of 13G5 light chain variable region (Seq ID No: 15 in U.S. Pat. No. 7,812,133) | QVQLQQPGAELVRPGASVKLSCKASGYTFTSYWLNWVKQRPGQGLE WIVMIDPSDSETHYNQVFKDKATLTVDKSSSTAYMQLSSLTSEDSAVY YCIRGRGNEYGGSHAMEYWGQGTLLTVSS |
| 234 13G5 heavy chain variable region | Amino acid sequence of 13G5 heavy chain variable region (Seq ID No: 16 in U.S. Pat. No. 7,812,133) | QVQLQQPGAELVKPGTSVKLSCKASGYSFTSYWMHGVRQRPGQGLE WIGEIDPSNGRTNYNEKFKSKATLTVDKSSSTAYIQLSSLTSEDSAVYY CTRERSPRYFDVWGAGTLLTVSS |

IMGT indicates that CDR is determined using IMGT nomenclature;
KABAT indicates that CDR is determined using Kabat nomenclature.
The numbering in the sequence correlation table takes precedence over any inconsistent numbering elsewhere in this text.

What is claimed herein is:

1. A method of treating or preventing graft versus host disease (GvHD) in a human subject in need thereof, comprising administering to the subject a therapeutically or prophylactically effective amount of:
   a. at least one anti-OX40L antibody or fragment thereof that antagonizes specific binding of OX40 to OX40L; and
   b. at least one mTOR inhibitor.

2. The method of claim 1, wherein the at least one anti-OX40L antibody or fragment thereof is administered at least one time before a transplant.

3. The method of claim 1, wherein the at least one anti-OX40L antibody or fragment thereof is administered at least one time after a transplant.

4. The method of claim 1, wherein the at least one mTOR inhibitor is administered at least one time after a transplant.

5. The method of claim 1, wherein the at least one mTOR inhibitor is administered at least one time before a transplant.

6. The method of claim 1, wherein the at least one anti-OX40L antibody or fragment thereof is administered at least one time before a transplant and at least one time after the transplant.

7. The method of claim 1, wherein the at least one mTOR inhibitor is administered at least one time before a transplant and at least one time after the transplant.

8. The method of claim 1, wherein the at least one anti-OX40L antibody or fragment thereof is administered at least one time before a transplant and the at least one mTOR inhibitor is administered at least one time after the transplant.

9. The method of claim 1, wherein the at least one mTOR inhibitor is administered at least one time before a transplant and the at least one anti-OX40L antibody or fragment thereof is administered at least one time after the transplant.

10. The method of claim 1, wherein the at least one anti-OX40L antibody or fragment thereof and the at least one mTOR inhibitor are administered at least one time before a transplant.

11. The method of claim 1, wherein the at least one anti-OX40L antibody or fragment thereof and the at least one mTOR inhibitor are administered at least one time after a transplant.

12. The method of claim 1, wherein the administration of the at least one anti-OX40L antibody or fragment thereof and the at least one mTOR inhibitor are continued at least until peripheral blood chimerism has been achieved in the human subject.

13. The method of claim 1, wherein the at least one anti-OX40L antibody or fragment thereof is administered at least one time before a transplant followed by once a week, bi-weekly or once a month administration of the same after the transplant; and wherein the at least one mTOR inhibitor is administered at least one time after the transplant.

14. The method of claim 1, wherein the at least one anti-OX40L antibody or fragment thereof is administered at least one time before a transplant followed by once a week, bi-weekly or once a month administration of the same after the transplant; and wherein the at least one mTOR inhibitor is administered daily after the transplant.

15. The method of claim 1, wherein the at least one anti-OX40L antibody or fragment thereof is humanized or human.

16. The method of claim 1, wherein the at least one anti-OX40L antibody or fragment thereof is selected from the group consisting of multispecific antibodies, bi-specific antibodies, single-chain Fv antibodies (scFv), camelized antibodies, Fab fragments, F(ab') fragments, disulfide-linked Fvs (sdFv), and epitope-binding fragments thereof.

17. The method of claim 1, wherein the at least one anti-OX40L antibody or fragment thereof competes for binding of OX40L with an antibody comprising the VH sequence of SEQ ID NO: 34 and the VL sequence of SEQ ID NO: 48.

18. The method of claim 1, wherein the at least one anti-OX40L antibody or fragment thereof comprises an HCDR3 of from 16 to 27 amino acids and derived from the recombination of a human VH gene segment, a human D gene segment, and a human JH gene segment; wherein the human JH gene segment is IGHJ6 or IGHJ6*02.

19. The method of claim 1, wherein the at least one anti-OX40L antibody or fragment thereof comprises a CDR selected from:
 a. the HCDR3 sequence of Seq ID No:40 or Seq ID No:46;
 b. the HCDR3 sequence of Seq ID No:8 or SEQ ID No:14;
 c. the HCDR3 sequence of Seq ID No:72 or Seq ID No:78;
 d. the HCDR3 sequence of Seq ID No:100 or Seq ID No:106;
 e. the HCDR3 sequence of an antibody having the variable region amino acid sequence of Seq ID No: 215, 217, 219, 221, 223, 225, 227, 229 or 230; and
 f. the HCDR3 sequence of an antibody having the variable region amino acid sequence of Seq ID No: 232 or 234.

20. The method of claim 1, wherein the at least one anti-OX40L antibody or fragment thereof comprises:
 a. the CDRs of Seq ID No:40 or Seq ID No:46 for CDRH3, SEQ ID No:38 or SEQ ID No:44 for CDRH2, SEQ ID No:36 or SEQ ID No:42 for CDRH1, SEQ ID No:50 or SEQ ID No:56 for CDRL1, SEQ ID No:52 or SEQ ID No:58 for CDRL2, and SEQ ID No:54 or SEQ ID No:60 for CDRL3;
 b. the CDRs of Seq ID No:8 or SEQ ID No:14 for CDRH3, SEQ ID No:6 or SEQ ID No:12 for CDRH2, SEQ ID No:4 or SEQ ID No:10 for CDRH1, SEQ ID No:18 or SEQ ID No:24 for CDRL1, SEQ ID No:20 or SEQ ID No:26 for CDRL2, and SEQ ID No:22 or SEQ ID No:28 for CDRL3;
 c. the CDRs of Seq ID No:72 or Seq ID No:78 for CDRH3, SEQ ID No:70 or SEQ ID No:76 for CDRH2, SEQ ID No:68 or SEQ ID No:74 for CDRH1, SEQ ID No:82 or SEQ ID No:88 for CDRL1, SEQ ID No:84 or SEQ ID No:90 for CDRL2, and SEQ ID No:86 or SEQ ID No:92 for CDRL3;
 d. the CDRs of Seq ID No:100 or Seq ID No:106 for CDRH3, SEQ ID No:98 or SEQ ID No:104 for CDRH2, SEQ ID No:96 or SEQ ID No:102 for CDRH1, SEQ ID No:110 or SEQ ID No:116 for CDRL1, SEQ ID No:112 or SEQ ID No:118 for CDRL2, and SEQ ID No:114 or SEQ ID No:120 for CDRL3;
 e. the heavy chain CDRs and the light chain CDRs of variable region amino acid sequences:
  i. SEQ ID NO: 215 and SEQ ID NO: 214;
  ii. SEQ ID NO: 217 and SEQ ID NO: 216;
  iii. SEQ ID NO: 219 and SEQ ID NO: 218;
  iv. SEQ ID NO: 221 and SEQ ID NO: 220;
  v. SEQ ID NO: 223 and SEQ ID NO: 222;
  vi. SEQ ID NO: 225 and SEQ ID NO: 224;
  vii. SEQ ID NO: 225 and SEQ ID NO: 226;
  viii. SEQ ID NO: 227 and SEQ ID NO: 214;
  ix. SEQ ID NO: 229 and SEQ ID NO: 228; or
  x. SEQ ID NO. 230 and SEQ ID NO: 214;
 f. the heavy chain CDRs and the light chain CDRs of variable region amino acid sequences:
  i. SEQ ID NO: 232 and SEQ ID NO: 231; or
  ii. SEQ ID NO: 234 and SEQ ID NO: 233;
 g. the VH and/or VL domains of Seq ID No:34 for VH and/or Seq ID No:48 for VL;
 h. the VH and/or VL domains of Seq ID No:2 for VH and/or Seq ID No:16 for VL;
 i. the VH and/or VL domains of Seq ID No:66 for VH and/or Seq ID No:80 for VL;
 j. the VH and/or VL domains of Seq ID No:94 for VH and/or Seq ID No:108 for VL;
 k. the VH domain and the VL domain of amino acid sequences:
  i. SEQ ID NO: 215 and SEQ ID NO: 214;
  ii. SEQ ID NO: 217 and SEQ ID NO: 216;
  iii. SEQ ID NO: 219 and SEQ ID NO: 218;
  iv. SEQ ID NO: 221 and SEQ ID NO: 220;
  v. SEQ ID NO: 223 and SEQ ID NO: 222;
  vi. SEQ ID NO: 225 and SEQ ID NO: 224;
  vii. SEQ ID NO: 225 and SEQ ID NO: 226;
  viii. SEQ ID NO: 227 and SEQ ID NO: 214;
  ix. SEQ ID NO: 229 and SEQ ID NO: 228; or
  x. SEQ ID NO: 230 and SEQ ID NO: 214; or
 l. the VH domain and the VL domain of amino acid sequences:

i. SEQ ID NO: 232 and SEQ ID NO: 231; or
ii. SEQ ID NO: 234 and SEQ ID NO: 233.

21. The method of claim 1, wherein the at least one anti-OX40L antibody or fragment thereof comprises the VH sequence of SEQ ID No:215 and the VL sequence of SEQ ID No:214.

22. The method of claim 1, wherein the at least one anti-OX40L antibody or fragment thereof is oxelumab.

23. The method of claim 1, wherein the at least one anti-OX40L antibody or fragment thereof is administered at least one time before a transplant and at least one time after the transplant and the at least one mTOR inhibitor is administered at least one time before a transplant and at least one time after the transplant.

24. A method of treating or preventing transplant rejection in a human subject in need thereof, comprising administering to the subject a therapeutically or prophylactically effective amount of:
  a. at least one anti-OX40L antibody or fragment thereof that antagonizes specific binding of OX40 to OX40L; and
  b. at least one mTOR inhibitor.

25. The method of claim 24, wherein the at least one anti-OX40L antibody or fragment thereof is administered at least one time before a transplant and at least one time after the transplant and the at least one mTOR inhibitor is administered at least one time before a transplant and at least one time after the transplant.

26. The method of claim 24, wherein the at least one anti-OX40L antibody or fragment thereof is humanized or human.

27. The method of claim 24, wherein the at least one anti-OX40L antibody or fragment thereof comprises:
  a. the CDRs of Seq ID No:40 or Seq ID No:46 for CDRH3, SEQ ID No:38 or SEQ ID No:44 for CDRH2, SEQ ID No:36 or SEQ ID No:42 for CDRH1, SEQ ID No:50 or SEQ ID No:56 for CDRL1, SEQ ID No:52 or SEQ ID No:58 for CDRL2, and SEQ ID No:54 or SEQ ID No:60 for CDRL3;
  b. the CDRs of Seq ID No:8 or SEQ ID No:14 for CDRH3, SEQ ID No:6 or SEQ ID No:12 for CDRH2, SEQ ID No:4 or SEQ ID No:10 for CDRH1, SEQ ID No:18 or SEQ ID No:24 for CDRL1, SEQ ID No:20 or SEQ ID No:26 for CDRL2, and SEQ ID No:22 or SEQ ID No:28 for CDRL3;
  c. the CDRs of Seq ID No:72 or Seq ID No:78 for CDRH3, SEQ ID No:70 or SEQ ID No:76 for CDRH2, SEQ ID No:68 or SEQ ID No:74 for CDRH1, SEQ ID No:82 or SEQ ID No:88 for CDRL1, SEQ ID No:84 or SEQ ID No:90 for CDRL2, and SEQ ID No:86 or SEQ ID No:92 for CDRL3;
  d. the CDRs of Seq ID No:100 or Seq ID No:106 for CDRH3, SEQ ID No:98 or SEQ ID No:104 for CDRH2, SEQ ID No:96 or SEQ ID No:102 for CDRH1, SEQ ID No:110 or SEQ ID No:116 for CDRL1, SEQ ID No:112 or SEQ ID No:118 for CDRL2, and SEQ ID No:114 or SEQ ID No:120 for CDRL3;
  e. the heavy chain CDRs and the light chain CDRs of variable region amino acid sequences:
    i. SEQ ID NO: 215 and SEQ ID NO: 214;
    ii. SEQ ID NO: 217 and SEQ ID NO: 216;
    iii. SEQ ID NO: 219 and SEQ ID NO: 218;
    iv. SEQ ID NO: 221 and SEQ ID NO: 220;
    v. SEQ ID NO: 223 and SEQ ID NO: 222;
    vi. SEQ ID NO: 225 and SEQ ID NO: 224;
    vii. SEQ ID NO: 225 and SEQ ID NO: 226;
    viii. SEQ ID NO: 227 and SEQ ID NO: 214;
    ix. SEQ ID NO: 229 and SEQ ID NO: 228; or
    x. SEQ ID NO: 230 and SEQ ID NO: 214;
  f. the heavy chain CDRs and the light chain CDRs of variable region amino acid sequences:
    i. SEQ ID NO: 232 and SEQ ID NO: 231; or
    ii. SEQ ID NO: 234 and SEQ ID NO: 233;
  g. the VH and/or VL domains of Seq ID No:34 for VH and/or Seq ID No:48 for VL;
  h. the VH and/or VL domains of Seq ID No:2 for VH and/or Seq ID No:16 for VL;
  i. the VH and/or VL domains of Seq ID No:66 for VH and/or Seq ID No:80 for VL;
  j. the VH and/or VL domains of Seq ID No:94 for VH and/or Seq ID No:108 for VL;
  k. the VH domain and the VL domain of amino acid sequences:
    i. SEQ ID NO: 215 and SEQ ID NO: 214;
    ii. SEQ ID NO: 217 and SEQ ID NO: 216;
    iii. SEQ ID NO: 219 and SEQ ID NO: 218;
    iv. SEQ ID NO: 221 and SEQ ID NO: 220;
    v. SEQ ID NO: 223 and SEQ ID NO: 222;
    vi. SEQ ID NO: 225 and SEQ ID NO: 224;
    vii. SEQ ID NO: 225 and SEQ ID NO: 226;
    viii. SEQ ID NO: 227 and SEQ ID NO: 214;
    ix. SEQ ID NO: 229 and SEQ ID NO: 228: or
    x. SEQ ID NO: 230 and SEQ ID NO: 214; or
  l. the VH domain and the VL domain of amino acid sequences:
    i. SEQ ID NO: 232 and SEQ ID NO: 231; or
    ii. SEQ ID NO: 234 and SEQ ID NO: 233.

28. The method according to claim 1, wherein the combination produces a synergistic effect, which is measured in a Rhesus macaque model of haploidentical hematopoietic stem cell transplantation.

29. The method according to claim 28, wherein survival in said model is increased by at least 14 days as compared to survival resulting from either of:
  a. a method of treating or preventing GvHD in a Rhesus macaque model of haploidentical hematopoietic stem cell transplantation, comprising administering to the Rhesus macaque a therapeutically or prophylactically effective amount of a monotherapy, said monotherapy comprising at least one anti-OX40L antibody or fragment thereof; or
  b. a method of treating or preventing GvHD in a Rhesus macaque model of haploidentical hematopoietic stem cell transplantation, comprising administering to the Rhesus macaque a therapeutically or prophylactically effective amount of a monotherapy, said monotherapy comprising at least one mTOR inhibitor.

* * * * *